(12) United States Patent
Bourget et al.

(10) Patent No.: US 7,338,805 B2
(45) Date of Patent: Mar. 4, 2008

(54) LABELING REAGENTS, METHODS FOR SYNTHESIZING SUCH REAGENTS AND METHODS FOR DETECTING BIOLOGICAL MOLECULES

(75) Inventors: Cecile Bourget, Grenoble (FR); Jean Lhomme, Meylan (FR); Ali Laayoun, Lyons (FR); Mitsuharu Kotera, Meylan (FR); Emmanuelle Trevisiol, Cornebarrieu (FR); Lionel Menou, Saint Genis Laval (FR); Eloy Bernal Mendez, Lyons (FR)

(73) Assignees: Bio Merieux, Marcy l'Etoile (FR); Universite Joseph Fourier Domaine, Grenoble (FR); Centre National de la Recherche Scientifique, Paris (FR)

( * ) Notice: Subject to any disclaimer, the term of this patent is extended or adjusted under 35 U.S.C. 154(b) by 40 days.

(21) Appl. No.: 10/137,454

(22) Filed: May 3, 2002

(65) Prior Publication Data

US 2003/0186448 A1    Oct. 2, 2003

Related U.S. Application Data

(60) Provisional application No. 60/310,241, filed on Aug. 7, 2001.

(30) Foreign Application Priority Data

May 4, 2001    (FR) ................... 01 06040

(51) Int. Cl.
*G01N 37/00*    (2006.01)
*G01N 33/48*    (2006.01)

(52) U.S. Cl. ............... 436/56; 436/63; 436/501; 436/544; 436/546; 435/6; 536/23.1

(58) Field of Classification Search ........... 436/56, 436/63, 501, 544, 546; 535/6; 536/23.1
See application file for complete search history.

(56) References Cited

U.S. PATENT DOCUMENTS

| | | | |
|---|---|---|---|
| 4,507,466 A | | 3/1985 | Tomalia et al. |
| 4,568,737 A | | 2/1986 | Tomalia et al. |
| 4,672,040 A | | 6/1987 | Josephson |
| 4,683,195 A | | 7/1987 | Mullis et al. |
| 4,683,202 A | | 7/1987 | Mullis |
| 4,775,745 A | * | 10/1988 | Ford et al. ............ 534/560 |
| 4,800,159 A | | 1/1989 | Mullis et al. |
| 5,234,809 A | | 8/1993 | Boom et al. |
| 5,328,824 A | | 7/1994 | Ward et al. |
| 5,399,491 A | | 3/1995 | Kacian et al. |
| 5,449,767 A | | 9/1995 | Ward et al. |
| 5,750,338 A | | 5/1998 | Collins et al. |
| 6,083,708 A | | 7/2000 | Singh et al. |
| 6,083,762 A | | 7/2000 | Papen et al. |
| 6,083,763 A | | 7/2000 | Balch |
| 6,110,426 A | | 8/2000 | Shalon et al. |

FOREIGN PATENT DOCUMENTS

| | | |
|---|---|---|
| DE | 39 10 151 A1 | 10/1990 |
| EP | 0 063 879 A2 | 11/1982 |
| EP | 0 097 373 A2 | 1/1984 |
| EP | 0 201 184 A2 | 12/1986 |
| EP | 0 286 898 A2 | 10/1988 |
| EP | 0 302 175 A2 | 2/1989 |
| EP | 0 350 407 B1 | 1/1990 |
| EP | 0 561 722 A1 | 9/1993 |
| EP | 0 567 841 A2 | 11/1993 |
| EP | 0 569 272 B1 | 6/1998 |
| WO | WO 90/01069 A1 | 2/1990 |
| WO | WO 90/06995 A1 | 6/1990 |
| WO | WO 90/08838 A | 8/1990 |
| WO | WO 91/02818 A1 | 3/1991 |
| WO | WO 93/16094 A2 | 8/1993 |
| WO | WO 95/08000 A2 | 3/1995 |
| WO | WO 97/35031 A1 | 9/1997 |
| WO | WO 97/45202 A1 | 12/1997 |
| WO | WO 98/05766 A1 | 2/1998 |
| WO | WO 99/15621 A1 | 4/1999 |
| WO | WO 99/35500 A1 | 7/1999 |
| WO | WO 99/53304 A1 | 10/1999 |
| WO | WO 99/65926 A1 | 12/1999 |

| WO | WO 00/05338 A1 | 2/2000 |
| WO | WO 00/07982 A1 | 2/2000 |
| WO | WO 00/40590 A2 | 7/2000 |
| WO | WO 00/60049 A1 | 10/2000 |
| WO | WO 01/44506 A1 | 6/2001 |
| WO | WO 01/92361 A1 | 12/2001 |

OTHER PUBLICATIONS

Shiga et al. "Diazonium Compounds Useful as Components for Nucleic Acid Probes", Anal. Sci., 1993, v. 9, No. 4, pp. 553-556.*
M. Shiga et al., "Fluorescence Detection of DNA Using A Novel Peroxidase Substrate, 4-(4-Hydroxyphenylcarbamoyl)butanoic Acid," *Analytical Sciences*, vol. 11, No. 4, 1995, pp. 591-595.
G. M. Makrigiorgos et al., "Fluorescent Labelling of Abasic Sites: A Novel Methodology to Detect Closely-Spaced Damage Sites in DNA," *International Journal of Radiation Biology*, vol. 74, No. 1, 1998, pp. 99-109.

* cited by examiner

*Primary Examiner*—Yelena G. Gakh
(74) *Attorney, Agent, or Firm*—Oliff & Berridge, PLC

(57) ABSTRACT

The present invention relates to a temperature-stable labeling reagent of formula:

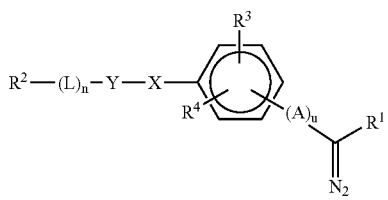

in which

R$^1$ represents H or an alkyl, aryl or substituted aryl group,

R$^2$ represents a detectable marker or at least two detectable markers linked together by at least one multimeric structure, L is a linking arm containing a linear succession of at least two covalent bonds and n an integer equal to 0 or 1, R$^3$ and R$^4$ represent independently of each other: H, NO$_2$, Cl, Br, F, I, R$^2$-(L)$_n$-Y—X—, OR, SR, NR$_2$, R, NHCOR, CONHR, COOR with R=alkyl or aryl, A is a linking arm containing at least one covalent double bond allowing conjugation of the diazo functional group with the aromatic ring and u is an integer between 0 and 2, preferably equal to 0 or 1, and —Y—X— represents —CONH—, —NHCO—, —CH$_2$O—, —CH$_2$S—.

The present invention also describes a method for synthesizing said markers as well as applications for labeling biological molecules, in particular nucleic acids, with a labeling reagent carrying the diazomethyl functional group.

The invention finds a preferred application in the field of diagnosis.

38 Claims, 13 Drawing Sheets

DPDAM
(DiPhényIDAM)

PMDAM
(PhénylMéthylDAM)

NPDAM
(NitroPhénylDAM)

PDAM
(PyrénylDiAzoMéthane)

BioDPDAM
(BiotinylDPDAM)

m-BioPMDAM
(meta-BiotinylPMDAM)

p-BioPMDAM
(para-BiotinylPMDAM)

o-BioPMDAM
(ortho-BiotinylPMDAM)

Cy5PMDAM

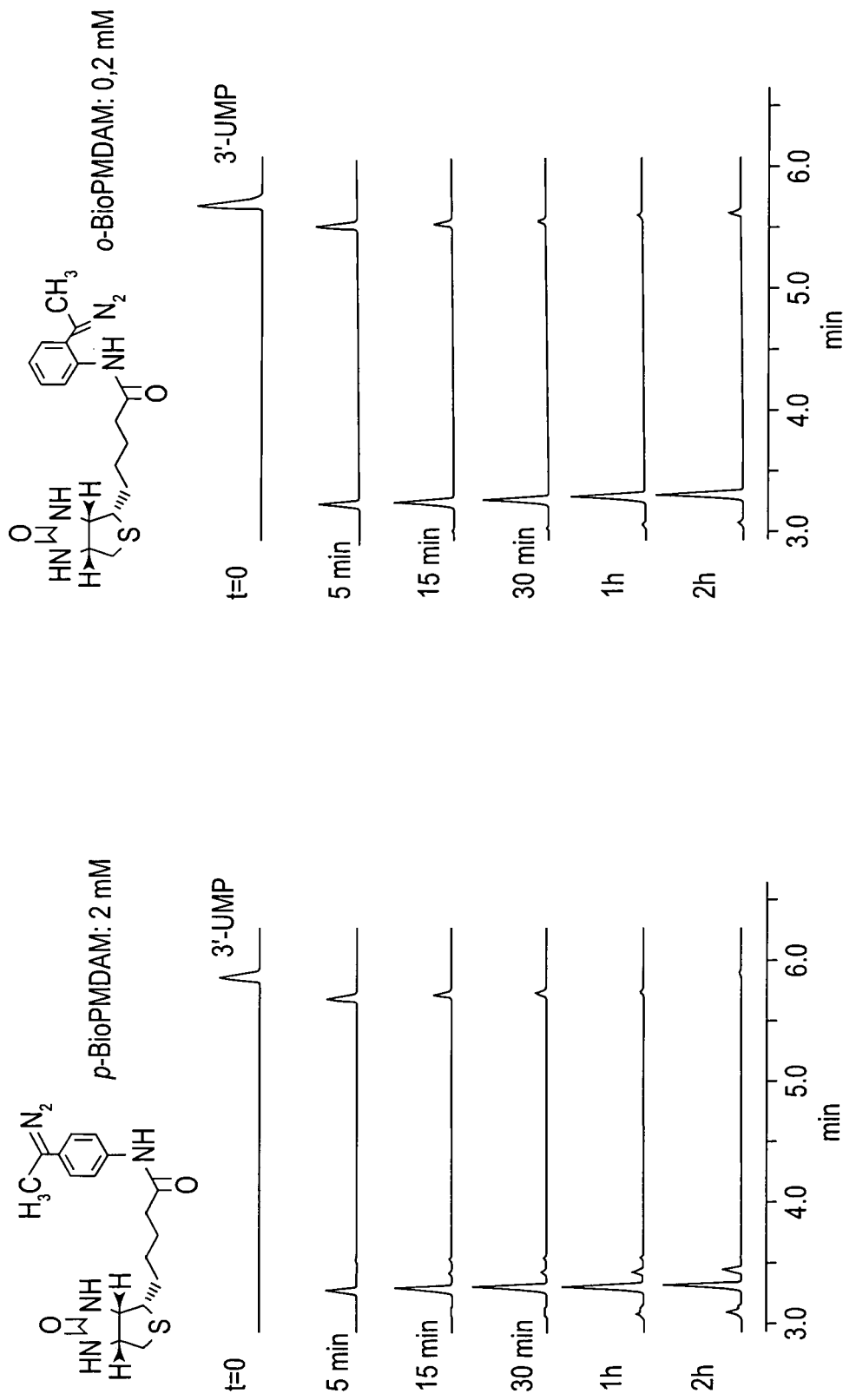

LABELING REAGENTS, METHODS FOR SYNTHESIZING SUCH REAGENTS AND METHODS FOR DETECTING BIOLOGICAL MOLECULES

This nonprovisional application claims the benefit of U.S. Provisional Application No. 60/310,241, filed Aug. 7. 2001.

BACKGROUND OF THE INVENTION

The present invention relates to novel reagents for labeling biological molecules, to a method for synthesizing said markers as well as to applications for labeling biological molecules, in particular in the field of diagnosis using nucleic probes.

DESCRIPTION OF THE PRIOR ART

The prior art shows that numerous methods exist for labeling nucleotides, oligonucleotides or nucleic acids.

A first method consists in attaching the marker to the base, whether the latter is a natural base or a modified base. A second method proposes attaching the marker to the sugar, here again whether it is a natural sugar or a modified sugar. A third method is aimed at attaching the marker to the phosphate.

Labeling on the base has been used in particular in the approach for labeling nucleic acids by incorporating directly labeled nucleotides.

Labeling on the sugar is often used in the case of the nucleic probes prepared by chemical synthesis.

Labeling on the phosphate has also been used to introduce arms which have been functionalized and markers during the chemical synthesis of oligonucleotides.

In fact, persons skilled in the art, who have to carry out a labeling of a nucleotide, or of a nucleotide analog or of a nucleic acid, are inclined to carry out this attachment onto the base or onto the sugar which offer them more convenience and alternatives. That is in fact what emerges from the study of numerous documents, such as EP-A-0,329,198, EP-A-0,302,175, EP-A-0,097,373, EP-A-0,063,879, U.S. Pat. No. 5,449,767, U.S. Pat. No. 5,328,824, WO-A-93/16094, DE-A-3,910,151, EP-A-0,567,841 for the base or EP-A-0,286,898 for the sugar.

The attachment of the marker to the phosphate is a technique which is more complex than the technique consisting in functionalizing the base or the sugar and has been used less in particular because of the low reactivity of the phosphate (see for example Jencks W. P. et al., J. Amer. Chem. Soc., 82, 1778-1785, 1960). Likewise, in the review by O'Donnel and McLaughlin ("Reporter groups for the analysis of nucleic acid structure", p. 216-243, in "Bioorganic Chemistry: Nucleic Acids", Ed. Hecht S. M., Oxford University Press, 1996) relating to the methods for introducing probes into oligonucleotide fragments, the effective alkylation of the internucleotide phosphodiester is considered as being impossible.

Patent application WO 99/65926 describes a method for labeling a synthetic or natural ribonucleic acid (RNA) which consists in fragmenting the RNA and in labeling at the level of the terminal phosphate. This document describes a number of functional groups which can be used for labeling in conjunction with fragmentation such as hydroxyl, amine, hydrazine, alkoxyamine, alkyl halide and benzyl-type alkyl halide functional groups, and in particular the 5'-(bromomethyl)fluorescein derivative. These functional groups make it possible to label nucleic acids, but it is necessary to associate a fragmentation step in order to have effective labeling because this labeling occurs on the phosphate released during fragmentation. Furthermore, it is necessary to add a large excess of labeling reagent relative to the RNA in order to obtain effective labeling, which induces problems of background noise generated by the marker in excess. Finally, this method does not work efficiently on double-stranded DNA.

A need therefore exists for novel reagents which are effective from the point of view of the labeling yield, which are specific at the level of the labeling position and in particular which do not affect the properties of hybridization of the bases involved in the formation of the double helix via hydrogen bonds, which can be used both for DNA and RNA and finally which make it possible to label either nucleotides, oligonucleotides, or nucleic acids which are of natural origin or which are prepared by enzymatic amplification.

SUMMARY OF THE INVENTION

The present invention describes novel markers which satisfy the abovementioned conditions and which use the diazomethyl functional group as reactive functional group for the labeling.

The diazomethyl functional group (of formula $-C(N_2)-$) has already been used for the alkylation of phosphate groups, but a number of problems exist. On the one hand, the diazo derivatives in general are themselves unstable, which poses problems for the use of these labeling reagents in a labeling kit, and, on the other hand, the product of coupling is unstable, which rules out its use if the role of the labeled product is to detect the presence of a target biological molecule in any sample.

Finally, the derivatives carrying the diazomethyl functional group are insoluble in water, which leads to two-phase conditions being used for the coupling with biological molecules, which are only soluble and stable in water or aqueous buffers, but these conditions slow down the rate of reaction and therefore hamper the efficiency of the coupling.

The novel labeling reagents of the invention also solve these technical problems.

According to a first embodiment, the present invention describes a temperature-stable labeling reagent of formula (0):

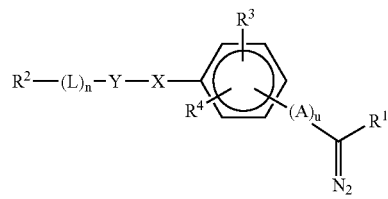

in which:
  $R^1$ represents H or an alkyl, aryl or substituted aryl group,
  $R^2$ represents a detectable marker or at least two detectable markers linked together by at least one multimeric structure,
  L is a linking arm containing a linear succession of at least two covalent bonds and n an integer equal to 0 or 1,
  $R^3$ and $R^4$ represent independently of each other: H, $NO_2$, Cl, Br, F, I, $R^2$-$(L)_n$-Y-X-, OR, SR, $NR_2$, R, NHCOR, CONHR, COOR with R=alkyl or aryl, A is a linking arm containing at least one covalent double bond allowing conjugation of the diazo functional group with the aromatic ring and u is an integer between 0 and 2, preferably equal to 0 or 1, and —Y—X— represents —CONH—, —NHCO—, —CH$_2$O—, —CH$_2$S—.

According to a second embodiment, the present invention describes a temperature-stable labeling reagent of formula (1):

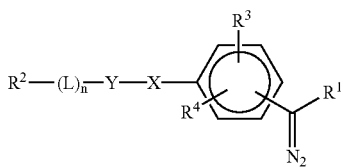

in which:

R$^1$ represents H or an alkyl, aryl or substituted aryl group,

R$^2$ represents a detectable marker or at least two detectable markers linked together by at least one multimeric structure, L is a linking arm containing a linear succession of at least two covalent bonds and n an integer equal to 0 or 1, R$^3$ and R$^4$ represent independently of each other: H, NO$_2$, Cl, Br, F, I, R$^2$-(L)$_n$-Y—X—, OR, SR, NR$_2$, R, NHCOR, CONHR, COOR with R=alkyl or aryl, and —Y—X— represents —CONH—, —NHCO—, —CH$_2$O—, —CH$_2$S—.

Advantageously, according to a first variant of the second embodiment, the temperature-stable reagent is of formula (2):

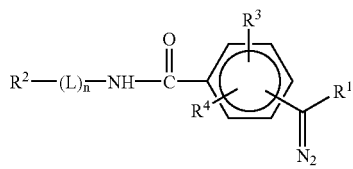

in which:

R$^1$ represents H or an alkyl, aryl or substituted aryl group,

R$^2$ represents a detectable marker or at least two detectable markers linked together by at least one multimeric structure, L is a linking arm containing a linear succession of at least two covalent bonds and n an integer equal to 0 or 1, and R$^3$ and R$^4$ represent independently of each other: H, NO$_2$, Cl, Br, F, I, R$^2$-(L)$_n$-Y—X—, OR, SR, NR$_2$, R, NHCOR, CONHR, COOR with R=alkyl or aryl.

Advantageously, according to a second variant of the second embodiment, the temperature-stable reagent is of formula (3):

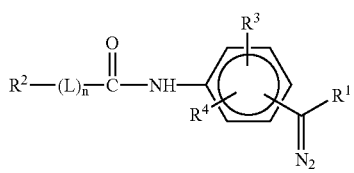

in which:

R$^1$ represents H or an alkyl, aryl or substituted aryl group,

R$^2$ represents a detectable marker or at least two detectable markers linked together by at least one multimeric structure, L is a linking arm containing a linear succession of at least two covalent bonds and n an integer equal to 0 or 1, and R$^3$ and R$^4$ represent independently of each other: H, NO$_2$, Cl, Br, F, I, R$^2$-(L)$_n$-Y—X—, OR, SR, NR$_2$, R, NHCOR, CONHR, COOR with R=alkyl or aryl.

Advantageously, according to a third variant of the second embodiment, the temperature-stable reagent is of formula (4):

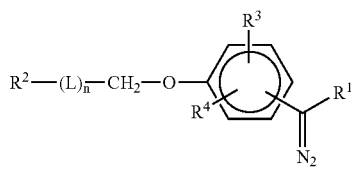

in which:

R$^1$ represents H or an alkyl, aryl or substituted aryl group,

R$^2$ represents a detectable marker or at least two detectable markers linked together by at least one multimeric structure, L is a linking arm containing a linear succession of at least two covalent bonds and n an integer equal to 0 or 1, R$^3$ and R$^4$ represent independently of each other: H, NO$_2$, Cl, Br, F, I, R$^2$-(L)$_n$-Y—X—, OR, SR, NR$_2$, R, NHCOR, CONHR, COOR with R=alkyl or aryl.

Advantageously, according to a first variant of the first embodiment, the temperature-stable reagent is of formula (21):

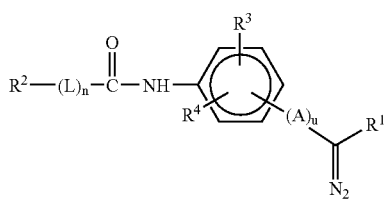

in which:

R$^1$ represents H or an alkyl, aryl or substituted aryl group,

R$^2$ represents a detectable marker or at least two detectable markers linked together by at least one multimeric structure, L is a linking arm containing a linear succession of at least two covalent bonds and n an integer equal to 0 or 1, A is a linking arm containing at least one covalent double bond allowing conjugation of the diazo functional group with the aromatic ring and u is equal to 1, and p1 R$^3$ and R$^4$ represent independently of each other: H, NO$_2$, Cl, Br, F, I, R$^2$-(L)$_n$-Y—X—, OR, SR, NR$_2$, R, NHCOR, CONHR, COOR with R=alkyl or aryl.

Advantageously, according to a second variant of the first embodiment, the temperature-stable reagent is of formula (22):

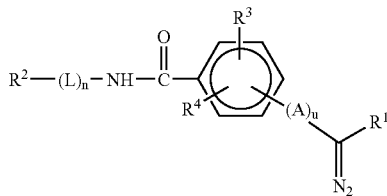

in which:
R$^1$ represents H or an alkyl, aryl or substituted aryl group,
R$^2$ represents a detectable marker or at least two detectable markers linked together by at least one multimeric structure,
L is a linking arm containing a linear succession of at least two covalent bonds and n an integer equal to 0 or 1,
A is a linking arm containing at least one covalent double bond allowing conjugation of the diazo functional group with the aromatic ring and u is equal to 1, and
R$^3$ and R$^4$ represent independently of each other: H, NO$_2$, Cl, Br, F, I, R$^2$-(L)$_n$-Y—X—, OR, SR, NR$_2$, R, NHCOR, CONHR, COOR with R=alkyl or aryl.

Advantageously, according to a third variant of the first embodiment, the temperature-stable reagent is of formula (23):

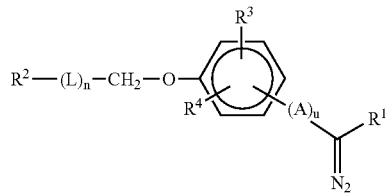

in which:
R$^1$ represents H or an alkyl, aryl or substituted aryl group,
R$^2$ represents a detectable marker or at least two detectable markers linked together by at least one multimeric structure,
L is a linking arm containing a linear succession of at least two covalent bonds and n an integer equal to 0 or 1,
A is a linking arm containing at least one covalent double bond allowing conjugation of the diazo functional group with the aromatic ring and u is equal to 1, and
R$^3$ and R$^4$ represent independently of each other: H, NO$_2$, Cl, Br, F, I, R$^2$-(L)$_n$-Y—X—, OR, SR, NR$_2$, R, NHCOR, CONHR, COOR with R=alkyl or aryl.

In the above formulae (0) to (4) and (21) to (23), advantageously R$^3$ and R$^4$ represent independently of each other: H, NO$_2$, OCH$_3$, —CO—NH—(CH$_2$)$_3$—(O—CH$_2$—CH$_2$)$_3$—CH$_2$—NH—R$^2$, —CO—NH—(CH$_2$)$_3$—(O—CH$_2$—CH$_2$)$_4$—CH$_2$—NH—R$^2$.

Thus, a preferred compound according to the third variant of the second embodiment (formula (4)) is of formula (4'):

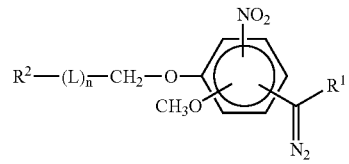

in which:
R$^1$ represents H or an alkyl, aryl or substituted aryl group,
R$^2$ represents a detectable marker or at least two detectable markers linked together by at least one multimeric structure, and
L is a linking arm containing a linear succession of at least two covalent bonds and n an integer equal to 0 or 1.

Similarly, a preferred compound according to the first variant of the second embodiment (formula (2)) is of formula (2'):

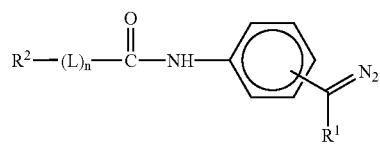

in which:
R$^1$ represents H or an alkyl, aryl or substituted aryl group,
R$^2$ represents a detectable marker or at least two detectable markers linked together by at least one multimeric structure, and
L is a linking arm containing a linear succession of at least two covalent bonds and n an integer equal to 0 or 1.

Advantageously, in formula (2'), the substituent carrying the diazomethyl functional group is in the ortho or meta position.

Similarly, a preferred compound according to the first variant of the first embodiment (formula (21) is of formula (24):

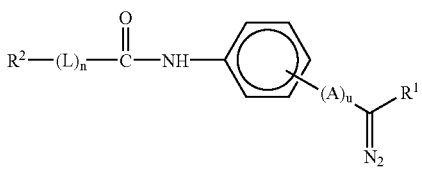

in which:
R$^1$ represents H or an alkyl, aryl or substituted aryl group,
R$^2$ represents a detectable marker or at least two detectable markers linked together by at least one multimeric structure, and
A is a linking arm containing at least one covalent double bond allowing conjugation of the diazo functional group with the aromatic ring and u is equal to 1.

The expression "multimeric structure" is understood to mean a polymer formed of repeating units of chemical or biological synthons. An example is cited in Example 34.2 of the description below. Many variants of such structures which can be used in the present invention are known, such as for example:
- linear polymers (EP-A-0,561,722, EP-A-0,669,991), branched polymers (WO-A-01/92361).
- particles (EP-A-0 827 552),
- dendrimers (U.S. Pat. No. 4,507,466; U.S. Pat. No. 4,568,737; U.S. Pat. No. 6,083,708),
- polynucleotides, and
- polypeptides.

The expression "detectable marker" is understood to mean at least one marker capable of directly or indirectly generating a detectable signal. A nonlimiting list of these markers follows:
- enzymes which produce a signal detectable for example by colorimetry, fluorescence, luminescence, such as horseradish peroxidase, alkaline phosphatase, β-galactosidase, glucose-6-phosphate dehydrogenase,
- chromophores such as fluorescent, luminescent or coloring compounds,
- groups with electron density detectable by electron microscopy or by their electrical property such as conductivity, amperometry, voltametry, impedance,
- detectable groups, for example whose molecules are of sufficient sizes to induce detectable modifications of their physical and/or chemical characteristics, this detection may be carried out by optical methods such as diffraction, surface plasmon resonance, surface variation, contact angle variation or physical methods such as atomic force spectroscopy, tunnel effect,
- radioactive molecules such as $^{32}P$, $^{35}S$ or $^{125}I$.

Preferably, the marker is not a radioactive marker in order to avoid the safety problems linked to these markers.

In a particular embodiment of the present invention, the marker is electrochemically detectable and in particular the marker is a derivative of an iron complex such as a ferrocene.

Indirect systems may also be used, such as, for example, ligands capable of reacting with an antiligand. The ligand/antiligand pairs are well known to persons skilled in the art, which is the case, for example, for the following pairs: biotin/streptavidin, hapten/antibody, antigen/antibody, peptide/antibody, sugar/lectin, polynucleotide/complementary strand of the polynucleotide. In this case, it is the ligand which carries the diazomethyl reactive functional group. The antiligand may be directly detectable by the markers described in the preceding paragraph or may itself be detectable by another ligand/antiligand pair. This stacking system is illustrated in the examples.

Another example of indirect systems uses a specific covalent bond between the ligand and the antiligand, for example methyl ketone and alkoxyamine.

Examples of this system are described in patent applications WO-A-00/40590 and WO-A-98/05766. These indirect detection systems may lead, under certain conditions, to amplification of the signal and reference may be made to prior patent applications WO-A-00/07982, WO-A-01/92361 and WO-A-95/08000 for examples of chemical amplification using polymers or to application WO-A-01/44506 for stacking chemical amplification systems.

In a particular embodiment of signal amplification, at least two markers are present on the labeling reagent.

In particular, a reagent which makes it possible to carry out the signal amplification according to the present invention possesses a structure $R^2\text{-}(L)_n\text{-}$ of formula (5) below:

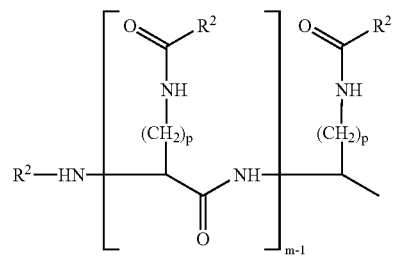

in which:
- $R^2$ represents a detectable marker,
- m is an integer between 1 and 100, preferably between 1 and 20, and
- p is an integer between 1 and 10, advantageously 2 to 6, preferably 4.

This structure of $R^2\text{-}(L)_n$ applies without distinction to formulae (0) to (4) and (21) to (23) above.

Another preferred labeling reagent for the signal amplification is the reagent of formula (6):

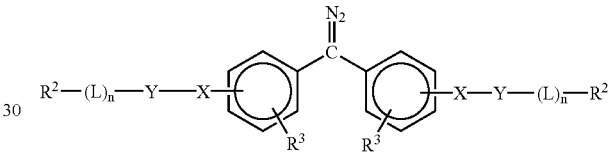

in which:
- $R^2$ represents a detectable marker,
- $R^3$ represents H, $NO_2$, Cl, Br, F, I, OR, SR, $NR_2$, R, NHCOR, CONHR, COOR with R=alkyl or aryl,
- L is a linking arm containing a linear succession of at least 2 covalent bonds and n an integer equal to 0 or 1, and
- —Y—X— represents —CONH—, —NHCO—, —CH$_2$O—, —CH$_2$S—.

Advantageously, the reagent for the signal amplification has the formula (7)

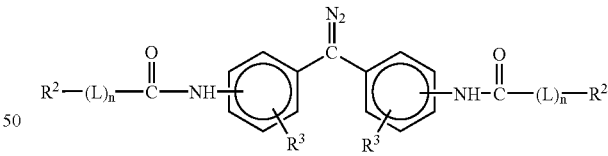

in which:
- $R^2$ represents a detectable marker or at least two detectable markers linked together by at least one multimeric structure,
- $R^3$ represents H, $NO_2$, Cl, Br, F, I, $R^2\text{-}(L)_n\text{-}Y\text{—}X\text{—}$, OR, SR, $NR_2$, R, NHCOR, CONHR, COOR with R=alkyl or aryl, preferably $R^3$ represents H, $NO_2$, $OCH_3$, —CO—NH—($CH^2$)$_3$—(O—$CH_2$—$CH_2$)$_3$—$CH_2$—NH—$R^2$ or —CO—NH—($CH_2$)$_3$—(O—$CH_2$—$CH_2$)$_4$—$CH_2$—NH—$R^2$, and
- L is a linking arm containing a linear succession of at least 2 covalent bonds and n an integer equal to 0 or 1.

Still another preferred labeling reagent for the signal amplification is the reagent of formula (25):

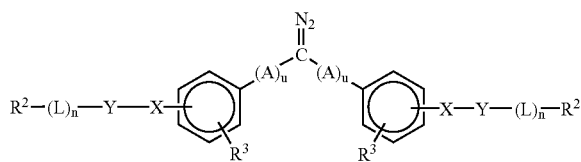

in which:
R² represents a detectable marker or at least two detectable markers linked together by at least one multimeric structure, R³ represents H, NO₂, Cl, Br, F, I, R²-(L)$_n$-Y—X—, OR, SR, NR₂, R, NHCOR, CONHR, COOR with R=alkyl or aryl, L is a linking arm containing a linear succession of at least two covalent bonds and n an integer equal to 0 or 1, A is a linking arm containing at least one covalent double bond allowing conjugation of the diazo functional group with the aromatic ring and u is equal to 1, and —Y—X— represents —CONH—, —NHCO—, —CH₂O—, —CH₂S—.

In a preferred embodiment of the invention, the tracer is a fluorescent compound of low steric hindrance such as fluorescein, dansyl, chromophores of the IR type (Li-COR Inc., Lincoln Nebr., USA), cyanine derivatives such as Cy5 and Cy3 (Randolph J. B. et al., Nucleic Acids Res., 25(14), p. 2923-2929, 1997) and in particular the Cy5 derivatives or alternatively the tracer is a hapten of low steric hindrance such as biotin or an abietane derivative (see application WO-A-00/07982). The expression low steric hindrance is understood to mean a molecular weight of less than 1000 g/mol.

In the case of a fluorophore, it is preferable to work with fluorophores whose excitation wavelength is greater than 450 nm, preferably greater than 600 nm.

In the case where the tracer is a hapten which does not produce a signal by itself, such as for example biotin, the detection is carried out by the recognition of an antiligand labeled as described above. In the case of biotin, streptavidin or an anti-biotin antibody coupled to a fluorescent compound such as fluorescein, Cy5 or phycoerythrin is preferably used. In the case of abietane, a monoclonal antibody as described in patent application WO-A-00/07982 is used.

In particular, the labeling reagents of the invention are soluble in polar solvents such as DMF, DMSO, CH₃CN, THF, DMA (dimethylacetamide), NMP (N-methylpyrrolidone), DME (dimethoxyethane).

Preferably, the labeling reagents are soluble in DMSO or water.

The expression water-miscible solvent is understood to mean a solvent which is miscible in a proportion of at least 5% by volume with water or an aqueous buffer containing salts.

Advantageously, in the preceding formulae, the arm L comprises an ethylene glycol or polyethylene glycol motif in order to increase the solubility of the reagent in water.

A is a linking arm containing at least one double bond of the ethylene type allowing conjugation of the diazomethyl functional group with the aromatic ring. The role of the linking arm A is to distance the diazomethyl functional group from the ring in order to reduce steric hindrance while preserving the stability of the diazomethyl functional group. The expression "conjugation" is understood to mean the electron delocalization of the aromatic ring along the carbon chain of the linking arm A. By way of example, the arm A may have the following structure:

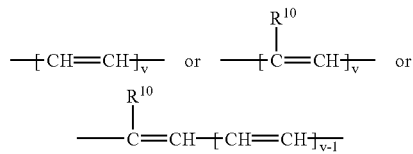

in which:
v is an integer between 1 and 10, preferably v is 1 or 2, and

R¹⁰ is H or an alkyl group, preferably R¹⁰ is H, methyl or ethyl.

These reagents can thus bind in the homogeneous phase to biological molecules, the homogeneous phase consisting of a substantially aqueous solution, that is to say containing at least 50% of water.

The expression "biological molecule" is understood to mean a compound which possesses at least one recognition site allowing it to react with a target molecule of biological interest. By way of example, there may be mentioned, as biological molecules, nucleic acids, antigens, antibodies, polypeptides, proteins and haptens.

The term "nucleic acid" means a succession of at least two deoxyribonucleotides or ribonucleotides optionally comprising at least one modified nucleotide, for example at least one nucleotide containing a modified base such as inosine, 5-methyldeoxycytidine, 5-dimethylaminodeoxyuridine, deoxyuridine, 2,6-diaminopurine, 5-bromodeoxyuridine or any other modified base allowing hybridization. This polynucleotide may also be modified at the level of the internucleotide bond, such as, for example, phosphorothioates, H-phosphonates, alkyl phosphonates, at the level of the backbone such as, for example, alpha-oligonucleotides (FR 2 607 507) or PNAs (M. Egholm et al., J. Am. Chem. Soc., 114, 1895-1897, 1992) or 2'-O-alkylriboses. The nucleic acid may be natural or synthetic, an oligonucleotide, a polynucleotide, a nucleic acid fragment, a ribosomal RNA, a messenger RNA, a transfer RNA, a nucleic acid obtained by an enzymatic amplification technique such as:

PCR (Polymerase Chain Reaction), described in patents U.S. Pat. No. 4,683,195, U.S. Pat. No. 4,683,202 and U.S. Pat. No. 4,800,159, and its RT-PCR (Reverse Transcription PCR) derivative, in particular in a one-step format as described in patent EP-B-0,569,272, LCR (Ligase Chain Reaction), disclosed for example in patent application EP-A-0,201,184, RCR (Repair Chain Reaction), described in patent application WO-A-90/01069, 3SR (Self Sustained Sequence Replication) with patent application WO-A-90/06995, NASBA (Nucleic Acid Sequence-Based Amplification) with patent application WO-A-91/02818, and TMA (Transcription Mediated Amplification) with patent U.S. Pat. No. 5,399,491.

The expression amplicons is then used to designate the nucleic acids generated by an enzymatic amplification technique.

Each of these modifications may be taken in combination as long as at least one phosphate is present in the nucleic acid.

The expression "polypeptide" is understood to mean a succession of at least two amino acids.

The expression "amino acids" is understood to mean:
primary amino acids which encode proteins,
amino acids derived after enzymatic action, such as trans-4-hydroxyproline,
amino acids which are natural but not present in proteins, such as norvaline, N-methyl-L-leucine, staline (see Hunt S. in Chemistry and Biochemistry of the amino acids, Barett G. C., ed., Chapman and Hall, London, 1985), and
amino acids protected with chemical functional groups which can be used in synthesis on a solid support or in a liquid phase and non-natural amino acids.

The term "hapten" denotes nonimmunogenic compounds, that is to say compounds incapable by themselves of promoting an immune reaction by production of antibodies, but capable of being recognized by antibodies obtained by immunizing animals under known conditions, in particular by immunizing with a hapten-protein conjugate. These compounds generally have a molecular mass of less than 3000 Da, and most often less than 2000 Da, and may be, for example, glycosylated peptides, metabolites, vitamins, hormones, prostaglandins, toxins or various medicaments, nucleosides and nucleotides.

The term "antibody" includes polyclonal or monoclonal antibodies, antibodies obtained by genetic recombination, and antibody fragments such as Fab or $F(ab')_2$ fragments.

The term "antigen" denotes a compound capable of generating antibodies.

The term "protein" includes holoproteins and heteroproteins such as nucleoproteins, lipoproteins, phosphoproteins, metalloproteins and glycoproteins, both fibrous and globular, in their characteristic conformational form.

Advantageously, the biological molecule possesses a phosphate group, that is to say a group having at least one motif:

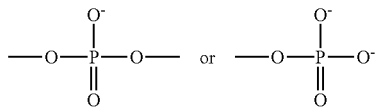

which is either naturally present in the biological molecule or may be introduced, for example, by chemical or enzymatic modification. Examples of chemical modification for proteins are given in "Chemistry of protein conjugation and cross linking", S. S. Wong, CRC Press, 1991.

Preferably, the biological molecule is a nucleic acid.

Some advantageous reagents of the invention are:

a) of formula (8):

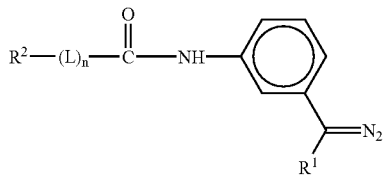

in which:
$R^1$ represents H or an alkyl or aryl or substituted aryl group,
$R^2$ represents a detectable marker or at least two detectable markers linked together by at least one multimeric structure,
L is a linking arm containing a linear succession of at least two covalent bonds, and
n an integer equal to 0 or 1.

b) of formula (9):

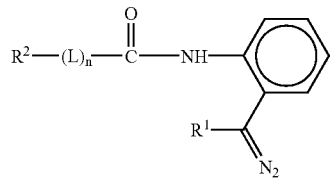

in which:
$R^1$ represents H or an alkyl or aryl or substituted aryl group,
$R^2$ represents a detectable marker or at least two detectable markers linked together by at least one multimeric structure,
L is a linking arm containing a linear succession of at least two covalent bonds, and
n an integer equal to 0 or 1.

c) of formula (10):

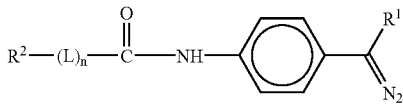

in which:
$R^1$ represents H or an alkyl or aryl or substituted aryl group,
$R^2$ represents a detectable marker or at least two detectable markers linked together by at least one multimeric structure,
L is a linking arm containing a linear succession of at least two covalent bonds, and
n an integer equal to 0 or 1.

Preferably, the labeling reagent has the:

a) of formula (11):

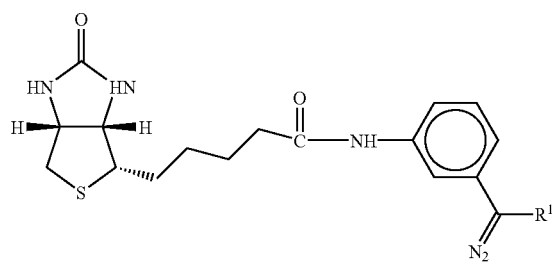

in which $R^1$ represents a methyl group or a phenyl, b) formula (12):

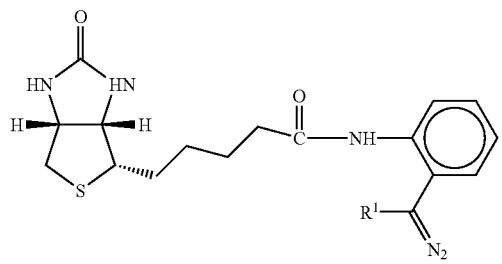

in which R¹ represents a methyl or phenyl group, c) of formula (13):

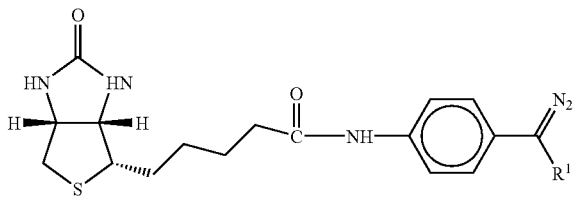

in which R¹ represents a methyl or phenyl group.

Other preferred reagents according to the invention have:

a) of formula (14):

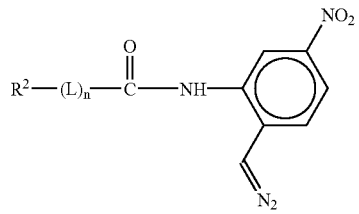

in which:
R² represents a detectable marker or at least two detectable markers linked together by at least one multimeric structure,
L is a linking arm containing a linear succession of at least two covalent bonds, and
n an integer equal to 0 or 1, b) of formula (26):

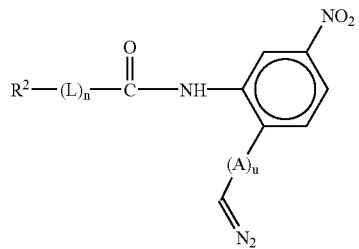

in which:

R² represents a detectable marker or at least two detectable markers linked together by at least one multimeric structure,
A is a linking arm containing at least one covalent double bond allowing conjugation of the diazo functional group with the aromatic ring and u is equal to 1, and
L is a linking arm containing a linear succession of at least two covalent bonds and n an integer equal to 0 or 1.

c) of formula (15):

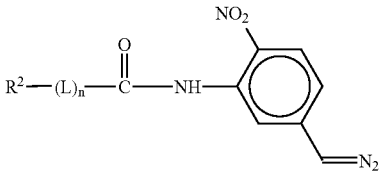

in which:
R² represents a detectable marker or at least two detectable markers linked together by at least one multimeric structure,
L is a linking arm containing a linear succession of at least two covalent bonds, and
n an integer equal to 0 or 1.

d) of formula (27):

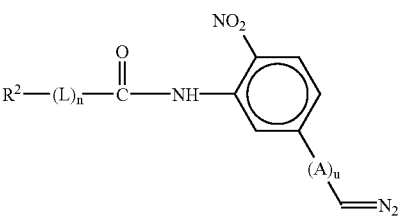

in which:
R² represents a detectable marker or at least two detectable markers linked together by at least one multimeric structure,
A is a linking arm containing at least one covalent double bond allowing conjugation of the diazo functional group with the aromatic ring and u is equal to 1, and
L is a linking arm containing a linear succession of at least two covalent bonds and n an integer equal to 0 or 1.

Regardless of the variant and embodiment of the reagent, L may comprise a unit —(O—CH₂—CH₂)—, repeated from 1 to 20 times, preferably from 1 to 10 times, and still more preferably from 2 to 5 times.

It is another object of the present invention to describe a method for synthesizing a labeling reagent as well as the labeling reagents, which are stable to temperature, capable of being obtained by said method comprising the following steps:

a) there is made available a derivative of formula (16a):

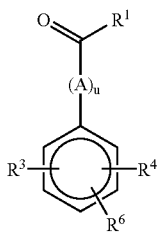

in which:
R$^1$ represents H or an alkyl or aryl or substituted aryl group,
R$^3$ and R$^4$ represent independently of each other: H, NO$_2$, Cl, Br, F, I, R , OR, SR, NR$_2$. R, NHCOR, CONHR, COOR with R=alkyl or aryl,
R$^6$ represents COOH, COOM, NH$_2$, OH or SH with M=alkyl, in particular methyl or ethyl, and
A is a linking arm containing at least one covalent double bond allowing conjugation of the diazomethyl functional group with the aromatic ring and u is an integer equal to 0 or 1, b) there is made available a marker or a marker precursor possessing a reactive functional group R$^7$ complementary to R$^6$, c) the complementary functional group of said marker or marker precursor is reacted with the functional group R$^6$ of the derivative of formula (16a) in the presence of at least one coupling agent to form a covalent bond, d) a hydrazine derivative or hydrazine is reacted with the ketone or aldehyde functional group to form a hydrazone, and e) the hydrazone is converted to a diazomethyl functional group using an appropriate treatment.

If the functional group R$^6$ is COOH or COOM, the complementary functional group R$^7$ is NH$_2$.

If the functional group R$^6$ is NH$_2$, the complementary functional group R$^7$ is COOH.

If the functional group R$^6$ is OH, the complementary functional group R$^7$ is chosen from: alkyl halide, sulfonate, tosylate.

If the functional group R$^6$ is SH, the complementary functional group R$^7$ is chosen from: alkyl halide, maleimide.

A variant of the method of synthesis comprises the following steps:

a) there is made available a derivative of formula (16a):

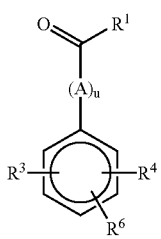

in which:
R$^1$ represents H or an alkyl or aryl or substituted aryl group,
R$^3$ and R$^4$ represent independently of each other: H, NO$_2$, Cl, Br, F, I, R$^6$, OR, SR, NR$_2$, R, NHCOR, CONHR, COOR with R=alkyl or aryl,
R$^6$ represents COOH, COON, NH$_2$, OH or SH with M=alkyl, in particular methyl or ethyl, and
A is a linking arm containing at least one covalent double bond allowing conjugation of the diazomethyl functional group with the aromatic ring and u is an integer equal to 0 or 1, b) there is made available a linking arm L possessing at least two reactive functional groups R$^8$ which are identical or different, the first functional group R$^8$ complementary to R$^6$ and the second functional group R$^8$ complementary to R$^7$, and there is made available, in addition, a marker or a marker precursor possessing a reactive functional group R$^7$, c) the first reactive functional group R$^8$ of the linking arm L is reacted with the derivative of formula (16a) in the presence of at least one coupling agent to form a covalent bond and then the second reactive functional group R$^8$ of the linking arm L is reacted with the marker or the marker precursor in the presence of at least one coupling agent to form a covalent bond, d) a hydrazine derivative or hydrazine is reacted with the ketone or aldehyde functional group to form a hydrazone, and e) the hydrazone is converted to a diazomethyl functional group using an appropriate treatment.

In this particular case, the method comprises an additional step in which the linking arm L is added to compound (16a) before reacting the marker or marker precursor. In this case, the linking arm L carries at least a first reactive functional group R$^8$ complementary to R$^6$, to allow coupling of the arm L to compound (16a), and at least a second functional group R$^8$, allowing coupling of the marker or marker precursor to the linking arm L, it being possible for the two functional groups R$^8$ carried by the arm L to be identical or different according to the coupling strategy and the reactive functional groups R$^6$ and R$^7$, carried by the compound (16a) and the marker or marker precursor, respectively.

If the functional group R$^6$ and/or the functional group R$^7$ is/are COOH or COOM, the first and/or the second complementary functional group R$^8$ is/are NH$_2$.

If the functional group R$^6$ and/or the functional group R$^7$ is/are NH$_2$, the first and/or the second complementary functional group R$^8$ is/are COOH.

If the functional group R$^6$ and/or the functional group R$^7$ is/are OH, the first and/or the second complementary functional group R$^8$ is/are independently chosen from: alkyl halide, sulfonate, tosylate.

If the functional group R$^6$ and/or the functional group R$^7$ is/are SH, the first and/or the second complementary functional group R$^8$ is/are independently chosen from: alkyl halide, maleimide.

In the case where R$^6$ is OH or SH, the coupling agent is a base such as potassium hydroxide or potassium carbonate or an organic base.

In the case where R$^6$ is COOH or NH$_2$, the coupling agent is chosen, for example, from the coupling agents used in peptide synthesis. Reference may be made to the manual "Peptide Chemistry, a practical textbook" by M. Bodansky, published by Springer Verlag, Berlin, 1988, chapter V, pages 55-73.

The expression "hydrazine derivative" is understood to mean a molecule possessing the NH$_2$—NH— functional group. Tosylhydrazine is an example of such a derivative.

The conversion of the hydrazone to diazomethyl is carried out by conventional methods, in particular oxidation with MnO$_2$.

Other methods can be used as described in X. Creary, Organic Syntheses, Wiley: New York, Coll. Vol. VII, p. 438-443, 1990; H. Zollinger, Diazo Chemistry II, VCH, Weinheim, p. 34-47, 1995; T. L. Holton and H. Shechter, J. Org. Chem., 60, 4725-4729, 1995.

In the case of the use of a tosylhydrazine derivative, the method is described in X. Creary, Organic Synthesis; Wiley: New York, Coll. Vol. VII, p. 438-443, 1990.

In a particular embodiment of any of the methods, said method comprises:
an additional step of protecting the ketone or aldehyde functional group (in the case where $R^1$ is H) of compound (16a), and
an additional subsequent step of deprotecting said ketone or aldehyde functional group.

This protection is achieved with an acetal group for example. The deprotection is carried out by an appropriate means, such as in an acidic medium for the acetal group. Persons skilled in the art determine, according to the compounds, at which stage of the synthesis these two protection and deprotection steps occur.

According to another embodiment of the present invention, there is described a method for synthesizing a labeling reagent as well as the labeling reagents, which are stable to temperature, capable of being obtained by said method comprising the following steps:
a) there is made available a derivative of formula (16):

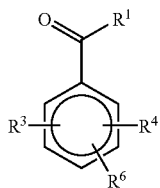

in which:
$R^1$ represents H or an alkyl or aryl or substituted aryl group,
$R^3$ and $R^4$ represent independently of each other: H, NO$_2$, Cl, Br, F, I, $R^6$, OR, SR, NR$_2$, R, NHCOR, CONHR, COOR with R=alkyl or aryl, and
$R^6$ represents COOH, NH$_2$, OH or SH.

b) there is made available a marker or a marker precursor possessing a reactive functional group $R^7$ complementary to $R^6$,
c) the complementary functional group of said marker or marker precursor is reacted with the $R^6$ functional group of the derivative of formula (16) in the presence of at least one coupling agent to form a covalent bond,
d) hydrazine or one of its derivatives is reacted with the ketone or aldehyde functional group to form a hydrazone, and
e) the hydrazone is converted to a diazomethyl functional group by means of an appropriate treatment.

If the functional group $R^6$ is COOH, the complementary functional group $R^7$ is NH$_2$.
If the functional group $R^6$ is NH$_2$, the complementary functional group $R^7$ is COOH.
If the functional group $R^6$ is OH, the complementary functional group $R^7$ is chosen from: alkyl halide, sulfonate, tosylate.

If the functional group $R^6$ is SH, the complementary functional group $R^7$ is chosen from: alkyl halide, maleimide.

In the case where $R^6$ is OH or SH, the coupling agent is a base such as potassium hydroxide or potassium carbonate.

In the case where $R^6$ is COOH or NH$_2$, the coupling agent is chosen, for example, from the coupling agents used in peptide synthesis. Reference may be made to the book "Peptide Chemistry, a practical textbook" by M. Bodansky, published by Springer Verlag, Berlin, 1988, Chapter V, pages 55-73.

The expression "hydrazine derivative" is understood to mean a molecule possessing the functional group NH$_2$—NH—. Tosylhydrazine is an example of such a derivative.

The conversion of the hydrazone to diazomethyl is carried out by the conventional methods, in particular oxidation with MnO$_2$.

Other methods can be used as described in X. Creary, Organic Syntheses, Wiley: New York, Coll. Vol. VII, p. 438-443, 1990; H. Zollinger, Diazo Chemistry II, VCH, Weinheim, p. 34-47, 1995; T. L. Holton and H. Shechter, J. Org. Chem., 60, 4725-4729, 1995.

In the case of the use of a tosylhydrazine derivative, the method is described in X. Creary, Organic Syntheses; Wiley: New York, Coll. Vol. VII, p. 438-443, 1990.

A preferred method according to the invention is a method where:
a) there is made available a derivative of formula (17):

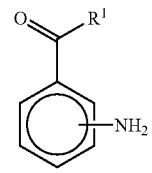

in which $R^1$ represents H or an alkyl or aryl or substituted aryl group,
b) there is made available a marker or a marker precursor possessing a carboxylic acid functional group,
c) the carboxylic functional group of said marker or marker precursor and the primary amine functional group of the derivative of formula (17) are reacted together in the presence of at least one coupling agent to form an amide bond,
d) hydrazine is reacted with the ketone or aldehyde functional group from the derivative of formula (17) to form a hydrazone, and
e) said hydrazone is oxidized in the presence of MnO$_2$ to form a diazomethyl functional group.

In all the methods described above and advantageously, the alkyl group is a linear or branched $C_1$-$C_4$ group and the aryl group is an optionally substituted phenyl group.

Preferably, $R^4$ is a methyl or a phenyl, that is to say that the derivative of formula (17) is acetophenone or benzophenone substituted with the amine at the ortho, meta or para position.

The amine functional group of the derivative (17) is in the ortho, meta or para position depending on the final product desired, preferably in the ortho or meta position.

The coupling agent is chosen from the coupling agents used in particular in peptide synthesis, as described above, and for example iBuOCOCl in the presence of a base such as N-methylmorpholine.

The expression "marker precursor" is understood to mean a compound having at least one optionally protected reactive functional group different from the diazomethyl functional group and compatible with said functional group which allows the subsequent attachment of a marker, that is to say after any one of the steps of the method and in particular before the oxidation step with $MnO_2$. In particular, the marker precursor may comprise the linking arm L. An example of a strategy using a marker precursor is given below in the case of signal amplification but other variants are possible using the various protective groups which are well known to persons skilled in the art.

In the case of signal amplification, the method of synthesis is similar. The marker precursor has the formula (18) below.

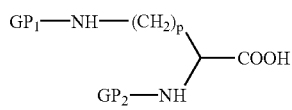

in which $GP_1$ and $GP_2$ represent two groups protecting an amine functional group which are identical or different and p is an integer between 1 and 10, advantageously 2 and 6, preferably 4. Advantageously, $GP_1$ and $GP_2$ are different in order to be able to add several motifs as is explained below.

Examples of protective groups GP1 or GP2 which can be used in the present invention are given in T. W. Greene and P. G. M. Wuts, Protective Groups in Organic Synthesis, 2$^{nd}$ edition, John Wiley and Sons, New York, 1991, preferably those commonly used in peptide synthesis such as Boc (tert-butyloxycarbonyl), Fmoc (9-fluorenylmethyleneoxycarbonyl), Cbz (carboxybenzyl) or Alloc (allyloxycarbonyl).

In particular, GP1 and GP2 are the protective groups Boc and Fmoc, respectively.

The reaction between this precursor which possesses a carboxyl functional group and the derivative of formula (17) takes place in the presence of a coupling agent to form the amide bond. After deprotection under customary conditions of one of the two protective groups, for example Fmoc with a base such as piperidine, the amine functional group released is used to couple another molecule of formula (18). This process is repeated as many times as necessary to obtain a multitude of $NH_2$ functional groups protected by a protective group, for example a Boc functional group. The motif is added between one (1) and one hundred (100) times, preferably between one (1) and twenty (20) times.

Hydrazine is reacted with the ketone functional group from the phenylketone derivative to form a hydrazone which is then oxidized in the presence of $MnO_2$ to form a diazomethyl residue. Then, after deprotection of the amine functional group carrying the Boc group, a tracer, for example a biotin activated with an N-hydroxysuccinimide group, is coupled to the amine functional groups to lead to a reagent whose unit $R^2\text{-}(L)_n\text{-}$ is that of formula (5).

It is another object of the present invention to describe a method as well as the products obtained by this method for labeling a biological molecule, in particular a nucleic acid, comprising bringing a biological molecule and a labeling reagent according to the invention into contact in solution in a substantially aqueous homogeneous solution.

The expression "substantially aqueous solution" is understood to mean a solution containing at least 50% of water. This solution preferably contains salts like a buffer solution.

The expression "homogeneous solution" is understood to mean a single-phase solution such as a water/DMSO solution by contrast to a two-phase solution such as a water/chloroform solution.

The particular conditions for the labeling reactions vary according to the biological molecules and the marker. As regards nucleic acids, a pH of between 5 and 8 allows efficient labeling. In particular, a pH of between 5.5 and 7.0 is preferred for all the reagents of the invention. With the reagent of formula (11), the pH range is broader for the labeling. A good labeling efficiency is obtained for a pH of between 3 and 8 for this reagent.

In particular, the method for labeling and fragmenting a single- or double-stranded nucleic acid comprises the following steps in any order:

fragmenting the nucleic acid, attaching a marker to at least one of the fragments via a labeling reagent chosen from the compounds: of formula (19):

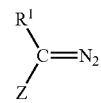

in which:

$R^1$ represents H or an alkyl, aryl or substituted aryl group, and

Z comprises a detectable marker, said reagent being covalently and predominantly coupled to at least one phosphate of said fragment.

The radicals Z and/or $R^1$ are chosen in order to stabilize the diazomethyl functional group, that is to say at least one of the two groups Z or $R^1$ has a phenyl nucleus.

The bond between the labeling reagent and the nucleic acid is covalent but it has been previously described that noncovalent interactions may be used in particular in stacking systems or in the case where the marker is indirectly detectable. The term "attach" therefore covers these various possibilities.

Preferably, the labeling reagent is chosen from the compounds of formula (20):

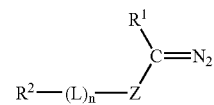

in which:

$R^1$ represents H or an alkyl, aryl or substituted aryl group, $R^2$ is a detectable marker or at least two detectable markers linked together by at least one multimeric structure, L is a linking arm containing a linear succession of at least two covalent bonds and n is equal to 0 or 1, and Z is chosen from:

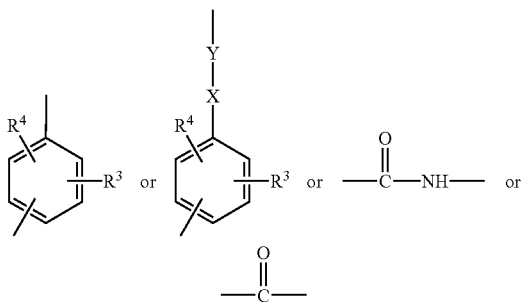

in which:
R³ and R⁴ represent independently of each other: H, $NO_2$, Cl, Br, F, I, OR, SR, $NR_2$, R, NHCOR, CONHR, COOR with R=alkyl or aryl, and
—Y—X— represents —CONH—, —NHCO—, —CH₂O—, —CH₂S—.

In a particular embodiment according to formula (19), Z has the following structure:

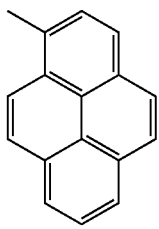

In this case and if $R^1$ is H, the labeling reagent is 1-Pyrenyldiazomethane (PDAM).

Although this marker is fluorescent, the excitation wavelength is too close to those of nucleic acids. An indirect detection using a monoclonal antibody directed against the pyrene motif is preferred. The method of producing this antibody is well known to persons skilled in the art (see for example patent application WO-A-00/07982).

The other novel reagents according to the invention which are described by the formulae (1) to (27) as well as the reagents capable of being obtained by the methods of synthesis according to the invention are also preferred reagents according to the method of fragmentation and labeling described above.

This method of labeling and fragmentation is particularly useful in the case where the labeled nucleic acid has to hybridize with a multitude of nucleic acids, in particular oligonucleotides, attached to the solid support at a predetermined position to form a DNA chip. The expression "DNA chip" is understood to mean a small-size solid support where a multitude of capture probes are attached at predetermined positions. Indeed, the density of the nucleic acids attached to the solid support imposes high steric constraints during hybridization, and the fragmentation makes it possible to improve this hybridization step. Examples of these DNA chips are given, for example, in the publications by G. Ramsay, Nature Biotechnology, 16, p. 40-44, 1998; F. Ginot, Human Mutation, 10, p. 1-10, 1997; J. Cheng et al., Molecular diagnosis, 1(3), p. 183-200, 1996;

T. Livache et al., Nucleic Acids Research, 22(15), p. 2915-2921, 1994; J. Cheng et al., Nature Biotechnology, 16, p. 541-546, 1998.

The fragmentation and the labeling are carried out in one step or in two steps and the labeling may be carried out either before, after or simultaneously with the fragmentation.

Preferably, the labeling and the fragmentation are carried out simultaneously, that is to say that the reagents necessary for these two steps are placed together in a substantially aqueous homogeneous solution with the nucleic acid for example. This is in particular the case for chemical or enzymatic fragmentation. In the case of mechanical fragmentation by a physical means, labeling and fragmentation being carried out simultaneously means that the physical means is applied to a substantially aqueous homogeneous solution containing at least the nucleic acids and the labeling reagent.

Fragmentation of the nucleic acid is carried out by the enzymatic, chemical or physical route.

Fragmentation by the enzymatic route of the nucleic acid is carried out, for example, by nucleases.

Fragmentation by the physical route of the nucleic acid is carried out, for example, by sonication or by radiation.

Fragmentation by the chemical route, if the nucleic acid is an RNA, is carried out by the customary methods (see for example Chem. Rev., 98, 961-990, 1998 by Oivanen M. et al.).

Metal complexes as described in the review by G. Pratviel et al., Adv. Org. Chem., 45, p. 251-312, 1998 or the review by G. Pratviel et al., Angew. Chem. Int. Ed. Engl., 34, p. 746-769, 1995 can be used for the fragmentation of DNA or RNA.

In a first embodiment, the chemical fragmentation of RNA is carried out by metal cations combined of otherwise with a chemical catalyst. In this case, the metal cations are $Mg^{2+}$, $Sr^{2+}$, $Ba^{2+}$, $Pb^{2+}$, $Zn^{2+}$, $Cd^{2+}$, $Mn^{2+}$, $Fe^{2+}$, $Co^{2+}$, $Ni^{2+}$, $Ru^{3+}$, $Ce^{3+}$, $Eu^{3+}$, $Tb^{3+}$, $Tm^{3+}$, $Yb^{3+}$ or $Lu^{3+}$ ions, the chemical catalyst consists of imidazole, or a substituted analog, for example N-methylimidazole, or any chemical molecule having affinity for RNA and carrying an imidazole nucleus or a substituted analog. The conditions for fragmentation using metals are indeed described in patent application WO-A-99/65926. Advantageously, the metals are $Mg^{2+}$, $Mn^{2+}$, $Zn^{2+}$, $Tb^{3+}$ or $Ce^{3+}$, preferably $Mg^{2+}$, $Mn^{2+}$, $Zn^{2+}$.

Efficient fragmentation conditions are obtained with a concentration of metal cation such as $Mn^{++}$ of between 2 and 100 mM, an imidazole concentration of between 2 and 100 mM.

Especially effective conditions are obtained with a concentration of cation such as $Mn^{++}$ of between 3 and 15 mM and an imidazole concentration of between 20 and 50 mM, in particular 30 mM.

The reaction pH should be between 5 and 8. Advantageously, the pH is between 5.5 and 6.5, preferably the pH is 6. The pH of 6 therefore represents a very advantageous compromise for carrying out the labeling and fragmentation combination with RNA (see preceding discussion on labeling).

In a second embodiment, chemical fragmentation of the RNA is carried out by the action of a polyamine such as spermine, putrescine or cadaverine. Concentrations of 5 to 100 mM allow fragmentation. The latter is complete from 10 mM polyamine.

In a third embodiment, chemical fragmentation of the RNA is carried out by the action of an artificial nuclease (see G. Pratviel et al., Adv. Inorg. Chem., 45, p. 251-312, 1998; D. S. Sigman et al. Chem. Rev., 93, p. 2295-2316, 1993)

such as 1,10-phenanthroline combined with a metal cation such as iron, copper or zinc. These cations are obtained from $FeSO_4$ or $CuCl_2$ or $ZnCl_2$, respectively, in solution. Concentrations of between 2 and 50 mM 1,10-phenanthroline are used for the fragmentation of RNA, in particular between 4 and 10 mM.

Fragmentation by the chemical route of DNA is carried out by bringing the nucleic acid into contact with a chemical means of creating an abasic site. The formation of an abasic site results from the cleavage of the N-glycoside bond which links the 2-deoxyribose sugar to the nucleic base. It involves a depurination for the loss of a purine (guanine, adenine) or a depyrimidination for pyrimidines (cytosine, thymine).

This depurination is spontaneous under physiological conditions (pH 7.4 at 37° C.) but the reaction rate is very low, of the order of $3\times10^{-11}$ depurination per second, that is to say unusable for efficient fragmentation. To increase the reaction rate, use is made of alkylating agents which make the N-glycoside bond fragile or enzymes such as DNA glycosylases, in particular uracil DNA glycosylase.

The abasic site obtained by depurination or depyrimidation is very unstable. Fragmentation at the level of this site is obtained at room temperature in a basic medium. In an acidic medium, the high temperature also accelerates this fragmentation. Using molecules capable of initiating the β-elimination phenomenon also accelerates the fragmentation.

A preferred embodiment of the fragmentation is obtained using an acidic pH, that is to say a pH of less than 5. Advantageously the pH is 3.

A sodium formate buffer at pH 3 makes it possible to efficiently fragment according to the invention. This buffer is compatible with the one-step labeling conditions as will be demonstrated in the examples. More advantageously still, an acidic medium (HCl, carbonate, $H_2SO_4$) is used.

In a particular embodiment of the present invention and with the aim of further increasing the fragmentation, the deoxyribonucleic acid contains at least one modified base capable of more easily generating an abasic site.

Various modified bases can be used such as N7-alkylpurines, N3-alkylpurines, O6-alkylpurines, 8-bromopurines, 8-thiopurines, 8-alkylthiopurines, 8-azidopurines or 8-alkylsulfonylpurines.

In the case where the nucleic acid to be labeled is generated by an enzymatic amplification technique such as PCR, the use of an 8-bromopurine makes it possible to have an efficient incorporation during the amplification, which correspondingly facilitates the method of fragmentation and labeling according to the invention while preserving excellent sensitivity for the enzymatic amplification step.

The present invention describes a labeled biological molecule and in particular a labeled nucleic acid capable of being obtained by any one of the methods according to the invention.

The present invention also relates to a kit for detecting a biological molecule, in particular a target nucleic acid comprising a labeling reagent according to the invention. Depending on the applications of the kit, other components such as, for example, lysis means (microorganisms and/or cells) and/or concentration means (such as silica or magnetic particles) and/or enzymatic amplification means are incorporated into the kit.

The invention relates to the use of a labeled biological molecule, in particular a labeled nucleic acid, as defined above, as probe for detecting a target biological molecule and in particular a target nucleic acid.

The invention also relates to the use of a nucleic acid as defined above, as labeled target which can bind to a capture probe.

To allow the detection and/or quantification and/or purification of the target biological molecule, the labeled biological molecule is capable of forming a complex with the target biological molecule. By way of example, for the detection of a target molecule of the nucleic acid type, the labeled nucleic acid is sufficiently complementary to the target to become specifically hybridized depending on the reaction conditions and in particular the temperature or the salinity of the reaction medium.

The method of detection is applicable for sequencing, messenger RNA expression profiling or screening of mutations for the purposes of research and screening of drugs in the pharmaceutical industry, the diagnosis of infectious or genetic diseases, or food or industrial control.

The trend in the field of diagnosis and in particular for infectious diseases (AIDS or Tuberculosis for example) is to lower the sensitivity level down to the detection of a single molecule in a sample which may represent several milliliters in the case of a liquid sample of the blood or urine or cerebrospinal fluid type. This sensitivity level can only be obtained if all the steps, from the taking of the sample to the issuing of results, are optimized. The various means of the invention allow this optimization without difficulty because the reagents, methods and processes of the invention are very widely applicable to various biological molecules. In particular, in the case where an enzymatic amplification step is necessary in order to obtain the necessary sensitivity (viral or bacterial infection such as HIV, HCV or Tuberculosis), a labeling and/or fragmentation method as described in the present invention makes it possible not to affect the sensitivity of the amplification technique either because it is not necessary to replace the deoxyribonucleotides used in the enzymatic amplification technique, or because the incorporated ribonucleotides or deoxyribonucleotides do not alter the sensitivity.

The chemistry of grafting described in the present invention possesses characteristics from the point of view of reactivity and specificity such that other applications are described below:

In a first embodiment, this chemisty of grafting is applied to the covalent attachment of nucleic acids to a solid support.

In a first variant of the method, a precursor of the diazomethyl functional group, such as a ketone or hydrazine as described above, is introduced during the chemical synthesis and the diazomethyl functional group is introduced onto the nucleic acids in a second step.

In a second preferred variant of the method, the diazomethyl functional groups are introduced onto the solid support and the nucleic acids are attached to the solid support via the phosphates of the nucleic acids and in particular the terminal (5' or 3') phosphates.

The introduction of a phosphate at the 3' or 5' end of nucleic acids is well known (see "Protocols for Oligonucleotides and Analogs, Synthesis and Properties" published by S. Agrawal, Humana Press, Totowa, N.J.).

In a specific embodiment of such a solid support, a labeling reagent carrying a ligand, in particular a hapten such as biotin or abietane, is attached to the solid support to which an antiligand, such as streptavidin or an antibody for example, is attached covalently or by adsorption. These solid supports are well known in the state of the art and are even commercially available (microtiter plate-streptavidin or latex-streptavidin for example). The role of the marker is no longer in this case to allow the detection but to allow the attachment of the labeling reagent to the solid support. The diazomethyl functional group is then available to react with nucleic acids. The derivatives of formula (11), (12), (13) or the PDAM derivative are examples of reagents which can be used for making such a solid support. Monoclonal antibody techniques make it possible to prepare antibodies against a large number of markers such as fluorescein or a derivative of Cy5. Persons skilled in the art can use a solid support with the labeling reagents of the present invention without too much difficulty by this indirect mode of preparation of the solid support in which a ligand/antiligand reaction is used to attach the diazomethyl functional group to the solid support.

A second embodiment of the solid support relates to particular supports such as latexes. Various modes of polymerization may be used to prepare the particles carrying a diazomethyl functional group from a polymerizable functional monomer carrying either a diazomethyl functional group or preferably a functional group which is a precursor of the diazomethyl functional group such as an aldehyde or a ketone and in particular:

Polymerization in a batch reactor: the monomers are introduced into the reactor before the beginning of the reaction with the other ingredients and without subsequent addition. Because of the difference in the reactivity of the monomers, this method often leads to the appearance of a composition drift. This is manifested by the production of macromolecules having compositions which vary considerably as a function of conversion. This method is not very efficient for incorporation at the surface because a large portion of the functional monomer risks being lost either inside the particles, or in the form of a water-soluble polymer. When the copolymerization is carried out batchwise with monomers of a polar nature, smaller particles are obtained in a large number, but with a limited conversion. This behavior is linked to the high water-solubility of these monomers, and it is attributed to the preponderance of the homogeneous nucleation mechanism.

Semicontinuous polymerization: at least a portion of the monomers is introduced into the reactor over a period between the start of the reaction and its end. This addition may be carried out at a fixed rate or according to a given profile. The aim is to control the addition of the mixture of monomers so as to obtain a copolymer of controlled composition (control of the composition of the interface); addition conditions thus often exist such that the rate of polymerization is higher than that of addition.

Shot addition polymerization: once the polymerization reaction is in progress, the functional monomer alone, or in the presence of the basic monomer, is introduced into the system in a controlled manner. The success of the operation therefore depends on the degree of prior knowledge of the kinetics of copolymerization. It is an efficient method for promoting superficial incorporation. The selection of the experimental conditions (degree of conversion at the time of addition, composition and concentration of the mixture of monomers) makes it possible to optimize the surface yields.

Seed polymerization: it consists in introducing the functional monomer into the system containing a latex already constituted and perfectly characterized. The functional monomer may be added alone or as a mixture with the basic monomer of the seed, in a single step or semicontinuously.

The seed polymerization, shot addition polymerization and semicontinuous polymerization techniques are preferred because they lead to a maximum incorporation of the derivative carrying the precursor of the diazomethyl functional group at the surface. Examples of particles carrying aldehyde functional groups are given for example in B. Charleux et al., Die Makromolecular Chem., 193, p. 187 and p. 205, 1992 or in patent EP-B-0,350,407.

It is another object of the present invention to describe a temperature-stable binding intermediate of formula (30):

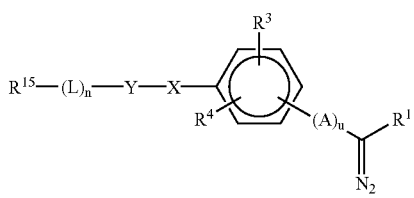

in which:

$R^1$ represents H or an alkyl, aryl or substituted aryl group, $R^{15}$ represents a nucleophilic or electrophilic reactive functional group, in particular COOH, $NH_2$, SH, OH, O—$NH_2$, alkyl ketone, aldehyde, isocyanate, isothiocyanate, maleimide, alkyl halide, activated ester, tosylate, L is a linking arm containing a linear succession of at least two covalent bonds and n an integer equal to 0 or 1, $R^3$ and $R^4$ represent independently of each other: H, $NO_2$, Cl, Br, F, I, $R^{15}$-(L)$_n$-Y—X—, OR, SR, $NR_2$, R, NHCOR, CONHR, COOR with R=alkyl or aryl, A is a linking arm containing at least one covalent double bond allowing conjugation of the diazo functional group with the aromatic ring and u is an integer between 0 and 2, preferably equal to 0 or 1, and —Y—X— represents —CONH—, —NHCO—, —$CH_2$O—, —$CH_2$S—.

Preferred binding intermediates according to the invention are of formula (30a):

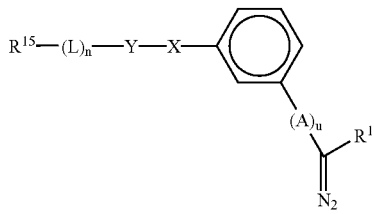

in which:

$R^1$ represents H or an alkyl, aryl or substituted aryl group, $R^{15}$ represents a nucleophilic or electrophilic reactive functional group, in particular COOH, $NH_2$, SH, OH, O—$NH_2$, alkyl ketone, aldehyde, isocyanate isothiocyanate, maleimide, alkyl halide, N-hydroxysuccinimide ester, tosylate, L is a linking arm containing a linear succession of at least two covalent bonds and n an integer equal to 0 or 1, A is a linking arm containing at least one covalent double bond allowing conjugation of the diazo functional group with the aromatic ring and u is an integer between 0 and 2, preferably equal to 0 or 1, and —Y—X— represents —CONH—, —NHCO—, —CH$_2$O—, —CH$_2$S—.

A third embodiment of the solid support consists in making available a solid support comprising a first nucleophilic or electrophilic reactive functional group, such as for example NH$_2$, SH, OH, O—NH$_2$, alkyl ketone, aldehyde, isocyanate, isothiocyanate, maleimide, alkyl halide, N-hydroxysuccinimide ester, tosylate, and then in reacting a binding intermediate, of formula (30) or (30a) described above, whose functional group R$^{15}$ is complementary to the first reactive functional group of the solid support. This reaction between the solid support and the binding intermediate optionally occurs in the presence of a coupling agent to form a covalent bond.

Such a solid support comprising at least one diazomethyl functional group, according to various embodiments described above, in particular a solid support to which a labeling reagent of the invention is indirectly attached, is also a subject of the present invention as well as the solid support comprising nucleic acids attached to the solid support via diazomethyl functional groups.

A first application of such a solid support is the manufacture of DNA chips. Methods exist for distributing nucleic acids on the solid support at discrete and predetermined positions.

Patent U.S. Pat. No. 6,110,426 proposes a method for producing these DNA chips using a capillary which is brought into contact on a solid surface to deliver a controlled volume of liquid. An effective contact takes place between the end of the capillary and the solid support so that the drop becomes deposited by capillarity. Likewise, patent U.S. Pat. No. 6,083,763 describes a set of capillaries sliding in a device so as to compensate for the differences in the height of each of them. They are brought into contact with a flat surface for the deposition, by capillarity of specific oligonucleotides.

Patent U.S. Pat. No. 6,083,762 proposes a system for distributing drops comprising a microdispenser coupled to a piezoelectric transducer in order to eject drop volumes of less than one nanoliter onto a solid surface. A similar result is obtained by applying a hot source to the wall of a capillary in order to form a bubble which ejects a defined volume of solution (see T. Okamoto et al., Nature Biotechnology, 18, p. 438-441, 2000).

The diazomethyl functional group thus makes it possible to covalently graft the nucleic acids onto the support. The grafting is simple, the linkage is stable, compared with adsorption in particular, and the selectivity of the reaction in relation to the terminal phosphate makes it possible to carry out an oriented coupling of the nucleic acid onto the solid support, which correspondingly facilitates subsequent hybridization steps by reducing steric hindrance.

A second application of a solid support according to the invention is the purification of nucleic acids.

In the case of purification, this purification is either direct (the solid support carrying diazomethyl functional groups reacts with the nucleic acids to be purified) or indirect (capture nucleic acids are attached to the solid support). These capture nucleic acids are sufficiently complementary to the target to be captured to hybridize thereto with the desired degree of specificity and it is the "capture nucleic acids/solid support" complex which allows the purification of the target nucleic acids.

The solid support is preferably in dispersed form for use in purification as latex particles, for example magnetic particles.

The expression "purification step" is understood to mean in particular the separation between the nucleic acids of microorganisms and the cellular constituents released in the lysis stage which precedes the purification of the nucleic acids. These lysis stages are well known. By way of example serving as a guide, there may be used the methods of lysis as described in patent applications:

WO-A-00/60049 on lysis by sonication,
WO-A-00/05338 on mixed magnetic and mechanical lysis,
WO-A-99/53304 on electric lysis, and
WO-A-99/15621 on mechanical lysis.

Persons skilled in the art will be able to use other well-known methods of lysis such as heat or osmotic shocks or treatments with chaotropic agents such as guanidium salts (patent U.S. Pat. No. 5,234,809).

This step generally makes it possible to concentrate the nucleic acids. By way of example, it is possible to use magnetic particles (see on this subject patents U.S. Pat. No. 4,672,040 and U.S. Pat. No. 5,750,338), and thus purify the nucleic acids, which have become attached to these magnetic particles, by a washing step. This step of purification of nucleic acids is particularly advantageous if it is desired to subsequently amplify said nucleic acids. A particularly advantageous embodiment of these magnetic particles is described in patent applications WO-A-97/45202 and WO-A-99/35500.

The term "solid support" as used here includes all materials to which a nucleic acid may be attached. Synthetic materials or natural materials, optionally chemically modified, may be used as solid support, in particular polysaccharides such as cellulose-based material, for example paper, cellulose derivatives such as cellulose acetate and nitrocellulose or dextran; polymers, copolymers, in particular based on styrene-type monomers, natural fibers such as cotton, and synthetic fibers such as nylon; inorganic materials such as silica, quartz, glass, ceramics; latexes; magnetic particles; metal derivatives, gels and the like. The solid support may be in the form of a microtiter plate, a membrane, a particle or a substantially flat plate made of glass or silicon or derivatives.

The invention finally relates to a method for capturing nucleic acids comprising the following steps:
 a solid support is made available to which at least one molecule comprising a diazomethyl functional group is directly or indirectly attached,
 a biological sample likely to contain free nucleic acids is brought into contact, and
 the solid support where the molecule(s) is (are) covalently attached at least to one nucleic acid is washed.

Additional information may be found in another patent application by the applicant, filed on May 4, 2001 under the registration number FR01/06039, as well as its international extension filed on the same day as the present invention.

BRIEF DESCRIPTION OF THE DRAWINGS

The accompanying figures and examples represent particular embodiments and cannot be considered as limiting the scope of the present invention.

FIGS. 2A to 2I represent the profiles as a function of time, analyzed by capillary electrophoresis, of the covalent coupling of various reagents carrying a diazomethyl functional group on the uridine 3'-monophosphate (3'-UMP) according to Example 6.1:
PDAM in FIG. 2A,
DPDAM at 2 millimoles per liter (mM) in FIG. 2B,
DPDAM at 20 mM in FIG. 2C,
PMDAM in FIG. 2D.
NPDAM in FIG. 2E,
BioDPDAM in FIG. 2F,
meta-BioPMDAM in FIG. 2G,
para-BioPMDAM in FIG. 2H,
ortho-BioPMDAM in FIG. 2I.

DESCRIPTION OF THE PREFERRED EMBODIMENTS

EXAMPLE 1

Synthesis of Reagents with Biotin

Figure 1:
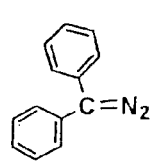
FIG. 1 represents the structural formulae of the various reagents used in the present invention as well as the abbreviation designating them. (o- means ortho, m- meta and p-para).
Figure 1:
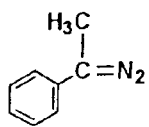
Figure 1:
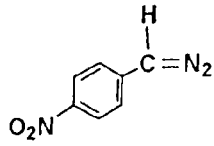
Figure 1:
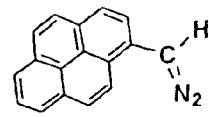
Figure 1:
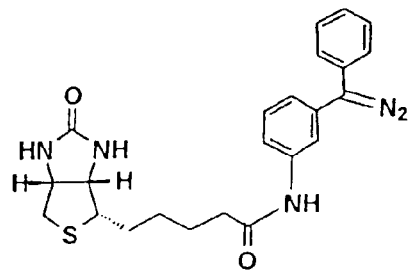
Figure 1:
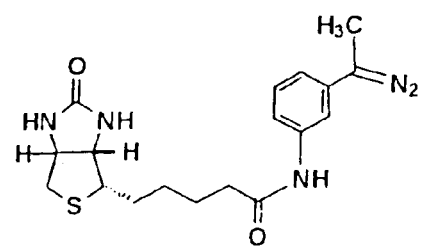
Figure 1:
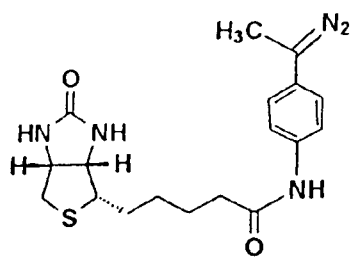
Figure 1:
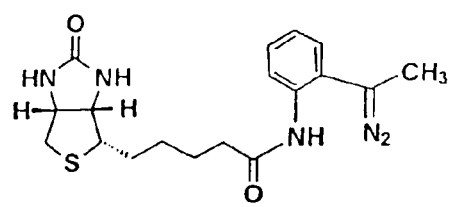
Figure 1:
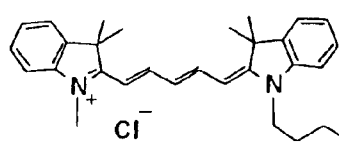
Figure 2A:
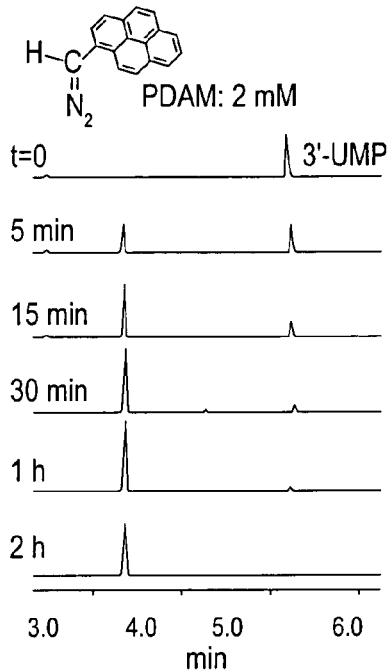
Figure 2B:
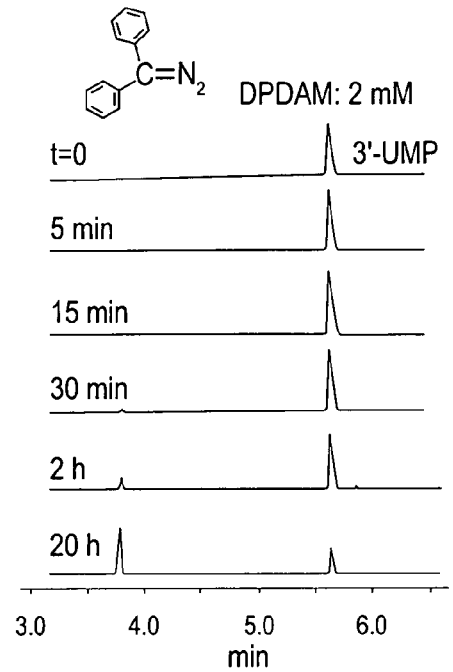
Figure 2C:
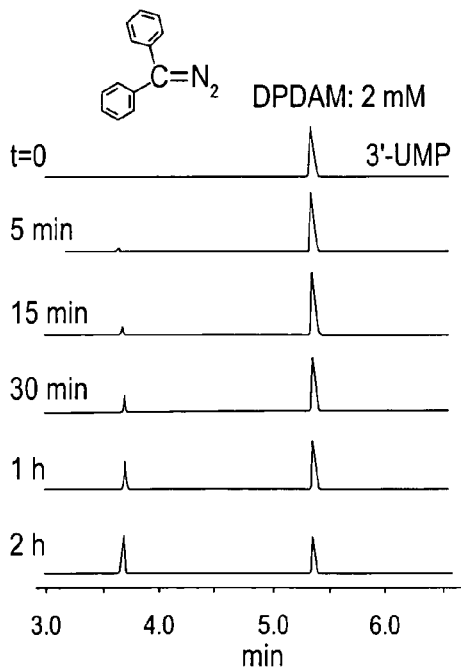
Figure 2D:
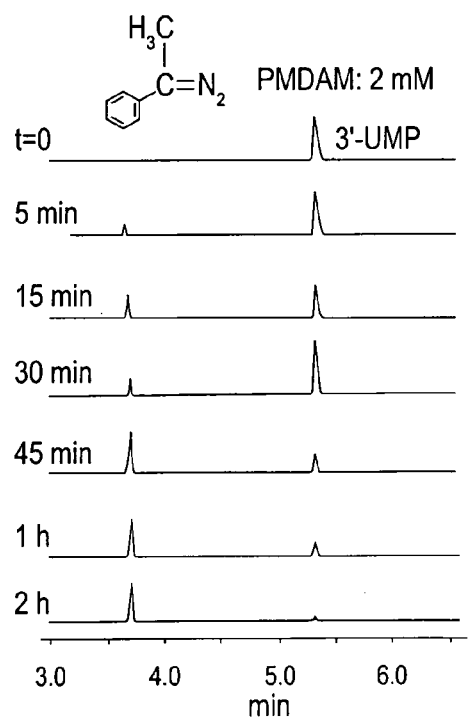
Figure 2E:
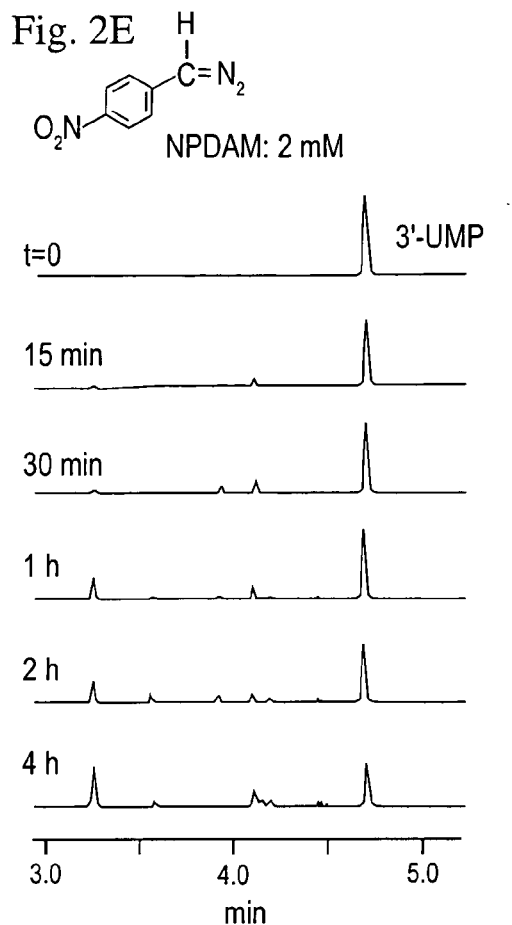
Figure 2F:
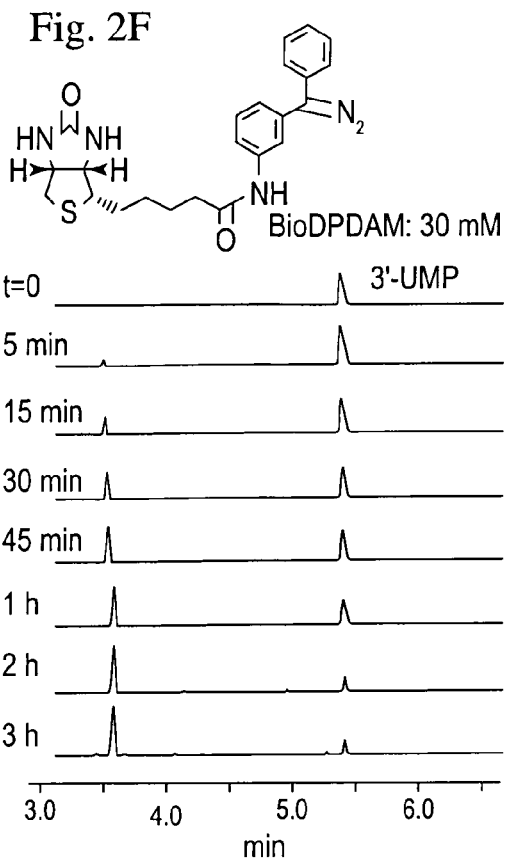
Figure 2G:
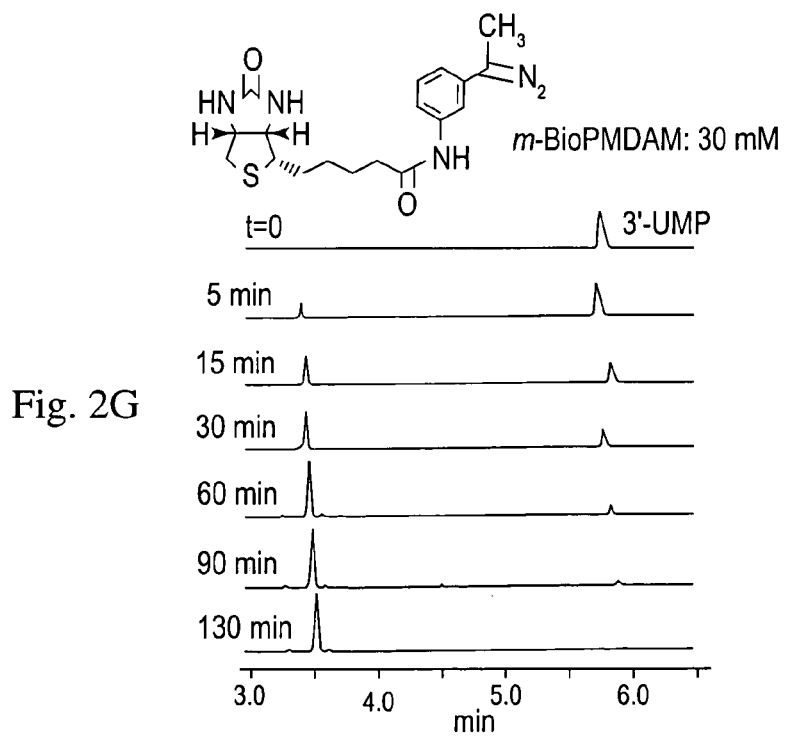

General synthesis scheme:

D-Biotin + [aminobenzoyl compound] →(N-methylmorpholine, iBuOCOCl, DMF)→

1a: R = $CH_3$, meta substituent
1b: R = $CH_3$, para substituent
1c: R = $CH_3$, ortho substituent
1d: R = Ph, meta substituent

↓ $N_2H_4$ — $H_2O$

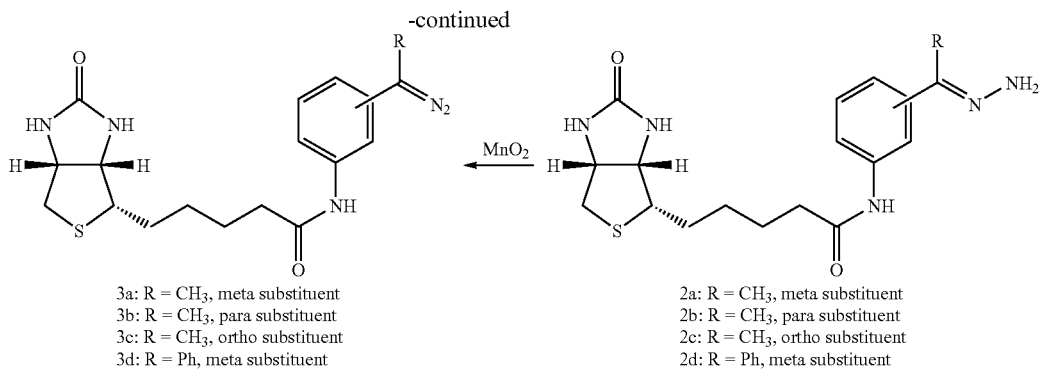

3a: R = CH₃, meta substituent
3b: R = CH₃, para substituent
3c: R = CH₃, ortho substituent
3d: R = Ph, meta substituent 2a: R = CH₃, meta substituent
2b: R = CH₃, para substituent
2c: R = CH₃, ortho substituent
2d: R = Ph, meta substituent Example 1.1

Synthesis of meta-BioPMDAM

Compound Biotin meta-acetophenone 1a:

The D-biotin (1.0 gram (g), 4.1 millimoles (mmol) is solubilized in 45 milliliters (ml) of anhydrous DMF in the hot state. The mixture is cooled to 0° C. under argon, and then N-methylmorpholine (590 microliters (μl), 5.33 mmol) and isobutyl chloroformate (840 μl, 6.60 mmol) are successively added. The mixture is kept stirred for 30 minutes (min), and then 3-aminoacetophenone (824 mg, 6.10 mmol) and N-methylmorpholine (480 μl, 4.35 mmol) in 10 ml of DMF are added. The solution is maintained stirred at 0° C. for 2 hours (h), and then evaporated to dryness. The residue is taken up in 3 ml of MeOH, and then 50 ml of water are added. The precipitate obtained is filtered, washed with water, $CH_2Cl_2$ and ether to give 1.2 g (80%) of crude product 1a. Recrystallization from the MeOH—$H_2O$ pair gives 1a (1.01 g, 70%) in the form of a white powder.

m.p. 145° C.—IR (KBr): 3280, 2931, 2857, 1691, 1590, 1540, 1487, 1434, 1298, 1266 cm$^{-1}$.—$^1$H NMR (300 MHz, DMSO-$d_6$) δ=1.3-1.7 (m, 6H); 2.33 (t, J=8 Hz, 2H); 2.55 (s, 3H); 2.58; (d, J=12 Hz, 1H); 2.83 (dd, J=12 and 5 Hz, 1H); 3.13 (m, 1H); 4.15 (m, 1H); 4.31 (m, 1H); 6.34 (s, 1H); 6.41 (s, 1H); 7.44 (t, J=8 Hz, 1H); 7.64 (d, J=8 Hz, 1H); 7.85 (d, J=8 Hz, 1H); 8.17 (s, 1H); 10.05 (s, 1H).—MS (FAB/glycerol), m/z: 362 [M+H]$^+$.

Compound meta-hydrazone 2a:

A solution of 1a (500 mg, 1.38 mmol) and of hydrazine monohydrate (200 μl, 4.15 mmol) in absolute ethanol (8 ml) is heated under reflux for 2 h. After cooling to room temperature, the white precipitate is filtered, washed with water, and then with ether and dried. 385 mg (74%) of product 2a are thus obtained in the form of a white powder.

m.p. 185° C.—IR (KBr): 3298, 2931, 2857, 1698, 1665, 1626, 1541, 1494, 1470, 1446, 1330, 1265 cm$^{-1}$.—$^1$H NMR (300 MHz, DMSO-$d_6$) δ=1.3-1.7 (m, 6H); 1.98 (s, 3H); 2.26 (t, J=8 Hz, 2H); 2.56 (d, J=12 Hz, 1H); 2.81 (dd, J=12 and 5 Hz, 1H); 3.11 (m, 1H); 4.13 (m, 1H); 4.29 (m, 1H); 6.39 (s, 3H); 6.42 (s, 1H); 7.22 (m, 2H); 7.50 (d, J=8 Hz, 1H); 7.84 (s, 1H); 9.82 (s, 1H).—MS (FAB/glycerol), m/z: 376 [M+H]$^+$.

Compound meta-diazomethane 3a:

2a (180 mg, 0.48 mmol) is solubilized in 2 ml of DMF. $MnO_2$ (340 mg, 3.9 mmol) is then added. After stirring for 30 minutes at room temperature, the mixture is filtered through a sintered funnel containing celite (thickness: 0.5 cm) and 3 Å powdered molecular sieves (0.5 cm). The reaction mixture is concentrated to a volume of about 0.5 ml, and then 5 ml of ether are added. The resulting precipitate is filtered, washed with water and then dried. Compound 3a (170 mg, 95%) is obtained in the form of a pink powder.

m.p. 160° C.—IR (KBr): 3278, 2935, 2859, 2038, 1704, 1666, 1605, 1577, 1536, 1458, 1430, 1263 cm$^{-1}$.—$^1$H NMR (300 MHz) δ=1.3-1.7 (m, 6H); 2.11 (s, 3H); 2.28 (t, J=8 Hz, 2H); 2.57 (d, J=12 Hz, 1H); 2.81 (dd, J=12 and 5 Hz, 1H); 3.11 (m, 1H); 4.13 (m, 1H); 4.29 (m, 1H); 6.33 (s, 1H); 6.41 (s, 1H); 6.60 (m, 1H); 7.25 (m, 3H); 9.84 (s, 1H).

Example 1.2

Synthesis of para-BioPMDAM

Compound Biotin para-acetophenone 1b:

The D-biotin (1 g, 4.1 mmol) is solubilized in 45 ml of anhydrous DMF in the hot state. The mixture is cooled to 0° C. under argon, and then N-methylmorpholine (590 μl, 5.33 mmol) and isobutyl chloroformate (840 μl, 6.60 mmol) are successively added. The mixture is kept stirred for 30 min, and then 4-aminoacetophenone (824 mg, 6.10 mmol) is added. The solution is maintained stirred at 0° C. for 2 h, and then evaporated to dryness. The residue is taken up in 50 ml of water. The precipitate obtained is filtered, washed with water and then with 50 ml of MeOH in the hot state. The white precipitate is dissolved in DMF while heating and then the solution obtained is filtered and washed with MeOH. The filtrate is recovered and evaporated to dryness to give 888 mg of 1b (2.46 mmol, 60%).

m.p. 260° C.—IR (KBr): 3260, 2930, 2358, 1706, 1673, 1610, 1526, 1401, 1380, 1322, 1257, 1150 cm$^{-1}$.—$^1$H NMR (200 MHz, DMSO-$d_6$) δ=8.82 (s, 1H, N$\underline{H}$—CO); 7.57 (d, 2H, J=9 Hz, Ar—H); 6.83 (d, 2H, J=9 Hz, Ar—H); 6.40 (broad s, 1H, N$\underline{H}$—CO—NH); 6.32 (broad s, 1H, NH—CO—N$\underline{H}$); 4.28 (m, 1H, $CH_2$—C$\underline{H}$—NH); 4.12 (m, 1H, CH—C$\underline{H}$—NH); 3.11 (m, 1H, CH—S); 2.80 and 2.55 (system ABX, 2H, $^2J_{AB}$=5 Hz, $^3J_{AX}$=12 Hz, $^3J_{BX}$=0 Hz, $CH_2$—S); 2.35 (t, 2H, J=8 Hz, $CH_2$—CO); 2.10 (s, 3H, $CH_3$); 1.60-1.34 (m, 6H, $(CH_2)_3$).

Compound para-hydrazone 2b:

Compound 1b (870 mg, 2.4 mmol) is dissolved in the hot state in ethanol (99%, 8 ml) and then hydrazine monohydrate (995 μl, 19.5 mmol) is added. The solution is heated under reflux for 3 h. The white precipitate obtained is filtered, and washed with ice-cold water. 820 mg (90%) of product 2b are thus obtained in the form of a white powder.

m.p. 305° C.—IR (KBr): 3281, 3183, 2930, 2857, 1698, 1658, 1593, 1521, 1459, 1401, 1325, 1263, 1187 cm$^{-1}$.—$^1$H NMR (200 MHz, DMSO-d$_6$) δ=9.68 (s, 1H, NH—CO); 7.52 (s, 4H, J=9 Hz, Ar—H); 6.43 (broad s, 1H, NH—CO—NH); 6.35 (broad s, 1H, NH—CO—NH); 6.21 (s, 2H, NH$_2$); 4.29 (m, 1H, CH$_2$—CH—NH); 4.12 (m, 1H, CH—CH—NH); 3.12 (m, 1H, CH—S); 2.81 and 2.56 (system ABX, 2H, $^2J_{AB}$=5 Hz, $^3J_{AX}$=12 Hz, $^3J_{BX}$=0 Hz, CH$_2$—S); 2.32 (t, 2H, J=8 Hz, CH$_2$—CO); 1.97 (s, 3H, CH$_3$); 1.63-1.36 (m, 6H, (CH$_2$)$_3$).

Compound para-diazomethane 3b:

2b (200 mg, 0.53 mmol) is solubilized in 10 ml of DMF. 800 mg of MnO$_2$ are then added. After stirring for 10 minutes, the mixture is filtered through a Celite (0.5 cm)-molecular sieve (0.5 cm in powdered form) mixed layer. The reaction mixture is evaporated to dryness and then washed with ether and dried. Compound 3b (190 mg, 96%) is obtained in the form of a pink powder.

m.p. 180° C. (dec.).—IR (KBr): 3257, 2930, 2857, 2032, 1698, 1597, 1524, 1510, 1455, 1404, 1307, 1259, 1180 cm$^{-1}$.—$^1$H NMR (200 MHz, DMSO-d$_6$) δ=10.18 (s, 1H, NH—CO); 7.88 (d, 2H, J=6 Hz, Ar—H); 7.7 (d, 2H, J=6 Hz, Ar—H); 6.41 (broad s, 1H, NH—CO—NH); 6.34 (broad s, 1H, NH—CO—NH); 4.28 (m, 1H, CH$_2$—CH—NH); 4.12 (m, 1H, CH—CH—NH); 3.11 (m, 1H, CH—S); 2.80 and 2.55 (system ABX, 2H, $^2J_{AB}$=5 Hz, $^3J_{AX}$=12 Hz, $^3J_{BX}$=0 Hz, CH$_2$—S); 2.35 (t, 2H, J=8 Hz, CH$_2$—CO); 2.10 (s, 3H, CH$_3$); 1.60-1.34 (m, 6H, (CH$_2$)$_3$).

Example 1.3

Synthesis of ortho-BioPMDAM

Compound Biotin ortho-acetophenone 1c:

The D-biotin (1 g, 4.1 mmol) is solubilized in 45 ml of anhydrous DMF in the hot state. The mixture is cooled to 0° C. under argon, and then N-methylmorpholine (590 μl, 5.33 mmol) and isobutyl chloroformate (840 μl, 6.60 mmol) are successively added. The mixture is kept stirred for 30 min, and then 2-aminoacetophenone (824 mg, 6.10 mmol) is added. The solution is maintained stirred at room temperature for 3 h 30 min, and then evaporated to dryness. The residue is taken up in 50 ml of water. The precipitate obtained is filtered, washed with water and then with 50 ml of MeOH in the hot state. The precipitate obtained is filtered and washed with water. Recrystallization is carried out by dissolving the product in MeOH in the hot state and reprecipitating by addition of water. The precipitate is filtered, washed with water, and then with ether to give 1.1 g (2.95 mmol, 72%) of crude product 1c.

m.p. 150° C.—IR (KBr): 3248, 2930, 2857, 2359, 1691, 1669, 1651, 1582, 1528, 1448, 1354, 1310, 1245, 1161 cm$^{-1}$.—$^1$H NMR (200 MHz, DMSO-d$_6$) δ=11.24 (s, 1H, NH—CO); 8.33 (d, 1H, J=8.5 Hz, Ar—H); 7.97 (d, 2H, J=8 Hz, Ar—H); 7.57 (t, 1H, J=7 Hz, Ar—H); 7.18 (t, 1H, J=7 Hz, Ar—H); 6.44 (broad s, 1H, NH—CO—NH); 6.35 (broad s, 1H, NH—CO—NH); 4.30 (m, 1H, CH$_2$—CH—NH); 4.14 (m, 1H, CH—CH—NH); 3.12 (m, 1H, CH—S); 2.80 and 2.55 (system ABX, 2H, $^2J_{AB}$=5 Hz, $^3J_{AX}$=12 Hz, $^3J_{BX}$=0 Hz, CH$_2$—S); 2.61 (s, 3H, CH$_3$); 2.37 (t, 2H, J=8 Hz, CH$_2$—CO); 1.62-1.38 (m, 6H, (CH$_2$)$_3$).

Compound ortho-hydrazone 2c:

Compound 1c (500 mg, 1.38 mmol) is dissolved in the hot state in ethanol (99%, 8 ml) and then hydrazine monohydrate (572 μl, 11.1 mmol) is added. The solution is heated under reflux for 50 minutes. The solution is evaporated to dryness. The white precipitate obtained is filtered, washed with water and then dried with ether. 416 mg (11.1 mmol, 80%) of product 2c are thus obtained in the form of a white powder.

m.p. 161° C.—IR (KBr): 3412, 3240, 2930, 2857, 2351, 1706, 1677, 1604, 1590, 1531, 1463, 1444, 1372, 1303, 1270, 1169 cm$^{-1}$.—$^1$H NMR (200 MHz, DMSO-d$_6$) δ=11.97 (s, 1H, NH—CO); 8.35 (d, 1H, J=8 Hz, Ar—H); 7.45 (d, 1H, J=7 Hz, Ar—H); 7.19 (t, 1H, J=7.5 Hz, Ar—H); 7.04 (t, 1H, J=7 Hz, Ar—H); 6.61 (s, 2H, NH$_2$); 6.42 (broad s, 1H, NH—CO—NH); 6.35 (broad s, 1H, NH—CO—NH); 4.32 (m, 1H, CH$_2$—CH—NH); 4.14 (m, 1H, CH—CH—NH); 3.12 (m, 1H, CH—S); 2.81 and 2.56 (system ABX, 2H, $^2J_{AB}$=5 Hz, $^3J_{AX}$=12 Hz, $^3J_{BX}$=0 Hz, CH$_2$—S); 2.31 (t, 2H, J=8 Hz, CH$_2$—CO); 2.09 (s, 3H, CH$_3$); 1.63-1.36 (m, 6H, (CH$_2$)$_3$).

Compound ortho-diazomethane 3c:

2c (200 mg, 0.53 mmol) is solubilized in 10 ml of DMF. 800 mg of MnO$_2$ are then added. After stirring for 15 minutes, the mixture is filtered through a Celite (0.5 cm)-molecular sieve (0.5 cm in powdered form) mixed layer. The reaction mixture is evaporated to dryness and then washed with ether and dried. Compound 3c (130 mg, 65%) is obtained in the form of a pink powder.

m.p. 110° C.—IR (KBr): 3248, 2930, 2857, 2367, 2342, 2038, 1699, 1521, 1456 cm$^{-1}$.—H NMR (200 MHz, DMSO-d$_6$) δ=9.37 (s, 1H, NH—CO); 7.26-7.00 (m, 4H, Ar—H); 6.43 (broad s, 1H, NH—CO—NH); 6.35 (broad s, 1H, NH—CO—NH); 4.30 (m, 1H, CH$_2$—CH—NH); 4.15 (m, 1H, CH CH NH); 3.12 (m, 1H, CH—S); 2.82 and 2.54 (system ABX, 2H, $^2J_{AB}$=5 Hz, $^3J_{AX}$=12 Hz, $^3J_{BX}$=0 Hz, CH$_2$—S); 2.24 (t, 2H, J=8 Hz, CH$_2$—CO); 2.12 (s, 3H, CH$_3$); 1.63-1.37 (m, 6H, (CH$_2$)$_3$).

Example 1.4

Synthesis of meta-BioDPDAM

Compound meta-coupling 1d:

The D-biotin (500 mg, 2.05 mmol) is solubilized in 23 ml of anhydrous DMF in the hot state. The mixture is cooled to 0° C. under argon, and then N-methylmorpholine (295 μl, 2.67 mmol) and isobutyl chloroformate (420 μl, 3.28 mmol) are successively added. The mixture is kept stirred for 30 min, and then 3-aminobenzophenone (605 mg, 3.07 mmol) and N-methylmorpholine (240 μl, 2.17 mmol) in 7 ml of DMF are added. The solution is maintained stirred at 0° C. for 2 h, and then evaporated to dryness. The residue is taken up in 1 ml of MeOH, and then 25 ml of water are added. The precipitate obtained is filtered, washed with water and then with ether to give 810 mg (93%) of crude product 1d. Recrystallization from the MeOH—H$_2$O pair gives 1d (630 mg, 72%) in the form of a white powder.

$^1$H NMR (200 MHz, DMSO-d$_6$) δ=10.10 (s, 1H, NH—CO); 8-7.39 (m, 9H, Ar—H); 6.43 (broad s, 1H, NH—CO—NH); 6.35 (broad s, 1H, NH—CO—NH); 4.27 (m, 1H, CH$_2$—CH—NH); 4.13 (m, 1H, CH—CH—NH); 3.12 (m, 1H, CH—S); 2.84 and 2.55 (system ABX, 2H, $^2J_{AB}$=5 Hz, $^3J_{AX}$=12 Hz, $^3J_{BX}$=0 Hz, CH$_2$—S); 2.31 (t, 2H, J=8 Hz, CH$_2$—CO); 1.59-1.36 (m, 6H, (CH$_2$)$_3$).

Compound meta-hydrazone 2d:

1d (350 mg, 0.83 mmol) is solubilized in 5.5 ml of absolute ethanol and then hydrazine monohydrate (140 μl, 2.48 mmol) is added. The solution is heated under reflux overnight. After evaporation, the product is taken up in 1 ml of ethanol and water. The white precipitate is recrystallized: it is dissolved in a minimum of ethanol in the hot state and water is added until a slight cloudiness appears. After cooling, the precipitate obtained is washed with water and then dried with ether. 264 mg (73%) of product 2d are thus obtained in the form of a white powder.

$^1$H NMR (200 MHz, DMSO-$d_6$) δ=9.99 (s, 1H, NH—CO); 9.80 (s, 2H, NH$_2$); 7.54-6.88 (m, 9H, Ar—H); 6.26 (broad s, 1H, NH—CO—NH); 6.21 (broad s, 1H, NH—CO—NH); 4.28 (m, 1H, CH$_2$—CH—NH); 4.13 (m, 1H, CH—CH—NH); 3.12 (m, 1H, CH—S); 2.78 and 2.59 (system ABX, 2H, $^2J_{AB}$=5 Hz, $^3J_{AX}$=12 Hz, $^3J_{BX}$=0 Hz, CH$_2$—S); 2.27 (t, 2H, J=8 Hz, CH$_2$—CO); 1.57-1.36 (m, 6H, (CH$_2$)$_3$).

Compound meta-diazodiphenyl 3d:

3d (500 mg, 0.53 mmol) is solubilized in 1 ml of THF. 80 mg of activated MnO$_2$ are then added. After stirring for 5 minutes at room temperature, the mixture is filtered through a Celite (0.5 cm)-molecular sieve (0.5 cm in powdered form) mixed layer. The reaction mixture is evaporated to dryness. Compound 3d (47 mg, 100%) is obtained in the form of a violet oil.

$^1$H NMR (200 MHz, DMSO-$d_6$) δ=9.95 (s, 1H, NH—CO); 7.60-6.9 (m, 9H, Ar—H); 6.42 (broad s, 1H, NH—CO—NH); 6.35 (broad s, 1H, NH—CO—NH); 4.28 (m, 1H, CH$_2$—CH—NH); 4.14 (m, 1H, CH—CH—NH); 3.12 (m, 1H, CH—S); 2.83 and 2.59 (system ABX, 2H, $^2J_{AB}$=5 Hz, $^3J_{AX}$=12 Hz, $^3J_{BX}$=0 Hz, CH$_2$—S); 2.27 (t, 2H, J=8 Hz, CH$_2$—CO); 1.58-1.35 (m, 6H, (CH$_2$)$_3$).

EXAMPLE 2

Reagent for Labeling with Cy5: Cy5PMDAM

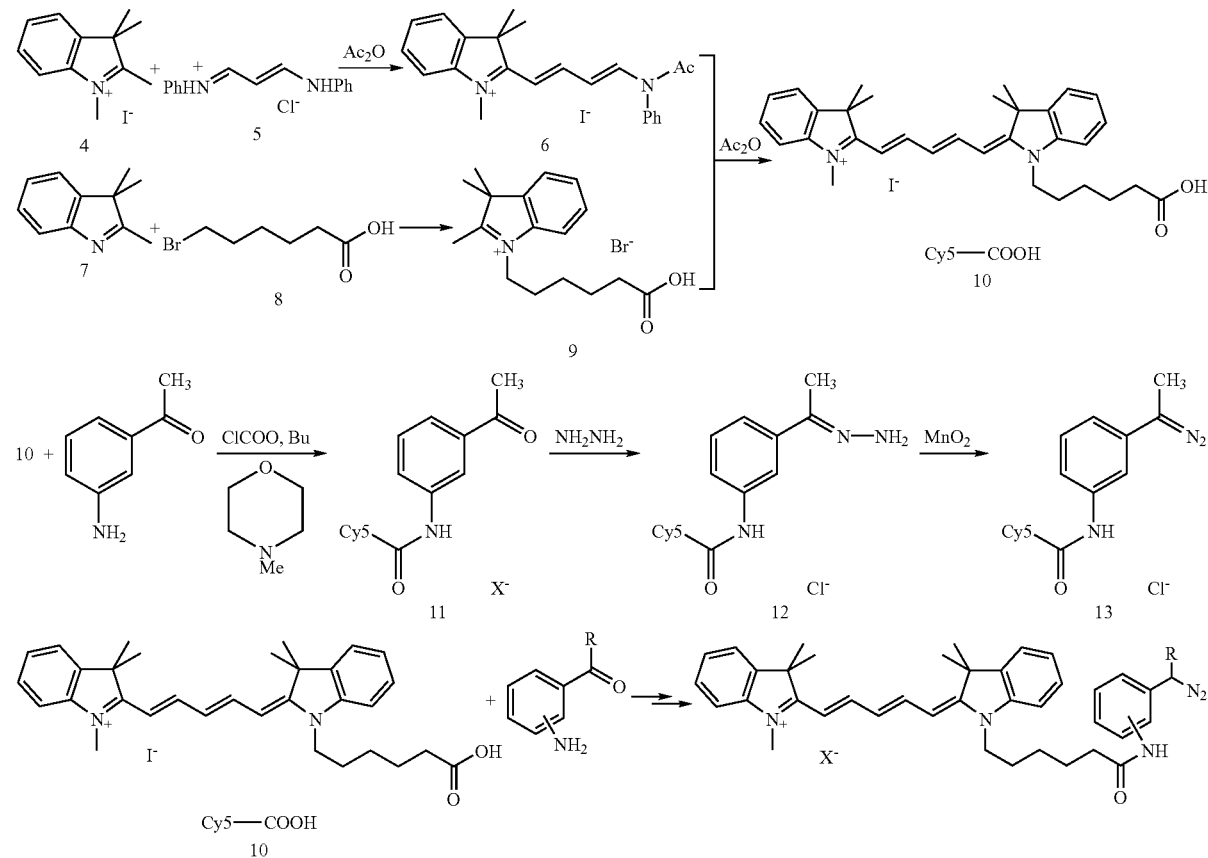

Compound 2-[4-(N-acetyl-N-phenylamino)buta-1,3-dienyl]-1,2,3,3-tetramethyl[3H]indolium iodide 6:

The mixture of malonaldehydebis(phenylimine) monohydrochloride 5 (18.3 g, 70.0 mmol), NaOAc (9.0 g, 110 mmol) and 1,2,3,3-tetramethyl[3H]indolium iodide 4 (4.25 g; 14.1 mmol) in acetic anhydride (75 ml) is heated at 110° C. for 20 min. After cooling, ether (350 ml) is added and the brown solid which precipitates is filtered, and washed with ether (3×100 ml). The solid is redissolved in 150 ml of CH$_2$Cl$_2$, filtered (elimination of the inorganic salts) and then evaporated to give a brown solid (6.0 g, 90%).

$^1$H NMR (CDCl$_3$): δ=8.64 (d, 1H, J=12 Hz, 1-H); 8.14 (t, 1H, J=16, 12 Hz, 3-H); 7.63-7.19 (m, 9H); 6.90 (d, 1H, J=15 Hz, 4-H); 5.82 (t, 1H, J=12, 13 Hz, 2-H); 4.06 (s, 3H, NCH$_3$); 2.16 (s, 3H, —COCH$_3$); 1.74 (s, 6H, CH$_3$).

Compound 1-(5-carboxypentyl)-2,3,3-trimethyl[3H]indolium bromide 9:

2,3,3-Trimethylindole 7 (10.0 g, 62.8 mmol) and 6-bromohexanoic acid 8 (12.3 g, 62.8 mmol) are mixed without solvent and heated at 110° C. for 12 h under argon. The violet-red pasty reaction mixture is washed with ethyl acetate (2×60 ml, the paste is triturated with the spatula and the supernatant is decanted off), and then with acetone (50 ml, the paste solidifies). The pink solid is filtered and then dried under vacuum (16.0 g; 73%).

Compound Cy5COOH 10:

The mixture of the iodide 6 (6.0 g, 12.7 mmol), bromide 9 (4.5 g, 12.7 mmol) and NaOAc (2.6 g, 32 mmol) in acetic anhydride (35 ml) is heated at 110° C. for 20 min. After cooling, ether (150 ml) is added and the precipitate is filtered and washed with ether (3×50 ml). The solid is dissolved in 100 ml of $CH_2Cl_2$, filtered and purified by chromatography on an $SiO_2$ column (eluent: MeOH 5-10%/$CH_2Cl_2$). 3.4 g (44%) are obtained.

$^1$H NMR (CDCl$_3$): δ=8.03 (t, 2H, J=10, 11 Hz, 2-H, 4-H); 7.38-6.91 (m, 9H, Ar—H, 3-H); 6.41 (d, 1H, J=14 Hz, 1-H); 6.31 (d, 1H, J=13 Hz, 5-H); 4.07 (t, 2H, J=7, 7 Hz, α-CH$_2$); 3.68 (s, 3H, NCH$_3$); 2.47 (t, 2H, J=7, 7 Hz, ε-CH$_2$); 1.71 (m, 18H, CH$_3$, β,γ and δ-CH$_2$).

Compound for coupling 3-aminoacetophenone with Cy5COOH 10 (product 11):

N-Methylmorpholine (360 μl, 3.2 mmol) is added to a solution of Cy5COOH 10 (1.19 g, 1.9 mmol) in 12 ml of $CH_2Cl_2$. The solution is cooled with an ice bath, and then isobutyl chloroformate (480 μl, 3.7 mmol) is added. After stirring for 5 minutes, 3-aminoacetophenone (488 mg, 3.6 mmol) is added. The mixture is stirred at room temperature for 3 h. On adding 250 ml of ether, a pasty solid is obtained. After stirring, the solid is allowed to stand at the bottom of the round-bottomed flask and the supernatant is decanted off. 50 ml of ether are again added and the medium is triturated with a spatula to give a solid. The latter is filtered, washed with water, with ether, and then dried under vacuum. The product (iodide) is then dissolved in ethanol, passed over an amberlite IRA900 (Cl$^-$; 15 g) column. The ethanolic solution recovered is evaporated to dryness and then passed over an $SiO_2$ column. 0.93 g (77%) of blue solid is obtained.

Compound Cy5-hydrazone 12:

There is added to a solution of acetophenone 11 (0.93 g, 1.46 mmol) in 5 ml of absolute ethanol hydrazine monohydrate (180 μl, 3.1 mmol) which is stirred at room temperature for 7 h. 50 ml of ether are added and the precipitate is filtered and washed with ether. The crude product is dissolved in 50 ml of $CH_2Cl_2$, the solution is filtered and then concentrated to 10 ml. The product is precipitated by adding 100 ml of ether, filtered, washed with ether and dried under vacuum. 540 mg of product 12 (57%) are obtained.

Compound Cy5PMDAM 12a:

300 mg of $MnO_2$ are added to a solution of 100 mg of hydrazone 12 in 2 ml of DMF, and the mixture is vigorously stirred for 10 min. The suspension is filtered through a layer of celite and washed with DMF (3×500 μl). 50 ml of ether are added and the oil which sediments is triturated with a spatula and the supernatant is decanted off. The washing operation is repeated 3 times with 25 ml of ether and the solid thus obtained is filtered, and dried. 65 mg (65%) of product 12a are obtained. The purity of the product is about 80-85% ($^1$H NMR).

EXAMPLE 3

Other Reagents Synthesized

Example 3.1

Synthesis of para-nitrophenyldiazomethane (NPDAM)

4-Nitrobenzaldehyde hydrazone is commercially available (reference 28, 118-2, Aldrich, France).

Work is therefore carried out on 600 mg (3.64 mmol) of this product which is dissolved in 9 ml of THF. The solution is kept stirred for 5 minutes and then 1.26 g (4 equivalents, 14.56 mmol) of $MnO_2$ are added with care. The mixture is kept stirred for 10 minutes, and then filtered. The filtrate recovered is evaporated to dryness. After washing with pentane, the compound para-nitrophenyldiazomethane is obtained in the form of a bright orange-colored powder with a yield of 79% (468 mg, 2.87 mmol).

m.p. 80-82° C.—$^1$H NMR (300 MHz, DMSO-d$_6$) δ=8.11 (d, 2H, J=9 Hz, Ar—H$_3$); 7.18 (d, 2H, J=9 Hz, Ar—H$_2$); 6.06 (s, 1H, CH$_1$—N$_2$).

Example 3.2

Synthesis of Phenylmethyldiazomethane (PMDAM)

Acetophenone hydrazone: acetophenone (2.0 g, 16 mmol) is diluted in 16 ml of absolute ethanol and then hydrazine (2.3 ml, 48 mmol) is added. The mixture is heated to reflux temperature. After 2 h, the solvent is evaporated and the residue is taken up in ether (150 ml). The medium is washed with water (100 ml). After drying over $Na_2SO_4$, the ether is evaporated off. A pale yellow oil (1.5 g, 11 mmol, 69%) is obtained.

Phenylmethyldiazomethane (PMDAM): hydrazone (150 mg, 1.1 mmol) is dissolved in 3 ml of THF. $MnO_2$ (480 mg, 5.5 mmol) is added. The medium is stirred for 30 min at room temperature. The medium becomes red in color. It is filtered and the solvent is evaporated off. A red oil (145 mg, 100%) is obtained. This reagent is used without purification.

Example 3.3

Synthesis of Diphenyldiazomethane (DPDAM)

Benzophenone hydrazone is of commercial origin (reference B 960-2 Aldrich, France).

Work is therefore carried out on 196 mg (1.0 mmol) which are dissolved in 5 ml of THF. 435 mg (5 eq, 5.0 mmol) of $MnO_2$ are added, the mixture is kept stirred for 10 minutes, and then filtered. The filtrate recovered is evaporated to dryness. 193 mg (0.99 mmol) are obtained. This reagent is used without purification.

Example 3.4

Synthesis of NVDAM

-continued

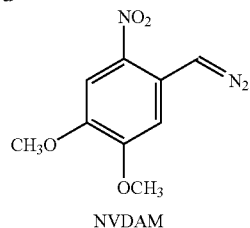
NVDAM

The synthesis is carried out according to the protocol described above, from 6-nitroveratraldehyde (Aldrich, reference 27,960-9).

EXAMPLE 4

Synthesis of the Biotinylated Derivative from NPDAM

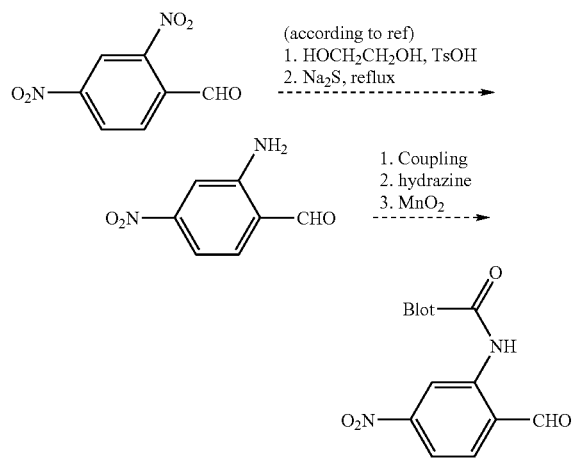

M. E. Wall et al., *J. Med. Chem.*, 1993, 36, 2689.

The 2-amino-4-nitrobenzaldehyde derivative is prepared according to the method of M E Wall et al. referenced above.

The preparation of the diazomethane NPDAM is identical to that described in Example 3.1 above.

EXAMPLE 5

Preparation of the DNA and RNA Nucleic Acids

Example 5.1

Preparation of the DNA Amplicons

The DNA amplicons are generated by PCR from 16S *Mycobacterium tuberculosis* genomic DNA targets ($10^E+4$ copies as starting targets) using the Fast Start kit from Roche, 0.2 mM of each deoxyribonucleotide (d-ATP, d-CTP, d-GTP, d-TTP), 0.3 µM of primers and 0.4 µl of enzyme.

The PCR parameters are as follows:
−95° C.: 4 min and then 35 cycles (95° C.:30 sec; 55° C.:30 sec; 72° C.:30 sec) and then 4° C.

The amplicons are qualitatively analyzed by agarose gel electrophoresis (1.5%, TBE 0.5×). The volume deposited is 5 µl and the migration takes place for 20 min at 100 volts (V). The visualization of the PCR products is carried out under a UV lamp after staining with ethidium bromide.

The conditions for the culture, the extraction of the Mycobacteria and the amplification primers are given in patent WO-A-99/65926.

Example 5.2

Preparation of the RNAs Transcribed

The transcriptions are carried out from the PCR target (*Mycobacterium tuberculosis* 16S RNA fragment) using the MEGAscript kit from Ambion: 7.5 mM of each nucleotide (ATP, CTP, GTP and UTP) and 2 µl of enzyme (RNA polymerase). The incubation time is 3 hours (h) at 37° C. The amplification primers for the PCR carry a T3 or T7 polymerase promoter as described in application WO-A-99/65926 or in the article J. Clin. Microbiol. 37(1), p. 49-55, 1999, which makes it possible to carry out the transcription.

The transcripts are analyzed by agarose gel electrophoresis (1.5%, TBE 0.5×). The volume deposited is 5 µl and the migration is performed for 20 min at 100 V. The visualization of the transcripts is carried out under a UV lamp after ethidium bromide staining.

Results which are identical from the point of view of the invention may be obtained using other amplification techniques such as NASBA or TMA which directly generate RNA amplicons.

EXAMPLE 6

Reactivity of the Labeling Reagents on Model Nucleotides

The synthesis of the labeling reagents is described in Examples 1 to 4. The PDAM described in the present invention is commercially available (reference P1405, Molecular Probes, Eugene, Oreg.).

Example 6.1

Labeling of the Monomers UMP 3'-phosphate

The reactivity of the labeling reagents carrying a diazomethyl functional group was studied in order to control the specificity of the reaction.

A protocol was developed which consists in studying this reactivity by capillary electrophoresis on a model compound 3'-UMP (Uridine 3'-monophosphate, reference U1126 Sigma) under the following standard conditions:

3'-UMP 0.04 mM; $H_3BO_3$ 2.0 mM; 2.0 mM Marker [added with an appropriate organic solvent (THF, AcOEt or DMSO)]; solvents $H_2O$—$CH_3CN$— organic solvent (ratio: 1/3/1).

This solution is divided into ten fractions of 250 µl which are heated to 60° C. After a defined period, each fraction is treated with 250 µl of dichloromethane. After stirring, the organic phase (bottom phase) is removed. This operation is repeated two more times. After centrifugation (5 min, 5000 revolutions per minute (rpm)), the aqueous phase is analyzed by capillary electrophoresis. The capillary electrophoresis (CE) conditions are as follows: CE analysis was carried out by the Beckman P/ACE 5000 apparatus. An untreated fused silica capillary (75 µm×50 cm) was used. The applied voltage is 30 kV (normal polarity) and the temperature of the capillary was maintained at 23° C. The electrophoretograms were recorded at 254 nm. The borate buffer solution (0.1 M, pH 8.3) was prepared from boric acid by adjusting the pH with an NaOH solution and filtered through a 0.2 μm filter. The samples were injected under pressure (0.5 psi, 5 sec). Each analysis is preceded by the regeneration of the capillary by successive passages of an NaOH solution (0.1 M, 2 min), water (2 min) and borate buffer (2 min) under pressure (20 psi).

The reaction is carried out by varying the reaction time between 0 and 4 hours as indicated in each figure and the results are presented for each reagent tested in FIGS. 2A to 2I with the reagent concentration used.

The reaction time is indicated on each electrophoretogram.

With all the reagents tested, the exclusive formation of a monoalkylated product is obtained, which proves the specificity of the reaction.

The reactivity, that is to say the half-reaction time of the reagent with 3'-UMP, may thus be calculated by comparing the height of the peaks, and the results are presented in Table 1 below (standard conditions described above):

reaction time) is 2 hours. The same result is obtained with BioDPDAM (FIG. 2F) where the reactivity is 45 min at a concentration of 30 mM.

Example 6.2

Test of Various Nucleotide 3'-monophosphates

In order to avoid any error of interpretation, an additional study on the meta-BioPMDAM marker, taken as a significant example, was carried out with the other nucleotide 3'-monophosphates.

Figure 3A:
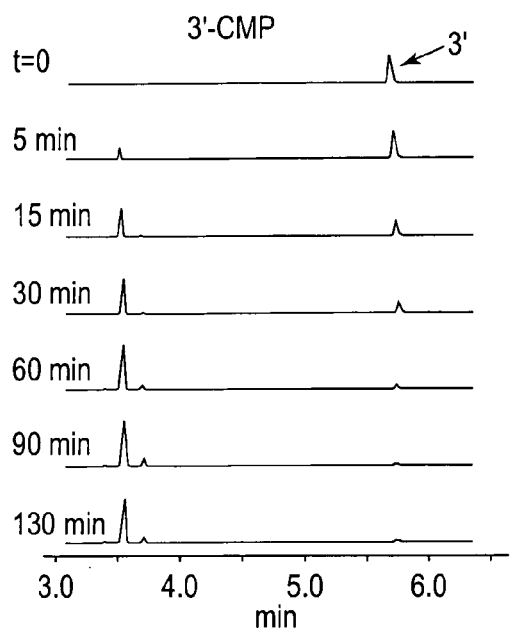
FIGS. 3A to 3D represent the profiles as a function of time, analyzed by capillary electrophoresis, of the reaction of meta-BioPMDAM with four (4) nucleotide 3'-monophosphates according to Example 6.2:
3'-CMP in the ribonucleotide series according to FIG. 3A,
3'-AMP in the ribonucleotide series according to FIG. 3B,
3'-GMP in the ribonucleotide series according to FIG. 3C, and
3'-TMP in the deoxyribonucleotide series according to FIG. 3D.
Figure 3B:
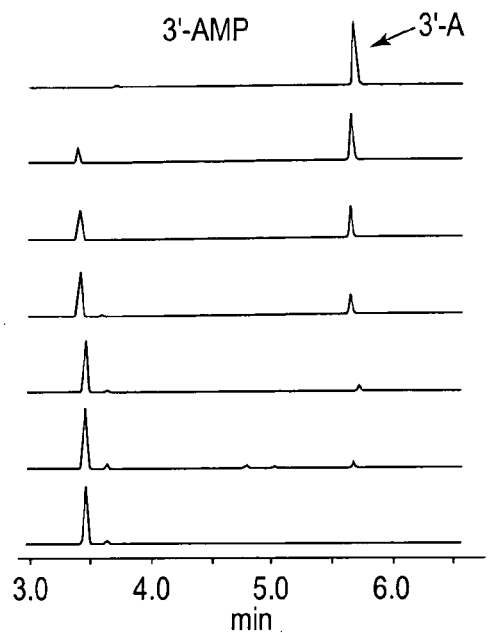
Figure 3C:
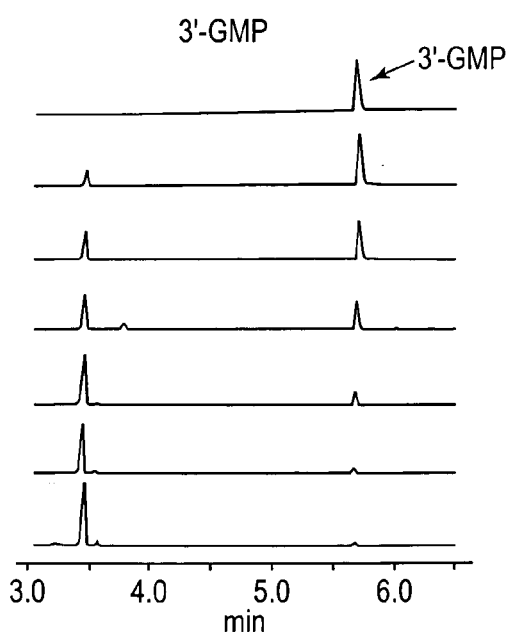
Figure 3D:
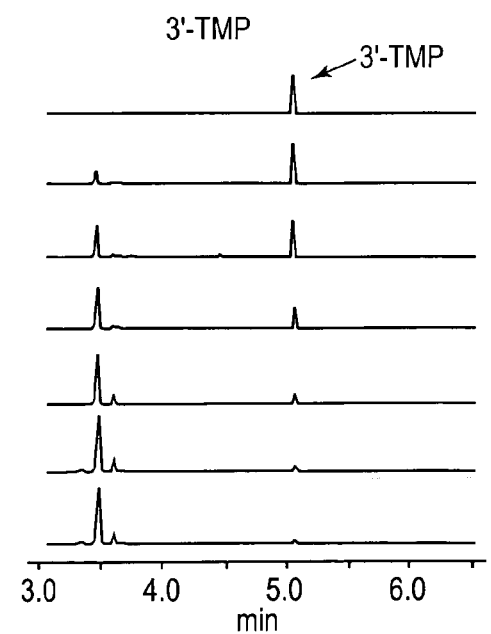

The nucleotides tested are as follows: 3'-AMP (reference 85,194-9 Aldrich), 3'-GMP (reference 151214, ICN), 3'-CMP (reference C1133, Sigma), 3'-TMP (deoxyribo series) (reference T1008, Sigma). The electrophoretograms obtained with the various nucleotides are represented in FIGS. 3A to 3D. The reaction times indicated in FIG. 3A are identical for FIGS. 3B to 3D.

TABLE 1

Reactivity (half-reaction time) of reagents

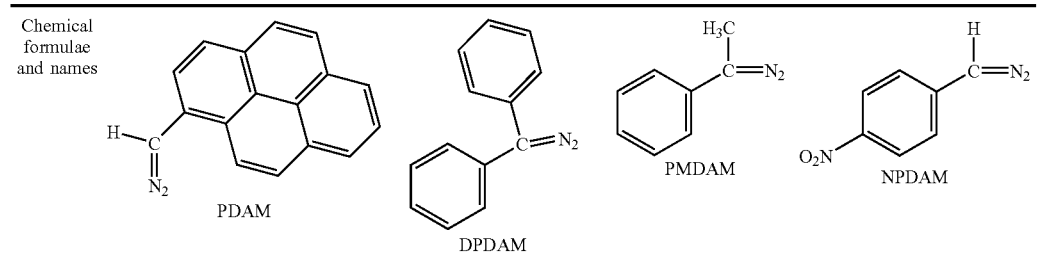

| Chemical formulae and names | PDAM | DPDAM | PMDAM | NPDAM |
|---|---|---|---|---|
| Reactivity | 5 min | 20 h | 30 min | 4 h |
| Chemical formulae and names | BioDPDAM | m-BioPMDAM | p-BioPMDAM | o-BioPMDAM* |
| Reactivity | 10 h | 15 min | 5 min | 1 min |

*With o-BioPMDAM, the reactivity is estimated because under the conditions of a 2 mM concentration of labeling reagent, the reaction is complete in less than 5 min. FIG. 2I therefore uses a concentration of 0.2 mM.

It can be noted nevertheless that, since the reaction is very specific and does not lead to by-products for all the reagents tested, it is possible to increase the concentration of the labeling reagent with no consequence from the selectivity point of view on the labeling.

Thus, for the DPDAM reagent, if the concentration is increased to 20 mM (see FIG. 2C), the reactivity (half- Regardless of the starting nucleotide (ribo or deoxyribo series), the exclusive and complete formation of the alkylated product is observed in 130 min at 60° C. It is important to note that in the case of guanine (the most reactive base with the customary alkylating reagents), only the product alkylated with phosphate is observed, proving the very high selectivity of the reaction.

This study also makes it possible to verify that the rate of the reaction does not depend on the nature of the nucleotide as substrate.

Example 6.3

Study of a Dinucleotide

Figure 4:
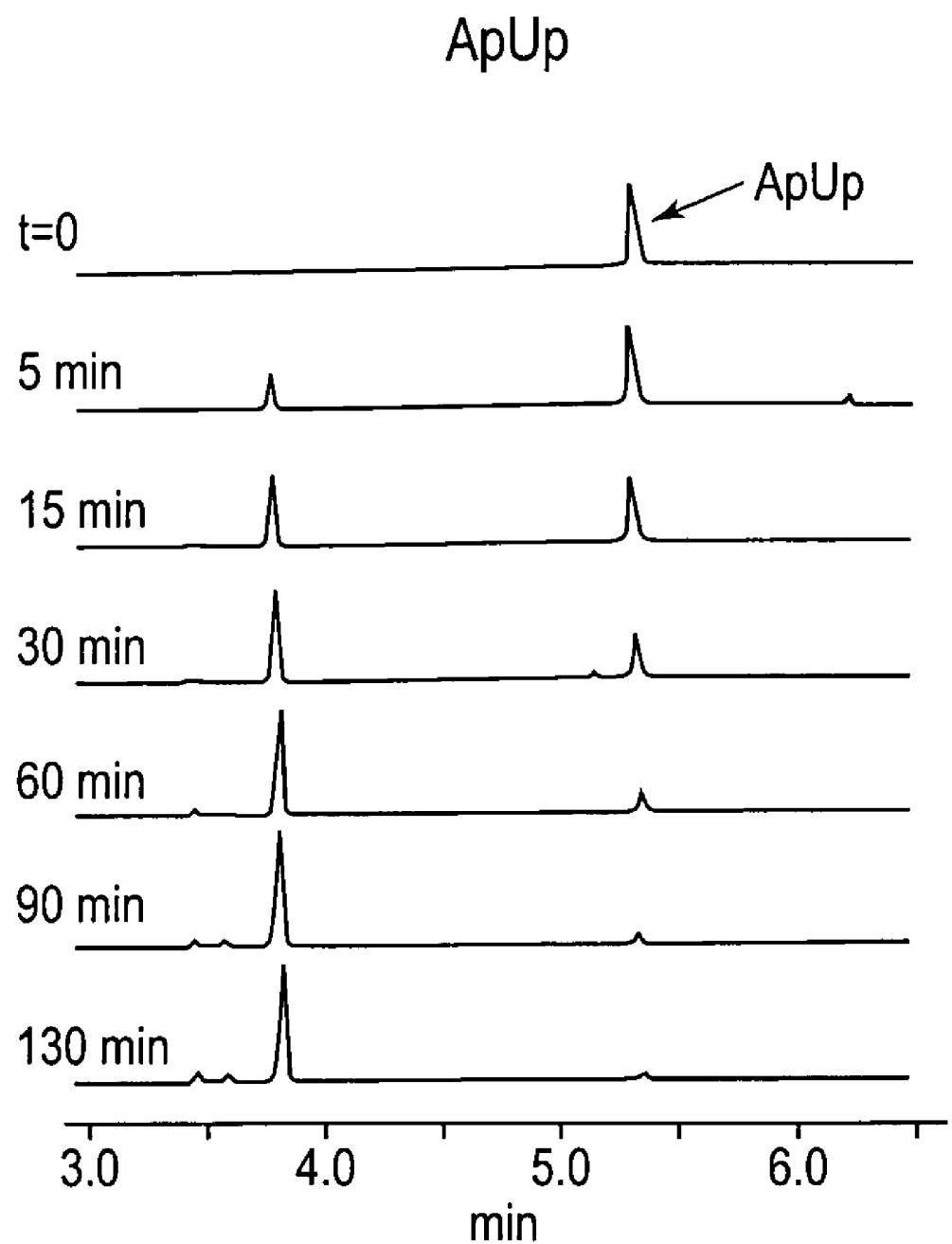
FIG. 4 represents the profiles as a function of time, analyzed by capillary electrophoresis, of the reaction of meta-BioPMDAM with a dinucleotide 5'-ApUp according to Example 6.3.
Figure 5A:
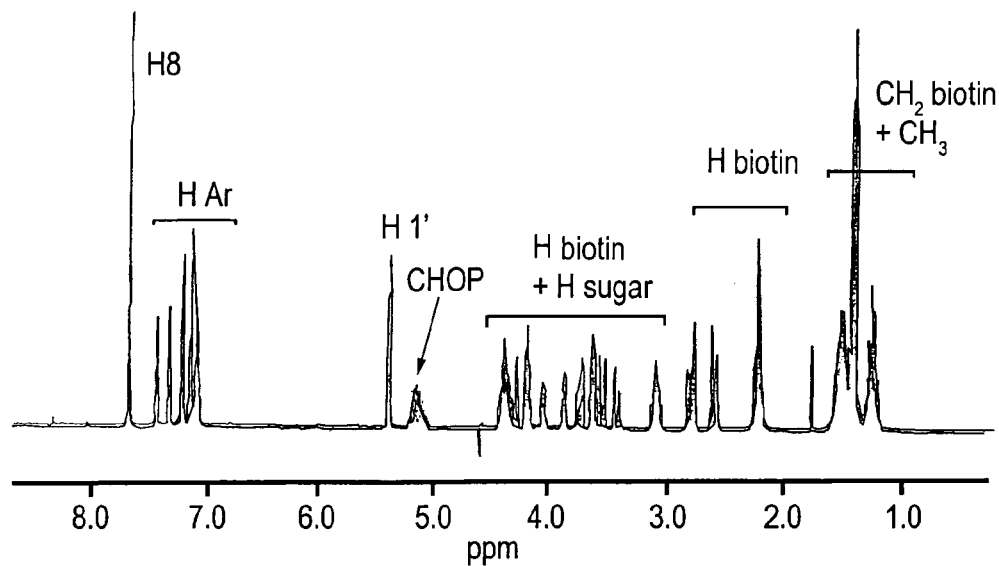
FIGS. 5A to 5D represent the proton NMR spectrum in $D_2O$ of various conjugates between the meta-BioPMDAM reagent and four (4) ribonucleotide 3'-monophosphates according to Example 6.4:
3'-GMP in FIG. 5A,
3'-AMP in FIG. 5B,
3'-CMP in FIG. 5C, and
3'-UMP in FIG. 5D.
Figure 5B:
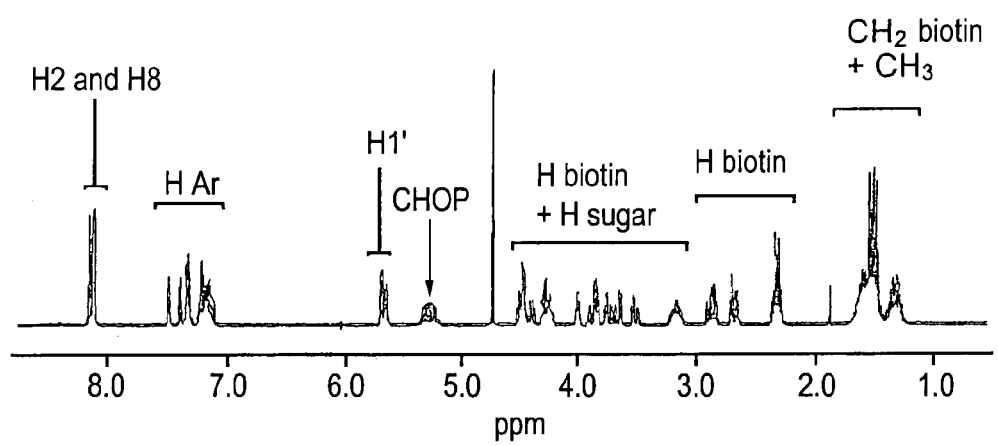
Figure 5C:
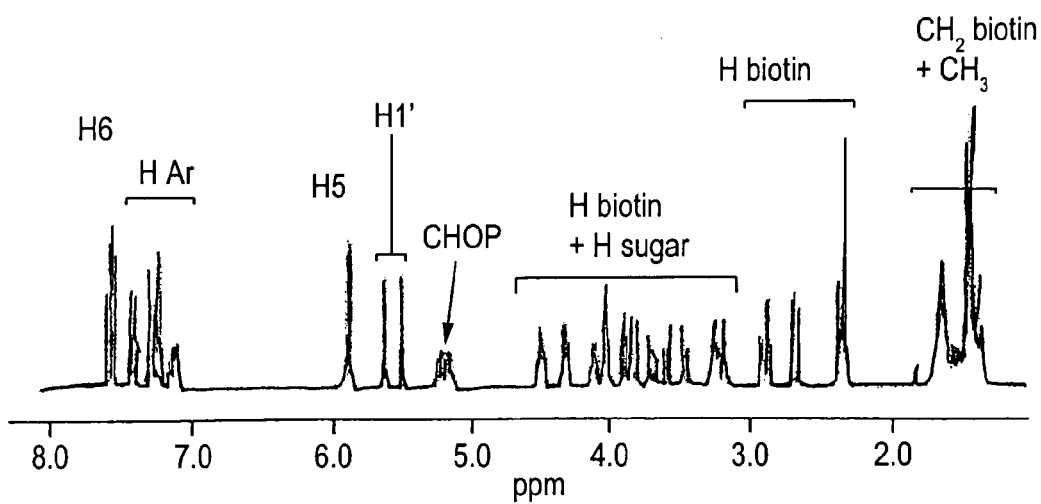
Figure 5D:
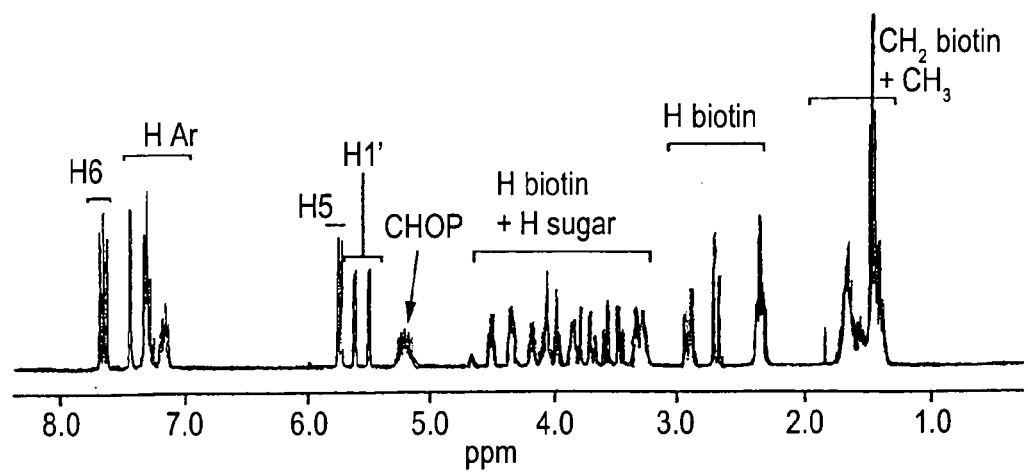
Figure 6:
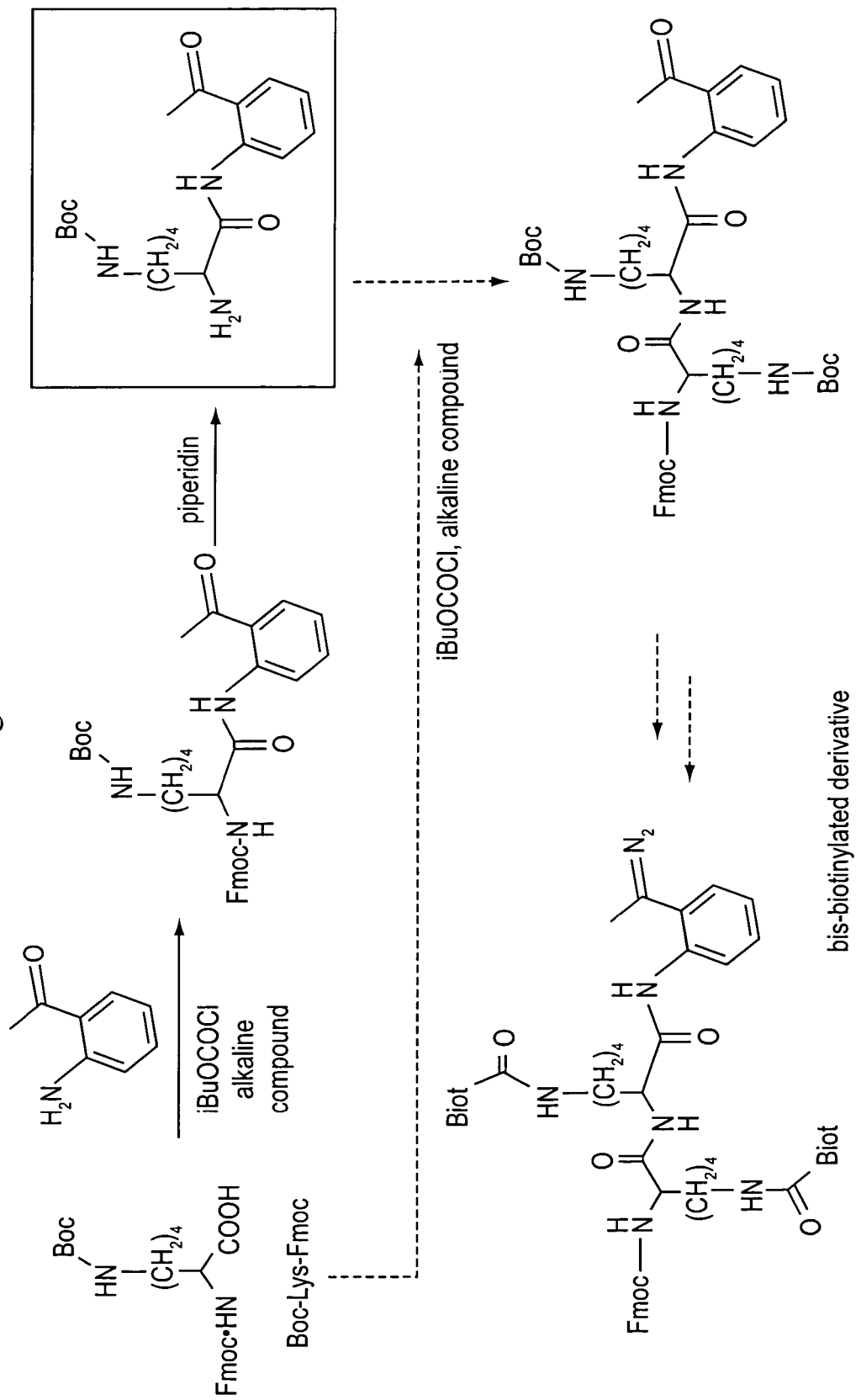
FIG. 6 represents a scheme for the synthesis of a labeling reagent carrying two (2) biotins for the chemical amplification of the signal.
Figure 7:
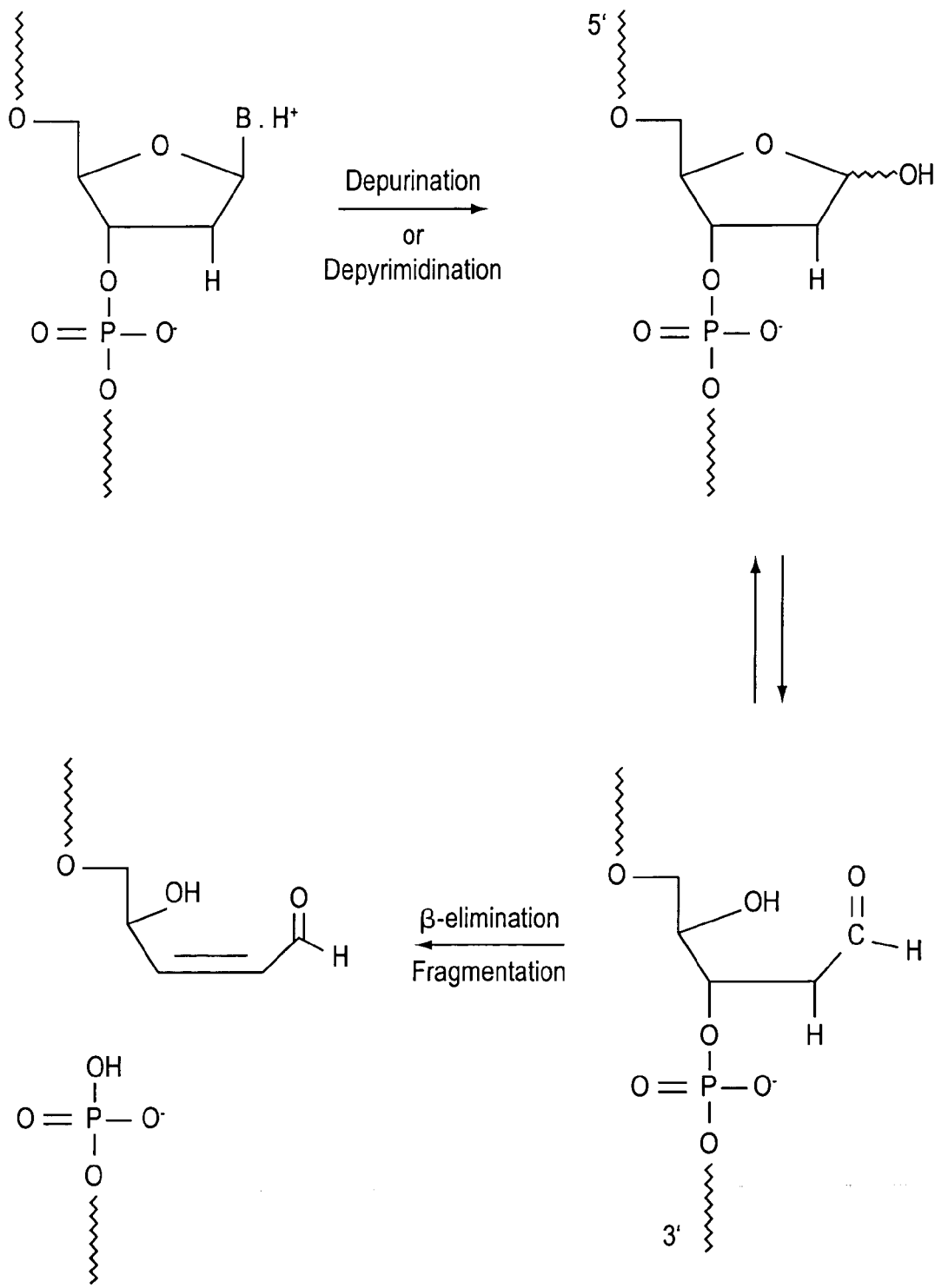
FIG. 7 represents the fragmentation mechanism in acidic medium by the formation of an abasic site.

The alkylation of the dinucleotide ApUp (reference A4298, Sigma) was carried out with meta-BioPMDAM in order to verify the selectivity of the reaction toward the terminal phosphate relative to the internucleotide phosphate. The monitoring of the reaction by electrophoresis is represented in FIG. 4. The conditions are the standard conditions of Example 6.1 already described.

The exclusive formation of a single product is observed, showing good selectivity of the meta-BioPMDAM reagent toward the terminal phosphate relative to the internucleotide phosphate.

Example 6.4

Characterization of the Adducts with the 4 Nucleotide 3'-monophosphates

To ensure that the products obtained indeed resulted from an alkylation with the phosphate, the synthesis of the adducts of the monophosphates 3'-UMP, 3'-CMP, 3'-GMP and 3'-AMP with the meta-BioPMDAM reagent was carried out. The alkylation reaction is carried out on the preparative scale as indicated below. The adducts, obtained with yields of the order of 70%, are purified and then studied by proton or phosphorus NMR.

Preparation Protocol:

3'-UMP (in disodium salt form, 9.3 mg, 21.1 μmol) is dissolved in 2 ml of a 0.1 M aqueous $H_3BO_3$ solution, and then 2 ml of $CH_3CN$, 6 ml of MeOH and then the meta-BioPMDAM reagent (75 mg; 0.20 mmol) are successively added. The reaction is carried out for 2.5 h at room temperature. It is monitored by capillary electrophoresis. 3 ml of water are added, and then the excess reagent is removed by extraction with $CH_2Cl_2$. The aqueous phase is evaporated off. The residue is dissolved in a small quantity of water and purified by passing over a reversed phase silica gel column (Lichroprep RP-18, Merck; elution MeOH/$H_2O$ (20/80)). 10 g (69%) of the adduct of 3'-UMP are obtained.

The proton NMR spectra obtained for the adducts of 3'-NMP (N=G, U, C, A) are presented in FIGS. 5A to 5D. The identification of the adducts was carried out by two-dimensional $^1H/^1H$ NMR experiments (COSY). Two diastereoisomers for each of these adducts in a 1/1 ratio are present.

Only one peak is present for the phosphorus NMR around 0 ppm (300 MHz, $D_2O$).

These experiments demonstrate that the reaction is indeed specific, that only one adduct is observed and that the labeling indeed takes place on the phosphorus. There is no alkylation side reaction on the bases. The products of labeling are therefore particularly suitable for a hybridization step.

EXAMPLE 7

Study of Stability

Example 7.1

Stability of the Labeling Reagents to Temperature

All the diazomethane derivatives, described in the table of Example 6.1 above, are preserved in the solid state in a freezer at −20° C. for at least three (3) months and no loss of reactivity is observed.

The stability at room temperature on the bench was determined by $^1H$ NMR for the two reagents NPDAM and meta-BioPMDAM. We observed no decomposition on leaving NPDAM for one month on the bench with no special precaution. We observed about 50% decomposition on leaving meta-BioPMDAM on the bench for twenty-five (25) days.

The stability of the labeling reagent to temperature is an essential characteristic. Indeed, the final destination of such a reagent for an industrial application is a labeling kit. A reagent which is not stable at least for fifteen (15) days at −20° C., preferably one (1) month, is unmarketable. Even if means of storage and of dispatch exist down to −110° C., a relationship exists between the stability at −110 20 C. and at −20° C. and that is why the value of fifteen (15) days at −20° C., preferably one (1) month at −20° C., is an industrial minimum. Beyond −110° C., laboratories do not have the required items of equipment (freezer) for storing these reagents from the point of view of the user and of the manufacturer, and there is no simple means of the dry ice type for shipping them from the point of view of the manufacturer.

As regards the stability at room temperature, a stability of a few hours, preferably one (1) day, is sufficient to allow the user to carry out the labeling.

Example 7.2

Hydrolysis of Various Nucleotide 3'-UMP Marker Conjugates

We tested the stability of the [3'-UMP-marker] conjugates in a basic medium. The mechanism of hydrolysis may be represented in the following manner:

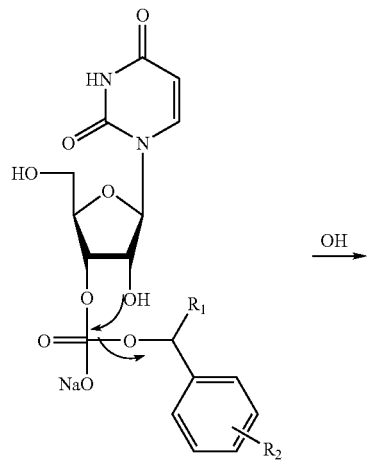
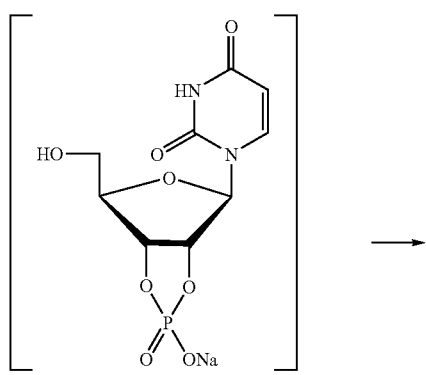
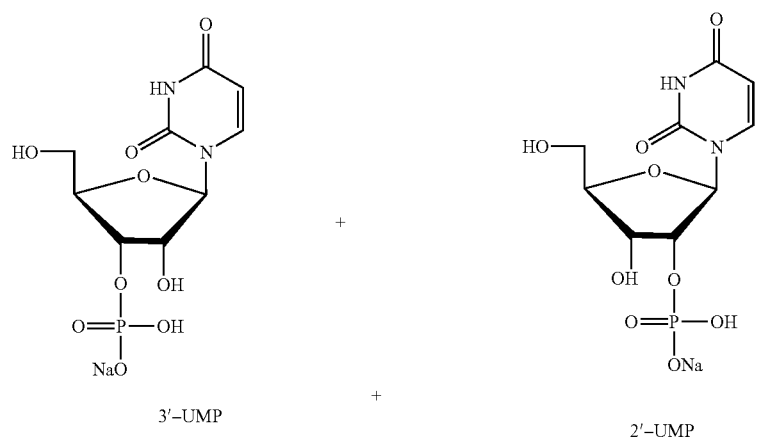
3'-UMP          2'-UMP
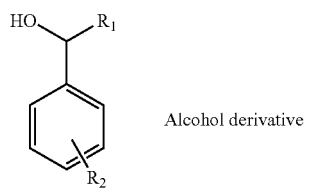
Alcohol derivative The various conjugates used were synthesized according to the protocol followed for the alkylation of the monophosphate 3'-UMP (ribonucleotide series) by meta-BioPMDAM.

The various labeling reagents tested with 3'-UMP are:
meta-BioPMDAM,
ortho-BioPMDAM,
para-BioPMDAM,
DPDAM, and
PDAM.

Procedure

A 20 mM solution of the labeling reagent is prepared in DMSO.

For the reaction, the following are mixed:
20 µl of this solution,
40 µl of 1N NaOH,
10 µl of reference product at 40 mM, and
130 µl of H₂O.

This solution is heated to 60° C. and samples were taken at precise times.

For the samples, the procedure is carried out in the following manner:
10 µl of heated solution,
40 µl of 0.5M H₃BO₃, and
150 µl of H₂O.

15 µl of this final solution are then injected by capillary electrophoresis, for each sample.

The rate of the hydrolysis reaction was determined by capillary electrophoresis by studying the reduction in the quantity of conjugate as a function of time (measurement of the surface area of the peak compared with that of an internal standard: 3,5-diaminobenzoic acid or naphthoic acid).

In this manner, we were able to compare the stability of the various conjugates.

The results are presented in Table 2 below:

TABLE 2

Reactivity (half-reaction period of reagents conjugated to nucleotide 3'-UMP-markers

| Labeling reagent coupled to 3'-UMP | Half-life period of the conjugate (min) |
|---|---|
| meta-BioPMDAM | 197 |
| ortho-BioPMDAM | 30 |
| para BioPMDAM | 8 |
| DPDAM | 54 |
| PDAM | 16 |

Thus, we found that the conjugate with meta-BioPMDAM had a half-life period of 197 min, that is a period twenty-five (25) times as high as that of the para-BioPMDAM derivative, seven (7) times as high as that of the DPDAM derivative and four (4) times as high as that of the ortho-BioPMDAM derivative.

The ortho and meta derivatives make it possible to better stabilize the conjugate, which allows better detection in the case of a diagnostic test.

EXAMPLE 8

Labeling of the Transcribed RNAs with the meta-bioPMDAM Derivative (3a)

Labeling:

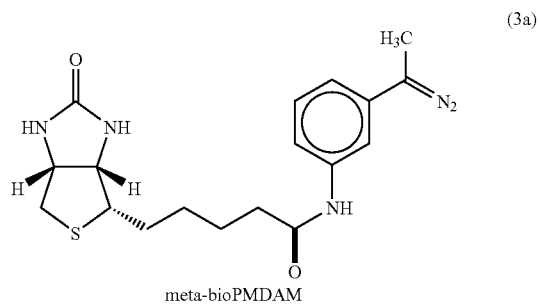

meta-bioPMDAM (3a)

The meta-bioPMDAM derivative (3a) was obtained according to the reaction scheme described in Example 1.1. The RNA targets were prepared by post-PCR transcription according to the procedure described in Example 5.2.

To 50 µl of a solution containing RNA transcripts, 9 µl of pure water (Sigma), 9 µl of 0.1M imadazole and 9 µl of 1M MnCl₂ were added. The concentration and of imidazole and MnCl₂ is 6 mM and 60 mM respectively. Before incubation, solution containing the RNA target and the buffer necessary for the fragmentation, 3 µl of meta-bioPMDAM (3a) at 100 mM in DMSO were added. The final concentration of meta-bioPMDAM marker is 2 mM. After having adjusted the solution to 150 µl with pure water, the reaction mixture is homogenized and incubated for 30 min at 60° C. After 30 min of incubation and addition of EDTA (100 mM final), the excess marker is removed by purification on QIAVAC™ columns (Qiagen, Hilden, Germany) using the supplier's buffers and protocol.

Hybridization:

After the labeling step during fragmentation, the fragments obtained are hybridized onto the DNA chips designed for the analysis of region 213-415 of the "Genbank" M20940 sequence of the *Mycobacterium tuberculosis* 16S RNA. This DNA chip is described in A. Troesch et al., J. Clin. Microbiol., 37(1), p. 49-55, 1999.

The hybridization steps were carried out on the fluidic stations (Affymetrix, Santa Clara, Calif.) using the hybridization protocol and the buffers described in A. Troesch et al., J. Clin. Microbiol., 37(1), p. 49-55, 1999. An additional step is necessary to reveal the biotin (indirect detection).

The biotinylated fragments hybridized to the capture probes at the surface of the DNA chip are revealed by introducing a streptavidin labeled with phycoerythrin (excitation: 488 nanometers (nm)) and with a Cy5 (excitation: 650 nm) using the following conditions: 300 µl of pure water; 300 µl of 100 mM Tris buffer pH 7/1M NaCl/0.05% Tween/0.005% Antifoam; 6 µl of BSA (50 mg/ml); 6 µl of labeled streptavidin (200 µg/ml). The references of the constituents used are:

Streptavidin-Phycoerythrin: reference R[0438], Dako, Denmark.
Streptavidin-CY5: reference C0050 Dako Denmark.
Antifoam reference M5-575, Ultra Additives Inc.
Tween reference P-7949, Sigma.

Reading of the DNA Chip:

The reading of the fluorescence emitted at the surface of the DNA chip after labeling and hybridization as well as the generation of data in terms of signal intensity and the percentage homology are performed by reading systems and the software provided by Affymetrix (GeneChip® Instrument System and GeneChip® Information System, Santa Clara Calif.).

The reading system provides signal and background noise intensities expressed in rfu (relative fluorescence unit). The percentage homology is given relative to a reference sequence which, in this case, is the *Mycobacterium tuberculosis* sequence.

The results in terms of mean intensity of the signal (I), of the background noise (B) and of the percentage homology (%) are given in Table 3 below.

In general, it is considered that a percentage homology greater than 90% is a satisfactory result although a result greater than 95% is generally sought. Above 95%, the values are no longer indicated because they are not significant in the case of the Mycobacteria DNA chip. A high intensity with a low background noise is the second result sought in the examples which follow. In all the results, the background noise B is deduced from the mean intensity I.

TABLE 3

Reading of the fluorescence emitted at the surface of the DNA chip after labeling and hybridization

| Marker | % homology | I (rfu) | B (rfu) | I/B |
|---|---|---|---|---|
| Phycoerythrin | >95% | 2358 | 397 | 6.9 |
| Cy5 | >95% | 4688 | 72 | 66.3 |

With the two markers, the percentage homology is greater than 95%. The intensities of the signals in rfu are greater than those obtained by standard labeling techniques.

These results show that the labeling reaction during fragmentation of the RNA transcripts using the meta-bioPMDAM derivative makes it possible to generate enough labeled fragments which are detectable on the DNA chip. The diazomethyl functional group therefore allows the introduction of the biotin marker into the sequence of an RNA transcript. This chemistry does not modify the properties of biotin-streptavidin interaction. Indeed, whether with the fluorophore phycoerythrin or Cy5, the intensity levels as well as the signal to background noise ratio (I/B) are good. This technique makes it possible to use a different fluorophore depending on the applications or even to detect at two different wavelengths (see for example Nature Genetics volume 14, pages 441-447, 1996).

EXAMPLE 9

Optimization of the Conditions for Labeling with the meta-bioPMDAM Derivative

Example 9.1

Optimization of the Concentration of Fragmentation Salt ($MnCl_2$)

The labeling of the RNA transcripts was carried out according to the protocol described in Example 8 using various concentrations of $MnCl_2$.

The hybridization and reading were also carried out according to the procedures described in Example 8.

The labeling results show that the high intensities are obtained with low concentrations of $MnCl_2$.

$MnCl_2$: 0 mM, Intensity I: 3857 rfu, Homology: 93.5%, $MnCl_2$: 5 mM, Intensity I: 3031 rfu, Homology: 93.5%, and $MnCl_2$: 10 mM, Intensity I: 2471 rfu, Homology: 94.1%.

The analysis of the fragmentation of the RNA transcripts at various concentrations of $MnCl_2$ show that the fragmentation is always efficient at 5 mM in relation to metal and by incubating at 60° C.

This shows that very good labeling results can be obtained using the labeling reagents under optimum labeling and fragmentation conditions.

Example 9.2

Optimization of the Imidazole Concentration

Four (4) tubes containing 50 µl of a solution of RNA transcripts (16S Mycobacteria) are brought into contact with 4.5 µl or 18 µl or 36 µl of imidazole (1M in pure water) in order to obtain 30, 120 and 240 mM final concentration, respectively. Three (3) µl of meta-bioPMDAM (100 mM in DMSO) are then added and the total volume is adjusted to 150 µl with pure water.

The solutions in the four tubes are vortexed and incubated for 10 minutes at 60° C.

Purification

The removal of the excess marker was carried out by purification of the four solutions of labeling reactions on QIAVAC™ columns.

The hybridization and reading steps are those of Example 8 (streptavidin phycoerythrin detection).

The results in terms of signal intensity are as follows:

Imidazole 30 mM intensity 3600 rfu,

Imidazole 120 mM intensity 1600 rfu, and

Imidazole 240 mM intensity 1400 rfu.

The best result in terms of labeling intensity is obtained with 30 mM imidazole. It is probable that high concentrations (120 and 240 mM) generate excessive fragmentations, and, consequently, generate shorter fragments.

This also shows that the chemistry of labeling based on the diazomethyl functional group may be optimized and adapted to the labeling conditions and to the target to be labeled.

Example 9.3

Effect of the Concentration of meta-bioPMDAM Marker

Six (6) tubes containing 50 µl of a solution of RNA transcripts (Example 5.2) are brought into contact with 4.5 µl of imidazole (1M in pure water) and with respectively a volume of 0.38; 0.75; 1.5; 3; 4.5 and 7.5 µl of meta-bioPMDAM (100 mM in DMSO). The total volume is adjusted to 150 µl with pure water.

The solutions are vortexed and incubated for 10 min at 60° C.

The purification, hybridization and reading conditions are in accordance with Example 8.

The results are given in Table 4 below:

TABLE 4

Summary table of the labeling results as a function of the concentrations of bioPMDAM marker. Visualization on DNA chip with streptavidin-phycoerythrin (PE) and streptavidin-Cy5 (Cy5).

| Concentration of meta-bioPMDAM | Marker | Homology (%) | I (rfu) | B (rfu) | I/B |
|---|---|---|---|---|---|
| 0.25 mM | PE | 72.4 | 193 | 786 | 0.2 |
|  | Cy5 | 60.5 | 3263 | 487 | 6.7 |
| 0.5 mM | PE | 88.6 | 454 | 785 | 0.61 |
|  | Cy5 | 77.3 | 7925 | 589 | 3.5 |
| 1.0 mM | PE | 91.4 | 891 | 809 | 1.1 |
|  | Cy5 | 84.3 | 11194 | 662 | 16.9 |
| 2.0 mM | PE | 94.6 | 2361 | 787 | 3.03 |
|  | Cy5 | 91.4 | 15375 | 417 | 6.8 |
| 3.0 mM | PE | 95.1 | 3944 | 797 | 5.0 |
|  | Cy5 | 93.5 | 23248 | 222 | 104.8 |
| 5.0 mM | PE | 93.5 | 6112 | 820 | 7.5 |
|  | Cy5 | 92.4 | 34794 | 479 | 72.6 |

From 2 mM meta-bioPMDAM, the percentage homologies and the labeling intensities are good. This is true in the case of the visualization of biotin with streptavidin carrying phycoerythrin and also in the case of streptavidin linked to Cy5. Above this concentration, the signal is increased and the percentage homology is not affected.

Example 9.4

Elimination of the Post-labeling Purification Step

With the aim of dispensing with the purification step, various labeling reaction volumes are hybridized onto a DNA chip without prior purification.

To 50 µl of a solution of RNA transcripts (Example 5.2), the labeling buffer during the fragmentation is added, the mixture is then incubated for 30 min at 60° C. The labeling conditions during fragmentation are: 30 mM imidazole (4.5 µl of a solution of imidazole at 1M in pure water), 10 mM $MnCl_2$ (1.5 µl of a solution of manganese chloride at 1M in pure water) and 2 mM meta-BioPMDAM (3 µl of a 100 mM solution in anhydrous DMSO).

After incubation, various volumes of the labeling solution were hybridized onto the DNA chip without any prior purification. The hybridization protocol used is described above. The biotinylated fragments hybridized to the capture probes at the surface of the DNA chip are revealed by introducing a streptavidin labeled with phycoerythrin (ex: 488 nm) using the conditions of Example 8.

The detection of the phycoerythrin marker and the analysis of the results were also carried out according to the protocol recommended by Affymetrix and which is described in Example 8.

The results are given in Table 5 below.

TABLE 5

Elimination of the post-labeling purification step

| Volume hybridized onto the DNA chip (µl) | Homology (%) | I (rfu) | B (rfu) | I/B |
|---|---|---|---|---|
| 20 | 94.1 | 932 | 801 | 1.2 |
| Ref.* | >95 | 728 | 752 | 1.0 |

Ref.*: post-labeling purification on columns of the total volume of the labeling reaction These results show that with 2 mM meta-BioPMDAM, it is possible to eliminate the purification if the entire reaction volume is not hybridized. With 20 µl hybridized onto the DNA chip, the results in terms of percentage homology and intensity of the signal are comparable to those obtained with the standard protocol using a purification step.

The same results, presented in Table 6, are obtained with labeling protocols without metal ($MnCl_2$). The signals are higher.

TABLE 6

Elimination of the post-labeling purification step without $MnCl_2$

| Volume hybridized onto the DNA chip (µl) | Homology (%) | I (rfu) | B (rfu) | I/B |
|---|---|---|---|---|
| 20 | 93.5 | 2057 | 875 | 2.3 |

These results also show that the use of fragmenting agents other than metals may be a solution for avoiding precipitates and the high background noise.

In this Example 9.4, the RNA transcripts used are degraded, which explains the weakness of the signals, but the reference use allows comparison.

EXAMPLE 10

Other Fragmenting Agents which can be used for Labeling RNA

Example 10.1

Use of a Polyamine Chain

To dispense with the problems of reduction in the labeling yield in the presence of salts, we used a "biogenic" polyamine, spermine, as fragmenting agent. Indeed, this polyamine chain is known for its interaction with the phosphates of nucleic acids.

Fifty (50) µl of RNA transcripts (Example 5.2) are incubated for 30 minutes at 60° C. with various concentrations of spermine (reference 13275-0010, Acros, FR, 0.5 M stock solution pH 7.5) and 2 mM meta-BioPMDAM (3 µl of a 100 mM solution of BioPMDAM in anhydrous DMSO) in 150 µl final.

The purification, hybridization and detection on DNA chip were carried out according to the protocol described in Example 8 (streptavidin-phycoerythrin detection).

The labeling results are presented in Table 7:

TABLE 7

Use of spermine as fragmenting agent

| Spermine (mM) | Homology (%) | I (rfu) | B (rfu) | I/B |
|---|---|---|---|---|
| 6 | 93.0 | 444 | 537 | 0.8 |
| 5 | 94.1 | 842 | 552 | 3.3 |
| 4 | 94.6 | 1884 | 461 | 4.1 |
| 1 | 94.6 | 2925 | 449 | 6.5 |

The labeling results during fragmentation, percentage homology and signal intensity, with spermine as fragmenting agent, are satisfactory. The polyamine chains can therefore be used to fragment RNA targets during their labeling with labeling reagents carrying a diazomethyl functional group.

Example 10.2

Use of Phenanthroline Derivatives

Trial 1: to 5 μl of RNA transcripts there are added 20 μl of phenanthroline-FeSO$_4$ (reference P1929, Sigma, 25 mM) and 2 μl of meta-BioPMDAM (100 mM in DMSO). The volume is adjusted to 100 μl. The tube is incubated for 60 min at 95° C.

Trial 2: to 5 μl of RNA transcripts there are added 3 μl of imidazole pH 9.5 (1M in pure water), 0.5 μl of MnCl$_2$ and 2 μl of meta-BioPMDAM (100 mM in DMSO). The volume is adjusted to 100 μl. The tube is incubated for 10 min at 60° C.

In both cases, the samples are hybridized, detected and analyzed on a DNA chip.

The biotinylated fragments hybridized to the capture probes at the surface of the DNA chip are revealed by introducing a streptavidin coupled to a fluorophore, phycoerythrin (excitation: 488 nm), as above.

TABLE 8

Use of phenanthroline derivatives

| Conditions | Homology (%) | I (rfu) | B (rfu) | I/B |
|---|---|---|---|---|
| 5 mM phenanthroline FeSO$_4$, 2 mM meta-bioPMDAM for 60 min at 95° C. | >95 | 21821 | 633 | 34.5 |
| 30 mM imidazole pH 9.5, 10 mM MnCl$_2$, 2 mM meta-bioPMDAM for 10 min at 60° C. | >95 | 10719 | 540 | 19.9 |

The results obtained, in Table 8, with phenanthroline as fragmenting agent are higher than those obtained with the standard protocol using metal and imidazole.

Other phenanthroline derivatives complexed with other metals apart from Fe$^{++}$ can be used. For example Cu$^{++}$, Zn$^{++}$ and the like.

EXAMPLE 11

Labeling and Fragmentation in Two Steps of RNA with meta-bioPMDAM

Fifty (50) μl of a solution of RNA transcripts obtained according to the protocol described in Example 5.2 are incubated for 30 minutes at 60° C. in the presence of the fragmentation buffer: 30 mM imidazole and 10 mM MnCl$_2$. The meta-bioPMDAM derivative is then added at a final concentration of 2 mM and incubated for an additional 5 min at 60° C.

Before hybridization, the labeled RNA fragments are purified on a column according to the protocol described above (Example 8).

TABLE 9

Labeling and fragmentation in two steps of RNA with meta-bioPMDAM

| Protocol used | Homology (%) | I (rfu) | B (rfu) | I/B |
|---|---|---|---|---|
| 1. Fragmentation and then labeling | 81.1 | 44245 | 791 | 56.0 |
| 2. Labeling during fragmentation | 91.9 | 20548 | 588 | 35.0 |

Here, comparison, according to Table 9, should be made taking into account the intensities and the I/B ratio because the signals obtained in the case of protocol 1 (fragmentation and then labeling) are too strong. Saturation of the reader is observed; which leads to lower percentage homology values (81%) compared with 91.9% obtained with the reference protocol.

However, this example shows that the fragmentation and labeling steps can be separated.

EXAMPLE 12

Amplification of the Signal for Labeling RNA with the meta-bioPMDAM Reagent

The aim of this approach is to amplify the fluorescence signal by introducing several fluorophores per molecule of meta-bioPMDAM.

Labeling Reaction

To 5 μl of transcripts (myco 16S), 89 μl of pure water (Sigma), 30 μl of imidazole (1M in pure water), 1 μl of MnCl$_2$ (1M in pure water) and 2 μl of meta-bioPMDAM (100 mM in DMSO) are added.

The tubes are vortexed and then incubated for 10 minutes at 60° C.

The column purification and the hybridization on a DNA chip are carried out according to the protocol described in Example 8.

Without Amplification of the Signal

The biotinylated fragments are revealed by the interaction with streptavidin (labeled with phycoerythrin: PE) with the labeling reagent meta-bioPMDAM. The protocol for addition of streptavidin onto the DNA chip is that described in Example 8.

With Amplification of the Signal

1$^{st}$ step: attachment of streptavidin (300 μl of pure water, 300 μl of 100 mM Tris buffer pH 7/1M NaCl/0.05% Tween/ 0.005% Antifoam; 6 μl of BSA at 50 mg/ml; 4 μl of streptavidin at 1.5 mg/ml).

2$^{nd}$ step: attachment of biotinylated anti-streptavidin antibody (300 μl of pure water, 300 μl of 100 mM Tris buffer pH 7/1M NaCl/0.05% Tween/0.005% Antifoam; 6 μl of BSA at 50 mg/ml; 3 μl of biotinylated anti-streptavidin antibody at 1 mg/ml).

3$^{rd}$ step: attachment of streptavidin labeled with phycoerythrin (300 μl of pure water, 300 μl of 100 mM Tris buffer pH 7 μM NaCl/0.05% Tween/0.005% Antifoam; 6 μl of BSA at 50 mg/ml; 6 μl of streptavidin labeled with phycoerythrin at 300 μg/ml).

The following biotinylated anti-streptavidin is used in the above steps: reference 216-065-084, Jackson Immuno Research.

The reading of the signals on the DNA chip is carried out according to the protocol described in Example 8. The results in terms of percentage homology and labeling intensity are given in Table 10 below:

TABLE 10

Amplification of the signal for labeling RNA with the meta-bioPMDAM reagent

| Post-hybridization labeling | Homology (%) | I (rfu) | B (rfu) | I/B |
|---|---|---|---|---|
| Without amplification of the signal | >95 | 2400 | 581 | 4.1 |
| With amplification of the signal | >95 | 13798 | 860 | 16.0 |

The amplification of the signal considerably improves the sensitivity of detection.

EXAMPLE 13

Labeling of RNA with para-bioPMDAM (3b) and ortho-bioPMDAM (3c) Derivatives

The two reagents were prepared according to the protocol described in Example 1.2 and 1.3 and were evaluated in the labeling approach during the fragmentation of the RNA transcripts.

The RNA transcripts were obtained according to the protocol described in Example 5.2.

The protocol for labeling, hybridization, introduction of the streptavidin labeled with phycoerythrin and the purification protocol are those described in Example 8.

The results are given in Table 11 below:

TABLE 11

A Labeling of RNA with para-bioPMDAM and ortho-bioPMDAM

| Molecule used | Homology (%) | I (rfu) | B (rfu) | I/B |
|---|---|---|---|---|
| para-bioPMDAM | >95 | 1665 | 620 | 2.7 |
| ortho-bioPMDAM | >95 | 3657 | 532 | 6.9 |

These results show that the substitutions in ortho and para also give useful results in terms of labeling intensity and percentage homology.

EXAMPLE 14

Labeling of the RNA Transcripts with a BioDPDAM Derivative (3d)

The BioDPDAM derivative (3d) was prepared according to the protocol described in Example 1.4.

The RNA transcripts were obtained according to the protocol described in Example 5.2.

The labeling and fragmentation method is carried out in one step compared with the meta-BioPMDAM reagent under the conditions described in Table 12 below (reaction volume 100 µl).

The protocol for hybridization, introduction of the streptavidin labeled with phycoerythrin and the purification protocol are those described in Example 8.

The results are given in the table below:

TABLE 12 labeling of RNA transcripts with BioDPDAM (3d)

| Labeling conditions | Homology (%) | I (rfu) | B (rfu) | I/B |
|---|---|---|---|---|
| Reference protocol: | | | | |
| 30 mM Im pH 9.5; 5 mM MnCl$_2$; 2 mM meta-bioPMDAM (3a) 10 min at 60° C. | 89.7 | 35519 | 528 | 67.2 |
| 30 mM Im pH 9.5; 5 mM MnCl$_2$; 2 mM BioDPDAM (3d) 10 min at 60° C. | >95 | 3252 | 446 | 7.3 |
| 30 mM Im pH 9.5; 5 mM MnCl$_2$; 2 mM BioDPADAM (3d) 15 min at 60° C. | >95 | 4482 | 435 | 10.3 |
| 30 mM Im pH 9.5; 5 mM MnCl$_2$; 2 mM BioDPDAM (3d) 30 min at 60° C. | >95 | 6429 | 428 | 15.0 |

Im = Imidazole

The derivative 3d gives good results for labeling of the RNAs on phosphate. This result shows that substitutions such as the phenyl group may be used to modulate the reactivity and the stability of the markers carrying the diazomethyl functional group.

EXAMPLE 15

Labeling of RNA with the Cy5-PMDAM Derivative (12a)

Cy5-PMDAM (12a)

The marker Cy5-PMDAM (12a) was prepared according to the protocol described in Example 2.

Five (5) µl of RNA trascript (Example 5.2) are labeled with Cy5-PMDAM under various fragmentation and labeling conditions. The general conditions are as follows:

final reaction volume 100 µl,
    30 mM imidazole pH 8 (3 µl of a 1M stock solution),
    5 mM MnCl$_2$ (6 µl of a 0.1M stock solution), and
    3 mM Cy5-PMDAM (3 µl of a 100 mM stock solution in anhydrous DMSO).

In a first trial, the labeling during fragmentation is carried out in a single step.

In a second trial, the labeling and the fragmentation were carried out in two steps: the fragmentation is carried out before the labeling.

After each incubation which contains MnCl$_2$, the salt is neutralized by addition of 20 µl of a 0.5 M EDTA solution.

The incubation was carried out at 60° C. for 30 min for the labeling and the fragmentation in one step. For the second trial where the labeling and the fragmentation were carried out in two steps, the incubation, a 15 min incubation, was used for each step.

The labeled fragments were purified, hybridized, and detected according to the protocol described in Example 8. The only difference lies in the fact that during the hybridization step, the addition of labeled streptavidin is no longer necessary because the marker is detected directly by an appropriate reader (GMS 418 Array Scanner, Affymetrix, Santa Clara, Calif.).

The labeling results are given in Table 13 below:

TABLE 13

Labeling of RNA transcripts with the Cy5-PMDAM derivative

| Labeling protocol | Homology (%) | I (rfu) | B (rfu) | I/B |
|---|---|---|---|---|
| Labeling during fragmentation | >95 | 6612 | 352 | 17.3 |
| Fragmentation and then labeling | 94.1 | 8378 | 158 | 53.1 |

The labeling on the phosphate of the RNA transcripts with a labeling reagent (12a) gives very satisfactory results in terms of labeling intensity and percentage homology.

It is also important to note that the signal to background noise ratio is very satisfactory in the case of this marker. Indeed, the excitation and emission wavelengths of the cyanine derivatives are distant from those of biological molecules.

These results also show that the diazomethyl functional group allows the introduction of markers other than biotin at the level of the phosphate groups of nucleic acids.

EXAMPLE 16

Study of the Fragmentation of DNA

Example 16.1

Hydrolysis of Various Nucleosides in Acidic Medium

The aim of the study is to demonstrate the difference in terms of stability to acidic pH between the natural nucleosides, the modified nucleosides as well as the purine and pyrimidine type nucleosides. This study also allows better control of the fragmentation of the DNA by taking into account its base composition.

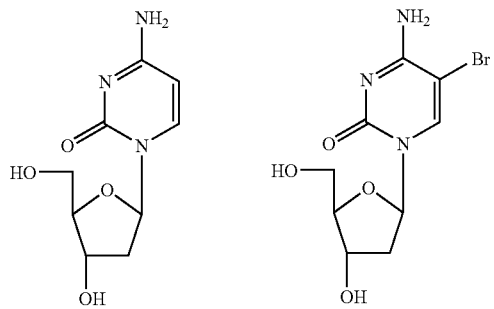

-continued

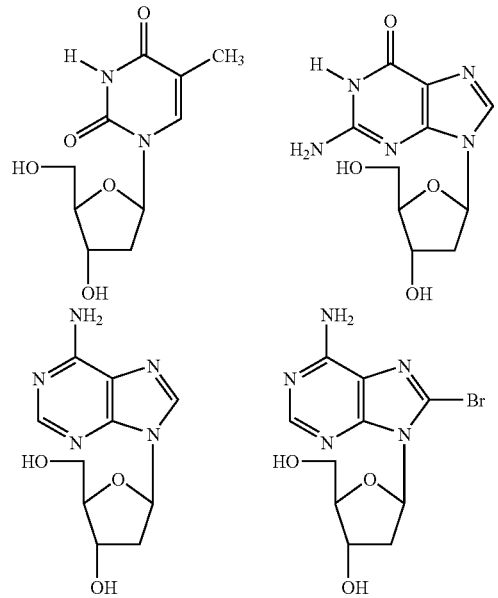

Two modified nucleosides, 8-bromo-2'-deoxyadenosine (8-BrdA) and 5-bromo-2'-deoxycytidine (5-BrdC) as well as the four (4) natural nucleosides (dA, dC, dG and dT) were used in this study.

50 nanomoles (nmol) of each nucleoside are incubated in 50 mM sodium formate pH 3 at 95° C. The incubation times vary from 0 to 45 min. After drying under vacuum and taking up in 20 µl of pure water, the samples (10 mmol) are then analyzed by reversed-phase HPLC. The results are given in the form of percentage hydrolysis of the starting nucleoside (on the y-axis) in relation to the incubation time in minutes (x-axis), see FIG. 8.

Figure 8:
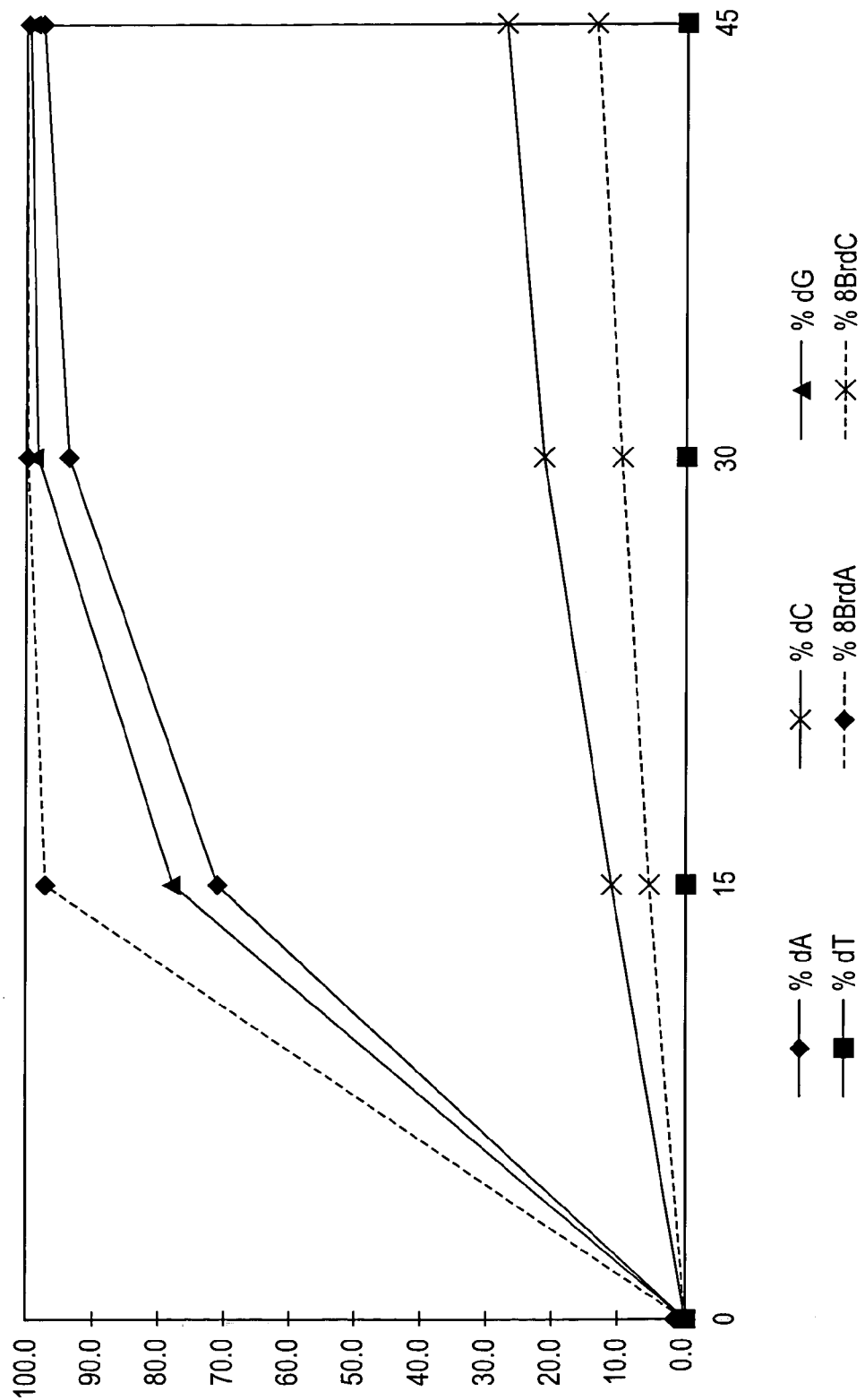
FIG. 8 shows, according to Example 16.1, the kinetics of degradation at acidic pH for various modified nucleosides (8-bromo-2'-deoxyadenosine (8-BrdA) and 5-bromo-2'-deoxycytidine (5-BrdC) as well as the four (4) natural nucleosides (dA, dC, dG and dT). The results are represented in the form of percentage hydrolysis of the starting nucleoside (on the y-axis) in relation to the reaction time in minutes (x-axis).

The curves of FIG. 8 show that the modification of adenine at the 8-position with a bromine atom renders this nucleoside less stable than the natural nucleoside. Moreover, the results show that under the conditions used, depurination is far greater than depyrimidination.

This study shows that the fragmentation of DNA by depurination or depyrimidination is controlled by optimizing the hydrolysis conditions or by incorporating either modified bases which are less stable than the natural bases or bases which can be modified and hydrolyzed after their incorporation.

Example 16.2

Fragmentation of Double-stranded DNA Incorporating a Modified Nucleotide or Otherwise Three PCR amplifications were carried out in parallel starting with 16S *Mycobacterium tuberculosis* genomic DNA target ($10^E+4$ initial copies) using the Fast Start kit from Roche, 0.2 mM of each deoxyribonucleotide (d-ATP, d-CTP, d-GTP, d-TTP), 0.3 µM of primers and 0.4 µL of enzyme.

The PCR parameters are those of Example 5.

In the first case, the protocol is used as such: in the case of so-called natural PCR.

In the second case, the protocol is modified in order to obtain a PCR at 30% of 8Br-dATP. This is achieved by introducing 0.2 mM d-CTP, d-GTP and d-TTP. 0.14 mM d-ATP and 0.06 mM 8-BrdATP are also introduced. (8-BrdATP is of commercial origin (reference N-2005-1, TriLink Biotechnologies, San Diego Calif.)).

In the third case, the protocol is modified in order to obtain a PCR at 50% of 8-BrdATP. This is achieved by introducing 0.2 mM d-CTP, d-GTP and d-TTP. 0.1 mM of d-ATP and 0.1 mM of 8-BrdATP are also introduced.

The study of the sole fragmentation of these amplicons was carried out under the conditions described above: 50 mM sodium formate pH 3 at 95° C.

The analysis was carried out on a denaturing polyacrylamide gel (8% polyacrylamide, 7 M urea, 1×TBE) using ethidium bromide staining.

After incubating for 15 min at 95° C. in 50 mM sodium formate pH 3, no difference is visible between the three (3) targets. In all cases, we observed complete fragmentation of the PCR amplicons.

The depurination of the PCR amplicons was also carried out at different pH values and at different temperatures and incubation times. Gel analysis, under the above conditions, shows that at pH 3 the fragmentation is complete after only 10 min of incubation at 95° C. At this pH, the fragmentation is also complete at 60° C. after 30 min of incubation.

At pH 4, 30 min of incubation are necessary to obtain complete fragmentation of the DNA amplicons even at 95° C. This result is very important and shows that the abasic site generated at acidic pH is unstable and therefore leads to the fragmentation of the DNA chain without any other particular treatment.

EXAMPLE 17

Labeling and Fragmentation of DNA with the meta-bioPMDAM Derivative (3a) in Two Steps The meta-bioPMDAM derivative (3a) was obtained according to the reaction scheme described in Example 1.1.

The DNA amplicons were prepared by PCR amplification according to the protocol described in Example 5.1.

Labeling

There are added to 10 µl of PCR, 38 µl of pure water (Sigma), 50 µl of sodium formate at pH 3 (100 mM in pure water) and the mixture is incubated for 30 minutes at 60° C. Next, 2 µl of meta-bioPMDAM (100 mM in DMSO) are then added. The solution was vortexed, and then incubated for an additional 15 minutes at 60° C.

The trials are carried out in duplicate in order to be able to analyze the fragmentation of the DNA on gel and the labeling efficiency by hybridization and reading of the DNA chip.

Purification

The purification is carried out on QIAQUICK™ columns (Nucleotide Removal kit, Qiagen, Hilden, Germany). The purification protocol used is that recommended by the supplier.

After purification, the eluate is transferred into a clean tube containing 400 µl of hybridization buffer (1.75 ml 20×SSPE; 2.9 ml 5M Betaine; 290 µl 0.1M DTAB; 10 µl Antifoam 30%). The references of these substances are, for:
   Betaine reference B-2754 Sigma, and
   DTAB reference D-5047 Sigma.

The solution is vortexed and incubated for 10 min at 95° C. in order to separate the DNA strands which are not separated during the labeling step during the fragmentation (denaturation step). The tube is then immersed in a water-ice mixture at 0° C. before hybridization onto a DNA chip.

Hybridization onto a DNA Chip

After the labeling step during fragmentation, the fragments obtained are hybridized onto the DNA chips designed for the analysis of region 213-415 of the "Genbank" M20940 sequence of the *Mycobacterium tuberculosis* 16S RNA. This DNA chip is described in A. Troesch et al., J. Clin. Microbiol, 37(1), p. 49-55, 1999.

The hybridization steps were carried out on the fluidic stations (Affymetrix, Santa Clara, Calif.) using the hybridization protocol and the buffers described in A. Troesch et al., J. Clin. Microbiol., 37(1), p. 49-55, 1999. An additional step is necessary to reveal the biotin (indirect detection).

The hybridization is revealed by the coupling of streptavidin labeled with phycoerythrin (PE) which interacts with the biotin of the meta-BioPMDAM under the following conditions: 300 µl of pure water; 300 µl of 100 mM Tris buffer pH 7/1M NaCl/0.05% Tween/0.005% Antifoam; 6 µl of BSA (50 mg/ml); 6 µl of streptavidin-PE (300 µg/ml).

The references of these substances are, for:
   Streptavidin-Phycoerythrin: reference: R[0438], Dako, Denmark,
   Streptavidin-CY5: reference: C0050 Dako, Denmark,
   Antifoam reference: M5-575, Ultra Additives Inc., and
   Tween reference: P-7949, Sigma.

Reading of the DNA Chip:

The reading of the fluorescence emitted at the surface of the DNA chip after labeling and hybridization as well as the generation of data in terms of signal intensity and the percentage homology are performed by reading systems and the software provided by Affymetrix (GeneChip® Instrument System and GeneChip® Information System, Santa Clara Calif.).

The reading system provides signal and background noise intensities expressed in rfu (relative fluorescence unit). The percentage homology is given relative to a reference sequence which, in this case, is the *Mycobacterium tuberculosis* sequence.

The results in terms of mean intensity of the signal (I), of the background noise (B) and of the percentage homology (%) are given in the table below:

In general, it is considered that a percentage homology greater than 90% is a satisfactory result although a result greater than 95% is generally sought. Above 95%, the values are no longer indicated because they are not significant in the case of the Mycobacteria DNA chip. A high intensity with a low background noise is the second result sought in the examples which follow. In all the results, the background noise B is deduced from the mean intensity I.

Analysis on Polyacrylamide Gel

The samples intended to be analyzed on gel are dried under vacuum, taken up in 10 µl of pure water and 10 µl of 2× blue formamide.

The migration is performed on an 8% acrylamide gel, in 1× TBE, for one (1) hour at 150 V.

Acid pH was used for the fragmentation of the DNA. Indeed, at this pH, the depurination phenomenon generates very unstable abasic sites leading to a practically immediate fragmentation of the DNA sequences at high temperature. This type of fragmentation produces DNA-5' phosphate fragments.

Gel analysis shows that the incubation of the PCR amplicons at 60° C. for 30 min in solution in formate buffer (50 mM, pH 3) leads to a complete fragmentation of these amplicons. This allowed us to evaluate the labeling during the fragmentation of the DNA amplicons in the presence of the meta-bioPMDAM marker.

The labeling results during the fragmentation of the DNA amplicons in terms of percentage homology, intensity of the signals and background noise are given in Table 14 below.

TABLE 14

Labeling and fragmentation of the DNA amplicons in terms of homology, intensity of the signals (I) and background noise (B)

| Conditions for labeling of the PCR amplicons | Homology (%) | I (rfu) | B (rfu) | I/B |
|---|---|---|---|---|
| Buffer: formate pH 3, 50 mM Marker: 2 mM meta-bioPMDAM Incubation: 30 min at 60° C. | >95 | 4456 | 593 | 7.5 |

This example shows that the reagents of the invention can be used for labeling the DNA fragments produced by enzymatic amplification in a two-step protocol. They can also be used for labeling nonamplified natural DNA.

EXAMPLE 18

Labeling of DNA with the Cy5-PMDAM Derivative (12a)

The labeling of DNA with this new marker carrying the diazomethyl functional group was evaluated using a synthetic DNA fragment.

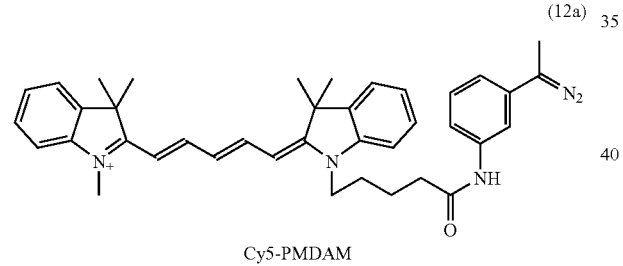

Cy5-PMDAM (12a)

The labeling reagent Cy5-PMDAM (12a) is prepared according to the protocol described in Example 2.

A twenty (20) mer oligodeoxyribonucleotide (ODN) is prepared according to the so-called phosphoramidite method. A phosphate is introduced at the 5' end by a standard phosphorylation reagent compatible with the phosphoramidite chemistry. The sequence of this ODN consists of all the natural bases of the DNA (sequence of the ODN: 5'-CT-GAACGGTAGCATCTTGAC-3'). This sequence is complementary to capture sequences of a so-called "model" DNA chip synthesized according to the Affymetrix technology. This DNA chip contains capture probes which are identical in terms of sequence and which show a checkered pattern on its surface. The reading of this DNA chip gives information as to the performance of the labeling in terms of intensity but not of result of homology.

Labeling: To 50 picomoles (pmol) of this ODN, 10 μl of Cy5-PMDAM (100 mM in DMSO) are added. The final volume is 100 μl. After homogenization, the incubation is carried out at 60° C. for 30 minutes.

Purification and reading: The purification, in order to remove the excess labeling reagent, is carried out according to Example 17. The reading on a DNA chip is carried out according to Example 17.

Results:

The mean of the labeling intensities (I) read on the DNA chip is 16 644 rfu for a background noise (B) of 450 rfu.

This intensity level is very high and shows that the labeling reagent Cy5-PMDAM (12a) is completely compatible with the labeling of the DNA fragments on the phosphate group.

EXAMPLE 19

Labeling and Fragmentation of DNA with the PDAM Reagent

Example 19.1

Labeling with 1-pyrenyldiazomethane (PDAM)

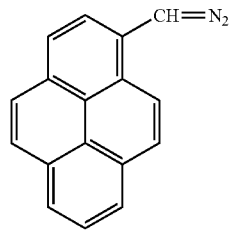

1-Pyrenyldiazomethane

PDAM is obtained from Molecular Probes (Eugene, Oreg.) and solubilized in anhydrous DMSO.

Two ODNs of twenty (20) mers were used as DNA models: one ODN of 20 mer 5'-hydroxyl and the same ODN of 20 mer carrying a phosphate at the 5' end. The sequence of the ODN is described in Example 18. The labeling reaction is carried out in a mixture containing 50% DMSO and 1.5 mM 1-pyrenyldiazomethane (PDAM) at 60° C. for 30 minutes or one hour.

The labeling efficiency was evaluated by thin-layer chromatography (in normal phase) in an isopropanol/ammonia/water 60/10/30 eluent. After 30 minutes, the coupling is complete on the ODN 5'-phosphate. One hour is required to obtain a partial coupling onto the ODN 5'-hydroxyl, that is to say about 50%.

The results of Example 6 are confirmed on a model sequence of 20 bases as regards the very preferential labeling of the reagents carrying a diazomethyl functional group on the terminal phosphate. The labeling on an intranucleotide phosphate is not a damaging inconvenience since it can lead to an increase in sensitivity by introducing more than one marker onto the nucleic acid fragment. This allows the nucleic acid to hybridize with a good sensitivity to the complementary target while preserving a good hybridization specificity.

Persons skilled in the art, by optimization reactions, can thus control the specificity of the labeling by varying, for example, the labeling reagent, the reaction time and the temperature, in order to have exclusive labeling on the terminal phosphate.

Example 19.2

Kinetic Study of the Labeling Reaction with PDAM

This study was carried out using the 20 mer ODN 5'-phosphate under the preceding conditions by varying the reaction time. The labeling yields were evaluated by reversed-phase high performance liquid chromatography (HPLC) analysis under the following conditions:

Reversed-phase column Spheri-5 RP-18 5 μm, 220×4.6 mm (Perkin Elmer). The buffers and the gradient used are:
 Buffer A: 0.1 M TEAA; Buffer B=50% Buffer A+50% $CH_3CN$, and
 Gradient from 10 to 50% of B over 30 min at 1 ml/min at room temperature.

Figure 9:
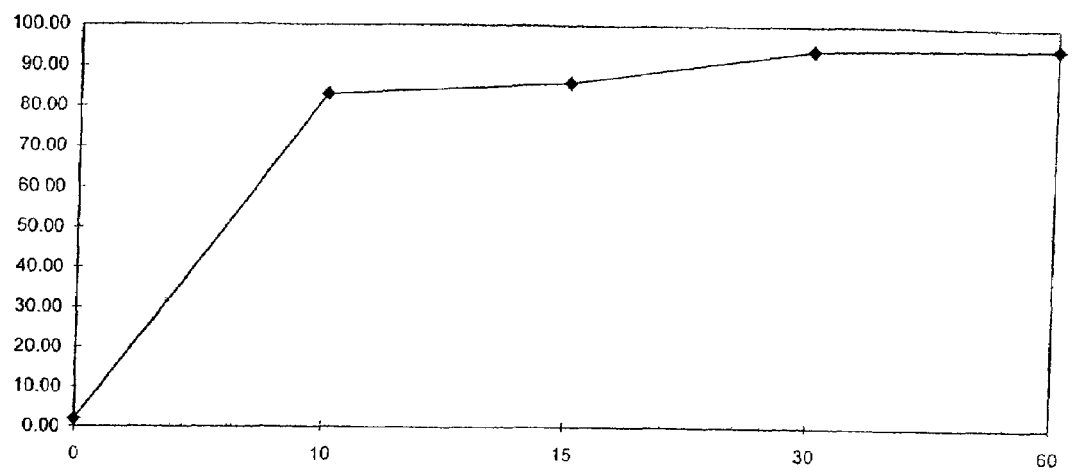
FIG. 9 represents, according to Example 19.2, the kinetics of labeling as a function of time at a temperature of 60° C. with the PDAM reagent on a synthetic oligodeoxynucleotide (ODN) 5'-phosphate. The results are represented in the form of percentage labeling in relation to the reaction time expressed in minutes (min) (on the x-axis).

The results are represented in FIG. 9 with, on the x-axis, the reaction time expressed in minutes, and, on the y-axis, the percentage labeling.

The yield is close to 90% after only 10 min of incubation at 60° C.

Example 19.3

Effect of the Temperature on the Labeling with PDAM

The labeling was carried out using the 20 mer ODN 5'-phosphate under the preceding conditions by varying the incubation temperature and with an incubation time of 10 min in each case.

The labeling yields were evaluated by reversed-phase HPLC analysis.

Figure 10:
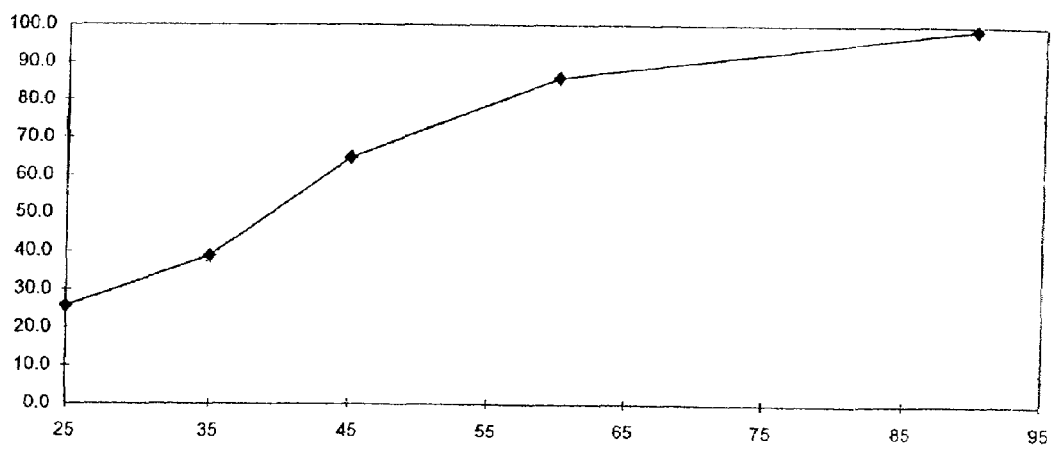
FIG. 10 represents, according to Example 19.3, the percentage labeling as a function of the reaction temperature. The results are presented in FIG. 10 with, on the y-axis, the percentage labeling and, on the x-axis, the reaction temperature in ° C.
Figure 11:
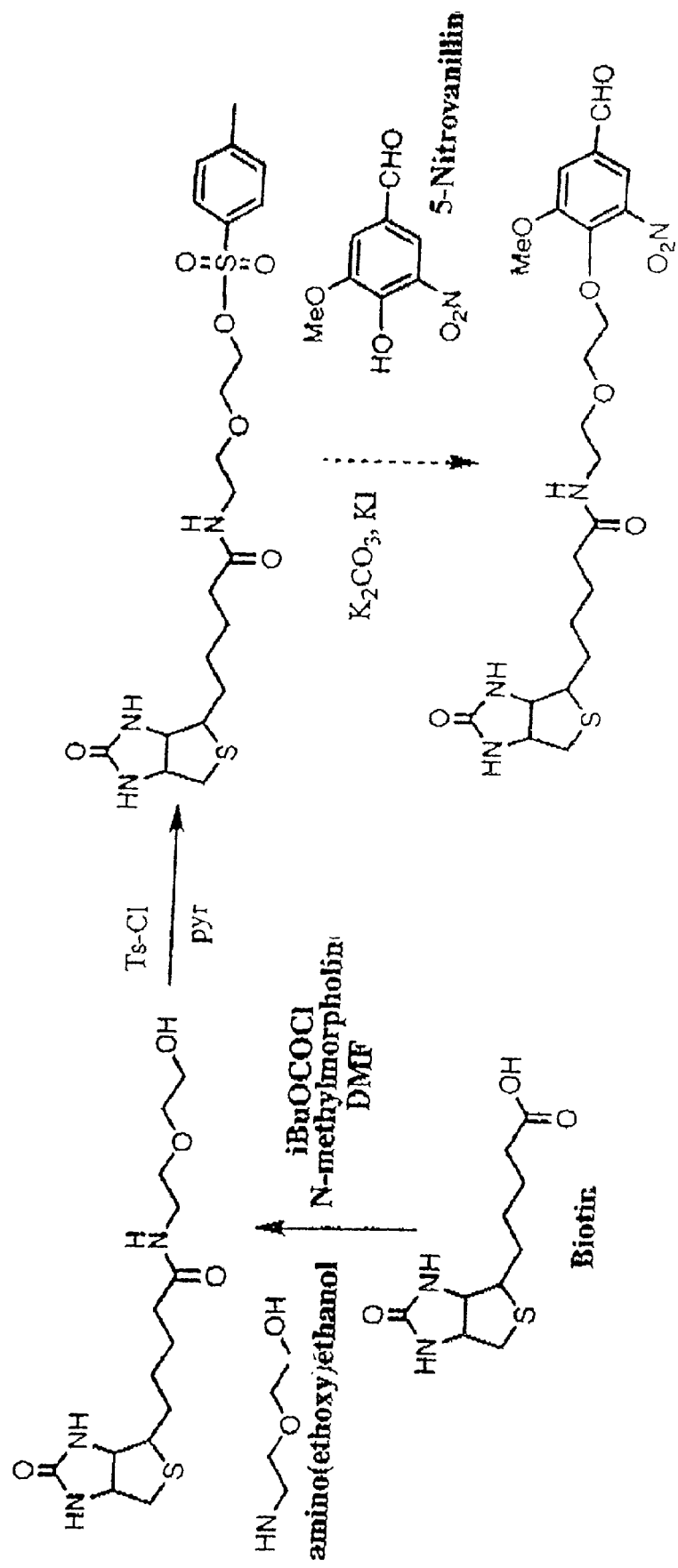
FIG. 11 represents a route of synthesis for a reagent according to formula (4') using the commercial reagent 5-Nitrovanillin. The aldehyde functional group makes it possible to obtain the diazomethyl functional group by formation of hydrazone and then oxidation of hydrazone with $MnO_2$.

The results are presented in FIG. 10 with, on the y-axis, the percentage labeling and, on the x-axis, the reaction temperature in ° C.

It is very important to note that even at room temperature (25° C.), a labeling of the ODN is observed. After 10 min of incubation at 25° C., the labeling yield is about 25%. At temperatures greater than 50° C., yields greater than 80% can be obtained.

This shows the efficiency and the flexibility of this chemistry of labeling of DNA with reagents carrying a diazomethyl functional group.

EXAMPLE 20

Labeling and Fragmentation of the DNA Amplicons Obtained by PCR Amplification with the Labeling Reagent meta-bioPMDAM (3a)

The meta-bioPMDAM derivative (3a) was obtained according to the reaction scheme described in Example 1.1.

The DNA amplicons were prepared by PCR amplification according to the protocol described in Example 5.1.

Example 20.1

Comparison of the Labeling with and without Fragmentation a. Labeling Under Fragmentation Conditions:

To 10 μl of PCR there are added 50 μl of sodium formate pH 3 (50 mM) and 2 μl of meta-BioPMDAM (100 mM in DMSO). The volume is adjusted to 100 μl. The solution is incubated for 30 min at 60° C.

b. Labeling Without Fragmentation:

To 10 μl of PCR there are added 2 μl of meta-BioPMDAM (100 mM in DMSO). The volume is adjusted to 100 μl. The solution is incubated for 30 min at 60° C.

The rest of the protocol is identical to that of Example 17.

Results

TABLE 15

Comparison of the labeling with and without fragmentation

| Protocol used | Homology (%) | I (rfu) | B (rfu) | I/B |
|---|---|---|---|---|
| a. Labeling under fragmentation conditions | >95 | 3995 | 569 | 7.0 |
| b. Labeling without fragmentation | 94.1 | 500 | 542 | 0.9 |

The results in Table 15 above show that, without fragmentation, the mean of the intensities obtained is at the same level as the background noise (500 rfu). The labeling during fragmentation gives a much higher intensity level (about 4 000 rfu) and a very good percentage homology. The combination of the two steps therefore indeed represents a significant improvement for the detection of a nucleic acid more than one hundred (100) nucleotides long.

Example 20.2

Effect of Denaturation Before Hybridization onto a DNA Chip

Two labeling reactions were carried out in parallel in two separate tubes according to the following protocol: to 10 μl of PCR there are added 50 μl of sodium formate buffer pH 3 (50 mM) and 2 μl of meta-bioPMDAM (100 mM in DMSO). The total volume is adjusted to 100 μl and incubated for 30 min at 60° C.

After purification on a column (Example 17), the solution resulting from the first tube is incubated for 10 min at 95° C. (in order to unpair the DNA double strand), and then the tube is immersed in a water-ice mixture at 0° C. until hybridization onto the DNA chip.

The solution resulting from the second tube is hybridized onto the DNA chip without prior denaturation.

The biotinylated fragments hybridized to the capture probes at the surface of the DNA chip are revealed by introducing a streptavidin labeled with phycoerythrin using the conditions described in Example 17.

Results

TABLE 16

Effect of denaturation before hybridization onto a DNA chip

| Conditions used | Homology (%) | I (rfu) | B (rfu) | I/B |
|---|---|---|---|---|
| With denaturation | >95 | 22812 | 570 | 40.1 |
| Without denaturation | 93.5 | 4795 | 681 | 7.0 |

The results obtained, presented in Table 16, with the prehybridization denaturation are higher than those obtained without the denaturation step. This shows that the denaturation of the DNA is necessary in order to obtain a good intensity level. Fragmentation via the abasic sites is a means for facilitating the denaturation of a double-stranded DNA and for strengthening the hybridization to the capture probes.

To test other labeling reagents and taking into account the results obtained with the various conditions above, we defined a reference protocol using fragmentation with sodium formate buffer (50 mM, pH 3) and a prehybridization denaturation step.

EXAMPLE 21

Labeling and Fragmentation of the PCR Amplicons with the Biotinylated Reagents in a One-step Protocol The meta-, ortho- and para-bioPMDAM derivatives were prepared according to the protocol described in Examples 1.1, 1.2 and 1.3. They were solubilized in anhydrous DMSO at a concentration of 100 mM.

The protocol is identical to that of Example 20.2 above (labeling and fragmentation in a single step followed by a prehybridization denaturation step).

Results

TABLE 17

Labeling and fragmentation of the PCR amplicons with the biotinylated reagents in a one-step protocol

| Marker | Homology (%) | I (rfu) | B (rfu) | I/B |
| --- | --- | --- | --- | --- |
| ortho-bioPMDAM | >95 | 25951 | 820 | 31.6 |
| meta-bioPMDAM | >95 | 22960 | 581 | 39.5 |
| para-bioPMDAM | 94.1 | 43785 | 1205 | 36.3 |

The optimized protocol with fragmentation and labeling in a single step gives excellent results with various labeling reagents containing the reactive diazomethyl functional group, as the results presented in Table 17 show.

EXAMPLE 22

Labeling and Fragmentation of DNA with BioDPDAM

The DNA amplicons were prepared by PCR amplification according to the protocol described in Example 5.1.

The synthesis of the labeling reagent is described in Example 1.

The protocol is identical to that of Example 20.2 including the denaturation at 95° C. before the hybridization step.

Results

TABLE 18

Labeling and fragmentation of DNA with BioDPDAM

| Marker used | Homology (%) | I (rfu) | B (rfu) | I/B |
| --- | --- | --- | --- | --- |
| BioDPDAM | 93.0 | 32359 | 3610 | 9.1 |

This result, described in Table 18, shows that substitutions as important as the phenyl group may be used to optimize the reactivity of the labeling reagents carrying a diazomethyl functional group.

EXAMPLE 23

Labeling and Fragmentation of DNA with 5-(bromomethyl)fluorescein

The DNA amplicons were prepared by PCR amplification according to the protocol described in Example 5.1.

To 10 µl of PCR there are added 50 µl of sodium formate pH 3 (100 mM) and 2 µl of 5-(bromomethyl)fluorescein (Molecular probes, Eugen, Oreg.) (100 mM in DMSO). The volume is adjusted to 100 µl. The solution is incubated for 30 min at 60° C.

The purification conditions are in accordance with those of Example 17. A denaturation step is carried out as described in Example 20.2.

The other conditions for hybridization and reading are identical to those described in the article by A. Troesch et al., J. Clin. Microbiol., 37(1), p. 49-55, 1999. The fluorescein is directly detectable on the reader.

TABLE 19

Labeling and fragmentation of DNA with 5-(bromomethyl) fluorescein

| Protocol used | Homology (%) | I (rfu) | B (rfu) | I/B |
| --- | --- | --- | --- | --- |
| Labeling and fragmentation of the PCR amplicons with 5-(bromomethyl) fluorescein | >95 | 855 | 183 | 4.7 |

This result in Table 19 shows that the fragmentation of DNA by the creation of abasic sites is completely compatible with a labeling reagent carrying a reactive alkyl halide functional group. This protocol is carried out in one step (fragmentation and labeling), but with lower intensities than with the markers carrying the diazomethyl functional group.

EXAMPLE 24

Labeling and Fragmentation of the DNA Amplicons in the Presence of Another Chemical Fragmentation Agent Derived from Phenanthroline DNA amplicons were prepared by PCR amplification according to the protocol described in Example 5.1. Two types of conditions are used:

Conditions a:

To 10 µl of PCR there are added 20 µl of phenanthroline-$FeSO_4$ and 2 µl of meta-BioPMDAM (100 mM in DMSO). The total volume is adjusted to 100 µl. The mixture is incubated for 60 min at 95° C.

Conditions b:

To 10 µl of PCR there are added 50 µl of sodium formate buffer pH 3 (100 mM in pure water) and 2 µl of meta-BioPMDAM (100 mM in DMSO). The total volume is adjusted to 100 µl. The mixture is incubated for 60 min at 95° C.

The other conditions for the protocol are identical to those of Example 17.

TABLE 20

Labeling and fragmentation of the DNA
amplicons in the presence of phenanthroline

| Conditions | Homology (%) | I (rfu) | B (rfu) | I/B |
|---|---|---|---|---|
| Phenanthroline FeSO$_4$ (5 mM) meta-bioPMDAM (2 mM) 60 min at 95° C. | >95 | 2236 | 500 | 4.5 |
| Formate buffer (50 mM) pH 3 meta-bioPMDAM (2 mM) 60 min at 95° C. | >95 | 6786 | 565 | 12.0 |

The two fragmentation conditions allow a satisfactory result as shown in Table 20.

The best result is obtained with conditions (b) using the fragmentation at acid pH.

EXAMPLE 25

Fragmentation of the PCR Amplicons Labeled by Incorporation of d-UTP-fluorescein Incorporation of the Labeled Nucleotide A PCR amplification was carried out according to the following protocol in order to generate PCR amplicons labeled with fluorescein (labeling on the bases).

Starting with 16S *Mycobacterium tuberculosis* genomic DNA target ($10^{+4}$ copies) using the Fast Start kit from Roche, 0.2 mM of the deoxyribonucleotides d-ATP, d-CTP and d-GTP as well as 0.14 mM d-TTP and 0.06 mM d-UTP-12-fluorescein, 0.3 μM of primers and 0.4 μl of enzyme. The percentage of labeled nucleotide relative to its natural homolog d-UTP is 30%. It is this ratio which is generally used in the reactions for labeling amplicons by incorporation of labeled nucleotides.

The d-UTP-12-fluorescein is commercially available from Roche Diagnostics reference 1373242, Mannheim, Germany).

The parameters for the PCR are those of Example 5.1.

a. Fragmentation of the PCR Amplicons Labeled at 30% with d-UTP-fluorescein:

To 10 μl of PCR there are added 50 μl of sodium formate buffer pH 3 (50 mM). The volume is adjusted to 100 μl. The solution is then incubated for 30 min at 60° C.

b. Labeling During the Fragmentation of the PCR Amplicons Containing 30% with d-UTP-fluorescein:

To 10 μl of PCR there are added 50 μl of sodium formate buffer pH 3 (50 mM) and 2 μl of meta-BioPMDAM (100 mM in DMSO). The volume is adjusted to 100 μl. The solution is then incubated for 30 min at 60° C. This trial corresponds to a reference protocol which makes it possible to compare the various labeling strategies by dispensing with the variability due to the amplification step.

A purification step on a column and a denaturation step at 95° C. are carried out in all cases as in Example 17.

Protocol (a1):

The nucleic acids obtained by fragmentation of the amplicons labeled with d-UTP-fluorescein (conditions a) are hybridized onto a DNA chip and detected in a first instance by direct reading of the fluorescent signals emitted by the fluorescein as described in Example 23.

Protocol (a2):

A signal amplification step was used to improve the labeling sensitivity. The amplification of the signal was carried out by introducing, during the hybridization step, a biotinylated anti-fluorescein antibody (reference 216-065-084, Jackson ImmunoResearch) and then a streptavidin labeled with phycoerythrin using the following successive conditions:

300 μl of pure water,
300 μl of 100 mM Tris buffer pH 7/1M NaCl/0.05% Tween/0.005% Antifoam; 2.4 μl of BSA (50 mg/ml), 1.2 μl of biotinylated anti-fluorescein antibody (1 mg/ml),
300 μl of pure water, and
300 μl of 100 mM Tris buffer pH 7/1M NaCl/0.05% Tween/0.005% Antifoam; 6 μl of BSA (50 mg/ml); 6 μl of streptavidin-PE (300 μg/ml).

In this protocol, the fluorescein acts as a hapten (tracer indirectly detectable with a labeled antibody) and not as a fluorophore.

Protocol (b)

The biotinylated fragments (condition b) hybridized onto a DNA chip are revealed by introducing a streptavidin labeled with phycoerythrin using the following conditions:

300 μl of pure water, and
300 μl of 100 mM Tris buffer pH 7/1M NaCl/0.05% Tween/0.005% Antifoam; 6 μl of BSA (50 mg/ml); 6 μl of labeled streptavidin (300 μg/ml).

The reading of the fluorescence emitted at the surface of the DNA chip after labeling and hybridization as well as the generation of data in terms of signal intensity and the percentage homology are carried out by the reading systems and the software provided by Affymetrix. In this respect it is important to note that the reading system used contains two filters which make it possible to directly detect:

the fluorescein in the case in which the amplicons are labeled with d-UTP-fluorescein only, according to protocol a1, or alternatively phycoerythrin in the case in which the amplicons are labeled:
with d-UTP-fluorescein with amplification of the signal, according to protocol a2, or
with meta-bioPMDAM during their fragmentation, according to protocol b.

In the two cases in which visualization is carried out by phycoerythrin, the use of a filter makes it possible to dispense with the signal generated by fluorescein and it is indeed the phycoerythrin signal which is detected.

Results

TABLE 21

Fragmentation of the PCR amplicons labeled
by incorporation of d-UTP-fluorescein

| | Protocol used | Marker detected | Homology (%) | I (rfu) | B (rfu) | I/B |
|---|---|---|---|---|---|---|
| a1. | Fragmentation of the PCR amplicons labeled with d-UTP-fluorescein | Flu* | 81.6 | 595 | 342 | 1.7 |
| a2. | Fragmentation of the PCR amplicons labeled with d-UTP-fluorescein with amplification of the signal | PE* | >95 | 22107 | 3461 | 6.4 |

TABLE 21-continued

Fragmentation of the PCR amplicons labeled by incorporation of d-UTP-fluorescein

|   | Protocol used | Marker detected | Homology (%) | I (rfu) | B (rfu) | I/B |
|---|---|---|---|---|---|---|
| b. | Fragmentation and labeling on the same PCR amplicons modified by d-UTP-fluorescein and labeled by meta-BioPMDAM | PE* | >95 | 21700 | 1503 | 14.4 |

*Flu = Fluorescein and PE = Phycoerythrin

The results, in Table 21 above, show that the chemical fragmentation using the creation of an abasic site is compatible with the enzymatic labeling of the DNA amplicons and that the labeling may take place before the fragmentation.

The intensity levels as well as the percentage homology which are obtained with this protocol for enzymatic incorporation of the fluorophore are low compared with those obtained with the labeling during fragmentation using the labeling reagent with a diazomethyl functional group such as meta-bioPMDAM (conditions (b)).

To reach the intensity level obtained with the meta-bioPMDAM derivative, a step for amplification of the signal is necessary (conditions a2). This indeed shows the efficiency of the diazomethyl reactive functional group relative to the traditional incorporation of modified base such as d-UTP fluorescein (reference protocol (b)).

EXAMPLE 26

Fragmentation of Double-stranded DNA by Sonication

DNA amplicons were obtained using the protocol described in Example 5.1. These amplicons were fragmented by sonication in the presence and in the absence of the marker.

a. Labeling of the PCR Amplicons During Sonication:

To 10 µl of PCR reaction there are added 2 µl of meta-BioPMDAM (100 mM in DMSO). The volume is adjusted to 100 µl with pure water and then the pH is adjusted to 6.5. The mixture is incubated for 30 min at 60° C. in a bath of an ultrasound vessel (frequency 35 kHz, model T460-H, Bioblock, France).

b. Labeling During Chemical Fragmentation of the PCR Amplicons (Single-step Reference Protocol):

To 10 µl of PCR there are added 50 µl of sodium formate pH 3 (50 mM) and 2 µl of meta-BioPMDAM (100 mM in DMSO). The volume is adjusted to 100 µl. The solution is incubated for 30 min at 60° C.

The trials are carried out in duplicate so as to be able to analyze the fragmentation of the DNA on a gel and the efficiency of labeling by hybridization and reading of the DNA chip as described above (Example 17 regarding phycoerythrin detection).

Analysis on a Gel

The analysis was carried out on a denaturing polyacrylamide gel (8% polyacrylamide, 7 M urea, 1×TBE) using ethidium bromide staining.

Gel analysis shows that the DNA amplicons are fragmented by sonication at 60° C.

Results

TABLE 22

Fragmentation of double-stranded DNA by sonication

| Conditions | Homology (%) | I (rfu) | B (rfu) | I/B |
|---|---|---|---|---|
| a. Labeling during fragmentation by sonication | 93.8 | 2271 | 631 | 3.6 |
| b. Labeling during chemical fragmentation (reference conditions) | >95 | 19639 | 1459 | 13.5 |

The results in Table 10 of labeling during sonication (conditions a) are satisfactory. This shows that physical fragmentation by sonication of the DNA targets is compatible with the chemistry of labeling with labeling reagents carrying a diazomethyl functional group.

The weak labeling results in this case are certainly due to the fact that the marker becomes degraded under the effect of the ultrasound. The results with fragmentation by creation of an abasic site by the action of acidic pH are better.

EXAMPLE 27

Labeling, Fragmentation and Denaturation of DNA in a Single Step

The DNA amplicons were prepared by PCR amplification according to the protocol described in Example 5.1.

Two labeling reactions were carried out:

a. Labeling, Fragmentation and Denaturation at 95° C. in a Single Step:

To 10 µl of PCR there are added 50 µl of sodium formate buffer pH 3 (50 mM) and 2 µl of meta-bioPMDAM marker (100 mM in anhydrous DMSO). The final volume is adjusted to 100 µl. The solution is then incubated for 30 min at 95° C. In this case, the reaction mixture was hybridized onto a DNA chip without any prior purification.

b. Labeling and Fragmentation at 60° C.:

To 10 µl of PCR there are added 50 µof sodium formate buffer pH 3 (50 mM) and 2 µl of meta-Bio-DPDAM marker (3d) (100 mM in anhydrous DMSO). The final volume is adjusted to 100 µl. The solution is then incubated for 30 min at 60° C. The reaction mixture was then purified according to the protocol described previously. In this protocol and before hybridization onto a DNA chip, the fragments were denatured according to the protocol described in Example 20.2.

Results

TABLE 23

Labeling, fragmentation and denaturation of DNA in a single step

| Protocol used | Homology (%) | I (rfu) | B (rfu) | I/B |
|---|---|---|---|---|
| a. Labeling, fragmentation and denaturation at 95° C. | >95 | 5426 | 506 | 10.7 |

TABLE 23-continued

Labeling, fragmentation and denaturation of DNA in a single step

| Protocol used | Homology (%) | I (rfu) | B (rfu) | I/B |
|---|---|---|---|---|
| b. Labeling and fragmentation at 60° C. followed by denaturation at 95° C. | >95 | 7015 | 818 | 6.8 |

Example 20.2 demonstrated the importance of the denaturation of the double-stranded DNA for detection sensitivity. These results in Table 23 show that with the fragmentation approach by creation of an abasic site, the labeling, fragmentation and denaturation of DNA can be carried out in a single step, which represents a notable improvement from the point of view of simplicity and time for the user, without affecting detection sensitivity.

EXAMPLE 28

Synthesis of para-Bio-EG3-PDAM

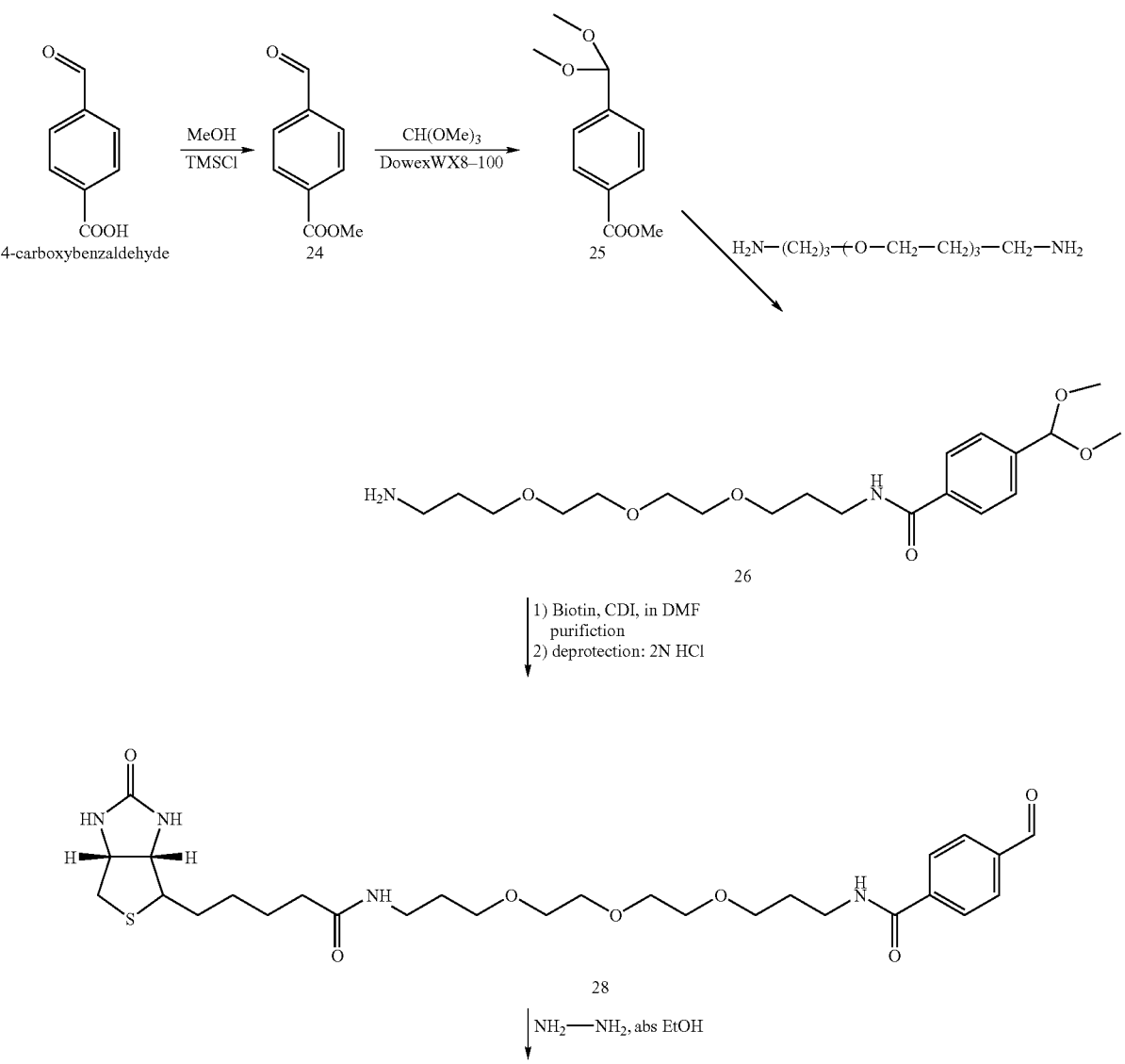

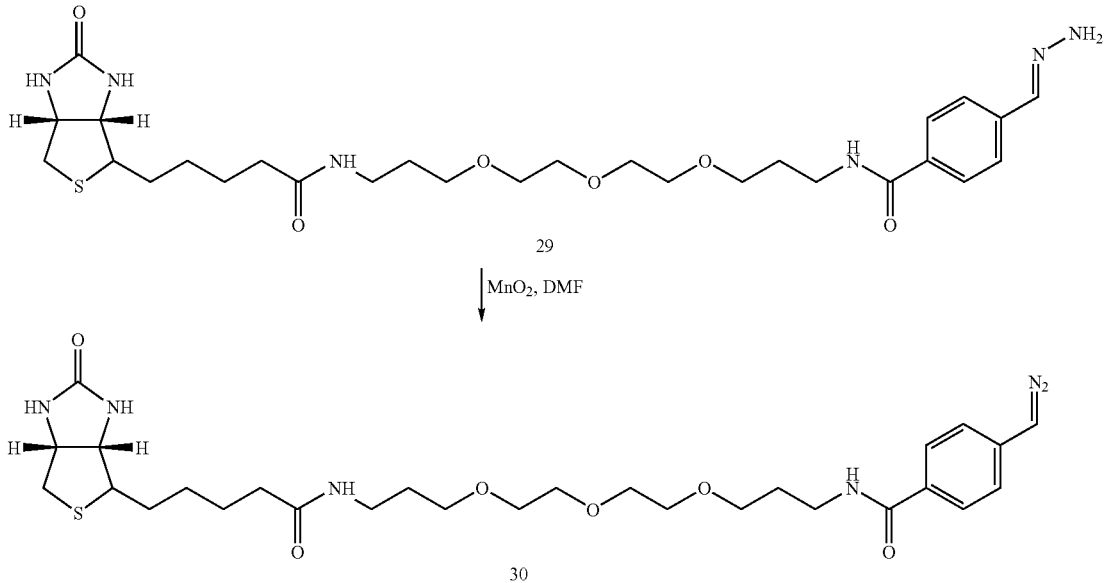

Protection of 4-carboxylbenzaldhyde:

The 4-carboxybenzaldehyde is of commercial origin. It is dissolved (3 g; 20 mmol) in a trimethylsilyl chloride solution (10 g; 92 mmol) in 100 ml of MeOH. The mixture is kept stirred for 40 h at room temperature. After evaporation, a white solid corresponding to 4-methoxycarbonylbenzaldehyde 24 is isolated, characterized by NMR and used as it is for the next reaction.

$^1$H NMR (200 MHz, CDCl$_3$) δ=10.07 (s, 1H, —CHO); 8.17 (d, 2H, J=8 Hz, Ar—H$_{2,6}$); 7.92 (d, 2H, J=8 Hz, Ar—H$_{3,5}$); 3.93 (s, 3H, CO—O—CH$_3$).

Protection of 4'-methoxycarbonylbenzaldehyde:

The 4-methoxycarbonylbenzaldehyde (3.35 g; 20 mmol) is dissolved with trimethyl orthoformate (4.8 g; 40 mmol) in the presence of Dowex 50WX8-100 (1 g). The mixture is heated under reflux for 2 h, and then filtered and evaporated. After a recrystallization trial, NMR analysis shows that the reaction is not complete and the latter is restarted in 30 ml of MeOH, 30 ml of CH(OMe)$_3$ and 1 g of Dowex 50WX8-100 at room temperature. Filtration and then evaporation are carried out so as to obtain 3.55 g (16.89 mmol, 84%) of product 25.

$^1$H NMR (200 MHz, CDCl$_3$) δ=8.01 (d, 2H, J=8 Hz, Ar—H$_{2,6}$); 7.50 (d, 2H, J=8 Hz, Ar—H$_{3,5}$); 5.41 (s, 1H, CH); 3.93 (s, 3H, —CO—O—CH$_3$); 3.29 (s, 6H, —O—CH$_3$).

Compound 26:

Compound 25 (3.1 g; 14.8 mmol) is solubilized in 16 ml (73 mmol) of 4,7,10-trioxa-1,13-tridecanediamine. The solution obtained is heated at 140-150° C. for 2 h. The mixture is then dissolved in 100 ml of DCM (dichloromethane or CH$_2$Cl$_2$) and washed 6 times with 10 ml of water. The organic phase is dried over MgSO$_4$ and then evaporated until an oil is obtained. This oil is washed with pentane 3 times in succession by decantation, and then a new extraction with DCM and H$_2$O is carried out. After drying over MgSO$_4$ and evaporation, product 26 is isolated with a yield of 63% (9.27 mmol).

$^1$H NMR (200 MHz, CDCl$_3$) δ=7.78 (d, 2H, J=8 Hz, Ar—H$_{2,6}$); 7.46 (d, 2H, J=8 Hz, Ar—H$_{3,5}$); 5.39 (s, 1H, CH); 3.62-3.47 (m, 14H, H$_{7',8',10',11'}$ and H$_{5',13'}$ and H$_{3'}$); 3.29 (s, 6H, —O—CH$_3$); 2.72 (m, 2H, H$_{15'}$) 1.87 (m, 2H, H$_{4'}$); 1.64 (m, 2H, H$_{14'}$); 1.30 (broad s, 2H, NH$_2$).

Biotinylated Compound 27:

Biotin (500 mg; 2.05 mmol) is suspended in 10 ml of DMF then 365 mg (2.25 mmol) of CDI are added. This solution is kept stirred for 30 min at room temperature. Compound 26 (900 mg; 2.26 mmol) is dissolved in 1 ml of DMF, and then added little by little to the preceding solution. The mixture thus obtained is kept stirred for 1 h at room temperature. After evaporation, purification by flash chromatography on a column (column 20 mm in diameter) is carried out with 250 ml of MeOH-DCM 6%, and then with 200 ml of MeOH-DCM 7% and finally 200 ml of MeOH-DCM 8%. The fractions corresponding to product 27 are combined and then evaporated to dryness to give 1.00 g of oil with a yield estimated at 50%.

$^1$H NMR (200 MHz, CDCl$_3$) δ=9.50 (broad s, 1H, NH$_{imidazole}$); 7.80 (d, 2H, J=8 Hz, Ar—H$_{2,6}$); 7.64 (s, 1H, H$_{imidazole}$); 7.46 (d, 2H, J=8 Hz, Ar—H$_{3,5}$ and 1H, NH$_{2'}$); 7-05 (s, 2H, H$_{imidazole}$); 6.76 (t, 1H, NH$_{16'}$), 6.20 (broad s, 1H, NH$_{B1}$); 5.44 (broad s, 1H, NH$_{B3}$); 5.37 (s, 1H, CH); 4.42 (m, 1H, H$_{B6a}$); 4.24 (m, 1H, H$_{B3a}$); 3.59-3.44 (m, 14H, H$_{7',8',10',11'}$ and H$_{5',13'}$ and H$_{3'}$); 3.29 (m, 8H, H$_{15'}$ and 2-O—CH$_3$); 3.07 (m, 1H, H$_{B4}$); 2.84 and 2.66 (system ABX, 2H, $^2J_{AB}$=5 Hz, $^3J_{AX}$=12 Hz, $^3J_{BX}$=0 Hz, H$_{B6}$); 2.13 (t, 2H, J=8 Hz, H$_{B10}$); 1.85 (m, 2H, H$_{4'}$); 1.66 (m, 2H, H$_{14'}$); 1.40-1.37 (m, 6H, H$_{B7, B8, B9}$).

Aldehyde Compound 28:

The acetal 27 is dissolved in 50 ml of chloroform, and then 20 ml of 2N HCl are added. The two-phase mixture is vigorously stirred for 15 min. The organic phase is recovered and dried over anhydrous NaHCO$_3$. It is filtered, evaporated and compound 28 is obtained in the form of a paste (495 mg; 0.855 mmol) with an overall yield of 42% from biotin.

$^1$H NMR (300 MHz, CDCl$_3$) δ=10.05 (s, 1H, CHO); 7.98 (d, 2H, J=8 Hz, Ar—H$_{2,6}$); 7.92 (d, 2H, J=8 Hz, Ar—H$_{3,5}$); 7.58 (t, 1H, NH$_{2'}$); 6.46 (t, 1H, NH$_{16'}$), 6.02 (broad s, 1H, NH$_{B1}$); 5.19 (broad s, 1H, NH$_{B3}$); 4.46 (m, 1H, H$_{B6a}$); 4.27 (m, 1H, H$_{B3a}$); 3.66-3.56 (m, 10H, H$_{7',8',10',11'}$ and H$_{5'}$); 3.50-3.29 (m, 4H, H$_{3',13'}$); 3.28 (m, 2H, H$_{15'}$); 2.95 (m, 1H, H$_{B4}$); 2.84 and 2.71 (system ABX, 2H, $^2J_{AB}$=5 Hz, $^3J_{AX}$=12 Hz, $^3J_{BX}$=0 Hz, H$_{B6}$); 2.15 (t, 2H, J=8 Hz, H$_{B10}$); 1.89 (m, 2H, H$_{4'}$); 1.72-1.63 (m, 6H, H$_{14'}$, H$_{B7, B9}$); 1.23 (m, 2H, H$_{B8}$).

Hydrazone Compound 29:

The aldehyde 28 (495 mg; 0.855 mmol) is dissolved in 10 ml of absolute ethanol. Hydrazine (350 μl; 7.20 mmol) is added, and then the reaction mixture is heated under reflux for 1 h. The oil obtained after evaporation is dissolved in abs. EtOH, in order to be evaporated again. A foam is then obtained which is triturated with pentane. The paste corresponding to product 29 (511 mg; 0.862 mmol) is obtained with a yield of 100%.

$^1$H NMR (300 MHz, CDCl$_3$) δ=7.76 (d, 2H, J=8 Hz, Ar—H$_{2,6}$); 7.72 (s, 1H, CH); 7.56 (d, 2H, J=8 Hz, Ar—H$_{3,5}$); 7.34 (t, 1H, NH$_{2'}$); 6.45 (t, 1H, NH$_{16'}$), 5.98 (broad s, 1H, NH$_{B1}$); 5.78 (broad s, 2H, NH$_2$); 5.18 (broad s, 1H, NH$_{B3}$); 4.44 (m, 1H, H$_{B6a}$); 4.26 (m, 1H, H$_{B3a}$); 3.62-3.56 (m, 10H, H$_{7',8',10',11'}$ and H$_{5'}$); 3.48-3.45 (m, 4H, H$_{3',13'}$); 3.27 (m, 2H, H$_{15'}$); 3.07 (m, 1H, H$_{B4}$); 2.84 and 2.68 (system ABX, 2H, $^2J_{AB}$=5 Hz, $^3J_{AX}$=12 Hz, $^3J_{BX}$=0 Hz, H$_{B6}$); 2.11 (t, 2H, J=8 Hz, H$_{B10}$); 1.86 (m, 2H, H$_{4'}$); 1.72-1.59 (m, 6H, H$_{14'}$, H$_{B7, B9}$); 1.21 (m, 2H, H$_{B8}$).

Diazo Compound 30:

The hydrazone 29 (357 mg; 0.602 mmol) is solubilized in 17.5 ml of DMF. MnO$_2$ (700 mg; 7.7 mmol) is then added. After stirring for 12 min at room temperature, the mixture is filtered on millipore containing celite (thickness: 2 cm) and 3 Å (0.5 cm) powdered molecular sieve. The reaction mixture is evaporated to dryness. The residual oil obtained is washed with ether three times in succession. Compound 30 (290 mg, 0.491 mmol) is obtained in the form of a slightly pink solid with a yield of 82%.

$^1$H NMR (300 MHz, DMSO-d$_6$) δ=8.28 (t, 1H, NH$_{2'}$); 7.77 (d, 2H, J=8 Hz, Ar—H$_{2,6}$); 7.74 (t, 1H, NH$_{16'}$); 7.00 (d, 2H, J=8 Hz, Ar—H$_{3,5}$); 6.38 (broad s, 1H, NH$_{B1}$); 6.32 (broad s, 1H, NH$_{B3}$); 5.80 (s, 1H, CH—N$_2$); 4.27 (m, 1H, H$_{B6a}$); 4.11 (m, 1H, H$_{B3a}$); 3.51-3.44 (m, 10H, H$_{7',8',10',11'}$ and H$_{5'}$); 3.37 (m, 2H, H$_{15'}$); 3.32 (m, 4H, H$_{3',13'}$); 3.05 (m, 1H, H$_{B4}$); 2.79 and 2.58 (system ABX, 2H, $^2J_{AB}$=5 Hz, $^3J_{AX}$=12 Hz, $^3J_{BX}$=0 Hz, H$_{B6}$); 2.02 (t, 2H, J=8 Hz, H$_{B10}$); 1.69 (m, 2H, H$_{4'}$); 1.59-1.48 (m, 6H, H$_{14'}$, H$_{B7, B9}$); 1.25 (m, 2H, H$_{B8}$).

The reactivity of compound 30 was tested on uridine 3'-monophosphate and monitored by capillary electrophoresis. The analytical conditions are those of Example 6.1. The results show a half-life period of 45 minutes.

The reagent is stable at −20° C. for at least 1 month.

EXAMPLE 29

Labeling and Fragmentation of DNA Amplicons with the Labeling Reagent para-Bio-EG3-PDAM The main advantages of this type of molecules, that is to say of PDAM derivatives carrying a polyethylene glycol-based linking arm, are to allow the diazo functional group and the biotin to be kept apart, and to increase the solubility and, in the final analysis, the reactivity of these molecules.

The para-Bio-EG3-PDAM derivative 30 was obtained according to the reaction scheme described in Example 28. The DNA amplicons were prepared by PCR amplification according to the protocol described in Example 5.1. Two labeling reactions were carried out.

a. Labeling with the para-Bio-EG3-PDAM Reagent:

To 10 μl of PCR there are added 10 μl of para-Bio-EG3-PDAM (100 mM in DMSO) and 77 μl of DNase/RNase-free water. The solution is homogeneous and has no precipitates. This solution is incubated for 10 min at 95° C., and then 3 μl of 0.1M HCl are added and the solution is incubated for 10 min at 95° C.

The remainder of the protocol is identical to that of Example 8.

b. Labeling with the meta-BioPMDAM Reagent:

To 10 μl of PCR there are added 10 μl of meta-BioPM-DAM (100 mM in DMSO) and 77 μl of DNase/RNase-free water. The synthesis of this product is mentioned in Example 11. The solution has a slight precipitate. This solution is incubated for 10 min at 95° C. 3 μl of 0.1M HCl are then added and the solution is incubated for 10 min at 95° C.

The remainder of the protocol is identical to that of Example 8.

Results:

TABLE 24

Comparative study of the labeling and fragmentation of DNA amplicons with para-Bio-EG3-PDAM and meta-BioPMDAM

| Protocol used | Homology (%) | I (rfu) | B (rfu) | I/B |
|---|---|---|---|---|
| a. Labeling with the para-Bio-EG3-PDAM reagent | >95% | 15151 | 621 | 24.4 |
| b. Labeling with the meta-BioPMDAM reagent | >95% | 11226 | 515 | 21.8 |

The signal intensities obtained in this Table 24 are very satisfactory and the percentage homology is high. This result shows that the introduction of a polyethylene glycol arm onto the diazo labeling molecule makes it possible to increase the aqueous phase solubility of the reagent. The test is therefore homogeneous. Furthermore, the increase in solubility makes it possible to increase the reactivity of the marker.

EXAMPLE 30
Synthesis of Other PDAM Derivatives Comprising a Polyethylene Glycol-based Linking Arm
Example 30.1
Synthesis of meta-Bio-EG3-PMDAM
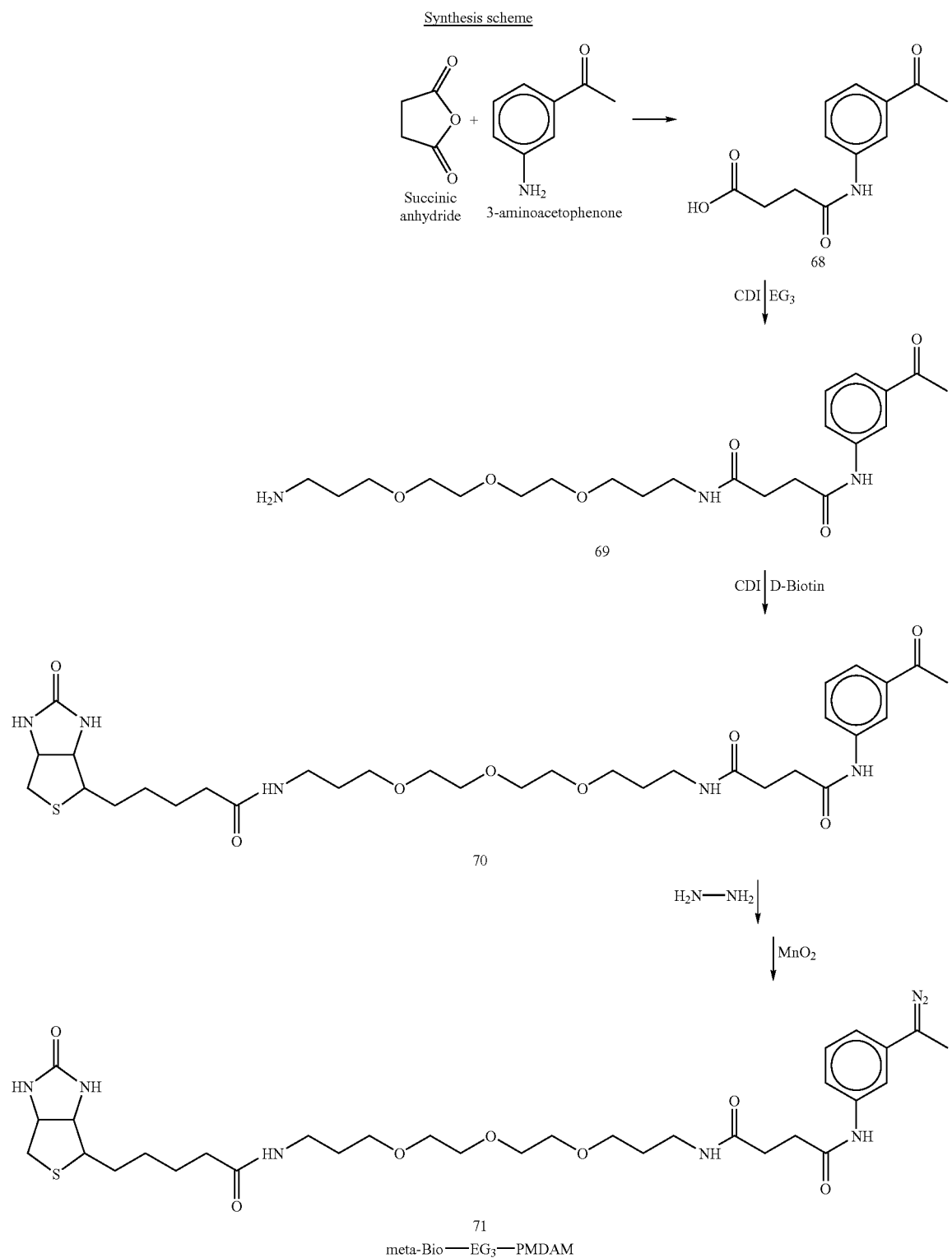
meta-Bio—EG3—PMDAM Compound 68:

3-Aminoacetophenone (14.5 g, 107 mmol) is solubilized in 50 ml of anhydrous DMF. Succinic anhydride (10.7 g, 107 mmol) is added and the mixture is kept stirred, under argon and at room temperature. After 6 h, the solution is concentrated under vacuum and 50 ml of methanol are added. The precipitate obtained is filtered and washed with methanol and ether. 19.4 g (81%) of product 68 are thus obtained in the form of a powder which is off-white in color.

$^1$H NMR (200 MHz, DMSO-$d_6$): δ=2.5-2.6 (m, 7H); 7.45 (t, H); 7.64 (d, 1H); 7.83 (d, 1H); 8.19 (s, 1H); 10.16 (s, 1H); 12.12 (s, 1H).

Compound 69:

5.07 g (22 mmol) of compound 68 are solubilized in 10 ml of anhydrous DMF, under argon. The mixture is placed on ice and 5.00 g (32 mmol) of carbonyldiimidazole are added. After 20 min, 20 ml (94.6 mmol) of 4,7,10-trioxatridecanediamine ($EG_3$) are slowly added. After 3 h of reaction at room temperature, the DMF is evaporated and the residue is taken up in 100 ml of $CH_2Cl_2$. Extractions are carried out with saturated $NaHCO_3$ and $H_2O$, after which the organic phase is dried with anhydrous $Na_2SO_4$ and the solvent evaporated. 4.34 g (46%) of product 69 are thus obtained.

$^1$H NMR (200 MHz, DMSO-$d_6$): δ=1.59 (m, 2H); 1.87 (m, 2H); 2.16 (s, 3H); 2.40 (m, 2H); 2.55 (m, 2H); 3.08 (m, 2H); 3.45 (m, 16H); 7.30 (t, 1H); 7.42 (d, 1H); 7.70 (d, 1H); 7.83 (t, 1H); 7.97 (s, 1H); 10.00 (s, 1H).

Biotinylated Compound 70:

D-biotin (1.0 g, 4.1 mmol) is solubilized in 10 ml of anhydrous DMF, under argon. The mixture is cooled on ice and carbonyldiimidazole (CDI) (0.665 g, 4.1 mmol) in 10 ml of anhydrous DMF is added. After 15 min, compound 69 (1.8 g, 4.1 mmol) in 2 ml of anhydrous DMF is added. The reaction is allowed to proceed for 3 h at 35° C., and then the DMF is evaporated and the residue is taken up in 100 ml of $CH_2Cl_2$. Extractions are carried out with saturated $NaHCO_3$ and $H_2O$, after which the organic phase is dried over anhydrous $Na_2SO_4$ and the solvent evaporated. NMR characterization of the product thus obtained shows that a mixture of product 70 and of free $EG_3$ is obtained. Another purification step is carried out before continuing the synthesis.

The final compound, meta-Bio-$EG_3$-PMDAM, is obtained after two synthesis steps according to the scheme described in Example 1.

The advantage of this synthesis is two-fold. On the one hand, product 69 is obtained in only two steps; this product may be used as a precursor of the diazo with the possibility of attaching thereto detectable molecules of a different nature, by means of the terminal amine group. This group also makes it possible to graft compound 69 onto solid supports, with the objective of immobilizing nucleic acids. On the other hand, compound 71 possesses the same reactive center as meta-Bio-PMDAM (our reference molecule), which facilitates the analysis of the advantages linked to the inclusion of the ethylene glycol ($EG_3$) arm.

The reagent is stable at −20° C. for at least 1 month.

Example 30.2

Synthesis of meta-Bio-EG4-PMDAM

Synthesis scheme:

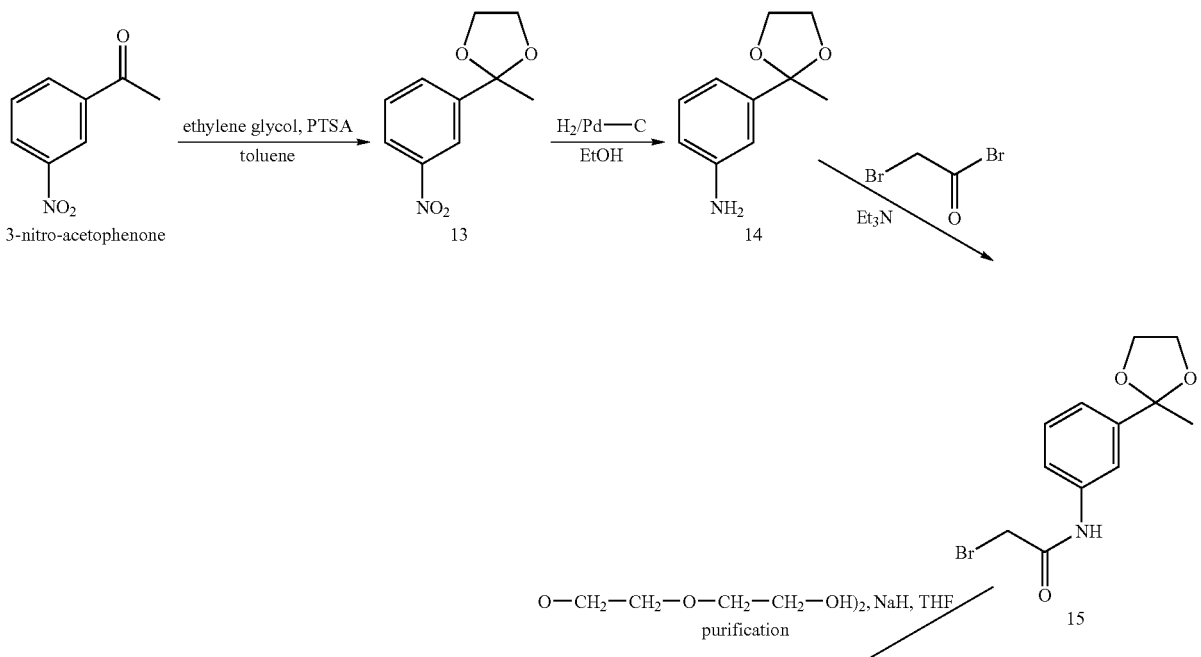

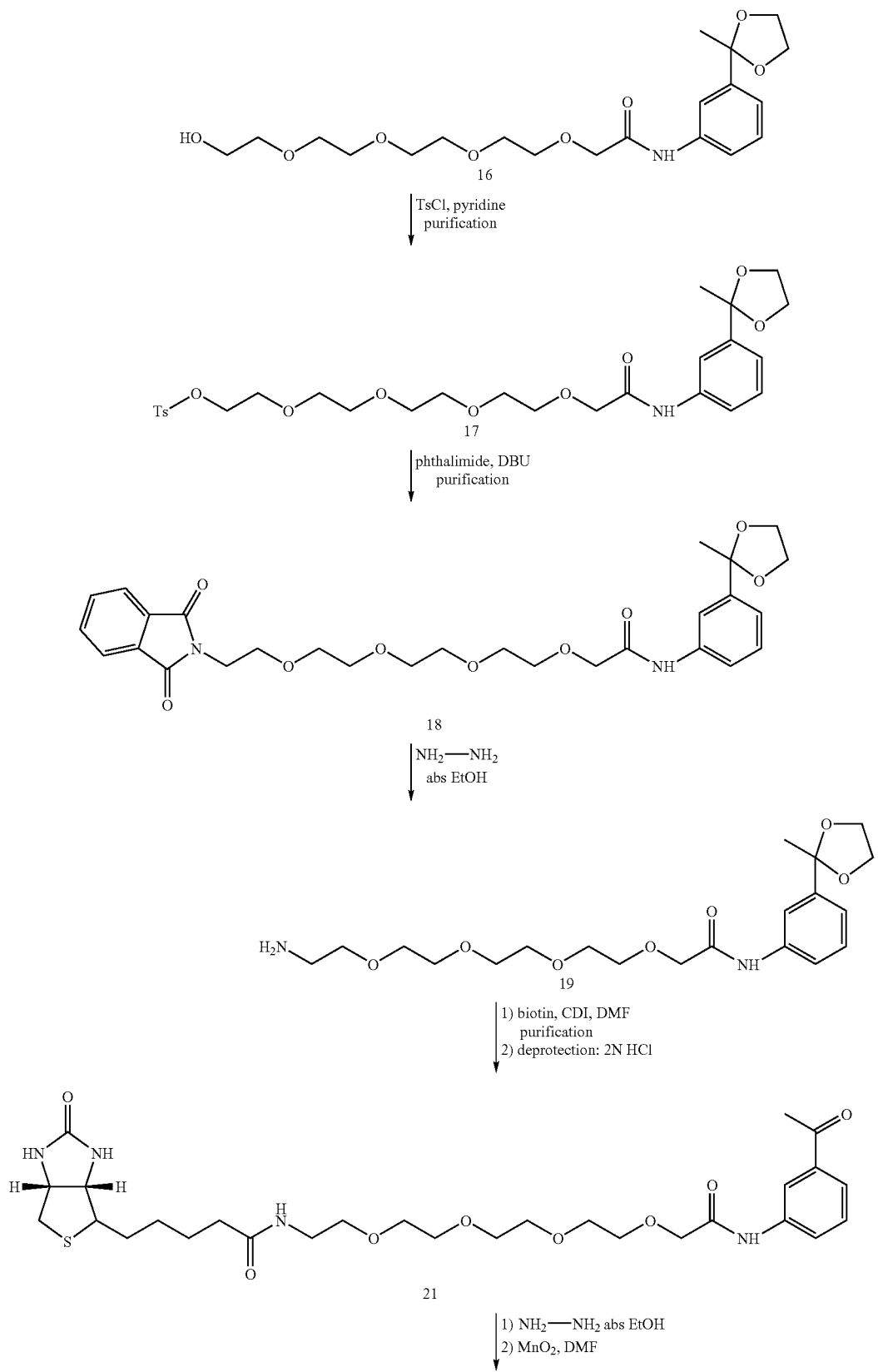

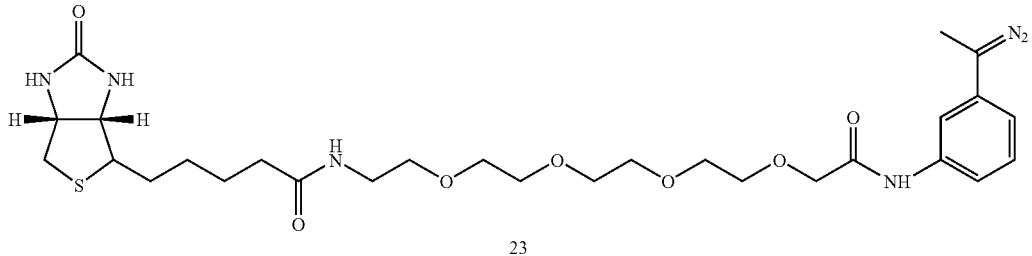

23

Protection of 3-nitroacetophenone 13:

33 g (0.20 mol) of 3-nitroacetophenone are dissolved in 400 ml of toluene, and then 40 ml (0.717 mol) of ethylene glycol and 600 mg (3.15 mmol) of para-toluenesulfonic acid (PTSA) are added. A Dean Stark system is mounted. The solution is heated for 3 h at 130° C. After having allowed the solution to return to room temperature, 400 ml of ethyl acetate are added, and then the solution is washed with 8 ml of a saturated NaHCO$_3$ solution. The organic phase is dried over MgSO$_4$. After evaporation, a pale yellow solid 13 is obtained (39.72 g; 0.190 mol) with a yield of 95%.

$^1$H NMR (200 MHz, CDCl$_3$) δ=7.11 (t, 1H, J=8 Hz, Ar—H); 6.87-6.78 (m, 2H, Ar—H); 6.59 (dd, 1H, J=6.5 Hz, Ar—H); 4.00 (m, 2H, H$_2$C$_{acetal}$); 3.79 (m, 2H, H$_2$C$_{acetal}$); 1.61 (s, 3H, CH$_3$).

Preparation of the Amine 14:

Compound 13 (39.7 g; 0.190 mol) is dissolved in 500 ml of EtOH, and then 1 g of 10% palladium on carbon is added. The mixture is heated in order to dissolve the whole, and then the solution is allowed to return to room temperature. After having created a vacuum and placed the solution under H$_2$, it is kept vigorously stirred for 5 h. The solution is then filtered in the hot state and then evaporated. The product 14 is washed with pentane, and isolated in the form of a solid (34 g; 0.189 mol) with a yield of 99%.

$^1$H NMR (200 MHz, CDCl$_3$) δ=7.14 (t, 1H, J=8 Hz, Ar—H); 6.85 (m, 2H, J=7.5 Hz, Ar—H); 6.79 (s, 1H, Ar—H); 6.59 (dd, 1H, J=6.5 Hz, Ar—H); 4.00 (m, 2H, H$_2$C$_{acetal}$); 3.77 (m, 2H, H$_2$C$_{acetal}$); 1.61 (s, 3H, CH$_3$).

Brominated Compound 15:

The amine 14 (12.3 g; 68.7 mmol) and triethylamine (7 g; 69 mmol) are dissolved in 150 ml of DCM under argon. A solution of 13.8 g (60 mmol) of bromoacetyl bromide dissolved in 150 ml of DCM is added dropwise at −5° C. At the end of the addition, 100 ml of aqueous 1N NaHCO$_3$ are added. The organic phase is washed twice in succession with aqueous NaHCO$_3$ and dried over MgSO$_4$. After evaporation to dryness, 22.6 g of a brown oil are obtained corresponding to compound 15 and used as it is for the next reaction.

$^1$H NMR (200 MHz, CDCl$_3$) δ=8.29 (broad s, 1H, NH); 7.62 (dt, 1H$_4$, J=5 Hz, Ar—H); 7.47 (s, 1H, Ar—H$_2$); 7.38-7.19 (m, 2H, Ar—H$_{5,6}$); 4.00 (m, 2H, Br—CH$_2$); 3.75 (m, 4H, H$_2$C—H$_2$C$_{acetal}$); 1.61 (s, 3H, CH$_3$).

Alcohol Compound 16:

Sodium hydride (3.3 g; 82.5 mmol) is washed three times with pentane and then suspended in 150 ml of THF, tetraethylene glycol (50 ml; 0.29 mol) is then added at room temperature. The reaction is kept stirred for 15 min. and then the solution is cooled to −5° C.

The addition of compound 15, diluted beforehand in 25 ml of THF, is made dropwise. The mixture is kept stirred for 30 min in order to allow it to return to room temperature. The solution is concentrated to 100 ml and then it is diluted with 500 ml CHCl$_3$. This organic phase is washed three times in succession with 250 ml of aqueous 1N NaHCO$_3$, and then it is dried over MgSO$_4$ before evaporating it. The product is purified by flash chromatography on a silica column (column 65 mm in diameter) with 1.5 l of MeOH-DCM 5%, and then with 500 ml of MeOH-DCM 7%, and finally 500 ml of MeOH-DCM 10%. The fractions corresponding to compound 16 are combined and then evaporated to dryness to give 17.4 g (42.1 mmol) of product, with a yield of 61%.

$^1$H NMR (200 MHz, CDCl$_3$) δ=8.86 (broad s, 1H, NH); 7.71 (d, 1H, J=7.5 Hz, Ar—H$_4$); 7.51 (s, 1H, Ar—H$_2$); 7.29-7.24 (m, 2H, Ar—H$_{5,6}$); 4.09 (m, 2H, CO—CH$_2$—O); 3.99 (m, 2H, H$_2$C$_{acetal}$); 3.72-3.53 (m, 20H, O—CH$_2$—CH$_2$—O, H$_2$C$_{acetal}$ and HO—CH$_2$); 1.61 (s, 3H, CH$_3$).

Tosylate Compound 17:

The alcohol 16 (4.13 g; 10.0 mmol) is dissolved in 5 ml of pyridine. 2.0 g (10.5 mmol) of tosyl chloride are then added at room temperature. The mixture is stirred under argon for 10 h. It is diluted with 100 ml of DCM, the organic phase is washed three times with 20 ml of aqueous 1N NaHCO$_3$, and then it is dried over MgSO$_4$ before coevaporating it with toluene. Purification by flash chromatography on a column (column 50 mm in diameter) is carried out with 500 ml of MeOH-DCM 2%, and then 500 ml of MeOH-DCM 3%, and finally 500 ml of MeOH-DCM 4%. The fractions corresponding to product 17 are combined and then evaporated to dryness to give 3.68 g (6.48 mmol) of oil with a yield estimated at 65%.

$^1$H NMR (300 MHz, CDCl$_3$) δ=8.86 (broad s, 1H, NH); 7.76 (d, 4H, J=5.5 Hz, Ar—H$_{tosyl}$); 7.60 (d, 1H, J=7.5 Hz, Ar—H$_4$); 7.50 (s, 1H, Ar—H$_2$); 7.32-7.22 (m, 2H, Ar—H$_{5,6}$); 4.10 (m, 2H, CO—CH$_2$—O); 4.00 (m, 2H, H$_2$C$_{acetal}$); 3.73-3.54 (m, 20H, O—CH$_2$—CH$_2$—O, H$_2$C$_{acetal}$ and HO—CH$_2$); 2.42 (s, 3H, Ar—CH$_3$); 1.61 (s, 3H, CH$_3$).

Phthalimide Compound 18:

The tosylate 17 (3.68 g; 6.48 mmol) is dissolved with 1.52 g (10.0 mmol) of DBU (1,8-diazobicyclo[5.4.0]undecene) and then the phthalimide (1.47 g; 10 mmol) is added. The solution thus obtained is heated at 85-90° C. for 17 h and then evaporated. The product is purified by flash chromatography on a silica column (column 50 mm in diameter) with 1 l of acetone-DCM 15%, and then with 1 l of acetone-DCM 20%. The fractions corresponding to compound 18 are combined and then evaporated to dryness to give 3.15 g (5.8 mmol) of product, with a yield of 90%.

$^1$H NMR (200 MHz, CDCl$_3$) δ=8.73 (broad s, 1H, NH); 7.79 (m, 2H, Ar—H$_{phtha}$); 7.99 (m, 2H, Ar—H$_{phtha}$ and Ar—H$_4$); 7.49 (s, 1H, Ar—H$_2$); 7.27-7.18 (m, 2H, Ar—H$_{5,6}$); 4.10 (m, 2H, CO—CH$_2$—O); 4.00 (m, 2H, H$_2$C$_{acetal}$); 3.69-3.56 (m, 20H, O—CH$_2$—CH$_2$—O, H$_2$C$_{acetal}$ and N$_{phtha}$—CH$_2$); 1.61 (s, 3H, CH$_3$).

Amine Compound 19:

The product 18 is dissolved in 20 ml of absolute EtOH by heating under reflux at 75-80° C. Hydrazine (1.07 ml; 22.1 mmol) is then added and the reaction is kept stirred for 1 h 15 min. The precipitate obtained is filtered on sintered glass and the ethanolic phase evaporated. The white precipitate is then washed with DCM, and the DCM phase is evaporated. The yellow oil obtained (2.3 g; 5.57 mmol) is directly used for the next reaction, even if it contains imidazole which may be subsequently removed during the step for deprotecting the acetal.

$^1$H NMR (300 MHz, CDCl$_3$) δ=8.83 (broad s, 1H, NH); 7.69 (d, 1H, J=7.5 Hz, Ar—H$_4$); 7.51 (s, 1H, Ar—H$_2$); 7.30-7.19 (m, 2H, Ar—H$_{5,6}$); 4.10 (m, 2H, CO—CH$_2$—O); 4.00 (m, 2H, H$_2$C$_{actal}$); 3.69-3.56 (m, 20H, O—CH$_2$—CH$_2$—O, H$_2$C$_{acetal}$ and H$_2$N—CH$_2$); 1.61 (s, 3H, CH$_3$).

Biotinylated Compound 20:

D-Biotin (1.05 g; 4.32 mmol) is solubilized in 10 ml of anhydrous DMF. 790 mg (4.87 mmol) of carbonyldiimidazole (CDI) are added under argon. After 10 min of stirring, the amine 19 diluted in 5 ml of DMF is added. The solution is kept stirred for 40 min and then evaporated before being purified by flash chromatography on a column.

For that, a column 50 mm in diameter is used with, as eluent, 500 ml of MeOH-DCM 5%, and then 500 ml of MeOH-DCM 10%, and finally 500 ml of MeOH-DCM 15%. The fractions corresponding to product 20 are combined and then evaporated to dryness to give a yellow oil (1.66 g; 2.6 mmol).

The yellow oil obtained (2.4 g) contains, according to the NMR spectrum, about 30% by weight of imidazole. It is therefore deduced therefrom that the yield of the reaction resulting in product 20 is about 60% relative to the starting biotin.

$^1$H NMR (300 MHz, CDCl$_3$) δ=8.80 (broad s, 1H, NH); 7.66 (m, 3H, Ar—H$_4$ and H$_{imidazole}$); 7.54 (s, 1H, Ar—H$_2$); 7.28-7.24 (m, 2H, Ar—H$_{5,6}$); 7.07 (s, 2H, H$_{imidazole}$), 6.59 (t, 1H, NH$_{15'}$); 6.06 (broad s, 1H, NH$_{B1}$); 5.19 (broad s, 1H, NH$_{B3}$); 4.45 (m, 1H, H$_{B6a}$); 4.27 (m, 1H, H$_{B3a}$); 4.10 (s, 2H, H$_{3'}$); 4.00 (m, 2H, H$_2$C$_{acetal}$); 3.75-3.49 (m, 18H, O—CH$_2$—CH$_2$—O and H$_2$C$_{acetal}$); 3.36 (m, 2H, H$_{14'}$); 3.09 (m, 1H, H$_{B4}$); 2.85 and 2.66 (system ABX, 2H, $^2J_{AB}$=5 Hz, $^3J_{AX}$=12 Hz, $^3J_{BX}$=0 Hz, H$_{B6}$); 2.16 (t, 2H, J=8 Hz, H$_{B10}$); 1.61 (s, 3H, CH$_3$); 1.59-1.3 (m, 6H, H$_{B9, B8, B7}$).

Ketone Compound 21:

The acetal 20 is dissolved in 80 ml of chloroform, and then 30 ml of 2N HCl are added. The mixture is kept vigorously stirred for 45 min. The organic phase is recovered and then dried over anhydrous NaHCO$_3$. After filtration, the solution is evaporated and the oil obtained is washed with pentane to give product 21 (1.48 g; 2.48 mmol) with a yield of 99%.

$^1$H NMR (300 MHz, CDCl$_3$) δ=8.99 (broad s, 1H, NH); 8.07 (s, 1H, Ar—H$_2$); 7.98 (d, 2H, J=8 Hz, Ar—H$_4$); 7.66 (d, 2H, J=8 Hz, Ar—H$_6$); 7.42 (t, 2H, J=8 Hz, Ar—H$_5$); 6.38 (t, 1H, NH$_{15'}$); 5.78 (broad s, 1H, NH$_{B1}$); 4.96 (broad s, 1H, NH$_{B3}$); 4.47 (m, 1H, H$_{B6a}$); 4.29 (m, 1H, H$_{B3a}$); 4.13 (s, 2H, H$_{3'}$); 3.76-3.37 (m, 16H, O—CH$_2$—CH$_2$—O); 3.32 (m, 2H, H$_{14'}$); 3.11 (m, 1H, H$_{B4}$); 2.89 and 2.75 (system ABX, 2H, $^2J_{AB}$=5 Hz, $^3J_{AX}$=12 Hz, $^3J_{BX}$=0 Hz, H$_{B6}$); 2.59 (s, 3H, CH$_3$); 2.16 (t, 2H, J=8 Hz, H$_{B10}$); 1.64-1.40 (m, 6H, H$_{B9, B8, B7}$).

Hydrazone Compound 22:

The ketone 21 is dissolved in 20 ml of absolute EtOH. The mixture is heated under reflux at 75-80° C. Hydrazine (816 µl; 16.81 mmol) is then added and the mixture is kept stirred for 3 h. After filtration, the mixture is evaporated to dryness, the residue is redissolved in ethanol until a sticky white foam is obtained. In a second instance, this foam is dissolved in 50 ml of chloroform and then 20 ml of a saturated NaHCO$_3$ solution are added. The mixture is thoroughly washed and then the organic phase is recovered. It is dried over anhydrous Na$_2$CO$_3$ and after filtration evaporated to dryness to give a new sticky foam. The latter corresponds to product 22 (842 mg; 1.38 mmol) and is obtained with a yield of 66%.

$^1$H NMR (300 MHz, CDCl$_3$) δ=8.81 (broad s, 1H, NH); 8.82 (s, 1H, Ar—H$_2$); 7.64 (d, 2H, J=8 Hz, Ar—H$_4$); 7.32 (m, 4H, Ar—H$_{5,6}$); 6.43 (t, 1H, NH$_{15'}$); 5.89 (broad s, 1H, NH$_{B1}$); 5.46 (broad s, 2H, NH$_2$); 4.99 (broad s, 1H, NH$_{B3}$); 4.44 (m, 1H, H$_{B6a}$); 4.27 (m, 1H, H$_{B3a}$); 4.11 (s, 2H, H$_{3'}$); 3.70-3.37 (m, 16H, O—CH$_2$—CH$_2$—O); 3.22 (m, 2H, H$_{14'}$); 3.08 (m, 1H, H$_{B4}$); 2.87 and 2.67 (system ABX, 2H, $^2J_{AB}$=5 Hz, $^3J_{AX}$=12 Hz, $^3J_{BX}$=0 Hz, H$_{B6}$); 2.11 (m, 5H, CH$_3$ and H$_{B10}$); 1.64-1.40 (m, 6H, H$_{B9, B8, B7}$).

Diazo Compound 23:

The hydrazone 22 (100 mg; 0.164 mmol) is dissolved in 1 ml of DMF under argon. 80 mg of activated MnO$_2$ are added and the mixture is kept vigorously stirred for 30 min. The mixture is filtered through a celite (3 cm)-powdered molecular sieve (1 cm) mixed layer. The solution is then evaporated to dryness. The oil obtained at the end of the evaporation is triturated until a pink powder is obtained which corresponds to compound 23 (78 mg; 0.128 mmol; 78%).

$^1$H NMR (300 MHz, DMSO-d$_6$) δ=9.60 (broad s, 1H, NH); 7.89 (s, 1H, Ar—H$_2$); 7.76 (t, 1H, NH$_{15'}$); 7.35-7.25 (m, 4H, Ar—H$_{5,6}$); 6.64 (d, 2H, J=8 Hz, Ar—H$_4$); 6.36 (broad s, 1H, NH$_{B1}$); 6.32 (broad s, 1H, NH$_{B3}$); 4.28 (m, 1H, H$_{B6a}$); 4.08 (m, 1H, H$_{B3a}$); 4.06 (s, 2H, H$_{3'}$); 3.55-3.31 (m, 16H, O—CH$_2$—CH$_2$—O); 3.17 (m, 2H, H$_{14'}$); 3.08 (m, 1H, H$_{B4}$); 2.80 and 2.59 (system ABX, 2H, $^2J_{AB}$=5 Hz, $^3J_{AX}$=12 Hz, $^3J_{BX}$=0 Hz, H$_{B6}$); 2.13 (m, 5H, CH$_3$); 2.13 (t, 2H, J=8 Hz, H$_{B10}$); 1.99-1.30 (m, 6H, H$_{B9, B8, B7}$).

The reactivity of compound 23 was tested on uridine 3'-monophosphate and monitored by capillary electrophoresis. The analytical conditions are those of Example 6.1. The results show a half-life period of 30 minutes.

The stability of the reagent is greater than 1 month at −2°° C.

Example 30.3
Synthesis of para-Bio-EG3-PMDAM
Synthesis scheme:
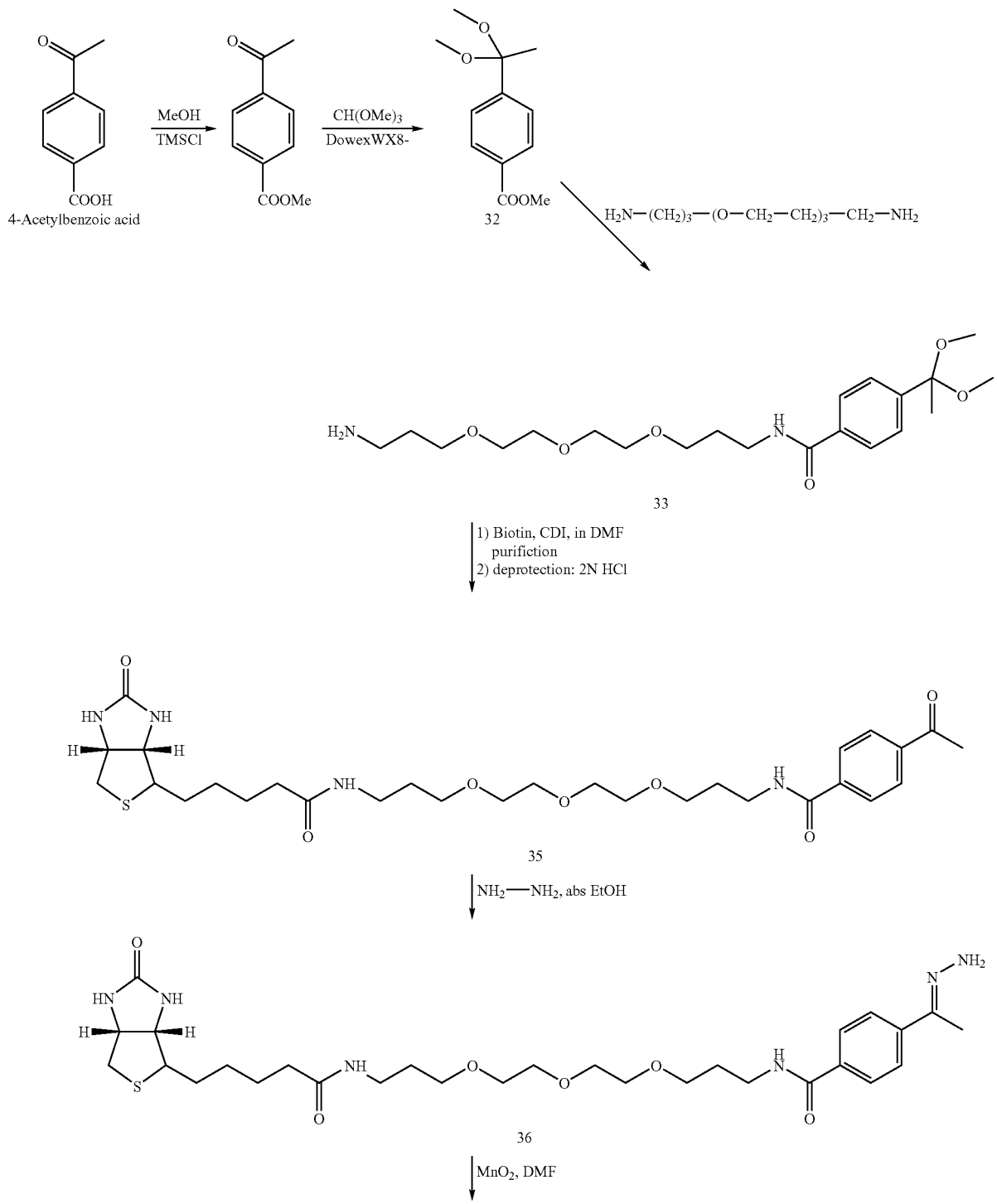

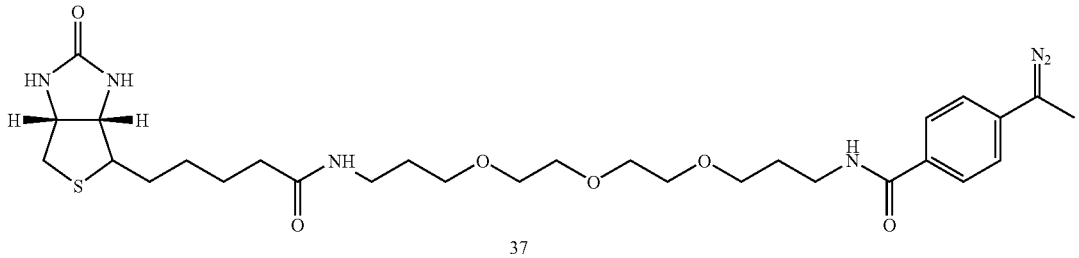

37

Protection of the 4-acetylbenzoic acid:

The 4-acetylbenzoic acid (1 g; 6.1 mmol) is dissolved in a trimethylsilyl chloride solution (TMSCl, 10 g; 92 mmol) in 5 ml of MeOH. The mixture is heated at 90° C. overnight. After evaporation, a white solid corresponding to compound 31 (1.21 g; 5.75 mmol) is isolated, characterized by NMR and used as it is for the next reaction.

$^1$H NMR (200 MHz, CDCl$_3$) δ=8.08 (d, 2H, J=8 Hz, Ar—H$_{2,6}$); 7.59 (d, 2H, J=8 Hz, Ar—H$_{3,5}$); 3.18 (s, 6H, —O—CH$_3$); 1.53 (s, 3H, CH$_3$).

Compound 32:

Compound 31 (1.21 g; 5.75 mmol) is dissolved in 5 ml of trimethyl orthoformate in the presence of Dowex 50WX8-100 (0.3 g). The mixture is heated at 60° C. overnight, and then filtered and evaporated to give compound 32 (1.19 g; 5.3 mmol) with a yield of 87%.

$^1$H NMR (200 MHz, CDCl$_3$) δ=8.00 (d, 2H, J=8 Hz, Ar—H$_{2,6}$); 7.54 (d, 2H, J=8 Hz, Ar—H$_{3,5}$); 3.89 (s, 1H, CO—O—CH$_3$); 3.16 (s, 6H, —O—CH$_3$); 1.51 (s, 3H, CH$_3$).

Compound 33:

Compound 32 (1.17 g; 5.22 mmol) is solubilized in 5 ml (22.7 mmol) of 4,7,10-trioxa-1,13-tridecanediamine. The solution obtained is heated at 140° C. for 4 h. The mixture is then dissolved in 30 ml of DCM and washed 3 times with 10 ml of water. The organic phase is dried over MgSO$_4$, and then evaporated until an oil corresponding to product 33 (1.44 g; 3.49 mmol) is obtained with a yield of 67%.

$^1$H NMR (200 MHz, CDCl$_3$) δ=7.76 (d, 2H, J=8 Hz, Ar—H$_{2,6}$); 7.51 (d, 2H, J=8 Hz, Ar—H$_{3,5}$); 3.62-3.47 (m, 14H, H$_{7',8',10',11'}$ and H$_{5',13'}$ and H$_{3'}$); 3.15 (s, 6H, —O—CH$_3$); 2.73 (m, 2H, H$_{15'}$) 1.88 (m, 2H, H$_{4'}$); 1.65 (m, 2H, H$_{14'}$); 1.38 (broad s, 2H, NH$_2$).

Biotinylated Compound 34:

Biotin (780 mg; 3.19 mmol) is suspended in 13 ml of DMF. 590 mg (3.60 mmol) of CDI are then added. This solution is kept stirred for 30 min at room temperature. Compound 33 is dissolved in 1 ml of DMF, and then the preceding solution is added little by little. The mixture thus obtained is kept stirred for 1 h at room temperature. After evaporating the DMF, purification by flash chromatography on a column (column 35 mm in diameter) is carried out with 500 ml of MeOH-DCM 6%, and then with 250 ml of MeOH-DCM 8%, and finally 250 ml of MeOH-DCM 8%. The fractions corresponding to product 34 are combined and then evaporated to dryness to give 1.05 g of oil with a yield estimated at 30%.

$^1$H NMR (300 MHz, CDCl$_3$) δ=8.49 (broad s, 1H, NH$_{imidazole}$); 7.79 (d, 2H, Ar—H$_{2,6}$); 7.66 (s, 1H, H$_{imidazole}$); 7.50 (d, 2H, J=8 Hz, Ar—H$_{3,5}$); 7.38 (t, 1H, NH$_{2'}$); 7.11 (s, 2H, H$_{imidazole}$); 6.67 (t, 1H, NH$_{16'}$); 5.99 (broad s, 1H, NH$_{B1}$); 5.15 (broad s, 1H, NH$_{B3}$); 4.46 (m, 1H, H$_{B6a}$); 4.27 (m, 1H, H$_{B3a}$); 3.61-3.45 (m, 14H, H$_{7',8',10',11'}$ and H$_{5',13'}$ and H$_{3'}$); 3.28 (m, 2H, H$_{15'}$); 3.15 (s, 6H, —OCH$_3$); 2.85 (m, 1H, H$_{B4}$); 2.85 and 2.69 (system ABX, 2H, $^2J_{AB}$=5 Hz, $^3J_{AX}$=12 Hz, $^3J_{BX}$=0 Hz, H$_{B6}$); 2.14 (t, 2H, J=8 Hz, H$_{B10}$); 1.86 (m, 2H, H$_{4'}$); 1.69 (m, 2H, H$_{14'}$); 1.49 (s, 3H, CH$_3$); 1.42-1.39 (m, 6H, H$_{B7, B8, B9}$).

Compound 35:

The acetal 34 is dissolved in 45 ml of chloroform, and then 10 ml of 2N HCl are added. The two-phase mixture is vigorously stirred for 5 min. The organic phase is recovered and dried over anhydrous NaHCO$_3$. It is filtered, evaporated, and compound 35 is obtained in the form of a light yellow solid (504 mg; 0.87 mmol) with an overall yield of 27% from biotin.

$^1$H NMR (300 MHz, CDCl$_3$) δ=7.97 (d, 2H, J=8 Hz, Ar—H$_{2,6}$); 7.91 (d, 2H, J=8 Hz, Ar—H$_{3,5}$); 7.51 (t, 1H, NH$_{2'}$); 6.50 (t, 1H, NH$_{16'}$), 6.05 (broad s, 1H, NH$_{B1}$); 5.23 (broad s, 1H, NH$_{B3}$); 4.45 (m, 1H, H$_{B6a}$); 4.27 (m, 1H, H$_{B3a}$); 3.62-3.56 (m, 10H, H$_{7',8',10',11'}$ and H$_{5'}$; 3.48-3.46 (m, 4H, H$_{3',13'}$); 3.27 (m, 2H, H$_{15'}$); 3.10 (m, 1H, H$_{B4}$); 2.85 and 2.71 (system ABX, 2H, $^2J_{AB}$=5 Hz, $^3J_{AX}$=12 Hz, $^3J_{BX}$=0 Hz, H$_{B6}$); 2.60 (s, 3H, CH$_3$); 2.14 (t, 2H, J=8 Hz, H$_{B10}$); 1.89 (m, 2H, H$_{4'}$); 1.72-1.61 (m, 6H, H$_{14'}$, H$_{B7\ B9}$); 1.40 (m, 2H, H$_{B8}$).

Hydrazone Compound 36:

The ketone 35 (500 mg; 0.864 mmol) is dissolved in 11 ml of absolute EtOH. The hydrazine (335 μl; 6.911 mmol) is added, and then the reaction mixture is heated under reflux for 1 h. The oil obtained after evaporation is dissolved in abs EtOH so as to be evaporated again. A sticky foam corresponding to product 36 (488 mg; 0.823 mmol) is then obtained with a yield of 95%.

$^1$H NMR (300 MHz, CDCl$_3$) δ=7.76 (d, 2H, J=8 Hz, Ar—H$_{2,6}$); 7.67 (d, 2H, J=8 Hz, Ar—H$_{3,5}$); 7.29 (t, 1H, NH$_{2'}$); 6.46 (t, 1H, NH$_{16'}$), 5.98 (broad s, 1H, NH$_{B1}$); 5.55 (broad s, 2H, NH$_2$); 5.14 (broad s, 1H, NH$_{B3}$); 4.45 (m, 1H, H$_{B6a}$); 4.24 (m, 1H, H$_{B3a}$); 3.62-3.51 (m, 10H, H$_{7',8',10',11'}$ and H$_{5'}$); 3.47-3.45 (m, 4H, H$_{3',13'}$); 3.27 (m, 2H, H$_{15'}$); 3.07 (m, 1H, H$_{B4}$); 2.84 and 2.69 (system ABX, 2H, $^2J_{AB}$=5 Hz, $^3J_{AX}$=12 Hz, $^3J_{BX}$=0 Hz, H$_{B6}$); 2.11 (t, 2H, J=8 Hz, H$_{B10}$ and s, 3H, CH$_3$); 1.86 (m, 2H, H$_{4'}$); 1.72-1.59 (m, 6H, H$_{14'}$, H$_{B7,\ B9}$); 1.21 (m, 2H, H$_{B8}$).

Diazo compound 37:

The hydrazone 36 (200 mg; 0.337 mmol) is solubilized in 5 ml of DMF. MnO$_2$ (450 mg; 5.17 mmol) is then added. After 15 min of stirring at room temperature, the mixture is filtered on millipore containing celite (thickness: 2 cm) and 3 Å (0.5 cm) powdered molecular sieve. The reaction mixture is evaporated to dryness. The residual oil obtained is washed with ether three times in succession, until a powder is obtained. Compound 37 (290 mg, 0.491 mmol) is obtained in the form of a pink solid with a yield of 93%.

¹H NMR (300 MHz, DMSO-$d_6$) δ=8.33 (t, 1H, $NH_{2'}$); 7.83 (d, 2H, J=8 Hz, Ar—$H_{2,6}$); 7.73 (t, 1H, $NH_{16'}$); 6.98 (d, 2H, J=8 Hz, Ar—$H_{3,5}$); 6.39 (broad s, 1H, $NH_{B1}$); 6.33 (broad s, 1H, $NH_{B3}$); 4.30 (m, 1H, $H_{B6a}$); 4.12 (m, 1H, $H_{B3a}$); 3.51-3.45 (m, 16H, $H_{7',8',10',11'\ and\ H5'}$ and $H_{15'}$ and $H_{3',13'}$); 3.07 (m, 1H, $H_{B4}$); 2.79 and 2.58 (system ABX, 2H, $^2J_{AB}$=5 Hz, $^3J_{AX}$=12 Hz, $^3J_{BX}$=0 Hz, $H_{B6}$); 2.14 (s, 3H, $CH_3$); 2.04 (t, 2H, J=8 Hz, $H_{B10}$); 1.77 (m, 2H, $H_{4'}$); 1.62-1.48 (m, 6H, $H_{14'}$, $H_{B7,\ B9}$); 1.31 (m, 2H, $H_{B8}$).

The reactivity of compound 37 was tested on uridine 3'-monophosphate and monitored by capillary electrophoresis. The analytical conditions are those of Example 6.1. The results show a half-life period of 60 minutes.

The reagent is stable at −20° C. for at least 1 month.

Example 30.4

Synthesis of meta-Bio-EG3-PDAM

Synthesis scheme:

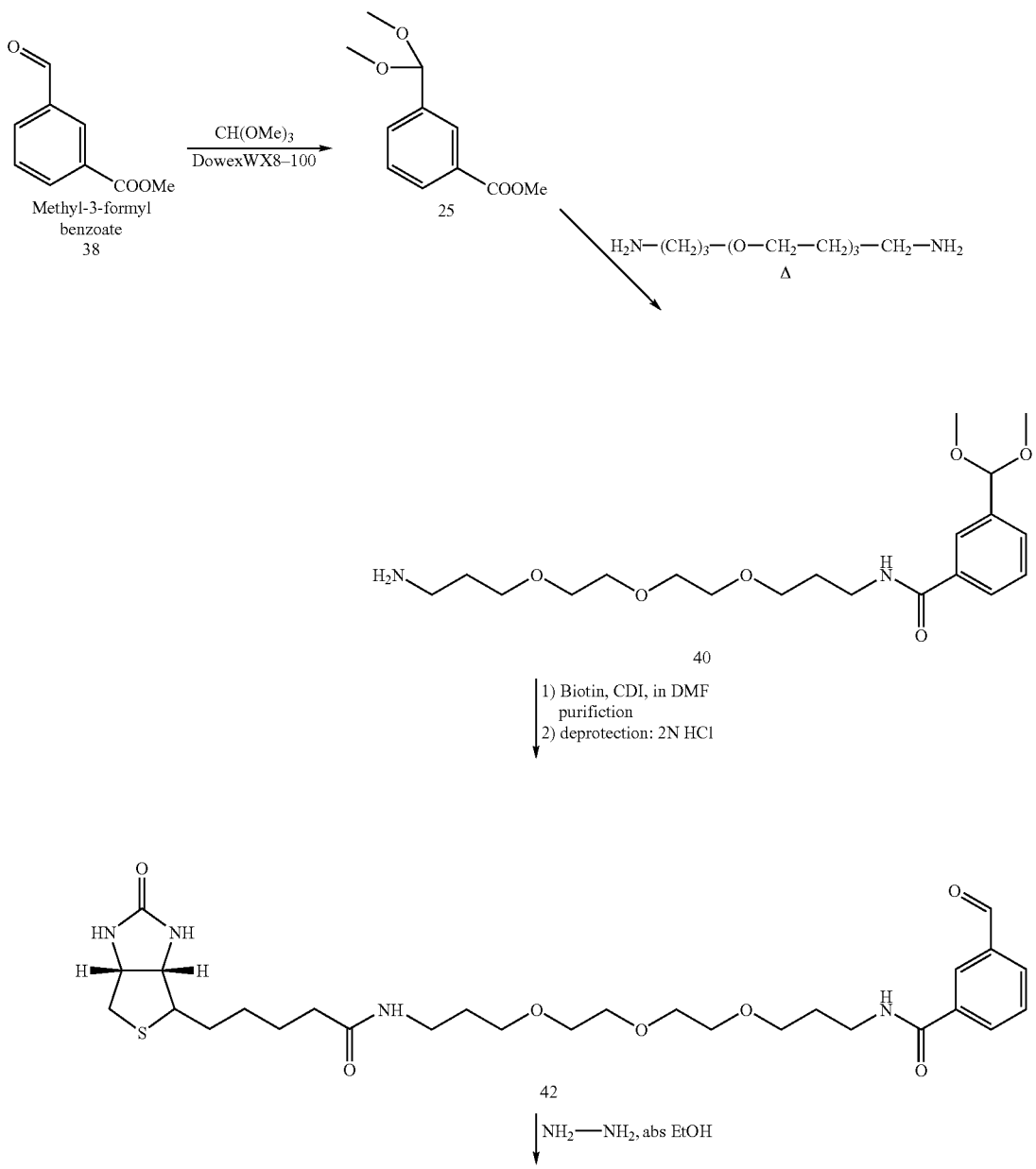

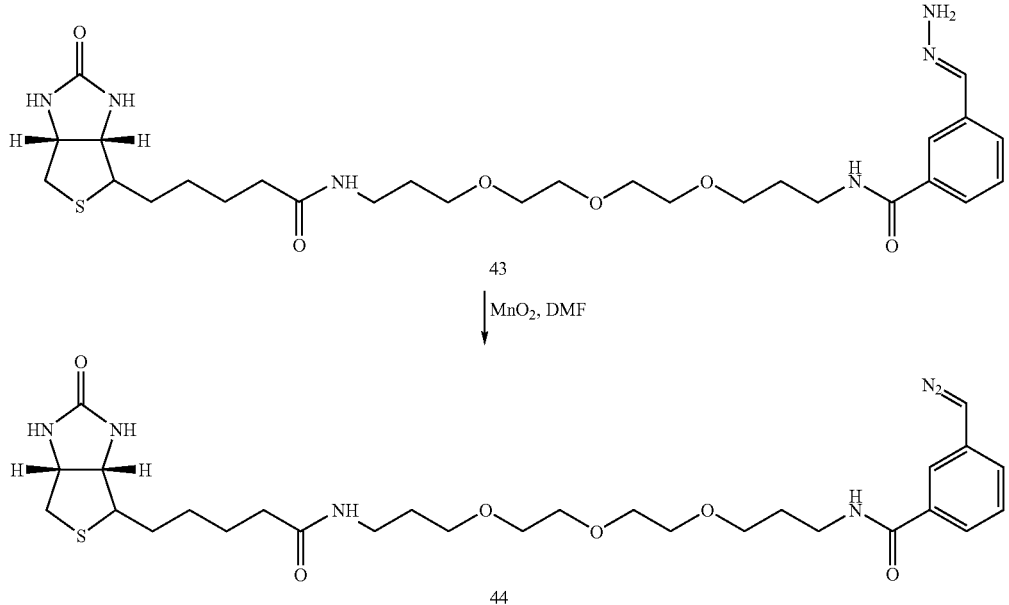

Protection of methyl 3-formylbenzoate 38:

The Dowex 50WX8-100 resin (2 g) is dissolved in 25 ml of MeOH and 25 ml of trimethyl orthoformate and the kept stirred for 15 min. After decantation, the resin is washed twice in succession with 20 ml of MeOH. This resin is then placed in 100 ml of MeOH, 50 ml of CH(OMe)$_3$ and 7.12 g (43.4 mmol) of methyl 3-formylbenzoate are added. The solution is kept stirred for 15 min, and then filtered on pleated paper before evaporation. Product 39 (9 g; 43.1 mmol) is isolated in the form of a light yellow liquid with a yield of 99%.

$^1$H NMR (200 MHz, CDCl$_3$) δ=8.10 (s, H, Ar—H$_2$); 7.9 (d, H, J=8 Hz, Ar—H$_4$); 7.63 (d, H, J=8 Hz, Ar—H$_6$); 7.42 (t, H, J=8 Hz, Ar—H$_5$); 5.40 (s, 1H, CH); 3.90 (s, 3H, —CO—O—CH$_3$); 3.31 (s, 6H, —O—CH$_3$).

Compound 40:

Compound 39 (2 g; 9.5 mmol) is solubilized in 10.4 ml (47.6 mmol) of 4,7,10-trioxa-1,13-tridecanediamine. The solution is then heated at 165° C. for 2 h. The mixture obtained is then dissolved in 80 ml of DCM and washed 4 times with 20 ml of water. After drying over MgSO$_4$ and evaporation, product 40 is 20 isolated with a yield of 60% (2.27 g; 5.69 mmol).

$^1$H NMR (200 MHz, CDCl$_3$) δ=7.84 (s, H, Ar—H$_2$); 7.75 (d, H, J=8 Hz, Ar—H$_4$); 7.53 (d, H, J=8 Hz, Ar—H$_6$); 7.39 (t, H, J=8 Hz, Ar—H$_5$); 5.38 (s, 1H, CH); 3.64-3.43 (m, 14H, H$_{7',8',10',11'}$ and H$_{5',13'}$ and H$_{3'}$); 3.29 (s, 6H, —O—CH$_3$); 2.72 (m, 2H, H$_{15'}$); 1.87 (m, 2H, H$_{4'}$); 1.64 (m, 2H, H$_{14'}$); 1.30 (broad s, 2H, NH$_2$).

Biotinylated Compound 41:

D-biotin (344 mg; 1.40 mmol) is suspended in 4 ml of DMF and then 250 mg (1.54 mmol) of CDI are added. This solution is kept stirred for 30 min at room temperature. Compound 40 (616 mg; 1.54 mmol) is dissolved in 2 ml of DMF, and then the preceding solution is added little by little. The mixture thus obtained is kept stirred for 50 min at room temperature. After evaporation, purification by flash chromatography on a column (column 30 mm in diameter) is carried out with 750 ml of MeOH-DCM 10%, and then with 250 ml of MeOH-DCM 15%. The fractions corresponding to product 41 are combined and then evaporated to dryness to give 740 mg of oil with a yield estimated at 50%.

$^1$H NMR (200 MHz, CDCl$_3$) δ=7.87 (S, H, Ar—H$_2$); 7.78 (d, H, J=8 Hz, Ar—H$_4$); 7.65 (S, 1H, H$_{imidazole}$); 7.53 (d, H, J=8 Hz, Ar—H$_6$); 7.39 (t, H, J=8 Hz, Ar—H$_5$); 7.07 (s, 2H, H$_{imidazole}$); 6.65 (t, 1H, NH$_{16'}$), 5.95 (broad s, 1H, NH$_{B1}$); 5.38 (s, 1H, CH); 5.15 (broad s, 1H, NH$_{B3}$); 4.43 (m, 1H, H$_{B6a}$); 4.27 (m, 1H, H$_{B3a}$); 3.59-3.44 (m, 14H, H$_{7',840,10',11'}$ and H$_{5',13'}$ and H$_{3'}$); 3.29 (m, 8H, H$_{15'}$ and 2-O—CH$_3$); 3.07 (m, 1H, H$_{B4}$); 2.84 and 2.66 (system ABX, 2H, $^2J_{AB}$=5 Hz, $^3J_{AX}$=12 Hz, $^3J_{BX}$=0 Hz, H$_{B6}$); 2.13 (t, 2H, J=8 Hz, H$_{B10}$); 1.85 (m. 2H, H$_{4'}$); 1.66 (m. 2H, H$_{14'}$); 1.40-1.37 (m, 6H, H$_{B7, B8, B9}$).

Aldehyde Compound 42:

The acetal 41 is dissolved in 20 ml of chloroform, and then 5 ml of 2N HCl are added. The two-phase mixture is vigorously stirred for 15 min. The organic phase is recovered and dried over anhydrous NaHCO$_3$. It is filtered, evaporated and compound 42 is obtained in the form of a yellow oil (593 mg; 1.02 mmol) with an overall yield of 87% from biotin.

$^1$H NMR (300 MHz, CDCl$_3$) δ=10.04 (s, 1H, CHO); 8.34 (s, H, Ar—H$_2$); 8.16 (d, H, J=8 Hz, Ar—H$_4$); 7.96 (d, H, J=8 Hz, Ar—H$_6$); 7.72 (t, 1H, NH$_2$); 7.39 (t, H, J=8 Hz, Ar—H$_5$); 6.51 (t, 1H, NH$_{16'}$); 6.00 (broad s, 1H, NH$_{B1}$); 5.30 (broad s, 1H, NH$_{B3}$); 4.46 (m, 1H, H$_{B6a}$); 4.27 (m, 1H, H$_{B3a}$); 3.66-3.56 (m, 10H, H$_{7',8',10',11'}$ and H$_{5'}$); 3.50-3.29 (m, 4H, H$_{3',13'}$); 3.28 (m, 2H, H$_{15'}$); 2.95 (m, 1H, H$_{B4}$); 2.84 and 2.71 (system ABX, 2H, $^2J_{AB}$=5 Hz, $^3J_{AX}$=12 Hz, $^3J_{BX}$=0 Hz, H$_{B6}$); 2.15 (t, 2H, J=8 Hz, H$_{B10}$); 1.89 (m, 2H, H$_{4'}$); 1.72-1.63 (m, 6H, H$_{14'}$, H$_{B7, B9}$); 1.23 (m, 2H, H$_{B8}$).

Hydrazone Compound 43:

The aldehyde 42 (593 mg; 1.02 mmol) is dissolved in 10 ml of absolute ethanol. The hydrazine (400 μl; 8.19 mmol) is added, and then the reaction mixture is heated under reflux for 50 min. The yellow oil obtained after evaporation is triturated with ether until a beige powder corresponding to product 43 (404 mg; 0.68 mmol) is obtained with a yield of 66%. Purification by flash chromatography on a column (column 15 mm in diameter) is then carried out on a 150 mg (0.253 mmol) sample with 200 ml of MeOH-DCM 20%. The fractions are combined and then evaporated to dryness to give 144 mg of product 43 with a yield of 76%.

$^1$H NMR (300 MHz, CDCl$_3$) δ=7.95 (s, H, Ar—H$_2$); 8.16 (d, H, J=8 Hz, Ar—H$_4$); 7.76 (s, 1H, CH); 7.96 (d, H, J=8 Hz, Ar—H$_6$); 7.38 (t, H, J=8 Hz, Ar—H$_5$); 6.45 (t, 1H, NH$_{16'}$); 5.98 (broad s, 1H, NH$_{B1}$); 5.72 (broad s, 2H, NH$_2$); 5.18 (broad s, 1H, NH$_{B3}$); 4.44 (m, 1H, H$_{B6a}$); 4.26 (m, 1H, H$_{B3a}$); 3.62-3.56 (m, 10H, H$_{7',8',10',11'}$ and H$_{5'}$); 3.48-3.45 (m, 4H, H$_{3',13'}$); 3.27 (m, 2H, H$_{15'}$); 3.07 (m, 1H, H$_{B4}$); 2.84 and 2.68 (system ABX, 2H, $^2J_{AB}$=5 Hz, $^3J_{AX}$=12 Hz, $^3J_{BX}$=0 Hz, H$_{B6}$); 2.11 (t, 2H, J=8 Hz, H$_{B10}$); 1.86 (m, 2H, H$_{4'}$); 1.72-1.59 (m, 6H, H$_{14'}$, H$_{B7, B9}$); 1.21 (m, 2H, H$_{B8}$).

Diazo Compound 44:

The hydrazone 43 (100 mg; 0.187 mmol) is solubilized in 4 ml of DMF. MnO$_2$ (200 mg; 2.3 mmol) is then added. After 13 min of stirring at room temperature, the mixture is filtered on millipore containing celite (thickness: 2 cm) and 3 Å (0.5 cm) powdered molecular sieve. The reaction mixture is evaporated to dryness. The residual oil obtained is washed with ether three times in succession. Compound 44 (290 mg, 0.491 mmol) is obtained in the form of an orange solid with a yield of 83%.

$^1$H NMR (300 MHz, DMSO-d$_6$) δ=8.39 (t, 1H, NH$_{2'}$); 7.78 (t, 1H, NH$_{16'}$); 7.39-7.34 (m, Ar—H); 7.09 (d, Ar—H); 6.38 (broad s, 1H, NH$_{B1}$); 6.32 (broad s, 1H, NH$_{B3}$); 5.78 (s, 1H, CH—N$_2$); 4.27 (m, 1H, H$_{B6a}$); 4.11 (m, 1H, H$_{B3a}$); 3.51-3.44 (m, 10H, H$_{7',8',10',11'}$ and H$_{5'}$); 3.37 (m, 2H, H$_{15'}$); 3.32 (m, 4H, H$_{3',13'}$); 3.05 (m, 1H, H$_{B4}$); 2.79 and 2.58 (system ABX, 2H, $^2J_{AB}$=5 Hz, $^3J_{AX}$=12 Hz, $^3J_{BX}$=0 Hz, H$_{B6}$); 2.02 (t, 2H, J=8 Hz, H$_{B10}$); 1.69 (m, 2H, H$_{4'}$); 1.59-1.48 (m, 6H, H$_{14'}$, H$_{B7, B9}$); 1.25 (m, 2H, H$_{B8}$).

The stability of the product is greater than 1 month at −20° C.

EXAMPLE 31

Synthesis of para-Cy5-EG3-PDAM

As has already been mentioned in Example 2, the biotin may be replaced with another marker such as Cy5. This example shows that the diazo functional group, carried by PDAM, may also be linked to this Cy5 marker via a polyethylene glycol linking arm.

Synthesis scheme: The counter-ion I⁻ is not represented in the formulae 46, 47, 50' and 51.

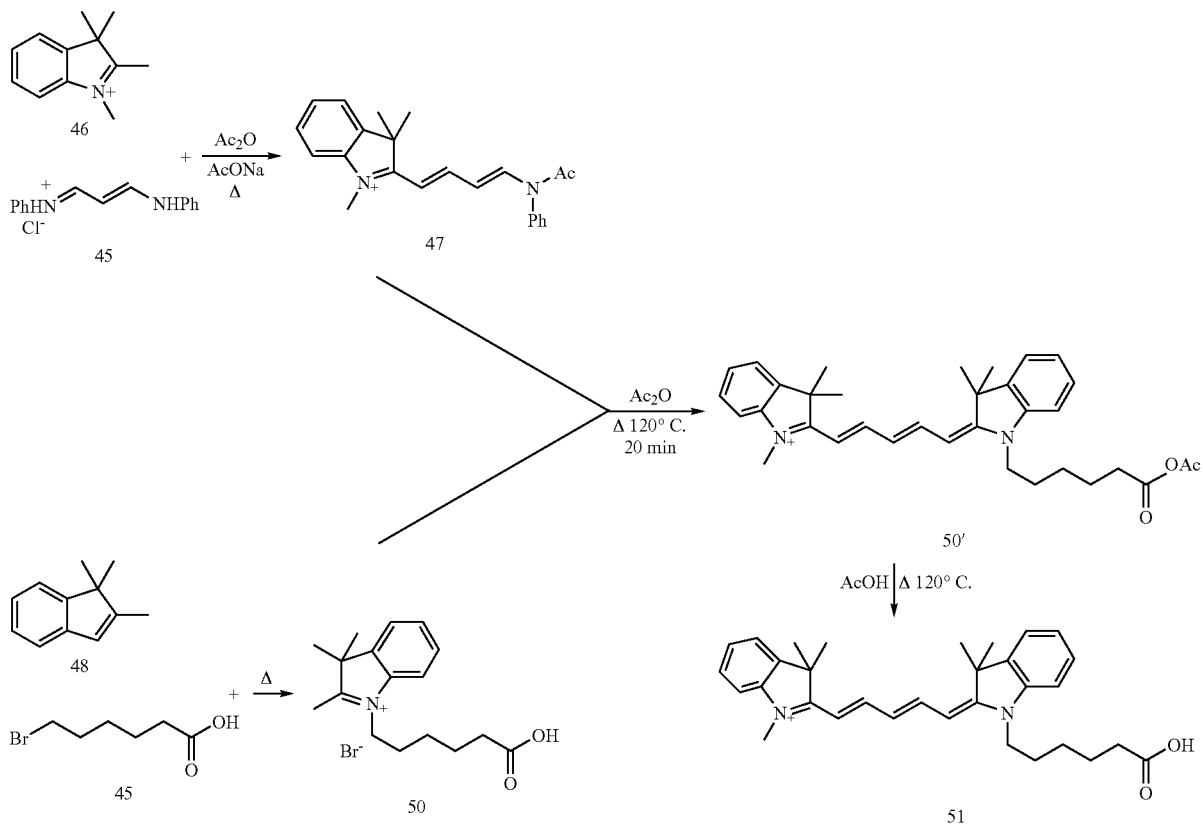

2-[4-(N-Acetyl-N-phenylamino)buta-1,3-dienyl]-1,2,3,3-tetramethyl[3H]indolium iodide 47:

The mixture of malonaldehydebis(phenylimine) monohydrochloride 45 (13 g; 50.2 mmol), NaOAc (6.0 g; 69.7 mmol) and 1,2,3,3-tetramethyl[3H]indolium iodide 46 (3.01 g; 10 mmol) in acetic anhydride (50 ml) is heated at 100° C. for precisely 20 min. After cooling, ether (350 ml) is added and the brown solid precipitated is filtered and washed with ether (3×100 ml). The solid is redissolved in 150 ml of CH$_2$Cl$_2$, filtered (removal of the inorganic salts) and then precipitated with 350 ml of ether to give a brown solid (3.54 g, 54%).

$^1$H NMR (CDCl$_3$): δ=8.64 (d; 1H; J=12 Hz; 1-H); 8.14 (t; 1H; J=16; 12 Hz; 3-H); 7.63-7.19 (m; 9H); 6.90 (d; 1H; J=15 Hz; 4-H); 5.82 (t; 1H; J=12; 13 Hz; 2-H); 4.06 (s; 3H; NCH$_3$); (2.16 (s; 3H; —COCH$_3$); 1.74 (s; 6H; CH$_3$)

1-(5-Carboxypentyl)-2,3,3-trimethyl[3H]indolium bromide 50:

2,3,3-Trimethylindole 48 (10.0 g; 62.8 mmol) and 6-bromohexanoic acid 49 (12.3 g; 62.8 mmol) are mixed without solvent and heated at 110° C. for 12 h under argon. The violet-red pasty reaction mixture is washed with ethyl acetate (2×60 ml, the paste is triturated with the spatula and the supernatant is decanted off), and then with acetone (50 ml, the paste solidifies). The pink solid is filtered and then dried under vacuum (16.0 g; 73%).

Cy5COOH Compound 51:

The mixture of the iodide 47 (2.5 g; 5.3 mmol), of the bromide 50 (1.87 g; 5.3 mmol) and of NaOAc (1.08 g; 12.1 mmol) in acetic anhydride (11 ml) is heated at 120° C. for 25 min. After cooling, ether (200 ml) is added and the precipitate is filtered and washed with ether (3×50 ml). The solid corresponding to product 50' is dissolved in 100 ml of CH$_2$Cl$_2$ and then evaporated. It is then dissolved in 15 ml of acetic acid and stirred for 30 min at 120° C. The precipitate corresponding to product 51 is then obtained after addition of 200 ml of ether and filtration on sintered glass, with a yield of 84% (2.71 g; 4.44 mmol).

$^1$H NMR (CDCl$_3$): δ=8.03 (t; 2H; J=10; 11 Hz, 2-H, 4-H); 7.38-6.91 (m; 9H; Ar—H, 3-H); 6.41 (d; 1H; J=14 Hz; 1-H); 6.31 (d; 1H; J=13 Hz; 5-H); 4,07 (t; 2H; J 7; 7 Hz; α-CH$_2$); 3.68 (s; 3H; NCH$_3$); 2.47 (t; 2H, J=7; 7 Hz; ε-CH$_2$); 1.71 (m; 18H; CH$_3$, β,γ and δ-CH$_2$).

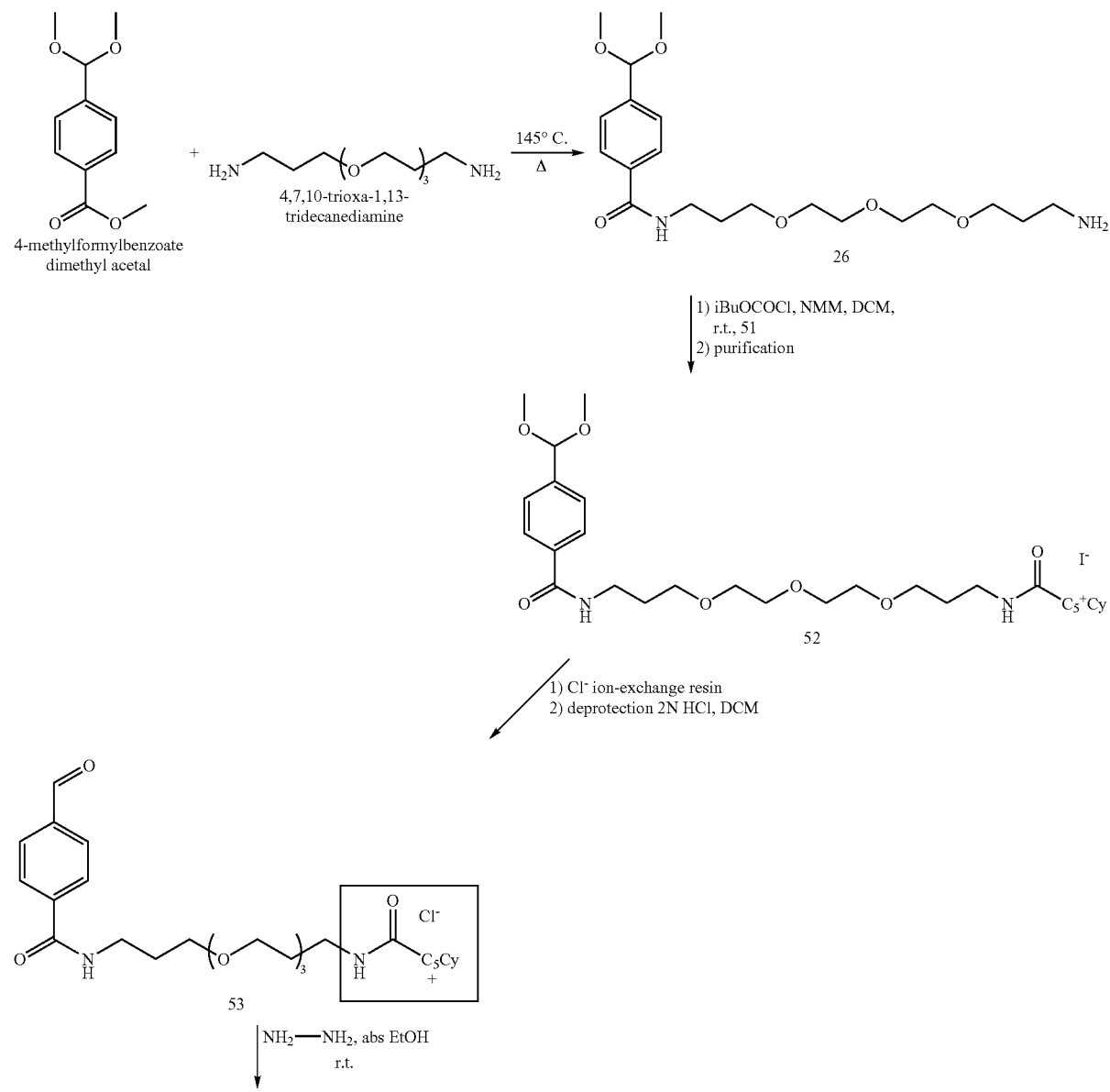

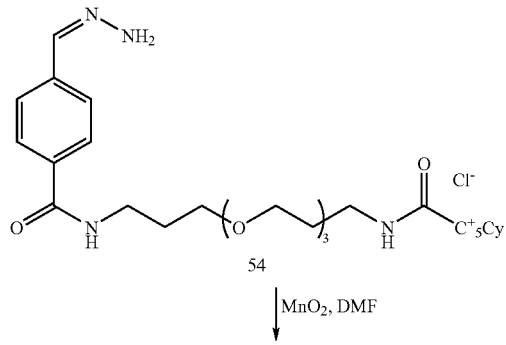

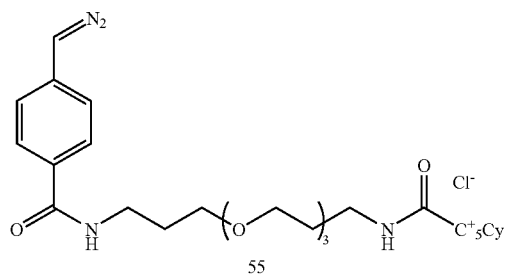

Coupling of Compound 26 with Cy5COOH 51 (Product 52):

To a solution of Cy5COOH 51 (1.5 g; 2.46 mmol) in 15 ml of CH$_2$Cl$_2$, N-methylmorpholine (NMM, 405 µl; 3.68 mmol) is added. The solution is cooled with an ice bath and placed under argon, and then isobutyl chloroformate (494 µl; 3.81 mmol) is added. After 10 min of stirring, the amine 26 (1.86 mg; 4.67 mmol) diluted in 8 ml of CH$_2$Cl$_2$ is added. The mixture is kept stirred at room temperature for 1 h 30 min. 20 ml of CH$_2$Cl$_2$ are added and the mixture is washed with 25 ml of NaHCO$_3$ (1N) three times in succession. After drying over Na$_2$CO$_3$, the solution is filtered in order to recover the dichloromethane phase which is evaporated.

Purification by flash chromatography on a column (column 45 mm in diameter, 20 ml fractions) is carried out with, as eluent, MeOH-DCM 10%. The fractions corresponding to product 52 are combined and then evaporated to dryness to give a blue solid which is dissolved in CH$_2$Cl$_2$. Product 52 is then precipitated and washed with ether to give a blue product with a yield of 72% (1.45 g; 1.77 mmol).

Product 52 (iodide) is then dissolved in 54 ml of methanol and then passed over an amberlite IRA900 column (Cl$^-$; 15 g). The methanolic solution recovered is evaporated to dryness to give a sticky oil which is redissolved in CH$_2$Cl$_2$. The evaporation makes it possible to obtain product 52' with a yield of 87%.

Aldehyde 53:

The acetal 52' is dissolved in 10 ml of DCM, and then 10 ml of 2N HCl are added. The solution is kept vigorously stirred for 3 h 30 min. After adding 20 ml of DCM, the dichloromethane phase is recovered and then dried over NaHCO$_3$. The product obtained after evaporation is washed with ether to give the aldehyde 53 with a yield of 90% (1.18 g; 1.46 mmol).

Hydrazone 54:

The aldehyde 53 (200 mg; 0.247 mmol) is dissolved in 1 ml of absolute ethanol and hydrazine monohydrate (15.6 µl; 0.321 mmol) is added. The solution is stirred at room temperature for 30 min. 8 ml of ether are added; the mixture is washed with ether by decantation three times in succession and then dried under vacuum. 172 mg of hydrazine 54 (0.209 mmol; 85% yield) is obtained and stored in a freezer.

Diazo 55:

To a solution of 20 mg (0.243 mmol) of hydrazone 54 in 2 ml of DMF, 100 mg of MnO$_2$ are added and the mixture is vigorously stirred for 5 min under argon at room temperature. The suspension is filtered through a layer of celite (thickness: 2 cm) and powdered molecular sieve 3 Å (0.5 cm) and washed with DMF. The solution is evaporated and then the residue is triturated with ether. The solid thus obtained is dried. 18 mg (0.185 mmol; 76%) of diazo 55 are obtained.

The stability of the reagent is greater than 1 month at −20° C.

EXAMPLE 32

Synthesis of meta-Fluo-EG3-PMDAM

As already mentioned in Examples 23 and 25, the biotin may be replaced with another marker. This example shows that it is also possible to link the diazo functional group, carried by PMDAM, to this fluorescein marker via a polyethylene glycol linking arm.

Synthesis scheme:

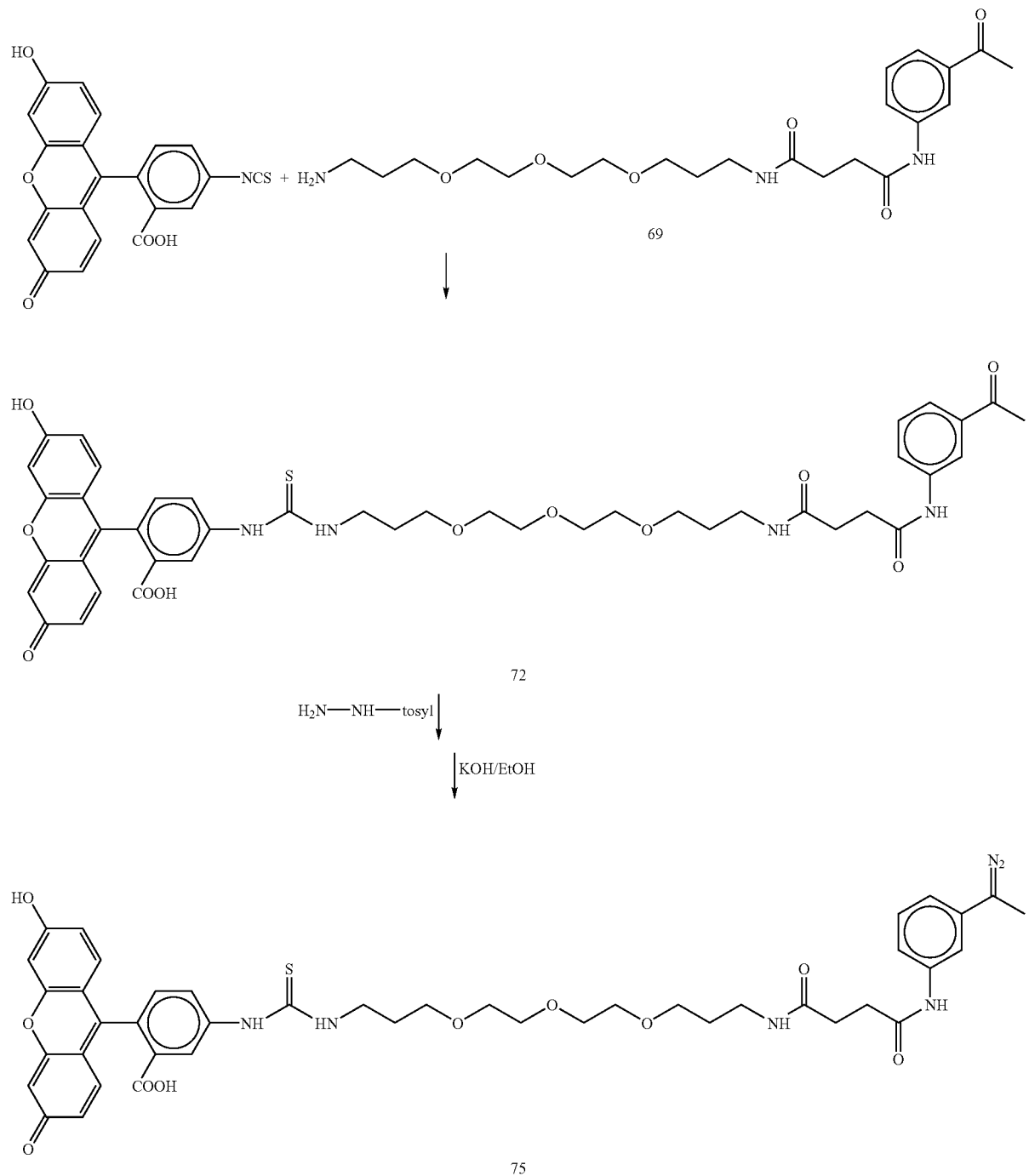

Compound 72: meta-Fluo-EG$_3$-PDAM 74

Fluorescein isothiocyanate (250 mg, 0.64 mmol) is solubilized in 1.6 ml of anhydrous DMF, with 2% of pyridine, under argon. The product 69 (0.356 g, 0.81 mmol), dissolved in 1.6 ml of anhydrous DMF, is added. The mixture is allowed to react for 3.5 h at room temperature, and then the DMF is evaporated and the residue is taken up in 25 ml of H$_2$O. Three extractions are then made with 50 ml Of CH$_2$Cl$_2$, and the aqueous phase is evaporated. 255 mg (48%) of product 72 are obtained.

meta-Fluo-EG$_3$-Hydrazone-Tosyl compound 75:

Compound 72 (255 mg, 0.31 mmol) is dissolved in 1.5 ml of ethanol under reflux. p-Toluenesulfonyl-hydrazine (69.2 mg, 0.37 mmol) in 1.5 ml of ethanol is added and the mixture is allowed to react for 6 h. The mixture is evaporated to dryness, and the solid is washed with $CH_2Cl_2$, $H_2O$ and ether. 18.5 mg (74%) of product 75 are obtained in the form of an orange powder.

$^1H$ NMR (200 MHz, DMSO-$d_6$): δ=1.6-1.8 (m, 4H); 2.13 (S, 1H); 2.28 (s, 1H); 2.36 (S, 1H); 2.80 (m, 1H); 3.07 (m, 2H); 3.46 (m, 12H); 6.5-6.7 (m, 6H); 7.1-8.3 (m, 9H).

meta-Fluo-EG$_2$-PMDAM compound 74:

The hydrazone 75 (176 mg, 0.18 mmol) is solubilized in 720 μl of a 10% KOH solution in anhydrous methanol. The solution is kept under reflux for 3 h. The solution is allowed to cool and a precipitate appears. The solution is filtered and evaporated to dryness. The residue is washed with ether and dried.

The NMR analysis shows the disappearance of signals at 2.36 and 2.13 ppm (corresponding to the methyls of the tosyl and of the hydrazone) and the appearance of a peak at 1.96 ppm (corresponding to the methyl of the diazo).

EXAMPLE 33

Diazomethyl Intermediate Allowing Subsequent Labeling

It may be advantageous to have not a direct labeling with the diazomethyl labeling reagent also carrying the marker $R^2$ but to proceed in two stages with an indirect labeling. In this case, the labeling reagent comprising the diazomethyl functional group is said to be prefunctionalized, that is to say that it also comprises a chemical functional group capable of subsequently reacting with direct or indirect markers. The prefunctionalization may occur by introducing a reactive covalent functional group into the labeling reagent which may react with an anti-reactive covalent functional group of the direct or indirect marker. These functional groups may consist of an electrophilic organic chemical functional group and a nucleophilic organic chemical functional group, or conversely.

An example of such a labeling strategy is illustrated by the scheme below

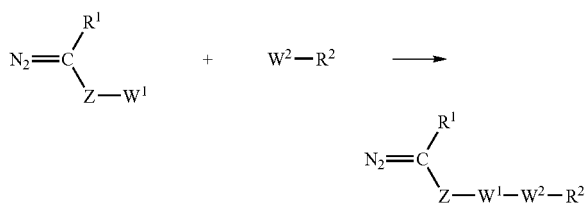

in which the labeling reagent comprises, in addition to a diazomethyl functional group, an electrophilic or nucleophilic functional group $W^1$ capable of reacting with a marker $R^2$ comprising a functional group $W^2$ complementary to $W^1$.

For example, if $W^1$ is a methyl ketone or aldehyde functional group, $W^2$ is an alkoxyamine functional group.

In a method for labeling a biological molecule such as a nucleic acid, the nucleic acid is brought into contact with the labeling reagent comprising the diazomethyl functional group and, in a subsequent step, the marker $W^2$—$R^2$ reacts with the nucleic acid via the functional group $W^1$.

One of the uses consists, for example, in a method for amplifying a sequence of a nucleic acid or in a method for signal amplification. Additional information on this type of labeling may be found in patent application WO-A-98/05766, under the priority of Aug. 2, 1996, and in patent application WO-A-00/40590 under the priority of Jan. 5, 1999.

Example 33.1

Synthesis of MeCO-PMDAM

Synthesis scheme:

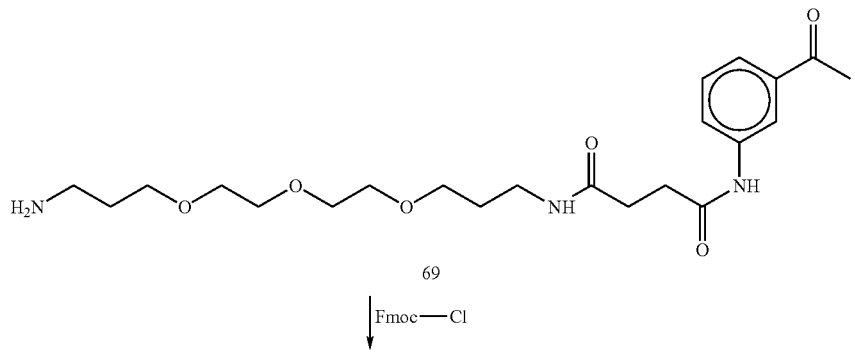

-continued
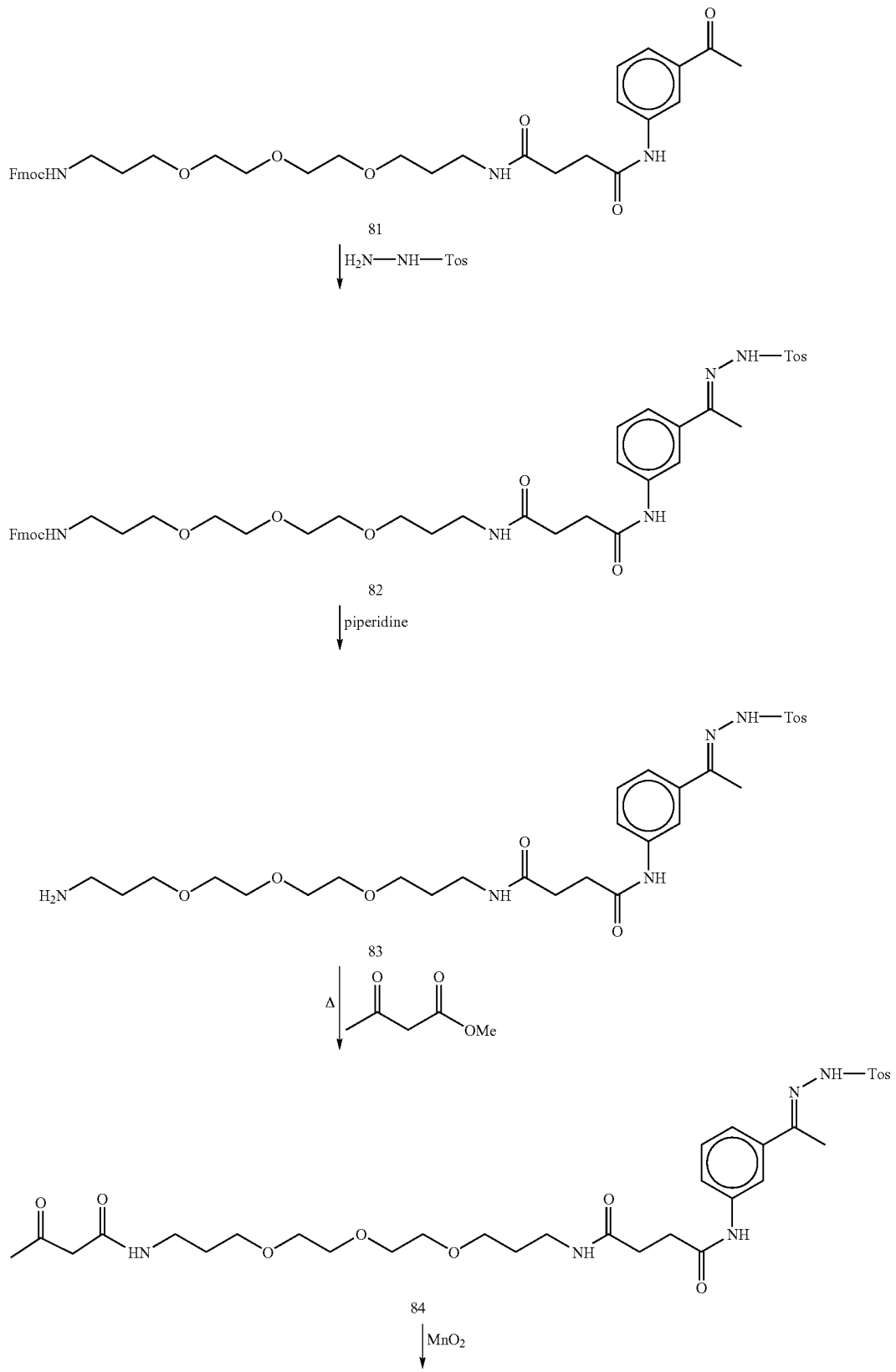

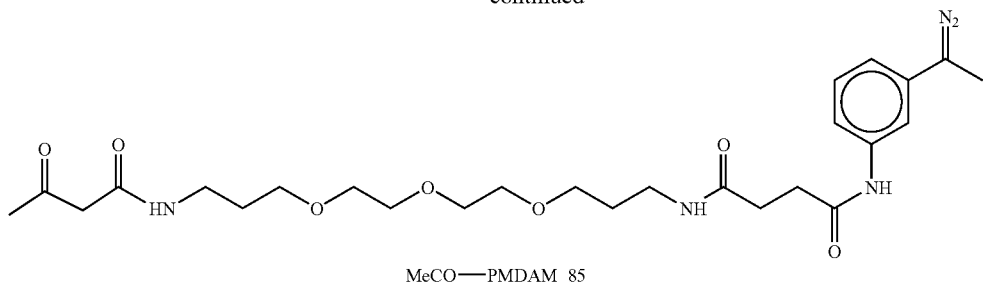

MeCO—PMDAM 85

Product 85, whose synthesis is described in this example, makes it possible to carry out the labeling of natural nucleic acids by virtue of the reactivity of the diazomethyl functional group with phosphate groups, and to thus introduce a methyl ketone functional group, which may be subsequently used to introduce a detectable (fluorescent, biotin) molecule possessing an alkoxyamine group.

This synthesis is based on known methods which are routinely used in chemistry. The starting material is the same as for the synthesis of the markers 71 and 74. The first step consists in the protection of the terminal amine with Fluorenylmethyl formate (Fmoc, 99). The choice of this protecting group is based on its stability and cleavage conditions.

99

After formation of the protected hydrazone 82 by the method previously used (meta-Fluo-EG$_3$-PMDAM example), the terminal amine is deprotected under gentle basic conditions which ensure the stability of the hydrazone. Methyl acetoacetate is used to create the methyl ketone functional group by a reaction of acylation of the terminal amine (see formation of compounds 26 and 36). The formation of the diazomethyl is then carried out by one of the methods described above.

Example 33.2

Synthesis of H$_2$NO-PMDAM

Synthesis scheme:

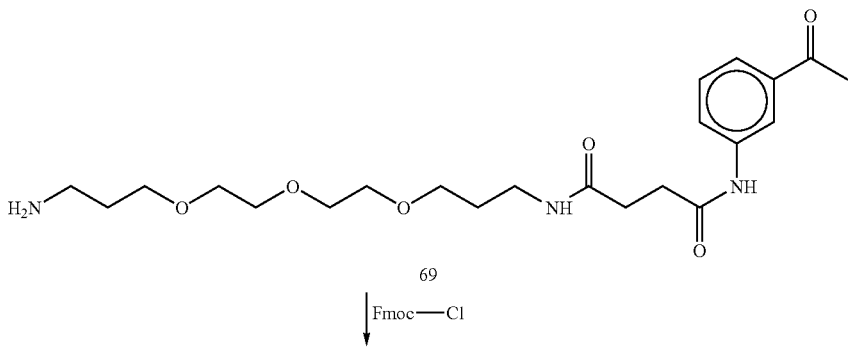

69

Fmoc—Cl

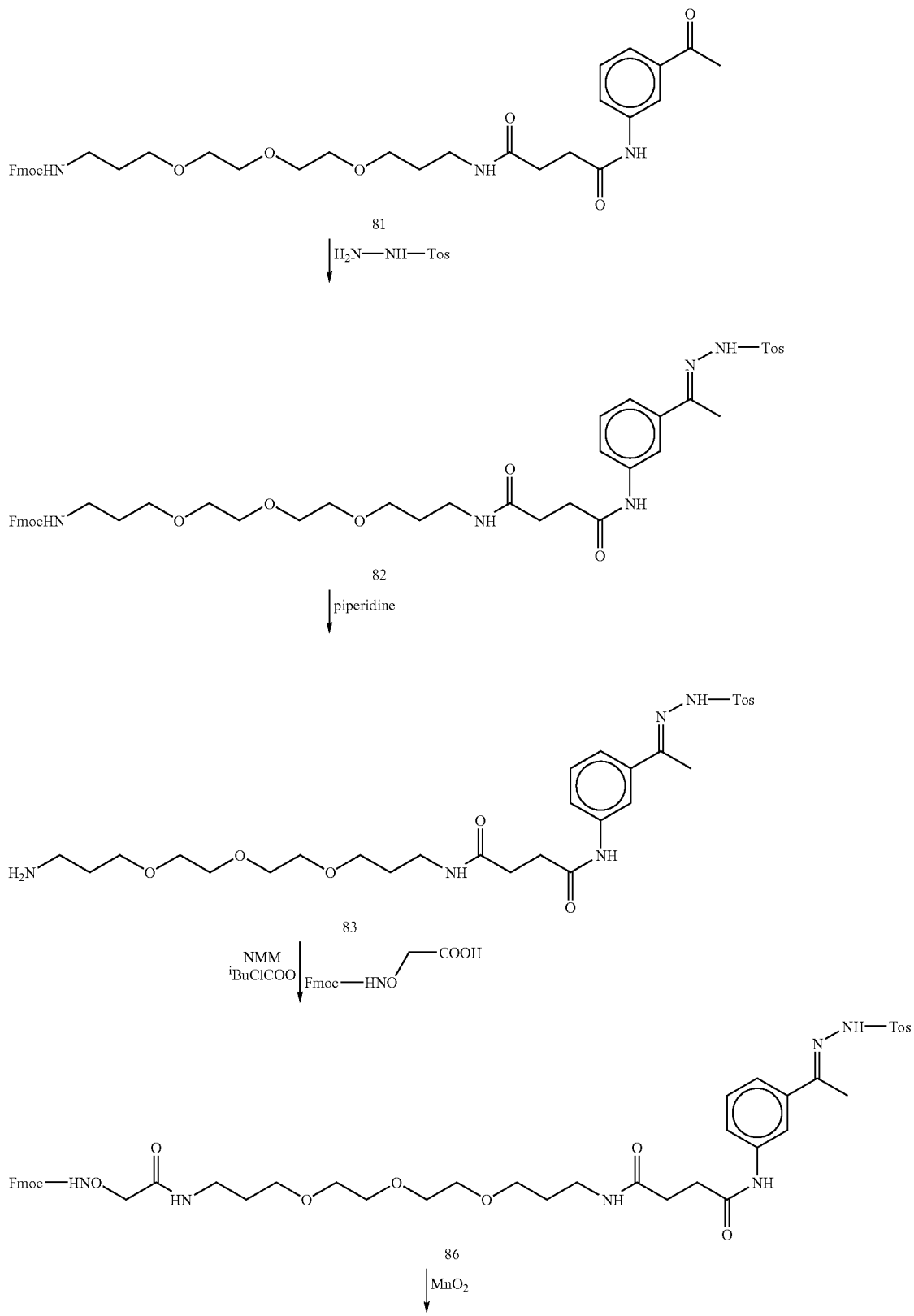

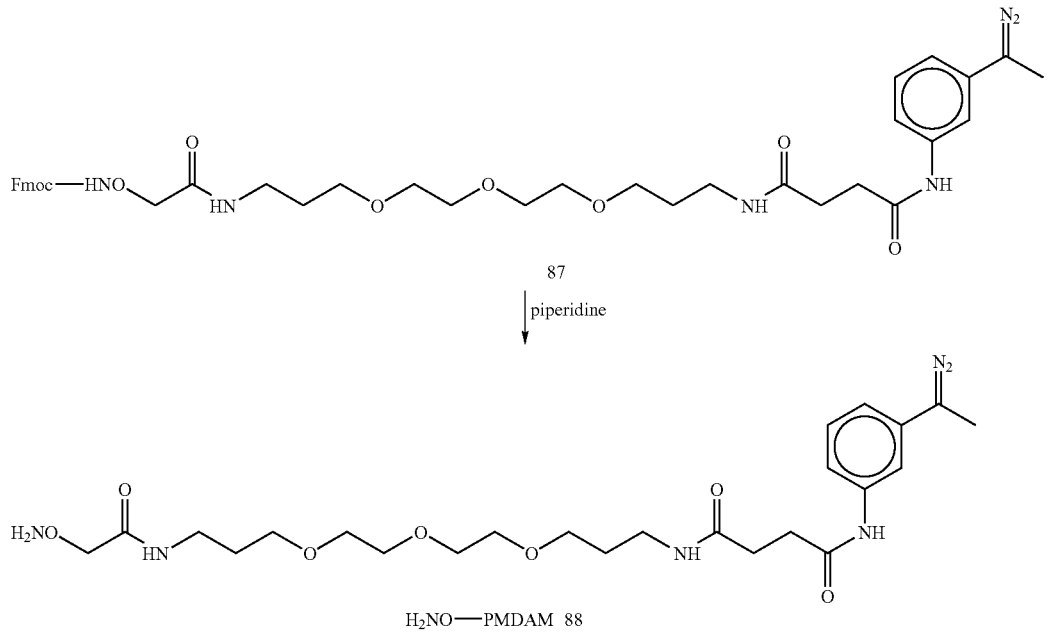

87

↓ piperidine

H₂NO—PMDAM 88

The product 88, whose synthesis is described in this example, makes it possible to carry out the labeling of natural nucleic acids, by virtue of the reactivity of the diazomethyl functional group with phosphate groups, and to thus introduce an alkoxyamine functional group, which may be subsequently used to introduce a detectable (fluorescent, biotin) molecule possessing a methyl ketone group.

This synthesis is based on the model of the preceding synthesis, that is to say the use of the precursor 69, of Fmoc for the protection of the amine and of tosyl for the protection of the hydrazone. The introduction of the alkoxyamine functional group (compound 86) takes place using the carboxymethoxylamine (commercial) protected by the Fmoc functional group (E. Trévisiol Thesis, LEDSS Grenoble, 1999). Given the gentle conditions for the final deprotection (compound 88), the latter is carried out immediately after the formation of the diazomethyl.

EXAMPLE 34

Preparation of the PDAM Derivatives Allowing the Amplification of the Signal

Example 34.1

Synthesis of the bis-biotinylated Markers such as [Bio-EG3]2-PDAM

Synthesis scheme:

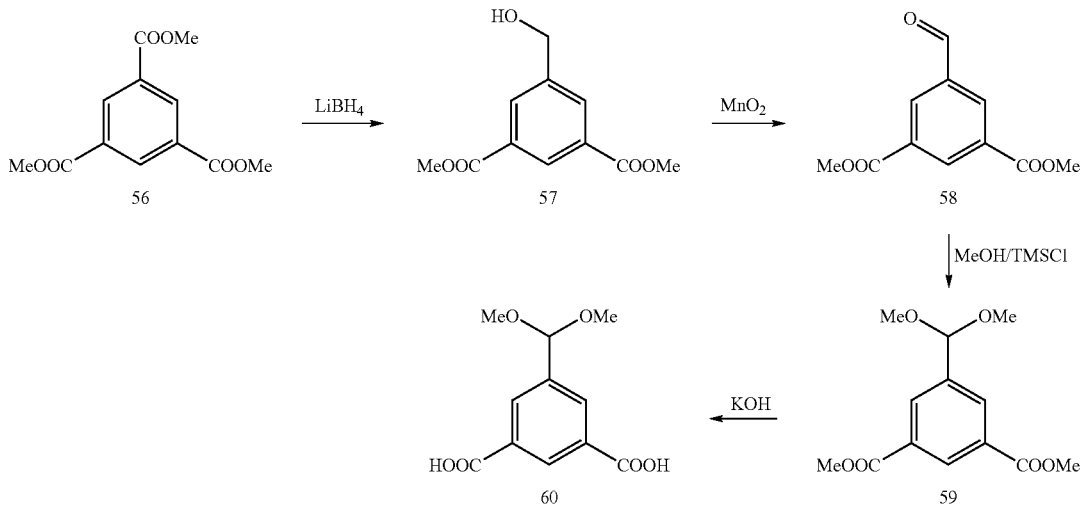

113 114
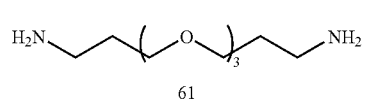 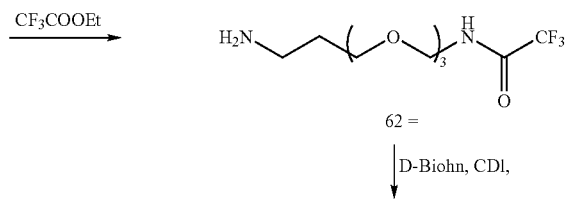
-continued
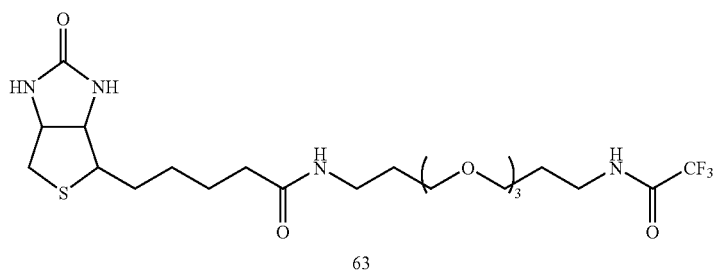
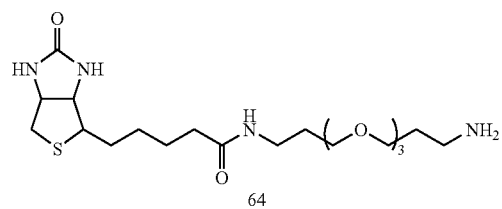
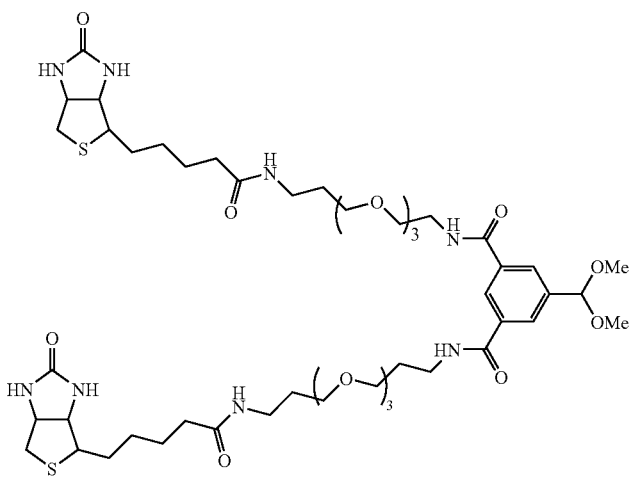

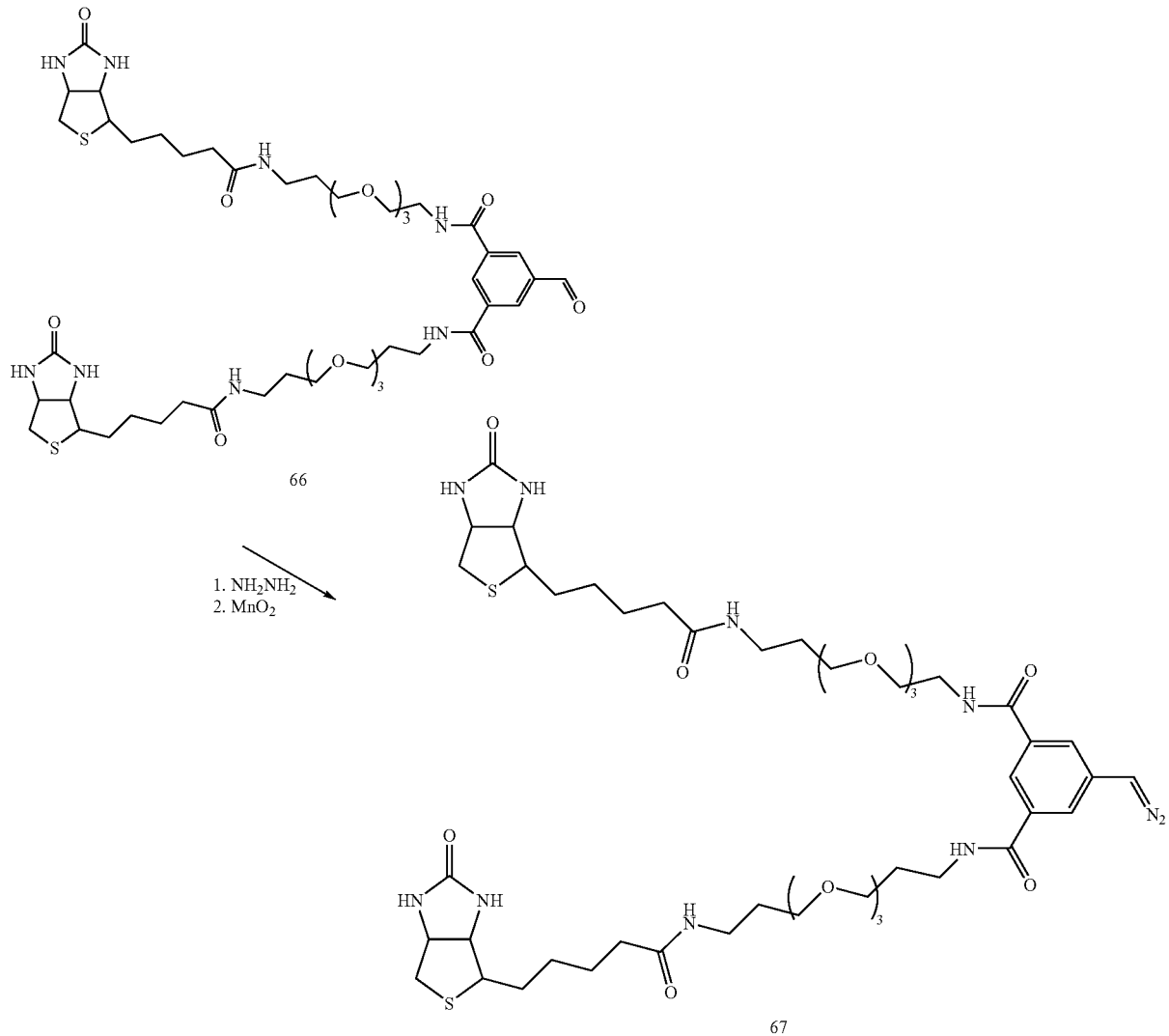

Reduction of trimethyl 1,3,5-benzenetricarboxylate 56 to the alcohol 57:

The triester 56 (12.6 g; 50.0 mmol) is dissolved in 100 ml of THF and then 1.1 g (50.5 mmol) of LiBH$_4$ are added at room temperature. The red solution is heated at 40-45° C., with stirring under argon, for 1 h. After cooling (ice), the excess hydride is carefully destroyed (emission of H$_2$) by addition of water (200 ml) and then of 2N HCl (30 ml). The change of color to light yellow is observed. This solution is extracted with CH$_2$Cl$_2$ (100 ml and then 3 times 50 ml), the organic phase is washed with anhydrous NaHCO$_3$, dried over MgSO$_4$, and then the solvent is evaporated until an oil (11.1 g) is obtained. Using flash chromatography on a silica column (diameter=40 mm, eluent: ethyl acetate/cyclohexane=1/1), the alcohol 57 (6.38 g, 57%) is obtained.

$^1$H NMR (200 MHz, CDCl$_3$): δ=8.53 (t, 1H, J=2 Hz); 8.18 (d, 2H, J=2 Hz); 4.76 (s, 2H); 3.91 (s, 6H); 2.30 (s, 1H).

Oxidation of the Alcohol 57 to Aldehyde 58:

The alcohol 57 (5.86 g; 26.1 mmol) is dissolved in 100 ml of THF and then 40.0 g of MnO$_2$ are added little by little over 5 min at room temperature. The solution is kept stirred overnight under argon. The solution is filtered through a Büchner funnel provided with a layer of celite 545, washed with CH$_2$Cl$_2$ and then the solvents are evaporated. The crude solid (4.4 g) is purified by flash chromatography on a silica column (diameter=50 mm, eluent: ethyl acetate/cyclohexane 3/7). 3.44 g (59%) of the aldehyde 58 are obtained.

$^1$H NMR (200 MHz, CDCl$_3$): δ=10.11 (s, 1H); 8.89 (t, 1H, J=1 Hz); 8.69 (d, 2H, J=1 Hz); 3.98 (s, 6H).

Formation of the Acetal 59:

The aldehyde 58 (3.21 g; 14.4 mmol) is dissolved in 30 ml of methanol and then 6.0 ml of TMSCl are added. The solution is kept stirred at room temperature under argon for 1 h. The solution is diluted with 200 ml of CH$_2$Cl$_2$, and stirred with 1M NaHCO$_3$ (100 ml) (caution emission of CO$_2$). The two phases are separated, the aqueous phase is extracted three times with CH$_2$Cl$_2$ (25 ml), the organic phases are combined, dried over MgSO$_4$ and then the solvent is evaporated. 3.55 g (92%) of the acetal 59 are obtained.

$^1$H NMR (200 MHz, CDCl$_3$): 8.63 (t, 1H, J=2 Hz); 8.29 (d, 2H, J=2 Hz); 5.45 (s, 2H); 3.93 (s, 6H); 3.32 (s, 6H).

Hydrolysis of the Diester 59 to the Diacid 60:

The diester 59 (3.18 g; 11.9 mmol) is dissolved in 10 ml of THF and then a KOH solution (2.0 g, pellet 85%) in 10 ml of methanol is added. After 15 min at room temperature, the solvents are evaporated. The residue is dissolved in $H_2O$ (50 ml). $H_3PO_4$ (about 2.5 ml, 85%) is added to pH 3 and the white precipitate is filtered on sintered glass (#3), washed with water and dried under vacuum. 2.59 g (91%) of the diacid 60 are obtained.

$^1$H NMR (200 MHz, DMSO-$d_6$): δ=8.43 (t, 1H, J=1 Hz) 8.15 (d, 2H, J=1 Hz); 5.53 (s, 1H); 3.27 (s, 6H).

Trifluoroacetamide 62:

The diamine 61 (66 g; 0.30 mol) is dissolved in 250 ml of $CH_2Cl_2$ and then ethyl trifluoroacetate (11.8 ml, 0.10 mol) is added dropwise over 5 min at 10° C. with stirring under argon. After 15 min at room temperature, the solution is transferred to a separating funnel, washed with $H_2O$ (3×100 ml), dried over $MgSO_4$ and the solvent evaporated. 22.4 g (71%) of the monoamide 62 having a purity of about 85% (determined by $^{19}F$ NMR) are obtained. This compound is stored at −20° C. and used without purification.

$^1$H NMR (200 MHz, CDCl$_3$): δ=3.5-3.6 (m, 12H); 3.42 (t, 2H, J=6 Hz); 2.75 (t, 2H, J=6 Hz); 1.81 (quantiplet, 2H, J=6 Hz); 1.67 (quantiplet, 2H, J=6 Hz); 1.30 (broad s, 2H). $^{19}F$ NMR (190 MHz, CDCl$_3$): δ=−76.3.

Compound 63:

To a suspension of D-biotin (6.39 g; 26.2 mmol) in 50 ml of DMF, carbonyldiimidazole (CDI, 6.32 g, 80%, 31.2 mmol) is added. The mixture is heated at 55-60° C., with stirring under argon, for 30 min. Complete dissolution of the material is initially observed followed by collection into a mass with precipitation of a white solid ($CO_2$ emission). The amine (oil) is added with the aid of 5 ml of $CH_2Cl_2$ in order to rinse and the mixture is heated at 55-60° C. for 3 h. The DMF is evaporated under vacuum (<1 mmHg) and the residue is stirred with $CH_2Cl_2$ (700 ml) and 2N HCl (100 ml). After filtration of the two phases through a layer of celite 545, the phases are separated, the aqueous phase is extracted with $CH_2Cl_2$ (15×100 ml), the organic phases are combined, dried over anhydrous $NaHCO_3$ and $MgSO_4$, and then the solvent is evaporated. The oily residue is triturated with 150 ml of ether to give a suspension. The pasty solid is difficult to filter. The supernatant is decanted off and the washing with ether is repeated. After drying under vacuum, 9.13 g (64%) of compound 63 are obtained.

$^1$H NMR (200 MHz, CDCl$_3$): δ=3.5-3.6 (m, 12H); 3.42 (t, 2H, J=6 Hz); 2.75 (t, 2H, J=6 Hz); 1.81 (quantiplet, 2H, J=6 Hz); 1,67 (quantiplet, 2H, J=6 Hz); 1.30 (broad s, 2H).

Compound 64:

A solution of compound 63 in aqueous ammonia (100 ml, 22% aqueous) is heated in a 250 ml round-bottomed flask with a septum at 55-60° C. for 2 h. After cooling, the solvent is evaporated. The residue is dissolved in methanol (20 ml) and passed over a column of Dowex 21K anion-exchange resin [height 12 cm×diameter 35 mm, OH$^-$ form obtained by prior washing with 1N NaOH (1.5 l) and then $H_2O$ (1.5 l) and then methanol (1.5 l)]. The compound 64 free of the trifluoroacetate ion passes in the first fractions with 200 ml of methanol. After evaporation, the residue is triturated with 50 ml of ether and then it is decanted off. The washing with ether is repeated five times in succession. After drying, the compound 64 (6.43 g, 86%) is obtained.

$^1$H NMR (300 MHz, CDCl$_3$): δ=6.77 (t, 1H, J=4 Hz); 6.32 (S, 1H); 5.52 (S, 1H): 4.45 (m, 1H); 4.28 (m, 1H), 3.50-3.68 (m, 12H); 3.30 (m, 2H), 3.11 (m, 1H); 2.86 (dd, 1H, J=13 and 5 Hz), 2.75 (t, 2H, J=13 Hz), 2.68 (d, 1H, J=13 Hz); 2.16 (t, 2H, J=7 Hz); 1.60-1.85 (m, 8H); 1.41 (m, 2H).

[Bio-EG$_3$]$_2$-acetal 65:

To a suspension of the diacid 60 (120 mg; 0.500 mmol) in dichloroethane (5 ml), carbonyl-diimdazole (225 mg, 90%, 1.25 mmol) is added and the mixture is heated at 55-60° C. for 30 min, with stirring under argon. The amine 64 (550 mg; 1.23 mmol) is added and the solution is heated at 55-60° C. for 6 h. After evaporation, the residue is passed over a silica column (diameter: 25 mm, eluent: methanol 15-30% in $CH_2Cl_2$). 413 mg (75%) of compound 65 are obtained.

$^1$H NMR (300 MHz, CDCl$_3$): δ=8.34 (s, 1H); 8.06 (s, 2H); 7.87 (m, 2H); 6.85 (m, 2H); 6.60 (s, 2H); 5.93 (s, 2H) 5.40 (s, 1H); 4.45 (m, 2H); 4.27 (m, 2H), 3.43-3.68 (m, 24H); 3.31 (s, 6H); 3.25 (m, 4H), 3.08 (m, 2H); 2.83 (dd, 2H, J=13 and 5 Hz), 2.70 (t, 2H, J=13 Hz); 2.13 (t, 4H, J=7 Hz); 1.89 (quintuplet, 4H, J=7 Hz); 1.55-1.70 (m, 12H); 1,37 (m, 4H).

[Bio-EG$_3$]$_2$-aldehyde 66:

The acetal 65 (413 mg; 0.376 mmol) dissolved in methanol is treated with 2N HCl (0.5 ml). After evaporation and washing with ether, the aldehyde 66 (0.37 g, 90%) is obtained.

$^1$H NMR (300 MHz, DMSO-$d_6$): δ=10.11 (s, 1H); 8.82 (t, 2H, J=6 Hz); 8.62 (s, 1H); 8.47 (s, 2H); 7.73 (t, 2H, J=5 Hz); 4.30 (m, 2H); 4.11 (m, 2H), 3.30-3.60 (m, 24H); 3.06 (m, 6H); 2.80 (dd, 2H, J=12 and 5 Hz), 2.56 (t, 2H, J=12 Hz); 2.03 (t, 4H, J=7 Hz); 1.78 (quintuplet, 4H, J=7 Hz); 1.35-1.60 (m, 12H); 1.28 (m, 4H).

[Bio-EG$_3$]$_2$-PDAM 67:

The aldehyde 66 is converted to the diazomethane 67 according to the method used for the preparation of diazomethanes (Example 1).

The stability of the reagent is greater than 1 month at −20° C.

Example 34.2

Synthesis of meta-Bio7-EG3-PMDAM

Synthesis scheme:

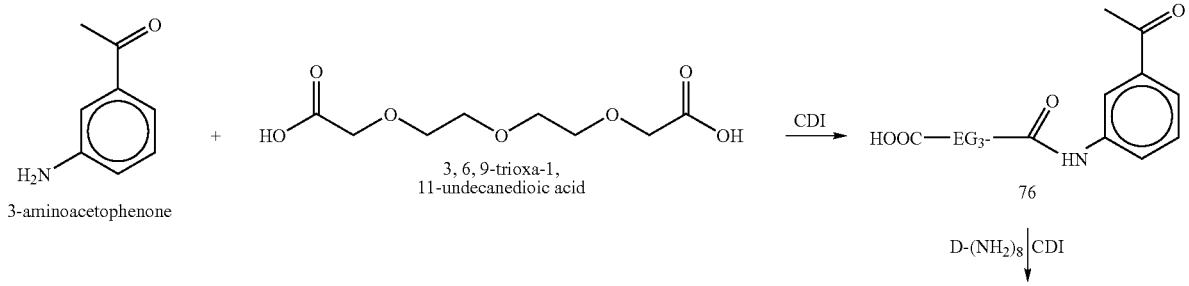

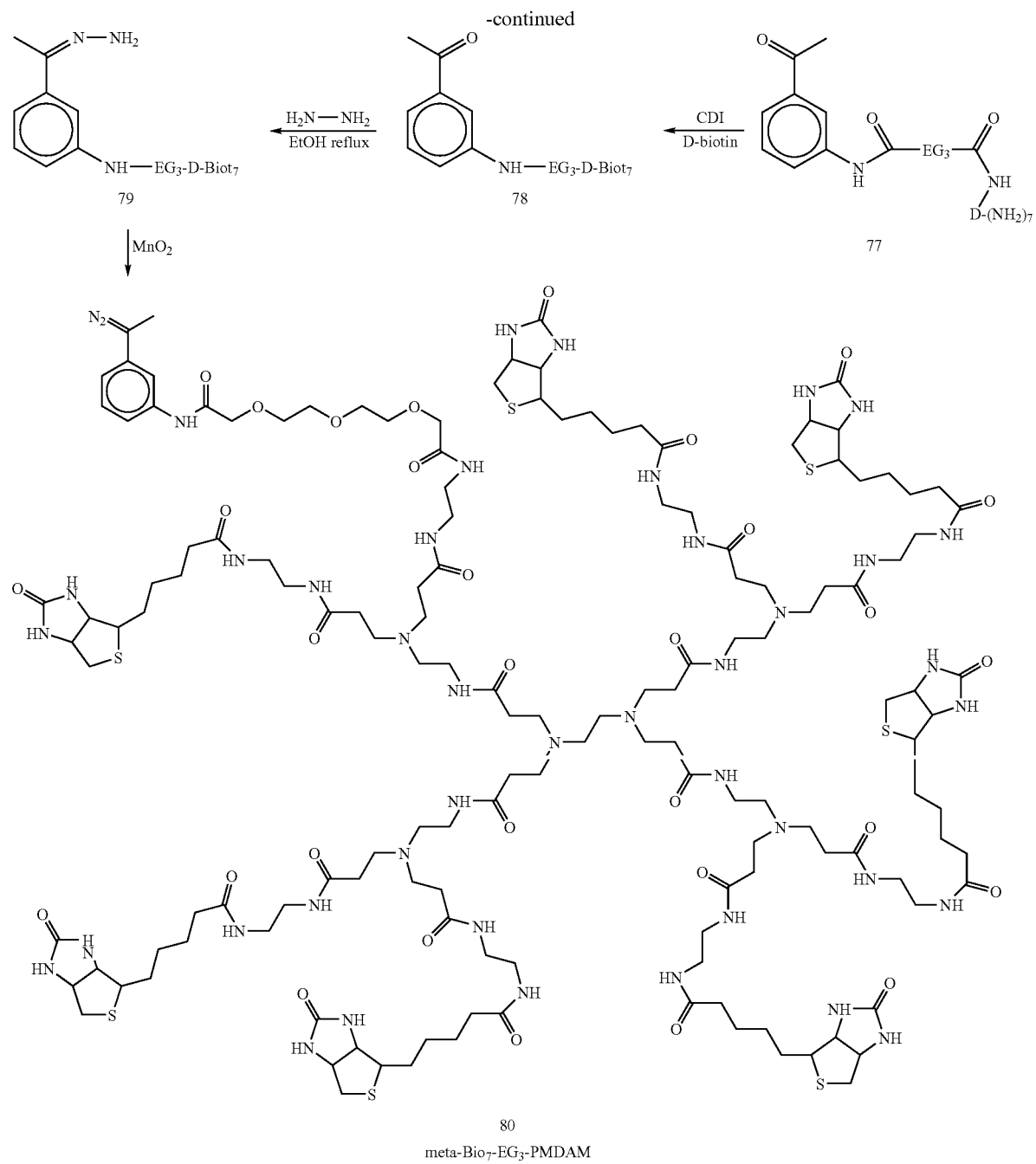

80
meta-Bio₇-EG₃-PMDAM

EG₃-acetophenone compound 76:

3,6,9-Trioxa-1,11-undecanedioic acid (EG₃, 12.64 ml, 74 mmol) is dissolved in 80 ml of anhydrous DMF under argon and cooled on an ice bath. Dicyclohexylcarbodiimide (DCC, 11.45 g, 55.5 mmol) is then dissolved in 20 ml of anhydrous DMF and slowly added. After 30 min, 3-aminoacetophenone (5.0 g, 37 mmol) is added and the reaction is allowed to proceed for 1 h at room temperature under argon. The DMF is then evaporated under vacuum and 70 ml of $CH_2Cl_2$ are added. The solution is filtered and extracted with 3×25 ml of 1% acetic acid. The aqueous phases are combined and washed with 25 ml of $CH_2Cl_2$. The organic phases are mixed, dried over anhydrous sodium sulfate and evaporated to dryness. The product is recrystallized from the MeOH: $H_2O$ pair. 8.74 g (70%) of product 76 are thus obtained.

$^1$H NMR (200 MHz, DMSO-d₆): δ=2.55 (s, 3H); 3.5-3.7 (m, 8H); 4.0 (s, 2H); 4.1 (s, 2H); 7.45 (t, 1H); 7.65 (d, 1H); 7.90 (d, 2H); 8.2 (s, 1H); 9.8 (s, 1H).

$(NH_2)_7$-EG₃-acetophenone compound 77:

The product 76 (120 mg, 0.35 mmol) is dissolved in 15 ml of anhydrous DMF under argon, cooled on ice, and DCC (110 mg, 0.53 mmol) is then added. After 30 min, this solution is added over a solution of the commercial dendrimer "Starburst PAMAM Dendrimer, Generation 1" (Aldrich, St Quentin Fallavier) (1 g, 0.71 mmol, in 5 ml of methanol), slowly and with vigorous stirring. The reaction is allowed to proceed for 1 h at room temperature and the mixture is evaporated. The residue is taken up in 10 ml of $CH_2Cl_2$ and extracted twice with 30 ml of 1% acetic acid.

Biot$_7$-EG$_3$-acetophenone compound 78:

D-biotin (1.73 g, 7.08 mmol) is solubilized in 80 ml of anhydrous DMF under argon, and the solution is cooled on ice. N-methylmorpholine (NMM, 856 µl, 7.7 mmol) and isobutyl chloroformate (1 022 µl, 7.7 mmol) are successively added. After 30 min, the product 77 (1.13 g, 0.7 mmol, in 5 ml of methanol) is added and the reaction is allowed to proceed for 3 h on ice and under argon. The mixture is concentrated under vacuum to 50 ml and 100 ml of $CH_2Cl_2$ are added. A precipitate forms, which is filtered, washed with ether and dried under vacuum. 1.3 g of 78 are obtained in the form of a white powder.

Biot$_7$-EG$_3$-Hydrazone compound 79:

The compound 78 (300 mg, 0.09 mmol) is dissolved in 10 ml of absolute ethanol under reflux. Hydrazine monohydrate (20 ml, 0.40 mmol) is added and the reaction is allowed to proceed for 3 h under reflux. After cooling, a precipitate forms, which is filtered, washed with ether and dried under vacuum. 109 mg (36%) of the product 79 are thus obtained in the form of a white powder.

Biot$_7$-EG$_3$-PMDAM compound 80:

The hydrazone 79 (100 mg, 0.03 mmol) is solubilized in 5 ml of anhydrous DMF at 70° C. The mixture is allowed to return to room temperature and $MnO_2$ (31 mg, 0.36 mmol) is added. The reaction is allowed to proceed for 10 min and the manganese oxide is removed by filtration on sintered glass with celite (0.5 cm) and powdered molecular sieve (0.5 cm). The filtrate is evaporated to dryness, washed with ether and dried under vacuum. 78 mg (78%) of product 80 are thus obtained.

Dendrimers are arborescent molecules possessing, at the ends, several reactive groups such as amines, carboxyls, hydroxyls and the like (for a review, see Newcome et al., (1996) *Dendritic Molecules: Concept, Syntheses, Perspectives.* VCH Ed., Weinheim, Germany). The synthesis of these molecules is nowadays perfectly controlled, and many dendrimers are marketed by the chemical industry. The choice of PAMAM (Sigma-Aldrich) was made on the basis of its stability, solubility and flexibility, since several versions of this molecule, with different number and type of endings, are available. "PAMAM Generation 1" makes it possible to add seven molecules of the marker (in a single synthesis step) for each diazomethyl group.

EXAMPLE 35

Labeling and Fragmentation in Two Steps of DNA Amplicons with meta-BioPMDAM

The DNA amplicons were prepared by PCR amplification according to the protocol described in Example 5.1. Two labeling reactions were carried out.

a. Labeling and Fragmentation in Two Steps:

To 10 µl of PCR there are added 10 µl of meta-BioPM-DAM (100 mM in DMSO) and 77 µl of DNase/RNase-free water. The solution is incubated for 10 min at 95° C. 3 µl of 0.1M HCl are then added and the solution is incubated for 10 min at 95° C.

b. Labeling and Fragmentation in One Step:

To 10 µl of PCR there are added 10 µl of meta-BioPM-DAM (100 mM in DMSO), 5 µl of 0.1M HCl and 75 µl of DNase/RNase-free water. The solution is incubated for 30 min at 60° C.

The remainder of the protocol is identical to that of Example 17.

Results:

TABLE 25

Comparative study of the labeling and fragmentation in two distinct steps and in a single step

| Protocol used | Homology (%) | I (rfu) | B (rfu) | I/B |
|---|---|---|---|---|
| a. Labeling and fragmentation in two steps | 99.5 | 14129 | 624 | 22.7 |
| b. Labeling and fragmentation in one step | 98.9 | 4431 | 667 | 6.6 |

As demonstrated in Table 25, the results obtained with the protocol in one step are satisfactory. Those obtained with a labeling and a fragmentation in two steps are even better. This example shows that the labeling and cleavage steps may be separated in order to improve the labeling according to the target used.

EXAMPLE 36

Labeling and Fragmentation of DNA Amplicons in Various Reaction Formats

The DNA amplicons were prepared by PCR amplification according to the protocol described in Example 5.1. Three labeling reactions were carried out.

a. Labeling and Fragmentation in a 250 µl Format:

To 50 µl of PCR there are added 75 µl of meta-BioPM-DAM (100 mM in DMSO) and 102.5 µl of DNase/RNase-free water. The solution is incubated for 25 min at 95° C. 22.5 µl of 0.1M HCl are then added and the solution is incubated for 5 min at 95° C.

b. Labeling and Fragmentation in a 200 µl Format:

To 50 µl of PCR there are added 75 µl of meta-BioPM-DAM (100 mM in DMSO) and 52.5 µl of DNase/RNase-free water. The solution is incubated for 25 min at 95° C. 22.5 µl of 0.1M HCl are then added and the solution is incubated for 5 min at 95° C.

c. Labeling and Fragmentation in a 150 µl Format:

To 50 µl of PCR there are added 75 µl of meta-BioPM-DAM (100 mM in DMSO) and 2.5 µl of DNase/RNase-free water. The solution is incubated for 25 min at 95° C.

22.5 µl of 0.1M HCl are then added and the solution is incubated for 5 min at 95° C.

The remainder of the protocol is identical to that of Example 17.

Results:

TABLE 26

Labeling and fragmentation according to different formats

| Protocol used | Homology (%) | I (rfu) | B (rfu) | I/B |
|---|---|---|---|---|
| a. 250 µl format | 100.0 | 5606 | 549 | 10.2 |
| b. 200 µl format | 99.4 | 5886 | 557 | 10.6 |
| c. 150 µl format | 99.4 | 6800 | 537 | 12.7 |

The results obtained in terms of signal and percentage homology are very satisfactory in all cases. Furthermore, although the reaction format varies from 150 to 250 μl, the results have similar values.

This example shows a flexibility of the reaction format of the labeling protocol which can accept different volumes and in particular different volumes of amplification products.

EXAMPLE 37

Comparison Between a Protocol Using a Purification Step Before Fragmentation and a Protocol Using a Purification Step After Fragmentation The DNA amplicons were prepared by PCR amplification according to the protocol described in Example 5.1. Two labeling reactions were carried out.

a. Labeling, Purification and then Fragmentation of the DNA Amplicons:

To 10 μl of PCR there are added 10 μl of meta-BioPM-DAM (100 mM in DMSO) and 80 μl of DNase/RNase-free water. The solution is incubated for 10 min at 95° C. The purification is then carried out according to the protocol described in Example 17. To the solution of purified labeled amplicons 6 μl of 0.1M HCl are added. The solution is incubated for 10 min at 95° C. Four hundred (400) μl of hybridization buffer, preheated at 95° C. for 10 min, are added.

The composition of the hybridization buffer and the remainder of the protocol are identical to that of Example 17.

b. Labeling, Fragmentation and then Purification of the DNA Amplicons:

To 10 μl of PCR there are added 10 μl of meta-BioPM-DAM (100 mM in DMSO) and 77 μl of DNase/RNase-free water. The solution is incubated for 10 min at 95° C. 3 μl of 0.1M HCl are then added and the solution is again incubated for 10 min at 95° C. The remainder of the protocol is identical to that of Example 17.

Results:

TABLE 27

Comparison between a protocol using a purification step before fragmentation and a protocol using a purification step after fragmentation

| Protocol used | Homology (%) | I (rfu) | B (rfu) | I/B |
| --- | --- | --- | --- | --- |
| a. Purification before fragmentation | 98.9 | 6256 | 473 | 13 |
| b. Fragmentation before purification | 96.1 | 6066 | 556 | 11 |

This result, presented in Table 27, shows that the purification step may be introduced between the labeling and fragmentation steps. Furthermore, the introduction of purification between the labeling and fragmentation steps makes it possible to carry out the denaturation during the cleavage and to hybridize onto the chip all of the labeled amplicon fragments.

EXAMPLE 38

Synthesis of 2-nitro-para-BioPDAM

Synthesis scheme:

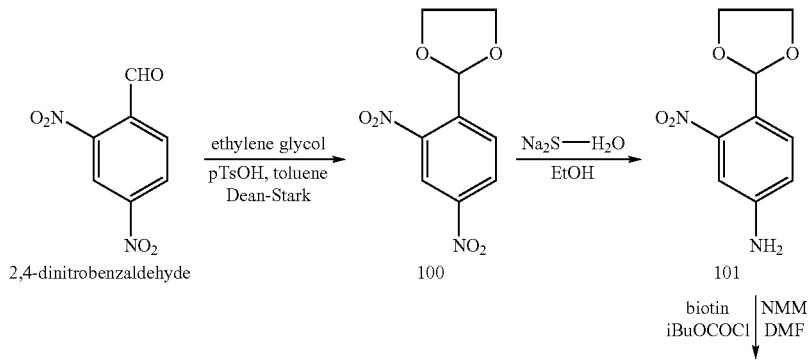

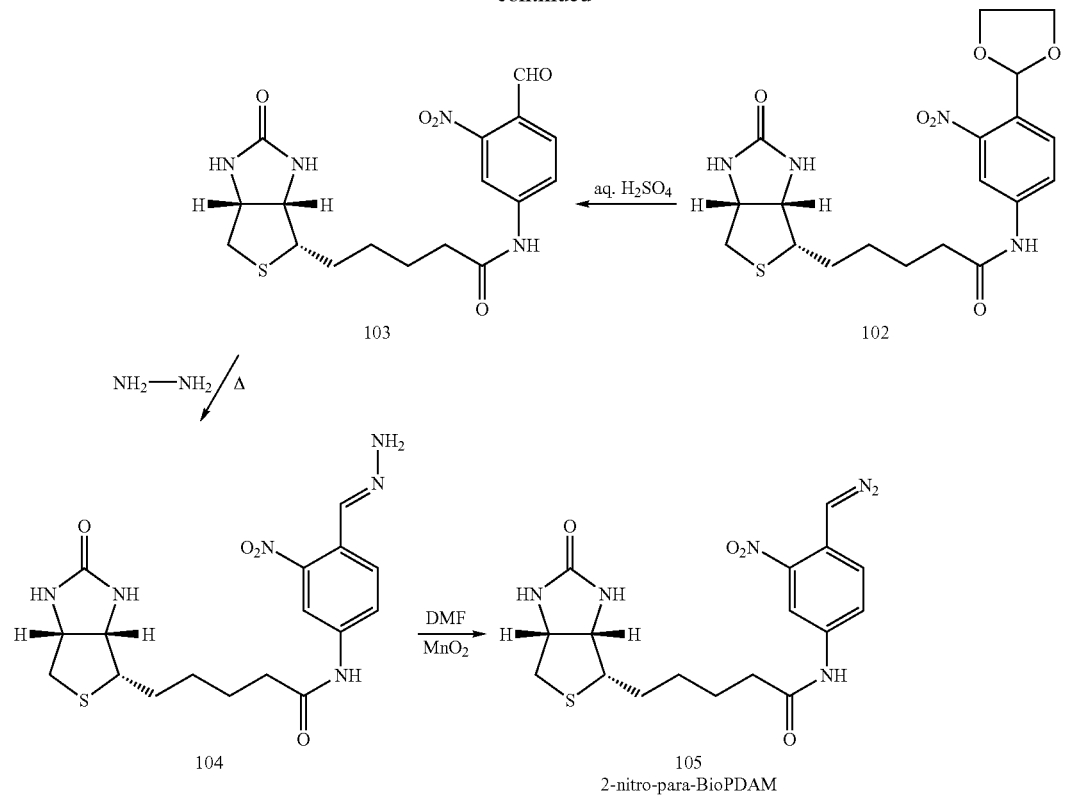

105
2-nitro-para-BioPDAM

Protection of the Aldehyde:

5 g (25.5 mmol) of 2,4-dinitrobenzaldehyde are dissolved in 250 ml of toluene, and 20 ml of ethylene glycol and 150 mg of para-toluenesulfonic acid are added. The mixture is heated under reflux, the water being recovered in a Dean-Stark system for 6 h. The mixture is treated with 150 ml of EtOAc and 100 ml of $H_2O$. The solution is extracted twice with ethyl acetate, the organic phase is dried with $MgSO_4$ and then evaporated. The oil obtained, corresponding to product 100, is used for the next reaction.

$^1$H NMR (200 MHz, $CDCl_3$): δ=8.70 (d, 1H$_{aro}$, J=2 Hz, H$_3$); 8.44 (dd, 1H$_{aro}$, J=2 Hz, J=6 Hz, H$_5$); 8.02 (d, 1H$_{aro}$, J=8 Hz, H$_6$); 6.49 (s, 1H, CH); 4.12-4.06 (m, 4H, $CH_2$—$CH_2$).

Reduction of the Dinitro Derivative 100:

The protected 2,4-dinitrobenzaldehyde (6.4 g; 25.5 mmol) is dissolved in an ethanol-water (6/1) mixture, and then 2 equivalents of $Na_2S$ nonahydrate (12.3 g; 51.1 mmol) are added. The reaction mixture is then heated for 30 min. Evaporation and then extraction using dichloromethane are carried out. After drying and filtration, the reaction medium is evaporated so as to obtain an oil which is directly purified on a silica column (cyclohexane/ethyl acetate 60/40). Compound 101 is isolated with a yield of 45%.

Compound 101: m.p. 58-60° C.—$^1$H NMR (200 MHz, $CDCl_3$): 7.49 (d, 1H$_{aro}$, J=2 Hz, H$_3$); 7.09 (d, 1H$_{aro}$, J=2 Hz, H$_6$); 6.80 (dd, 1H$_{aro}$, J=2 Hz, J=6 Hz, H$_5$); 6.27 (s, 1H, CH); 3.99-3.97 (m, 4H, $CH_2$—$CH_2$).

Coupling with Biotin:

D-biotin (1.0 g; 4.1 mmol) is solubilized in 20 ml of anhydrous DMF and 600 μl of N-methylmorpholine. Isobutyl chloroformate (700 μl; 5.5 mmol) is added under argon while cooling on an ice bath. The mixture is kept stirred for 5 min, and then 1 g (4.75 mmol) of compound 101 and 500 μl of N-methylmorpholine are added. The solution is kept stirred at room temperature for 4 h, and then evaporated to dryness. The oil obtained is directly passed over a silica column with, as elution solvent, MeOH-DCM 7% and then 10%. Product 102 (1.1 g; 2.52 mmol) is obtained with a yield of 62%.

$^1$H NMR (200 MHz, DMSO-d$_6$) δ=10.40 (s, 1H, NH—CO); 8.31 (d, 1H$_{aro}$, J=2 Hz, H$_3$); 7.77 (dd, 1H$_{aro}$, J=2 Hz, J=6 Hz, H$_5$); 7.68 (d, 1H$_{aro}$, J=2 Hz, H$_6$); 6.43 (broad s, 1H, NH—CO—NH); 6.36 (broad s, 1H, NH—CO—NH); 6.23 (s, 1H, CH); 4.28 (m, 1H, $CH_2$—CH—NH); 4.14 (m, 1H, CH—CH—NH); 3.92 (s, 4H, $CH_2$—$CH_2$); 3.12 (m, 1H, CH—S); 2.85 and 2.76 (system ABX, 2H, $^2J_{AB}$=5 Hz, $^3J_{AX}$=12 Hz, $^3J_{BX}$=0 Hz, $CH_2$—S); 2.29 (t, 2H, J=8 Hz, $CH_2$—CO); 1.61-1.39 (m, 6H, $(CH_2)_3$).

Deprotection of the Acetal:

The product 102 (768 mg; 1.76 mmol) is suspended in 25 ml of THF. The whole is dissolved after addition of 4 ml of 2N $H_2SO_4$. The mixture is kept stirred for 2 h. It is evaporated and then rinsed and washed with water on sintered glass. Compound 103 (694 mg) is obtained in the form of a yellow powder with a yield of 90%.

m.p. 165° C.—$^1$H NMR (200 MHz, DMSO-d$_6$) δ=10.69 (s, 1H, NH—CO); 10.09 (s, H, CHO); 8.43 (d, 1H$_{aro}$, J=2 Hz, H$_3$); 7.91 (s, 2H$_{aro}$, H$_5$ and H$_6$); 6.42 (broad s, 1H, NH—CO—NH); 6.35 (broad s, 1H, NH—CO—NH); δ=6.23 (s, 1H, CH); 4.29 (m, 1H, $CH_2$—CH—NH); 4.13 (m, 1H, CH—CH—NH); 3.12 (m, 1H, CH—S); 2.84 and 2.78

(system ABX, 2H, $^2J_{AB}$=5 Hz, $^3J_{AX}$=12 Hz, $^3J_{BX}$=0 Hz, CH$_2$—S); 2.29 (t, 2H, J=8 Hz, CH$_2$—CO); 1.61-1.39 (m, 6H, (CH$_2$)$_3$).

Formation of the Hydrazone 104:

The aldehyde 103 is suspended in ethanol and the suspension is heated to 80° C. When hydrazine is added, the whole dissolves and the solution is immediately colored orange. A precipitate forms after 5 min. The mixture is heated with stirring for 1 h. It is filtered on sintered glass and then the precipitate is dried. Product 104 (700 mg; 690 mmol) is obtained with a yield of 98%.

m.p. 169° C.—$^1$H NMR (200 MHz, DMSO-d$_6$) δ=10.31 (s, 1H, NH—CO); 8.31 (d, 1H$_{aro}$, J=2 Hz, H$_3$); 7.96 (s, H, CHO); 7.87 (d, 1H$_{aro}$, J=2 Hz, H$_6$); 7.68 (dd, 1H$_{aro}$, J=2 Hz, J=6 Hz, H$_5$); 7.31 (s, 2H, NH$_2$); 6.42 (broad s, 1H, NH—CO—NH); 6.34 (broad s, 1H, NH—CO—NH); 4.29 (m, 1H, CH$_2$—CH—NH); 4.13 (m, 1H, CH—CH—NH); 3.12 (m, 1H, CH—S); 2.84 and 2.78 (system ABX, 2H, $^2J_{AB}$=5 Hz, $^3J_{AX}$=12 Hz, $^3J_{BX}$=0 Hz, CH$_2$—S); 2.29 (t, 2H, J=8 Hz, CH$_2$—CO); 1.61-1.39 (m, 6H, (CH$_2$)$_3$).

Formation of the Diazo 105:

Compound 104 (200 mg; 0.492 mmol) is dissolved in 8 ml of DMF. 400 mg of MnO$_2$ are added. The mixture is vigorously stirred for 10 min. It is filtered on millipore containing celite (thickness: 2 cm) and powdered molecular sieve 3 Å (0.5 cm). It is evaporated to dryness and then washed with ether. The mixture is again filtered on millipore. Compound 105 (180 mg; 0.445 mmol) is obtained in the form of an orange powder with a yield of 98%.

m.p. 155° C.—$^1$H NMR (200 MHz, DMSO-d$_6$) δ=10.21 (s, 1H, NH—CO); 8.60 (d, 1H$_{aro}$, J=2 Hz, H$_3$); 7.77 (d, 1H$_{aro}$, J=6 Hz, H$_5$); 7.22 (d, 1H$_{aro}$, J=6 Hz, H$_6$); 6.60 (s, H, CH—N); 6.41 (broad s, 1H, NH—CO—NH); 6.33 (broad s, 1H, NH—CO—NH); 4.29 (m, 1H, CH$_2$—CH—NH); 4.13 (m, 1H, CH—CH—NH); 3.12 (m, 1H, CH—S); 2.84 and 2.78 (system ABX, 2H, $^2J_{AB}$=5 Hz, $^3J_{AX}$=12 Hz, $^3J_{BX}$=0 Hz, CH$_2$—S); 2.29 (t, 2H, J=8 Hz, CH$_2$—CO); 1.61-1.39 (m, 6H, (CH$_2$)$_3$).

The reactivity of compound 105 was tested on uridine 3'-monophosphate followed by capillary electrophoresis. The analytical conditions are those of Example 6.1. The results show a half-reaction period of 45 minutes.

The stability of the reagent is greater than 1 month at −20° C.

EXAMPLE 39

Labeling of RNA with the 2-nitro-para-BioPDAM derivative

The 2-nitro-para-BioPDAM derivative 105 was prepared according to the protocol described in Example 38. The RNA transcripts were obtained according to the protocol described in Example 5.2. The labeling and fragmentation method is carried out in a single step with the 2-nitro-para-BioPDAM reagent under the conditions described in Table 28 below. Two labeling reactions were carried out:

a. Labeling with the 2-nitro-para-BioPDAM derivative:

To 10 μl of transcripts there are added 2 μl of 2-nitro-para-BioPDAM (100 mM in DMSO), 3 μl of imidazole (1M in water). 5 μl of MnCl$_2$ and 85 μl of DNase/RNase-free water. This solution is incubated for 10 min at 60° C.

The remainder of the protocol is identical to that of Example 8.

b. Labeling with the meta-BioPMDAM reagent:

To 10 μl of transcripts there are added 2 μl of meta-BioPMDAM (100 mM in DMSO), 3 μl of imidazole (1M in water), 5 μl of MnCl$_2$ and 85 μl of DNase/RNase-free water. This solution is incubated for 10 min at 60° C.

The remainder of the protocol is identical to that of Example 8.

Results:

TABLE 28

Comparative study of the labeling of RNA with the 2-nitro-para-BioPDAM derivative compared with the meta-BioPMDAM derivative

| Protocol used | Homology (%) | I (rfu) | B (rfu) | I/B |
|---|---|---|---|---|
| 30 mM Im pH 9.5; 5 mM MnCl$_2$ 2 mM 2-nitro-para-BioPDAM 5 min at 60° C. | 98.9 | 14911 | 656 | 22.7 |
| 30 mM Im pH 9.5; 5 mM MnCl$_2$ 2 mM meta-BioPMDAM 10 min at 60° C. | 98.4 | 13611 | 694 | 19.6 |

It can indeed be seen in Table 28 that the 2-nitro-para-BioPDAM derivative gives good labeling results on the RNAs. Substitutions such as the nitro group may be used to modulate the reactivity and the stability of the markers carrying the diazomethyl functional group.

EXAMPLE 40

Labeling and Fragmentation of the DNA Amplicons with the Labeling Reagent 2-nitro-para-BioPDAM The 2-nitro-para-BioPDAM derivative was obtained according to the reaction scheme described in Example 38. The DNA amplicons were prepared by PCR amplification according to the protocol described in Example 5.1. Two labeling reactions were carried out.

a. Labeling with the 2-nitro-para-BioPDAM reagent:

To 10 μl of PCR there are added 2 μl of 2-nitro-para-BioPDAM (100 mM in DMSO), 5 μl of 0.1M HCl and 83 μl of DNase/RNase-free water. This solution is incubated for 30 min at 60° C.

b. Labeling with the meta-bioPMDAM reagent:

To 10 μl of PCR there are added 2 μl of meta-BioPMDAM (100 mM in DMSO), 5 μl of 0.1M HCl and 83 μl of DNase/RNase-free water. This solution is incubated for 30 min at 60° C.

The remainder of the protocol is identical to that of Example 17.

Result:

TABLE 29

Comparative study of the labeling of DNA with the 2-nitro-para-BioPDAM derivative compared with the meta-BioPMDAM derivative

| Protocol used | Homology (%) | I (rfu) | B (rfu) | I/B |
|---|---|---|---|---|
| a. Labeling with the 2-nitro-para-BioPDAM reagent | 100.0 | 24392 | 899 | 27.1 |
| b. Labeling with the meta-BioPMDAM reagent | 98.9 | 21883 | 774 | 28.3 |

The 2-nitro-para-BioPDAM reagent used for the labeling of the DNA gives advantageous results in terms of labeling intensity and percentage homology.

EXAMPLE 41

Insertion of a Double Bond Between the Diazomethyl Functional Group and the Phenyl Nucleus, Distancing of the DAM and Synthesis of a Molecule which is Particularly Suitable for this Distancing The objective aimed at is the distancing of the diazomethyl (DAM) functional group of the aromatic structure in order to minimize the effect of steric hinderance during the alkylation of the phosphates and also during the hybridization of the labeled nucleic acid with its complementary sequence.

For the aldol reaction for formation of (para-methoxycarbonyl)styrylmethyl methoxycarbonyl)styrylmethyl ketone 89, ethyl acetoacetate is used for the high acidity of the protons of the methylene, which facilitates attack of the formyl group, with subsequent elimination of H$_2$O (promoted by the conjugation of the double bond with the aromatic ring) and decarboxylation with hydrolysis due to the basic medium. The remainder of the synthesis is similar to what was shown in the other examples.

The final product para-Bio-EG$_3$-SMDAM 90 possesses two more carbons between the diazomethyl and the aromatic ring, which limits the possible steric problems, while preserving the stabilization of the diazomethyl by the aromatic system by conjugation.

Synthesis scheme:

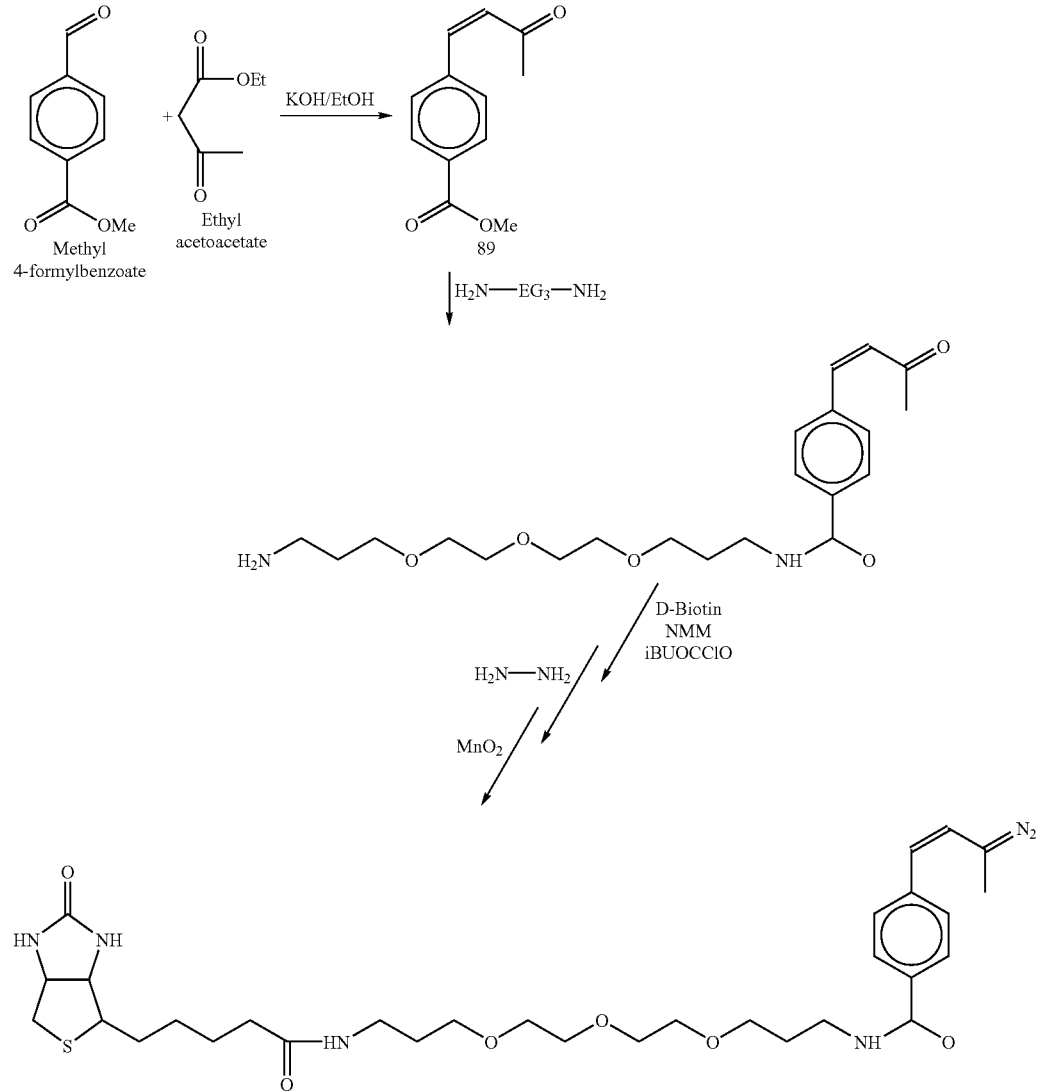

EXAMPLE 42

Capture and Detection of a Nucleic Acid on a Solid Support Carrying Diazomethyl Groups The reactivity of a resin carrying diazomethyl groups was studied to determine its capacity to bind nucleic acids.

4-(Diazomethyl)phenoxymethylpolystyrene (reference 17338, Fluka) is a resin described for its capacity to bind carboxyl groups, in particular those present in proteins (G. Bhalay, A. R. Dunstan, Tetrahedron Lett. 39, 7803-1998), but it is not described for its capacity to bind DNA molecules. We tested the possibility of capturing nucleic acids with this reagent, and of visualizing them by a calorimetric test.

The experiment is carried out with a portion of the reagents present in the HLA-DR oligo-detection kit (reference 33 202, bioMérieux, France, basic principle described in patent EP 549 776-B1), allowing the detection of nucleic acids amplified by PCR in microplates, by calorimetric reading. In the context of the experiment described, nucleic acids produced by PCR are caused to simultaneously react with the resin tested, and with a molecule of para-Bio-EG3-PDAM, whose synthesis is mentioned in Example 28. If the DNA reacts with the diazomethyl functional groups present on the two compounds, it will be possible to visualize it, after washing and removing the molecules which are non-covalently bound, using a calorimetric reaction involving an enzyme coupled to streptavidin. The streptavidin is combined with horseradish peroxidase, it being possible for this enzyme to decompose an OrthoPhenyleneDiamine molecule (Color 1 reagent of the kit) to a compound which can be detected at a wavelength of 492 nm.

Example 42.1

Capture and Detection of the DNA 10 mg of resin are incubated for 30 minutes at 60° C. with 50 µl of PCR performed as described in Example 5.1, in 400 µl of pure water (Sigma) supplemented with 5 µl of para-Bio-EG3-PDAM. This resin is then washed with 500 µl of PBS Tween buffer (Color 0 HLA reagent of the kit, PBS pH 7.0; 1% Tween, 0.2 g/l BND; 0.01 g/l Ciproflaxacin). The resin is then resuspended in 100 µl of PBS Tween, and 250 µl of streptavidin hybridization buffer (PBS pH 7.0 0.5% TWEEN) supplemented with streptavidin HRP(S-911, MOLECULAR PROBES, EUGENE, OREG., USA) diluted 1/10 000. The reaction mixture is incubated for 30 min at room temperature. The resin is then washed three (3) times with 500 µl of PBS Tween buffer, and it is incubated at room temperature in the presence of a chromogenic reagent (1 Color 1 Tablet, ortho-phenylenediamine hydrochloride, diluted in 5 ml of Color 2 buffer, 100 mM sodium phosphate, 50 mM citric acid, 0.03% $H_2O_2$) After an incubation of 20 min in the dark, the reaction is then blocked with 50 µl of $H_2SO_4$ (1.8N Color 3reagent). The supernatant is then pipetted and placed in a microplate in order to read the absorbence of the reaction medium at 492 nm.

Example 42.2

Control Without Nucleic Acid 10 mg of resin are incubated for 30 minutes at 60° C. in 425 µl of pure water (Sigma) supplemented with 5 µl of Dara-Bio-EG3-PDAM. This resin is then washed with 500 µl of PBS buffer. The sample is then treated in a manner identical to the procedure described in Example 42.1.

Example 42.3

Control with PCR Carried out Without Targets 10 mg of resin are incubated in 400 µl of pure water supplemented with 5 µl of para-Bio-EG3-PDAM for 30 minutes at 60° C., with 50 µl of PCR performed with a volume of 25 µl of pure water in place of the volume of the genomic DNA described. This resin is then washed with 500 µl of PBS buffer. The sample is then treated in a manner identical to the procedure described in Example 42.1.

Example 42.4

Control with PCR Without a Revealing Molecule 10 mg of resin are incubated with 50 µl of PCR in 400 µl of pure water for 30 minutes at 60° C. This resin is then washed with 500 µl of PBS buffer. The sample is then treated in a manner identical to the procedure described in Example 42.1.

Example 42.5

Control with Noncaptured Nucleic Acid 10 mg of resin are incubated for 30 minutes at 60° C. with 400 µl of pure water supplemented with 5 µl of para-Bio-EG3-PDAM. This resin is then washed with 500 µl of PBS Tween buffer (Color 0 HLA reagent of the kit, PBS pH 7.0; 1% Tween, 0.2 g/l BND; 0.01 g/l Ciproflaxacin). The resin is then resuspended in 100 µl of PBS Tween, and 250 µl of streptavidin hybridization buffer supplemented with streptavidin HRP diluted 1/10 000. To this preparation are added 50 µl of a DNA preparation prepared as follows:

5 µl of para-Bio-EG3-PDAM and 70 µl of pure water are added to 25 µl of DNA obtained from a PCR prepared as described in Example 5.1. This mixture is incubated for 30 min at 60° C., and then the excess marker is removed by subjecting the preparation to purification on a QIAquick column (Nucleotide Removal Kit, Qiagen, Hilden, Germany) according to the protocol recommended by the supplier, carrying out a final elution in a volume of 50 µl.

The reaction mixture is incubated for 30 min at room temperature, and then it is treated according to the procedure described in Example 42.1.

Results

TABLE 30

Study of the reactivity of a resin carrying diazomethyl groups

| Conditions | Absorbence at 492 nm |
| --- | --- |
| Ex. 42.1: DNA captured on Resin | 527 |
| Ex. 42.2: without nucleic acid | 249 |
| Ex. 42.3: PCR without target | 261 |
| Ex. 42.4: Control without marker | 264 |
| Ex. 42.5: Noncaptured nucleic acid | 249 |

In Table 30, a high calorimetric value indicates a high concentration of enzymes in the reaction medium, corresponding to a large presence of nucleic acid carrying biotin derivatives. The controls indicate that the signal is not due to a nonspecific adsorption of the DNA to the bead, to a reaction of the para-Bio-EG3-PDAM on the resin, or to an adsorption of the streptavidin HRP on the resin, but indeed to the presence of DNA captured covalently and labeled with para-Bio-EG3-PDAM.

EXAMPLE 43

Labeling of a PCR Product Allowing its Capture and its Detection in a Microplate The possibility of labeling a DNA molecule with only one type of molecule carrying a diazomethyl functional group, so as to capture and to detect this nucleic acid in a single step, on a microplate, is shown in this example.

The experiment is carried out with a portion of the reagents present in the HLA-DR oligo-detection kit (reference 33 202, bioMérieux), allowing the detection of nucleic acids amplifed by PCR in microplates, by calorimetric reading. In the context of the experiment described, para-Bio-EG3-PDAM, whose synthesis is described in Example 28, is reacted with nucleic acids produced by PCR. The DNA reacts with the diazomethyl groups of the molecule, and thus becomes equipped with biotins grafted on its phosphate. It will then be possible to capture the nucleic acid by incubation on a microplate where streptavidin molecules are adsorbed, and to visualize it by a calorimetric reaction. A detection reagent is used which is also a streptavidin molecule, combined with horseradish peroxidase (HRP). Under the conditions used, the peroxidase can decompose an OrthoPhenyleneDiamine molecule (Color 1 reagent of the kit) to a compound which can be detected at a wavelength of 492 nm.

Example 43.1

Capture and Detection of the DNA Derived from PCR, on a Microplate

10 µl of DNA obtained by PCR amplification as described in Example 5.1 are labeled by incubating them for 30 min at 60° C. in 80 µl of pure water (Sigma) supplemented with 10 µl of para-Bio-EG3-PDAM. After labeling, the DNA is purified on a QIAquick column (Nucleotide Removal Kit, Qiagen, Hilden, Germany) according to the protocol recommended by the supplier, and the final eluate is collected in 50 µl of EB buffer (10 mM Tris EDTA, pH 8.5). Twenty (20) µl of this eluate are diluted in 180 µl of PEG buffer (0.1M NaPO$_3$; 0.5M NaCl; 0.65% Tween 20; 0.14 mg/ml salmon sperm DNA (Gibco); 2% PEG 4000) supplemented with streptavidin HRP (S-911, Molecular Probes, Eugene, Oreg., USA) diluted to 1/10 000. One hundred (100) µl of this preparation are then incubated for 1 hour at 37° C., either in a well of a streptavidin-coated Combiplate 8 (reference 95029263, Labsystem, Helsinki, Finland) or in a control well, from a Maxisorb strip (Nunc, Denmark).

Example 43.2

Preparation of Controls

Controls are simultaneously prepared in the following manner:

A—Labeling Control Without DNA:

Ninety (90) µl of pure water supplemented with 10 µl of para-Bio-EG3-PDAM are incubated for 30 min at 60° C. The reaction mixture is then treated in a manner similar to the procedure described above in Example 43.1.

B—Labeling Control Without Markers:

Ten (10) µl of DNA obtained by PCR amplification, as described in Example 5.1, are incubated for 30 min at 60° C. in 90 µl of pure water. The reaction mixture is then treated in a manner similar to the procedure described above in Example 43.1.

All the strips are then washed with three times 100 µl of PBS Tween buffer (Color 0 HLA reagent of the kit, PBS pH 7.0; 1% Tween, 0.2 g/l BND; 0.01 g/l Ciproflaxacin) and the presence of streptavidin HRP is then visualized by addition of 100 µl of chromogenic reagent (1 Color 1 tablet, ortho-phenylenediamine hydrochloride, diluted in 5 ml of Color 2 buffer, 100 mM sodium phosphate, 50 mM citric acid, 0.03% H$_2$O$_2$), incubated for 20 min in the dark, the reaction then being blocked with 50 µl of H$_2$SO$_4$ (1.8N Color 3 reagent). The absorbence of the reaction medium is then measured at 492 nm.

Results:

TABLE 31

Detection of DNA captured and labeled with para-Bio-EG3-PDAM

| Conditions | Combiplate | Maxisorp control |
|---|---|---|
| A - labeled DNA | 1382 | 152 |
| B - nonlabeled DNA | 178 | 136 |
| C - without DNA | 140 | 192 |

The experiment, presented in Table 31, therefore shows that the DNA labeled with para-Bio-EG3-PDAM can be captured and detected in a single step in a microplate well. As the reaction controls indicate, the signal generated is only due to the DNA and does not result from a nonspecific adsorption of the nucleic acid to the wall of the microplate, or to streptavidin, or alternatively to a nonspecific reaction of streptavidin HRP with nonlabeled DNA, or with the plastic of the microplate.

EXAMPLE 44

Double Labeling of a PCR Product Allowing its Capture and its Detection on a Microplate Type Solid Support The possibility of labeling with two molecules, carrying diazomethyl functional groups, and in a single step, a DNA molecule, so as to capture it and to detect it on a microplate, is shown in this example.

The experiment is carried out with a portion of the reagents present in the HLA-DR oligo-detection kit, allowing the detection of nucleic acids amplified by PCR in microplates, by simple calorimetric reading. In the context of the experiment described:

1-pyrenyldiazomethane (PDAM), and para-Bio-EG3-PDAM.

are simultaneously reacted with nucleic acids produced by PCR.

If the DNA reacts with the diazomethyl functional groups present on the two compounds, it will be able to bind to a support carrying anti-pyrene antibodies, and it will be possible to visualize it with a streptavidin molecule combined with horseradish peroxidase. This enzyme can decompose a molecule of Ortho-PhenyleneDiamine, acting as revealing reagent, to a compound which can be detected at a wavelength of 492 nm.

Example 44.1

Double Labeling of the DNA and Detection on a Microplate

Anti-pyrene antibodies were adsorbed onto eight (8)-well Maxisorp strips by incubating overnight at room temperature 100 µl of a solution of 1.1 µl pf anti-pyrene antibodies diluted in 100 µl of bicarbonate buffer (0.05M pH 9.6). Such antibodies, called Rabbit anti-pyrene (Ref.: YSRT-AHP236) are available from Accurate Chemical & Scientific (Westbury, N.Y., United States of America). Of course, this might have been carried out with other commercially available antibodies, without there being divergent results compared with those which were obtained in this example.

10 µl of DNA obtained by PCR amplification, as described in Example 5.1, were then labeled by incubating them for 30 min at 60° C. in 40 µl of pure water (Sigma), 10 µl of para-Bio-EG3-PDAM, 2 µl of PDAM (P-1405, 1-pyrenyldiazomethane, Molecular Probes, Eugene, Oreg., USA) and 38 µl of DMSO.

After labeling, the DNA was purified using a QIAquick kit (QIAGEN) and the final eluate was collected in 50 µl of EB buffer (10 mM Tris EDTA, pH 8.5). Twenty (20) µl of this eluate were diluted in 180 µl of PEG buffer (0.1M $NaPO_3$; 0.5M NaCl; 0.65% Tween 20; 0.14 mg/ml salmon sperm DNA (Gibco); 2% PEG 4000) supplemented with streptavidin HRP(S-911, MOLECULAR PROBES, EUGENE, OREG., USA) diluted 1/10 000. One hundred (100) µl of this preparation were then incubated for 1 hour at 37° C., either in an adsorbed Maxisorp strip well, or in a nonadsorbed control well.

Example 44.2

Preparation of Controls

Controls were simultaneously prepared in the following manner:

A—Control for Labeling with para-Bio-EG3-PDAM Alone:

Ten (10) µl of DNA obtained by PCR amplification, as described in Example 5.1, are labeled by incubation for 30 min at 60° C. in 90 µl of pure water supplemented with 10 µl of para-Bio-EG3-PDAM. After labeling, the DNA is purified using a QIAquick kit and the final eluate is collected in 50 µl of EB buffer. Twenty (20) µl of this eluate are diluted in 180 µl of PEG buffer supplemented with streptavidin HRP diluted 1/10 000. One hundred (100) µl of this preparation are then incubated for 1 hour at 37° C., either in an adsorbed Maxisorp strip well, or in a nonadsorbed well.

B—Control for Labeling with PDAM Alone:

Ten (10) µl of DNA obtained by PCR amplification, as described in Example 5.1, are labeled by incubation for 30 min at 60° C. in 90 µl of pure water supplemented with 2 µl of PDAM and 38 µl of DMSO. After labeling, the DNA is purified using a QIAquick kit and the final eluate is collected in 50 µl of EB buffer. Twenty (20) µl of this eluate are diluted in 180 µl of PEG buffer supplemented with streptavidin HRP diluted 1/10 000. One hundred (100) µl of this preparation are then incubated for 1 hour at 37° C., either in an adsorbed Maxisorp strip well, or in a nonadsorbed well.

C—Control Without Labeling:

Ten (10) µl of DNA obtained by PCR amplification, as described in Example 5.1, are incubated for 30 min at 60° C. in 100 µl of pure water. After labeling, the DNA is purified using a QIAquick kit and the final eluate is collected in 50 µl of EB buffer. Twenty (20) µl of this eluate are diluted in 180 µl of PEG buffer supplemented with streptavidin HRP diluted 1/10 000. One hundred (100) µl of this preparation are then incubated for 1 hour at 37° C., either in an adsorbed Maxisorp strip well, or in a nonadsorbed well.

The strips are then washed with three times 100 µl of PBS Tween buffer (Color 0) and then the presence of streptavidin HRP is visualized by addition of 100 µl of chromogenic reagent (Color 2), incubated for 20 min in the dark, the reaction then being blocked with 50 µl of $H_2SO_4$ (Color 3). The absorbence of the reaction medium is then measured at 492 nm.

Results:

TABLE 32

Double labeling of the DNA with PDAM and para-Bio-EG3-PDAM

| Conditions | Anti-pyrene antibodies adsorbed on a plate (rfu) | Nonadsorbed control plate (rfu) |
|---|---|---|
| Ex. 44.1: PDAM + para-Bio-EG3-PDAM-labeled DNA | 348 | 16 |
| Ex. 44.2.A: para-Bio-EG3-PDAM-labeled DNA | 44 | 19 |
| Ex. 44.2.B: PDAM-labeled DNA | 68 | 12 |
| Ex. 44.2.C: nonlabeled DNA | 75 | 19 |

The result of Table 32 clearly shows a large signal resulting from the capture of the DNA in the wells by the anti-pyrene antibodies, as well as the simultaneous labeling thereof with streptavidin HRP, which has become attached. As the absence of signal in the controls shows, this detection is specific for the labeled DNA, and is not due to the nonspecific adsorption of the DNA or of the streptavidin HRP to the plastic, or to a nonspecific binding of the enzyme to the captured DNA. This example therefore shows that it is possible to carry out a double labeling of the DNA in a single step, it being possible for this double labeling to be used to capture it and to detect it simultaneously.

EXAMPLE 45

Labeling of a PCR Product Simultaneously Allowing its Capture and its Detection by Complementary Nucleic Probes This experiment makes it possible to demonstrate that it is possible to specifically detect a DNA, said DNA being captured on a solid surface using the reactivity of the diazomethyl functional group toward a phosphate group of the DNA.

The experiment is carried out with a portion of the reagents present in the HLA-DR oligo-detection kit (reference 33 202, bioMérieux, France), allowing the detection of nucleic acids amplifed by PCR in microplates, by calorimetric reading. In the context of the experiment described, para-Bio-EG3-PDAM is reacted with nucleic acids produced by PCR. The DNA reacts with the diazomethyl functional groups of the molecule, and thus becomes equipped with biotins grafted on its phosphates. It will then be possible to capture the nucleic acid by incubation on a microplate where streptavidin molecules are adsorbed, and to visualize it by a probe consisting of an oligonucleotide complementary to the captured sequence, combined with horseradish peroxidase, it being possible for this enzyme to decompose colorless molecules of OrthoPhenyleneDiamine (Color 1 reagent of the kit) to a compound which can be detected at a wavelength of 492 nm.

Example 45.1

Capture and Specific detection of the DNA on a Microplate

The labeling of 10 µl of DNA obtained by PCR amplification is carried out in duplicate by incubating them for 30 min at 60° C. with 20 µl of para-Bio-EG3-PDAM. After labeling, the DNA is purified on a QIAquick column (Nucleotide Removal Kit, Qiagen, Hilden, Germany) according to the protocol recommended by the supplier and the final eluate is collected in 50 µl of EB buffer (10 mM Tris-HCl, pH 8.5). Eighty-five (85) µl of the mixture of these eluates are denatured with 8.5 µl of reagent R4 (2N NaOH) for 5 min at room temperature, and the solution is then neutralized with 8.5 µl of reagent R5 (2N acetic acid). 850 µl of hybridization buffer (R6—10 mM Tris-HCl, pH 7.0, 0.2 g/l BND, 0.01 g/l Ciproflaxacin) and 85 µl of detection oligonucleotide (R7—4 mM sodium phosphate, 1 mM potassium phosphate, pH 7.0, 0.1% bovine serum albumin, 0.5% phenol) are added to the mixture. One hundred (100) µl of this preparation are deposited either on the positive control of a strip R1 provided with the kit (capture by a consensus sequence of the amplified gene), or on a streptavidin-coated Combiplate 8 plate (reference 95029263, Labsystem, Helsinki, Finland), or on a control Maxisorp plate (Nunc, Denmark).

In parallel, the same hybridization reaction is carried out on a ten-fold and one hundred-fold dilution, in EB buffer, of the DNA preparation in order to test the sensitivity of the technique.

Example 45.2

Preparation of the Controls

Controls were simultaneously prepared in the following manner:

A—Comparison to the HLA-DR Kit

Ten (10) µl of DNA obtained by PCR amplification, as described in Example 5.1, are incubated for 30 min at 60° C. with 20 µl of para-Bio-EG3-PDAM. After labeling, the DNA is purified on a QIAquick column, the final eluate is collected in a volume of 50 µl EB buffer. The 45 µl of eluate are denatured with 4.5 µl of reagent R4 for 5 min at room temperature, and the solution is neutralized with 4.5 µl of reagent R5. 450 µl of hybridization buffer R6 and 45 µl of detection oligonucleotide are added to the mixture. One hundred (100) µl of this preparation are deposited either on the positive control of a strip R1 provided with the kit (hybridization with a consensus sequence of the amplified gene), or on a streptavidin Combiplate 8 plate, or on a control Maxisorp plate.

B—Hybridization Performed on a DNA Which Does Not Hybridize to the Specific Probe:

Ten (10) µl of DNA obtained by PCR amplification, as described in Example 5.1, are incubated for 30 min at 60° C. with 20 µl of para-Bio-EG3-PDAM. The sample is then treated in a manner identical to the procedure described above in Example A.

C—Control Without DNA:

Ten (10) µl of reagent R6 (hybridization buffer) and 100 µl of reagent R7 (detection oligonucleotide) are deposited either on the positive control of a strip R1 provided with the kit, on a streptavidin plate, or on a Maxisorp-type control plate.

All the strips of the above protocols are incubated for one and a half hours at 37° C., and then washed with three times 100 µl of PBS Tween buffer (Color 0 HLA reagent) and then the presence of the specific detection probe is visualized by addition of 100 µl of chromogenic reagent (Color 2 reagent, PBS pH 7.0; 1% Tween, 0.2 g/l BND; 0.01 g/l Ciproflaxacin), incubated for 20 min in the dark, the reaction then being blocked with 50 µl of $H_2SO_4$ (1.8N Color 3 reagent). The absorbence of the reaction medium is then measured at 492 nm.

Results:

TABLE 33

Specific detection on a microplate of a DNA obtained from PCR

| Conditions | R1 strip HLA DR Kit (Specific capture) | Combiplate (Streptavidin) | Maxisorp (Control) |
|---|---|---|---|
| A - Labeled DNA - Ex. 45.1 | 1215 | 2160 | 16 |
| A - Labeled DNA (diluted 1/10) | NA | 900 | NA |
| A - Labeled DNA (diluted 1/100) | NA | 53 | NA |
| B - Control nonlabeled DNA - Ex. 45.2 A | 1153 | 40 | 17 |
| C - Control bacterial DNA - Ex. 45.2 B | 24 | 15 | NA |
| D - Control without DNA - Ex. 45.2 C | 13 | 12 | 17 |

The results of Table 33 indicate excellent amplification of the target which makes it possible to envisage a use in a diagnostic context. This example shows that the labeling on the phosphate groups allows the capture of DNA and does not prevent specific hybridization thereto.

EXAMPLE 46

Capture and Amplification of DNA Obtained from a Bacterial Lysate and Labeled with para-Bio-EG3-PDAM This example shows that it is possible to capture and to amplify a bacterial DNA using a capture based on the reactivity of the diazomethyl functional group on the phosphate of the nucleic acid.

In the present case, the nucleic acids contained in a bacterial lysate and labeled with para-Bio-EG3-PDAM are captured on streptavidin-coated magnetic beads. The use of magnetic beads makes it possible to immobilize the latter by magnetization during successive washings aimed at removing the cellular residues present in the reaction medium, it being necessary to remove these residues because they can inhibit the PCR amplification which is subsequently performed.

The amplification products were able to be analyzed by passage over DNA chips.

The bacterial DNA is obtained by lysing the cells contained in a *Mycobacterium tuberculosis* culture. The lysis is performed by mechanical lysis. More precisely, it is carried out by sonication, the treated liquid sample containing glass beads. Such a method is already indeed described by the applicant in its patent application WO-A-99/15621, as regards the beads, and in its patent application WO-A-00/60049, as regards the sonication. The sonication may also be carried out using a liquid bath.

However, other techniques, known to a person skilled in the art, may be used, such as those described in U.S. Pat. No. 5,902,746 and patent applications WO-A-98/54306 and WO-A-00/05338. All these Industrial Property titles belong to the applicant.

The bacterial DNA was quantified by Picogreen (P-7589; Molecular Probes, Eugene, Oreg., USA) according to the protocol described by the supplier, at a concentration of $10^7$ copies per µl.

Ten (10) µl of lysate are incubated in the presence of 20 µl of para-Bio-EG3-PDAM for 30 minutes at 60° C. In parallel, 10 µl of lysate are incubated in 20 µl of pure water (Sigma) under the same conditions.

The reaction medium is then purified on a QIAquick column (Nucleotide Removal Kit, Qiagen, Hilden, Germany). The purification protocol used is that recommended by the supplier. The final elution volume is 50 µl.

The labeled DNA fragments are then captured on Dynal magnetic beads (Dynabeads M-280 streptavidin; reference 112.05; Dynal Biotech ASA, Oslo, Norway), which are prepared according to the following protocol:

Ninety (90) µl of Dynal beads are washed twice with 200 µl of Free pure water (Sigma), and are then taken up in 200 µl of PEG buffer (0.1M NaPO$_4$, pH 7, 0.5M NaCl; 0.65% Tween 20; 0.14 ml Herring sperm DNA (reference 15634-017, GibcoBRL); 2% PEG 4000) and incubated for 30 min at 37° C. They are then washed twice with 200 µl 1×PBS buffer containing 0.5% Tween 20, and finally taken up in 90 µl of the same buffer.

Ten (10) µl of the labeled or nonlabeled DNA eluates are incubated for 5 min at room temperature with 40 µl of PEG buffer and 2.5 µl of the magnetic bead preparation described above.

The beads are then washed three times with 200 µl of 1×PBS buffer containing 0.5% Tween, taken up in 200 µl of water and incubated for 20 min at 60° C., and then washed again four times with 200 µl of PBS Tween. The beads are finally taken up in 25 µl of water and a PCR is carried out according to the protocol described in Example 5.1. Two reaction controls are performed, one with 25 µl of pure water and the other with 2.5 µl of beads prepared and washed under the same conditions as the biological samples, and taken up in 25 µl of water.

Result:

The PCR products are then quantified by Picogreen (P-7589; Molecular Probes, Eugene, Oreg., USA) according to the protocol described by the supplier. This method is based on the use of a molecule (Picogreen) having the characteristic of becoming fluorescent only when it is positioned inside a DNA molecule (by becoming intercalated between the bases). Because of the very specific character of this intercalation, and because the fluorescent signal produced is directly proportional to the quantity of DNA present in the medium, it is possible to assay in this manner, very accurately, the concentration of nucleic acid present in a sample. The signal is then expressed in rfu (relative fluorescent unit).

Analysis of the results of PCR on gel shows the presence of a single specific band at the expected size in the samples prepared from genomic DNA labeled with para-Bio-EG3-PDAM. The bands are not detected when the PCR was carried out using a nonlabeled genomic DNA. Quantification of the DNA with Picogreen makes it possible to confirm the production of DNA from genomic DNA captured on beads.

TABLE 34

Quantification of the DNA produced by PCR, from a bacterial lysate, captured and purified by para-Bio-EG3-PDAM

| Conditions | rfu |
|---|---|
| Nonlabeled controls | 51 |
| Labeled DNAs | 170 |
| Background noise | 20 |

Analysis on a DNA chip, according to the protocol described in Example 8, makes it possible to confirm the specificity of the amplification as shown in Table 35 below.

TABLE 35

Specific detection of the target captured and purified with para-Bio-EG3-PDAM

| | Homology | I (rfu) | B (rfu) | I/B |
|---|---|---|---|---|
| Sample | 98 | 11531 | 723 | 16 |

This example shows that it is possible to prepare a biological sample so as to amplify the nucleic acid which it contains, using a capture technique based on the reactivity of the diazomethyl functional group on the phosphate groups thereof.

EXAMPLE 47

Successive Amplification of Two Genes from a Bacterial DNA Captured on a Solid Support This example shows that it is possible to amplify several times and on different targets a DNA captured by virtue of the reactivity of the diazomethyl functional group on the phosphate groups thereof.

In the present case, the nucleic acids, contained in a bacterial lysate and labeled with para-Bio-EG3-PDAM, are captured on streptavidin-coated magnetic beads. The use of magnetic beads makes it possible to preserve the latter by magnetization during successive washings aimed at removing the cellular residues present in the reaction medium, it being necessary for these residues to be removed because they can inhibit the PCR amplifications which will be subsequently performed. These amplifications will take place on two different genes present in the genomic DNA, designated by the names 16S and rpoB respectively. These two genes are then analyzed using DNA chips.

The bacterial DNA is obtained by lysing the cells contained in a *Mycobacterium tuberculosis* culture, according to the protocol already described in Example 46. The bacterial DNA was quantified with Picogreen according to the protocol described by the supplier, at a concentration of $10^7$ copies per µl.

Ten (10) µl of lysate are incubated in the presence of 20 µl of para-Bio-EG3-PDAM for 30 minutes at 60° C. In parallel, 10 µl of lysate are incubated in 20 µl of pure water (Sigma) under the same conditions.

The reaction medium is then purified on a QIAquick column (Nucleotide Removal Kit, Qiagen, Hilden, Germany). The purification protocol used is that recommended by the supplier. The final elution volume is 50 µl.

The labeled DNA fragments are then captured on Dynal magnetic beads, which are prepared according to the following protocol:

Ninety (90) μl of Dynal beads are washed twice with 200 μl of Free pure water (Sigma), and are then taken up in 200 μl of PEG buffer (0.1M NaPO$_4$, pH 7, 0.5M NaCl; 0.65% Tween 20; 0.14 ml salmon sperm DNA (GibcoBRL); 2% PEG 4000) and incubated for 30 min at 37° C. They are then washed twice with 200 μl 1×PBS buffer containing 0.5% Tween 20, and finally taken up in 90 μl of the same buffer.

Ten (10) μl of the labeled or nonlabeled DNA eluates are incubated for 5 min at room temperature with 40 μl of PEG buffer and 2.5 μl of the magnetic bead preparation described above.

The beads are then washed three times with 200 μl of 1×PBS buffer containing 0.5% Tween, taken up in 200 μl of water and incubated for 20 min at 60° C., and then washed again four times with 200 μl of PBS Tween. The beads are finally taken up in 25 μl of water and a PCR is carried out according to the protocol described in Example 5.1. Two reaction controls are performed, one with 25 μl of pure water (Sigma) and the other with 2.5 μl of beads prepared and washed under the same conditions as the biological samples, and taken up in 25 μl of water.

After amplification, the reaction medium is collected, and the beads are separated and washed with 150 μl of 1×PBS containing 0.5% Tween, and then resuspended in 25 μl of pure water (Sigma). Another amplification is performed on the beads, but in the presence of primers intended to amplify the rpoB gene.

Control amplifications performed using noncaptured genomic DNA are performed in parallel on the two amplification systems (rpoB and 16S).

Result:

The PCR products obtained are then analyzed using DNA chips according to the protocol described in Example 8.

TABLE 36

Analysis on DNA chips of the DNA amplicons obtained from PCRs amplified successively or otherwise

| Conditions | | Homology (%) | I (rfu) | B (rfu) | I/B |
| --- | --- | --- | --- | --- | --- |
| Control PCR 16S | 16S | 96 | 4662 | 387 | 12 |
| Results on rpoB sequence | RpoB | 23 | 237 | 358 | 1 |

TABLE 36-continued

Analysis on DNA chips of the DNA amplicons obtained from PCRs amplified successively or otherwise

| Conditions | | Homology (%) | I (rfu) | B (rfu) | I/B |
| --- | --- | --- | --- | --- | --- |
| Control PCR rpoB | RpoB | 98 | 5438 | 397 | 14 |
| Results on 16S sequence | 16S | 17 | 183 | 391 | 1 |
| PCR 16S on beads | 16S | 98 | 2726 | 534 | 5 |
| Results on rpoB sequence | RpoB | 8 | 161 | 480 | >1 |
| PCR rpoB on washed beads | RpoB | 97 | 3205 | 349 | 9 |
| Results on 16S sequence | 16S | 14 | 84 | 358 | >1 |

Analysis of the results of PCR on gel shows the presence of a single specific band at the expected size in the samples prepared from genomic DNA labeled with para-Bio-EG3-PDAM. The bands are not detected when the PCR was carried out using nonlabeled genomic DNA.

Analysis using a DNA chip, as presented in Table 36 above, makes it possible to confirm the specificity of the two successive amplifications, and therefore the capacity to carry out a successive amplification of several genes from DNA immobilized on a solid support, this making it possible to avoid the development of multiplex systems, which often substantially reduce the sensitivity and efficiency of nucleic acid amplifications.

EXAMPLE 48

Capture and Amplification of DNA on a Nylon Membrane Carrying Diazomethyl Groups A Nylon membrane activated so as to carry diazomethyl groups was used to capture bacterial DNA, with the aim of amplifying it by PCR.

Example 48.1

Modification of the Biodyne C Filter

Synthesis scheme:

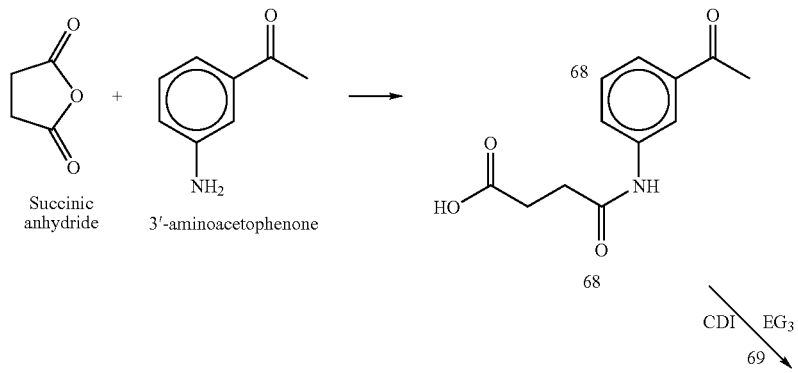

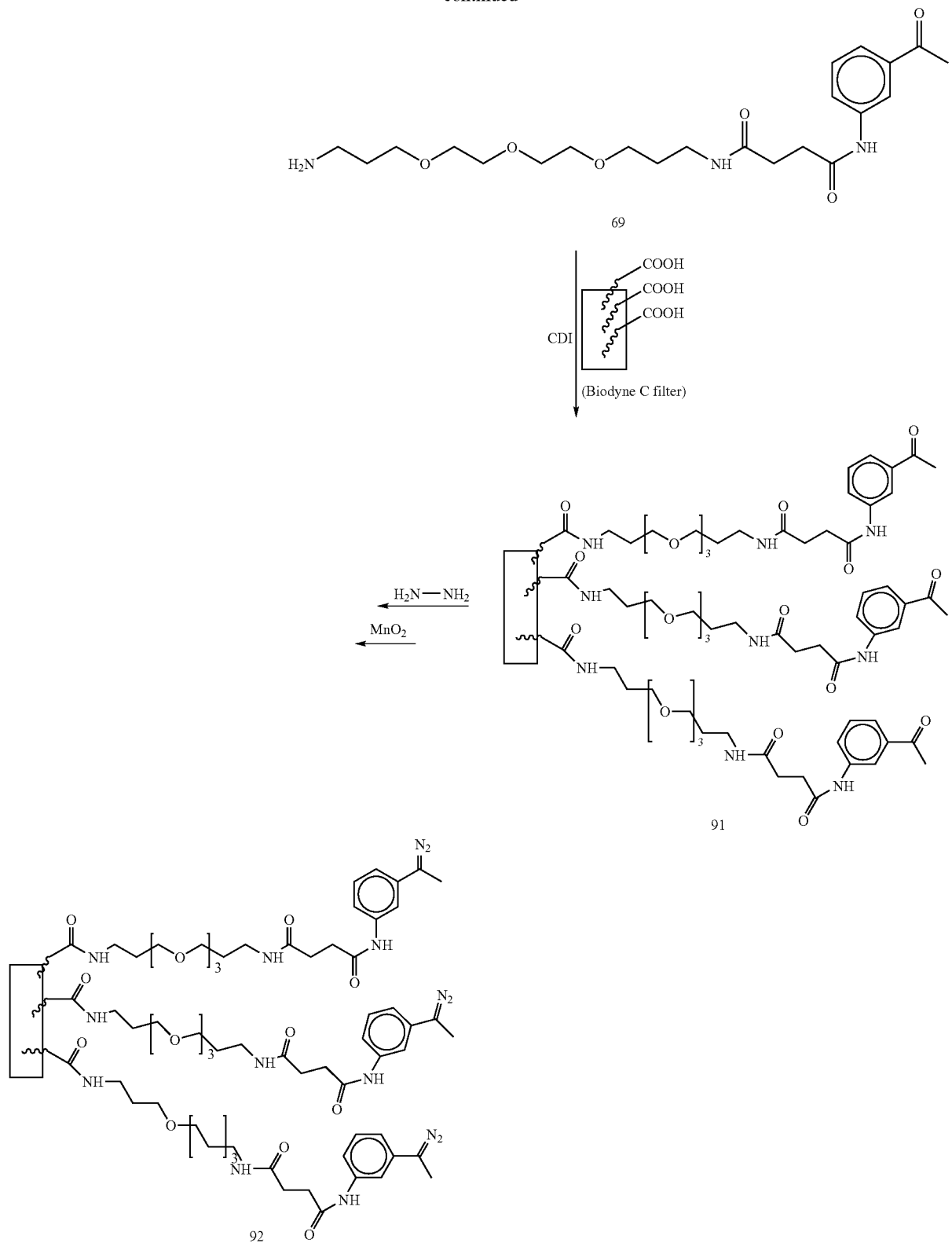
Compound 68:
3'-Aminoacetophenone (14.5 g, 107 mmol) is solubilized in 50 ml of anhydrous DMF. Succinic anhydride (10.7 g, 107 mmol) is added and the mixture is kept stirred under argon and at room temperature. After 6 h, the solution is concentrated under vacuum and 50 ml of methanol are added. The precipitate obtained is filtered and washed with methanol and ether. 19.4 g (81%) of product 68 are thus obtained in the form of an off-white powder.

$^1$H NMR (200 MHz, DMSO-d$_6$) δ=2.5-2.6 (m, 7H); 7.45 (t, 1H); 7.64 (d, 1H); 7.83 (d, H); 8.19 (s, 1H); 10.16 (s, 1H); 12.12 (s, 1H).

Compound 69:

5.07 g (22 mmol) of compound 68 are solubilized in 10 ml of anhydrous DMF, under argon. The solution is placed on ice and 5.00 g (32 mmol) of carbonyldiimidazole are added. After 20 min, 20 ml (94.6 mmol) of 4,7,10-trioxatridecanediamine (EG$_3$) are slowly added. After 3 h of reaction at room temperature, the DMF is evaporated and the residue is taken up in 100 ml of CH$_2$Cl$_2$. Extractions are carried out with saturated NaHCO$_3$ and H$_2$O, after which the organic phase is dried with anhydrous Na$_2$SO$_4$ and the solvent evaporated. 4.34 g (46%) of product 69 are thus obtained.

$^1$H NMR (200 MHz, DMSO-d$_6$): δ=1.59 (m, 2H); 1.87 (m, 2H); 2.16 (s, 3H); 2.40 (m, 2H); 2.55 (m, 2H); 3.08 (m, 2H); 3.45 (m, 16H); 7.30 (t, 1H); 7.42 (d, 1H); 7.70 (d, 1H); 7.83 (t, 1H); 7.97 (s, 1H); 10.00 (s, 1H).

Compound 91:

A 4 cm$^2$ rectangle is cut out on a sheet of Biodyne C filter (reference 60314; Pall Gelman Laboratory, Ann Arbor; Mich.; USA), introduced into a bottle and brought into contact with 0.97 g (6 mmol) of carbonyldiimidazole (CDI) in 3 ml of anhydrous DMF, on ice, under argon and with vigorous stirring. After 20 min, the solution is removed and the filter washed with DMF. A quantity of 0.53 g of product 68 (1 mmol) in 3 ml of anhydrous DMF is then added, and the reaction occurs overnight at room temperature. The solution is then removed and the filter is rinsed with ethanol, dried under vacuum and kept under argon.

Compound 92:

The modified filter 91 is placed in a solution of 97 ml of hydrazine hydrate (2 mmol) in 4 ml of absolute ethanol. The solution is refluxed for 5 h. After having allowed it to cool, the filter is washed with H$_2$O, ethanol and ether, dried under vacuum and placed under argon. Next, 4 ml of anhydrous DMF and 86 mg of MnO$_2$ (1 mmol) are added, and the mixture is allowed to react, with vigorous stirring. After 20 min, the solution is discarded, and the filter is rinsed with DMF and ether. The diazomethyl-modified filter 92 is stored under argon, at a temperature of −19 to −31° C.

Example 48.2

Biological Tests

The activated membrane is cut into small fragments of 2 mm$^2$ which will be incubated for 30 minutes at room temperature in 25 μl of *Mycobacterium tuberculosis* bacterial lysate, prepared by mechanical lysis, using the same technique and the same final concentration as in Example 46, and 375 μl of pure water (Sigma).

The membrane is then placed at 65° C. for 60 min in 100 ml of washing buffer (5% Formamide (Sigma), 1×SSPE (Perbio), 0.01% Triton X-100) so as to remove the nonspecific nucleic acids adsorbed onto the membrane, and then the latter is stored in 1 ml of pure water before amplification.

The PCR is carried out as described in paragraph 5.1, the reaction volume being adjusted with a sufficient quantity of pure water.

In parallel, controls are made according to the same procedure with membranes which cannot covalently bind nucleic acids:

nonmodified Biodyne C membrane (membrane A),

Biodyne membrane chemically modified according to the procedure described, but not treated with anhydrous DMF and MnO$_2$; this control makes it possible to verify the behavior of the membrane in the absence of diazomethyl groups (membrane B), and Biodyne C membrane which has not been modified, but has been treated for 20 min, with vigorous stirring, with anhydrous DMF and MnO$_2$, this control making it possible to verify that the latter step does not modify the adsorption of DNA to the membrane (membrane C).

To check for the absence of inhibition of PCR caused by the treatment of the membranes, another fragment of the membranes A, B and C is amplified simultaneously with 25 μl of bacterial lysate (tubes A', B' and C').

The PCR products are then quantified with Picogreen according to the protocol described by the supplier.

Result:

TABLE 37

Quantification of the DNA obtained by PCR from DNA of bacterial lysate captured on solid support

| Tests performed | Signal (rfu) |
|---|---|
| Modified membrane | 111 |
| Nonmodified membrane (A) | 18 |
| Nonmodified membrane, coamplified with 25 μl of bacterial lysate (A') | 260 |
| Nonactivated modified membrane (B) | 26 |
| Nonactivated modified membrane, coamplified with 25 μl of bacterial lysate (B') | 264 |
| Nonmodified membrane which has undergone activation (C) | 21 |
| Nonmodified membrane which has undergone activation, coamplified with 25 μl of bacterial lysate (C') | 268 |

These results of Table 37 indicate that it is possible to covalently capture on a solid support nucleic acids, obtained from a lysate, by virtue of the diazomethyl chemistry. The amplification observed is not due to nonspecific adsorption of the DNA to the membrane. On the other hand, it is observed, with the controls performed with the PCRs, that the membranes do not cause inhibition of the amplification reaction.

In order to check the nature of the amplified product on the membrane, the amplification product was analyzed by passing over a DNA chip, according to the protocol described above.

The invention claimed is:

1. A temperature-stable labeling reagent of formula (0):

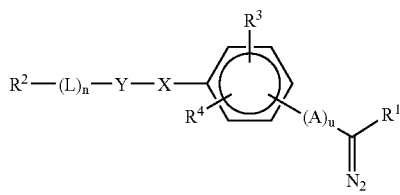

in which:
R[1] represents H or an alkyl, aryl or substituted aryl group,
R[2] represents a detectable marker or at least two detectable markers linked together by at least one multimeric structure,
L is a linking arm containing a linear succession of at least two covalent bonds and n an integer equal to 0 or 1,
R[3] and R[4] represent independently of each other: H, $NO_2$, Cl, Br, F, I, $R^2$-$(L)_n$-Y—X—, OR, SR, $NR^2$, R, NHCOR, CONHR, COOR with R=alkyl or aryl,
A is a linking arm containing at least one covalent double bond allowing conjugation of the diazo functional group with the aromatic ring and u is an integer from 0 to 2, and
—Y—X— represents —CONH—, —NHCO—, —$CH_2$O—, or —$CH_2$S—, with the proviso that when n is equal to 1, L comprises a unit including at least one —(O—$CH_2$—$CH_2$)—, or —Y—X— represents —NHCO—, $CH_2$— or —$CH_2$S—,
wherein the labeling reagent is stable for roughly 2 days at −20° C.,
wherein the labeling reagent is an ortho or meta species of formula (0), and
wherein the detectable marker is at least one marker capable of directly or indirectly generating a detectable signal, and the detectable marker is selected from the group consisting of an enzyme, a chromophore, a group with an electron density detectable by electron microscopy, a group with an electron density detectable by its electrical property, or a radioactive molecule.

2. The labeling reagent as claimed in claim 1 of formula (1):

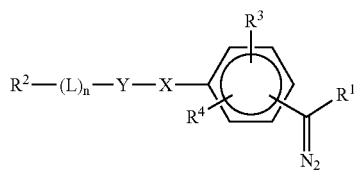

in which:
R[1] represents H or an alkyl, aryl or substituted aryl group,
R[2] represents a detectable marker or at least two detectable markers linked together by at least one multimeric structure,
L is a linking arm containing a linear succession of at least two covalent bonds and n an integer equal to 0 or 1,
R[3] and R[4] represent independently of each other: H, $NO_2$, Cl, Br, F, I, $R^2$-$(L)_n$-Y—X—, OR, SR, $NR^2$, R, NHCOR, CONHR, COOR with R=alkyl or aryl, and
—Y—X— represents —CONH—, —NHCO—, —$CH_2$O—, or —$CH_2$S—.

3. The reagent as claimed in claim 1 of formula (2):

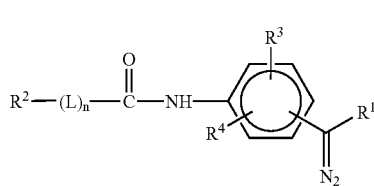

in which:
R[1] represents H or an alkyl, aryl or substituted aryl group,
R[2] represents a detectable marker or at least two detectable markers linked together by at least one multimeric structure,
L is a linking arm containing a linear succession of at least two covalent bonds and n an integer equal to 0 or 1, and
R[3] and R[4] represent independently of each other: H, $NO_2$, Cl, Br, F, I, $R^2$-$(L)_n$-Y—X—, OR, SR, $NR^2$, R, NHCOR, CONHR, COOR with R=alkyl or aryl.

4. The reagent as claimed in claim 1 of formula (3):

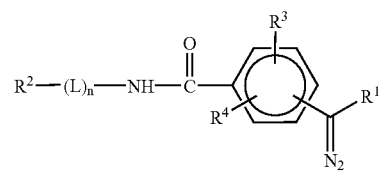

in which:
R[1] represents H or an alkyl, aryl or substituted aryl group,
R[2] represents a detectable marker or at least two detectable markers linked together by at least one multimeric structure,
L is a linking arm containing a linear succession of at least two covalent bonds and n an integer equal to 0 or 1, and
R[3] and R[4] represent independently of each other: H, $NO_2$, Cl, Br, F, I, $R^2$-$(L)_n$-Y—X—, OR, SR, $NR^2$, R, NHCOR, CONHR, COOR with R=alkyl or aryl.

5. The reagent as claimed in claim 1 of formula (4):

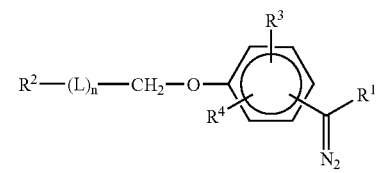

in which:
R[1] represents H or an alkyl, aryl or substituted aryl group,
R[2] represents a detectable marker or at least two detectable markers linked together by at least one multimeric structure,
L is a linking arm containing a linear succession of at least two covalent bonds and n an integer equal to 0 or 1, and
R[3] and R[4] represent independently of each other: H, $NO_2$, Cl, Br, F, I, $R^2$-$(L)_n$-Y—X—, OR, SR, $NR^2$, R, NHCOR, CONHR, COOR with R=alkyl or aryl.

6. The reagent as claimed in claim 1 of formula (21):

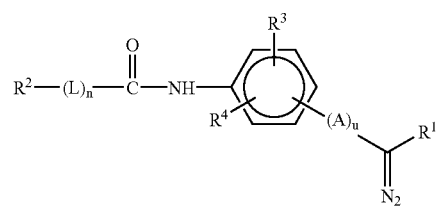

in which:
- $R^1$ represents H or an alkyl, aryl or substituted aryl group,
- $R^2$ represents a detectable marker or at least two detectable markers linked together by at least one multimeric structure,
- L is a linking arm containing a linear succession of at least two covalent bonds and n an integer equal to 0 or 1,
- A is a linking arm containing at least one covalent double bond allowing conjugation of the diazo functional group with the aromatic ring and u is equal to 1, and
- $R^3$ and $R^4$ represent independently of each other: H, $NO_2$, Cl, Br, F, I, $R^2$-$(L)_n$-Y—X—, OR, SR, $NR^2$, R, NHCOR, CONHR, COOR with R=alkyl or aryl.

7. The reagent as claimed in claim 1 of formula (22):

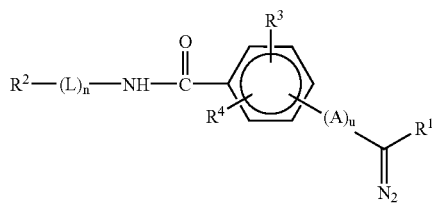

in which:
- $R^1$ represents H or an alkyl, aryl or substituted aryl group,
- $R^2$ represents a detectable marker or at least two detectable markers linked together by at least one multimeric structure,
- L is a linking arm containing a linear succession of at least two covalent bonds and n an integer equal to 0 or 1,
- A is a linking arm containing at least one covalent double bond allowing conjugation of the diazo functional group with the aromatic ring and u is equal to 1, and
- $R^3$ and $R^4$ represent independently of each other: H, $NO_2$, Cl, Br, F, I, $R^2$-$(L)_n$-Y—X—, OR, SR, $NR^2$, R, NHCOR, CONHR, COOR with R=alkyl or aryl.

8. The reagent as claimed in claim 1 of formula (23):

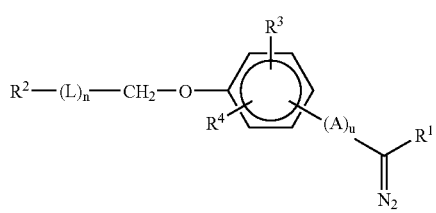

in which:
- $R^1$ represents H or an alkyl, aryl or substituted aryl group,
- $R^2$ represents a detectable marker or at least two detectable markers linked together by at least one multimeric structure,
- L is a linking arm containing a linear succession of at least two covalent bonds and n an integer equal to 0 or 1,
- A is a linking arm containing at least one covalent double bond allowing conjugation of the diazo functional group with the aromatic ring and u is equal to 1, and
- $R^3$ and $R^4$ represent independently of each other: H, $NO_2$, Cl, Br, F, I, $R^2$-$(L)_n$-Y—X—, OR, SR, $NR^2$, R, NHCOR, CONHR, COOR with R=alkyl or aryl.

9. The reagent as claimed in claim 1, wherein $R^3$ and $R^4$ represent independently of each other: H, $NO_2$, $OCH_3$, —CO—NH—$(CH_2)_3$—(O—$CH_2$—$CH_2)_3$—$CH_2$—NH—$R^2$, —CO—NH—$(CH_2)_3$—(O—$CH_2$—$CH_2)_4$—$CH_2$—NH—$R^2$.

10. The reagent as claimed in claim 1 of formula (2'):

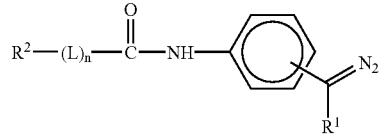

in which:
- $R^1$ represents H or an alkyl, aryl or substituted aryl group,
- $R^2$ represents a detectable marker or at least two detectable markers linked together by at least one multimeric structure, and
- L is a linking arm containing a linear succession of at least two covalent bonds and n an integer equal to 0 or 1.

11. A method for synthesizing a labeling reagent as claimed in claim 10, comprising the following steps:

a) providing a derivative of formula (17):

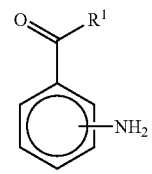

in which $R^1$ represents H or an alkyl or aryl or substituted aryl group, and $NH_2$ is in ortho- or meta-position, and, b) providing a marker or a marker precursor possessing a carboxylic acid functional group, c) reacting the carboxylic functional group of said marker or marker precursor and the primary amine functional group of the derivative of formula (17) together in the presence of at least one coupling agent to form an amide bond, d) reacting hydrazine with the ketone or aldehyde functional group from the derivative of formula (17) to form a hydrazone, and e) oxidizing said hydrazone in the presence of $MnO_2$ to form a diazomethyl functional group.

12. The reagent as claimed in claim 1 of formula (24):

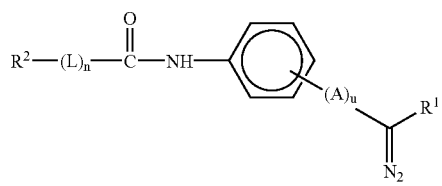

in which:
- $R^1$ represents H or an alkyl, aryl or substituted aryl group,
- $R^2$ represents a detectable marker or at least two detectable markers linked together by at least one multimeric structure, and
- A is a linking arm containing at least one covalent double bond allowing conjugation of the diazo functional group with the aromatic ring and u is equal to 1.

13. The reagent as claimed in claim 1, in which the structure $R^2\text{-}(L)_n\text{-}$ is of formula (5):

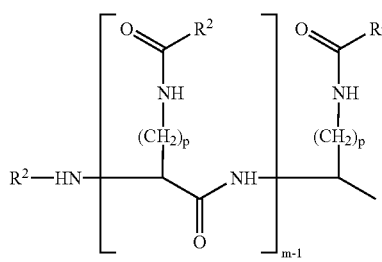

in which:

$R^2$ represents a detectable marker, m is an integer between 1 and 100, and p is an integer between 1 and 10.

14. The reagent as claimed in claim 1 of formula (6):

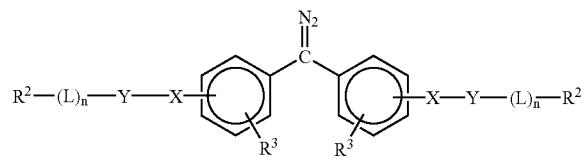

in which:

$R^2$ represents a detectable marker or at least two detectable markers linked together by at least one multimeric structure, $R^3$ represents H, $NO_2$, Cl, Br, F, I, $R^2\text{-}(L)_n\text{-}Y\text{—}X\text{—}$, OR, SR, $NR^2$, R, NHCOR, CONHR, COOR with R=alkyl or aryl, L is a linking arm containing a linear succession of at least two covalent bonds and n an integer equal to 0 or 1, and —Y—X— represents —CONH—, —NHCO—, —$CH_2O$—, or —$CH_2S$—.

15. The reagent as claimed in claim 1 of formula (25):

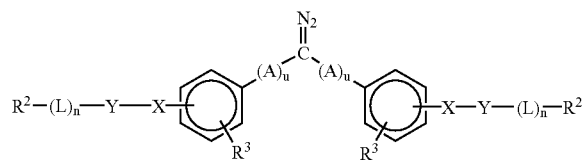

in which:

$R^2$ represents a detectable marker or at least two detectable markers linked together by at least one multimeric structure, $R^3$ represents H, $NO_2$, Cl, Br, F, I, $R^2\text{-}(L)_n\text{-}Y\text{—}X\text{—}$, OR, SR, $NR^2$, R, NHCOR, CONHR, COOR with R=alkyl or aryl, L is a linking arm containing a linear succession of at least two covalent bonds and n an integer equal to 0 or 1, A is a linking arm containing at least one covalent double bond allowing conjugation of the diazo functional group with the aromatic ring and u is equal to 1, and —Y—X— represents —CONH—, —NHCO—, —$CH_2O$—, or —$CH_2S$—.

16. The reagent as claimed in claim 1 of formula (14):

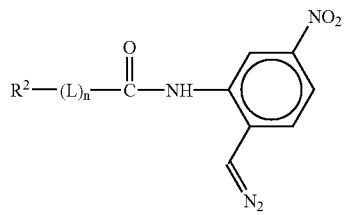

in which:

$R^2$ represents a detectable marker or at least two detectable markers linked together by at least one multimeric structure, and L is a linking arm containing a linear succession of at least two covalent bonds and n an integer equal to 0 or 1.

17. The reagent as claimed in claim 1 of formula (26):

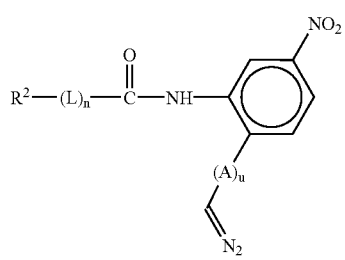

in which:

$R^2$ represents a detectable marker or at least two detectable markers linked together by at least one multimeric structure, A is a linking arm containing at least one covalent double bond allowing conjugation of the diazo functional group with the aromatic ring and u is equal to 1, and L is a linking arm containing a linear succession of at least two covalent bonds and n an integer equal to 0 or 1.

18. The reagent as claimed in claim 1 of formula (15):

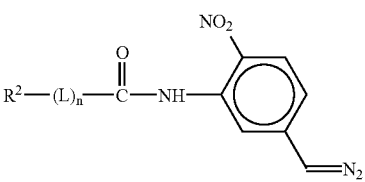

in which:

$R^2$ represents a detectable marker or at least two detectable markers linked together by at least one multimeric structure, L is a linking arm containing a linear succession of at least two covalent bonds and n an integer equal to 0 or 1.

19. The reagent as claimed in claim 1 of formula (27):

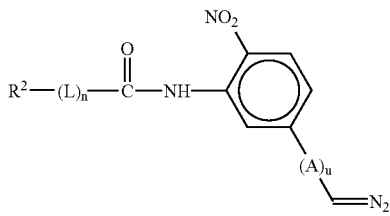

in which:
R² represents a detectable marker or at least two detectable markers linked together by at least one multimeric structure,
A is a linking arm containing at least one covalent double bond allowing conjugation of the diazo functional group with the aromatic ring and u is equal to 1, and
L is a linking arm containing a linear succession of at least two covalent bonds and n an integer equal to 0 or 1.

20. The reagent as claimed in claim 1, wherein L comprises a unit —(O—CH₂—CH₂)—, repeated from 1 to 20 times.

21. A method for synthesizing a labeling reagent, as claimed in claim 1, comprising the following steps:
a) providing a derivative of formula (16a):

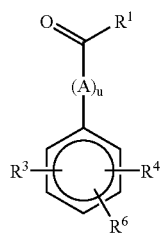

in which:
R¹ represents H or an alkyl or aryl or substituted aryl group,
R³ and R⁴ represent independently of each other: H, NO₂, Cl, Br, F, I, R⁶, OR, SR, NR², R, NHCOR, CONHR, COOR with R=alkyl or aryl,
R⁶ represents COOH, COOM, NH₂, OH or SH with M=alkyl, and R⁶ is in ortho- or meta-position, and,
A is a linking arm containing at least one covalent double bond allowing conjugation of the diazomethyl functional group with the aromatic ring and u is an integer equal to 0 or 1,
b) providing a marker or a marker precursor possessing a reactive functional group R⁷ complementary to R⁶,
c) reacting the complementary functional group of said marker or marker precursor with the functional group R⁶ of the derivative of formula (16a) in the presence of at least one coupling agent to form a covalent bond,
d) reacting hydrazine or one of its derivatives is with the ketone or aldehyde functional group to form a hydrazone, and
e) converting the hydrazone is to a diazomethyl functional group using an appropriate treatment.

22. The method of synthesis as claimed in claim 21, which comprises:
an additional step of protecting the ketone or aldehyde functional group of compound (16a), and
an additional subsequent step of deprotecting said ketone or aldehyde functional group.

23. The method of synthesis as claimed in claim 21, which consists in carrying out the following steps:
a) providing a derivative of formula (16):

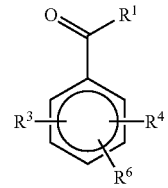

in which:
R¹ represents H or an alkyl or aryl or substituted aryl group,
R³ arid R⁴ represent independently of each other: H, NO₂, Cl, Br, F, I, R⁶, OR, SR, NR², R, NHCOR, CONHR, COOR with R=alkyl or aryl, and
R⁶ represents COOH, NH₂, OH or SH and NH₂ is in ortho- or meta-position, and,
b) providing a marker or a marker functional precursor possessing a reactive functional group R⁷ complementary to R⁶,
c) reacting the complementary functional group of said marker or marker precursor with the R⁶ functional group of the derivative of formula (16) in the presence of at least one coupling agent to form a covalent bond,
d) reacting hydrazine or one of its derivatives with the ketone or aldehyde functional group to form a hydrazone, and
e) converting the hydrazone to a diazomethyl functional group by means of an appropriate treatment.

24. The method of synthesis as claimed in claim 21, wherein M in R⁶=COOM is methyl or ethyl.

25. A method for synthesizing a labeling reagent, as claimed in claim 1, comprising the following steps:
a) providing a derivative of formula (16a):

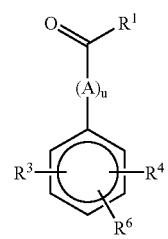

in which:
R¹ represents H or an alkyl or aryl or substituted aryl group,
R³ and R⁴ represent independently of each other: H, NO₂, Cl, Br, F, I, R⁶, OR, SR, NR², R, NHCOR, CONHR, COOR with R=alkyl or aryl,
R⁶ represents COOH, COOM, NH₂, OH or SH with M=alkyl, and R⁶ is in ortho- or meta-position, and,
A is a linking arm containing at least one covalent double bond allowing conjugation of the diazomethyl functional group with the aromatic ring and u is an integer equal to 0 or 1,
b) providing a linking arm L possessing at least two reactive functional groups R⁸ which are identical or different, the first functional group $R^8$ complementary to $R^6$ and the second functional group $R^8$ complementary to $R^{7'}$ and providing in addition, a marker or a marker precursor possessing a reactive functional group $R^7$, c) reacting the first reactive functional group $R^8$ of the linking arm L with the derivative of formula (16a) in the presence of at least one coupling agent to form a covalent bond and then reacting the second reactive functional group $R^8$ of the linking arm L with the marker or the marker precursor in the presence of at least one coupling agent to form a covalent bond, d) reacting hydrazine or one of its derivatives with the ketone or aldehyde functional group to form a hydrazone, and e) converting the hydrazone to a diazomethyl functional group using an appropriate treatment.

26. The method of synthesis as claimed in claim 25, wherein M in $R^6$=COOM is methyl or ethyl.

27. A method for labeling a biological molecule, in particular a nucleic acid, comprising bringing a biological molecule and a reagent as claimed in claim 1 into contact in a homogeneous solution, in a substantially aqueous buffer.

28. A labeled biological molecule obtained by the method as claimed in claim 27.

29. A method for labeling and fragmenting a single- or double-stranded nucleic acid, comprising the following steps:
    fragmenting the nucleic acid,
    attaching a marker to at least one of the fragments via a labeling reagent chosen from the compounds of formula of claim 1,
wherein:
    said reagent is covalently and predominantly coupled to at least one phosphate of said fragment.

30. The method as claimed in claim 29, wherein the labeling reagent is chosen from the compounds of formula (1) of claim 2.

31. The method as claimed in claim 29, wherein the fragmentation and the labeling are carried out in two steps.

32. The method as claimed in claim 29, wherein the fragmentation and the labeling are carried out in one step.

33. The method as claimed in claim 29, wherein the labeling is carried out in a substantially aqueous homogeneous solution.

34. The method as claimed in claim 29, wherein the fragmentation is carried out by the enzymatic, physical or chemical route.

35. A labeled nucleic acid obtained by the method as claimed in claim 29.

36. A kit for detecting a target nucleic acid comprising a labeled nucleic acid as claimed in claim 35.

37. A solid support onto which a reagent as claimed in claim 1 is attached.

38. The reagent as claimed in claim 1, wherein the reagent is stable for at least 15 days at a temperature of at least −20° C.

* * * * *

UNITED STATES PATENT AND TRADEMARK OFFICE
CERTIFICATE OF CORRECTION

PATENT NO. : 7,338,805 B2  Page 1 of 1
APPLICATION NO. : 10/137454
DATED : March 4, 2008
INVENTOR(S) : Cecile Bourget et al.

It is certified that error appears in the above-identified patent and that said Letters Patent is hereby corrected as shown below:

Claim 29, lines 6-7 (col. 155, lines 31-32), change "compounds of formula of claim 1" to -- compounds of formula (0) of claim 1 --.

Signed and Sealed this

First Day of July, 2008

JON W. DUDAS
*Director of the United States Patent and Trademark Office*